US008753846B2

(12) United States Patent
Heap et al.

(10) Patent No.: US 8,753,846 B2
(45) Date of Patent: Jun. 17, 2014

(54) METHODS OF MODIFYING NUCLEIC ACIDS IN HOST CELLS

(75) Inventors: John Timothy Heap, Nottingham (GB); Nigel Peter Minton, Nottingham (GB)

(73) Assignee: The University of Nottingham, Nottingham (GB)

( * ) Notice: Subject to any disclaimer, the term of this patent is extended or adjusted under 35 U.S.C. 154(b) by 162 days.

(21) Appl. No.: 12/867,579

(22) PCT Filed: Feb. 13, 2009

(86) PCT No.: PCT/GB2009/000380
§ 371 (c)(1),
(2), (4) Date: Oct. 22, 2010

(87) PCT Pub. No.: WO2009/101400
PCT Pub. Date: Aug. 20, 2009

(65) Prior Publication Data

US 2011/0027835 A1 Feb. 3, 2011

(30) Foreign Application Priority Data

Feb. 15, 2008 (GB) .................................. 0802842.5

(51) Int. Cl.
*C12N 1/20* (2006.01)
*C12Q 1/68* (2006.01)

(52) U.S. Cl.
USPC ............................ 435/91.5; 435/471; 435/6.1

(58) Field of Classification Search
None
See application file for complete search history.

(56) References Cited

FOREIGN PATENT DOCUMENTS

WO 2006/130925 A 12/2006

OTHER PUBLICATIONS

Manoj et al., Negative selection of *Plasmodium falciparum* reveals targeted gene deletion by double crossover recombination, International Journal for Parasitology 32 (2002) 81-89.*

O'Connor et al., Construction and analysis of chromosomal *Clostridium* difficile mutants, Molecular Microbiology (2006) 61(5), 1335-1351.*

Heap, J.T., at al., "The ClosTron: a Universal Gene Knock-Out System for the Genus *Clostridium*," Journal of Microbiological Methods 70(3):452-464, Sep. 2007.

International Search Report, mailed Sep. 15, 2009, issued in corresponding International Application No. PCT/GB2009/000380, filed Feb. 13, 2009, 7 pages.

International Preliminary Report on Patentability and Written Opinion, mailed Aug. 17, 2010, issued in corresponding International Application No. PCT/GB20091000380, filed Feb. 13, 2009, 8 pages.

* cited by examiner

*Primary Examiner* — Anne Gussow
*Assistant Examiner* — Reza Ghafoorian
(74) *Attorney, Agent, or Firm* — Christensen O'Connor Johnson Kindness PLLC

(57) ABSTRACT

A method of double crossover homologous recombination in a host cell comprising: a first homologous recombination event between a donor DNA molecule comprising a first element of a selectable allele and an acceptor DNA molecule comprising a second element of the selectable allele in the host cell, thereby to form a product of the first homologous recombination event in the host cell; and a second homologous recombination event within the product of the first homologous recombination event, thereby to form a product of the second homologous recombination event in the host cell which confers a selectable phenotype on the host cell, wherein the selectable phenotype arises following and in dependency on the formation of a selectable allele from the first and second elements of the selectable allele.

30 Claims, 65 Drawing Sheets

Figure 3

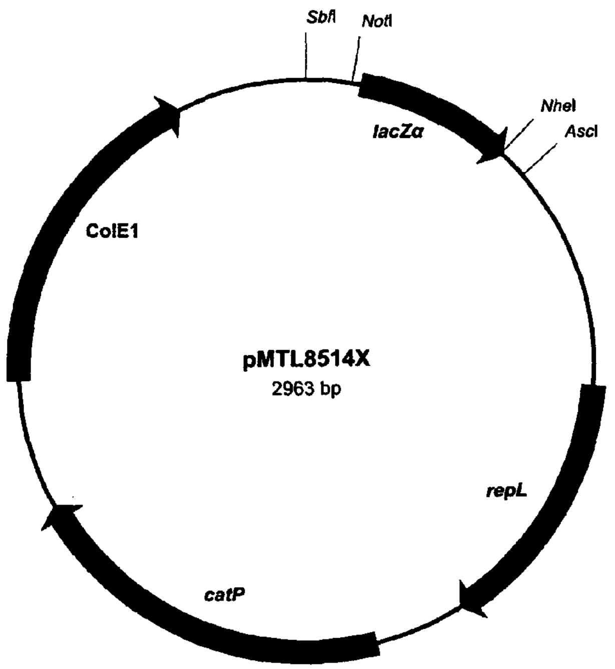

```
   1 ggataaaaaaattgtagataaatttataaaatagttttatctacaattttttttatcagg 60
  61 aaacagctatgaccgcggccgctgtatccatatgaccatgattacgaattcgagctcggt 120
 121 acccggggatcctctagagtcgacgtcacgcgtccatggagatctcgaggcctgcagaca 180
 181 tgcaagcttggcactggccgtcgttttacaacgtcgtgactgggaaaaccctggcgttac 240
 241 ccaacttaatcgccttgcagcacatccccctttcgccagctggcgtaatagcgaagaggc 300
 301 ccgcaccgatcgcccttcccaacagttgcgcagcctgaatggcgaatggcgctagcataa 360
 361 aaataagaagcctgcatttgcaggcttcttatttttatggcgcgccgcattcacttcttt 420
 421 tctatataaatatgagcgaagcgaataagcgtcggaaaagcagcaaaaagtttcctttt 480
 481 gctgttggagcatgggggttcaggggggtgcagtatctgacgtcaatgccgagcgaaagcg 540
 541 agccgaagggtagcatttacgttagataaccccctgatatgctccgacgctttatataga 600
 601 aaagaagattcaactaggtaaaatcttaatataggttgagatgataaggtttataaggaa 660
 661 tttgtttgttctaatttttcactcattttgttctaatttcttttaacaaatgttcttttt 720
 721 tttttagaacagttatgatatagttagaatagtttaaaataaggagtgagaaaaagatga 780
 781 aagaaagatatggaacagtctataaaggctctcagaggctcatagacgaagaaagtggag 840
 841 aagtcatagaggtagacaagttataccgtaaacaaacgtctggtaacttcgtaaaggcat 900
 901 atatagtgcaattaataagtatgttagatatgattggcggaaaaaaacttaaaatcgtta 960
 961 actatatcctagataatgtccacttaagtaacaatacaatgatagctacaacaagagaaa 1020
1021 tagcaaaagctacaggaacaagtctacaaacagtaataacaacacttaaaatcttagaag 1080
1081 aaggaaatattataaaaagaaaaactggagtattaatgttaaaccctgaactactaatga 1140
1141 gaggcgacgaccaaaaacaaaaatacctcttactcgaatttgggaactttgagcaagagg 1200
1201 caaatgaaatagattgacctcccaataacaccacgtagttattgggaggtcaatctatga 1260
1261 aatgcgattaagggccggccagtgggcaagttgaaaaattcacaaaaatgtggtataata 1320
1321 tctttgttcattagagcgataaacttgaatttgagagggaacttagatggtatttgaaaa 1380
1381 aattgataaaaatagttggaacagaaaagagtattttgaccactactttgcaagtgtacc 1440
1441 ttgtacctacagcatgaccgttaaagtggatatcacacaaataaaggaaaagggaatgaa 1500
1501 actatatcctgcaatgctttattatattgcaatgattgtaaaccgccattcagagtttag 1560
1561 gacggcaatcaatcaagatggtgaattggggatatatgatgagatgataccaagctatac 1620
1621 aatatttcacaatgatactgaaacattttccagcctttggactgagtgtaagtctgactt 1680
1681 taaatcatttttagcagattatgaaagtgatacgcaacggtatggaaacaatcatagaat 1740
1741 ggaaggaaagccaaatgctccggaaaacatttttaatgtatctatgataccgtggtcaac 1800
```

```
1801 cttcgatggctttaatctgaatttgcagaaaggatatgattatttgattcctatttttac 1860
1861 tatggggaaatattataaagaagataacaaaattatacttcctttggcaattcaagttca 1920
1921 tcacgcagtatgtgacggatttcacatttgccgttttgtaaacgaattgcaggaattgat 1980
1981 aaatagttaacttcaggtttgtctgtaactaaaaacaagtatttaagcaaaaacatcgta 2040
2041 gaaatacggtgtttttgttaccctaagtttaaactccttttgataatctcatgaccaa 2100
2101 aatcccttaacgtgagttttcgttccactgagcgtcagaccccgtagaaaagatcaaagg 2160
2161 atcttcttgagatcctttttttctgcgcgtaatctgctgcttgcaaacaaaaaaaccacc 2220
2221 gctaccagcggtggtttgtttgccggatcaagagctaccaactctttttccgaaggtaac 2280
2281 tggcttcagcagagcgcagataccaaatactgtccttctagtgtagccgtagttaggcca 2340
2341 ccacttcaagaactctgtagcaccgcctacatacctcgctctgctaatcctgttaccagt 2400
2401 ggctgctgccagtggcgataagtcgtgtcttaccgggttggactcaagacgatagttacc 2460
2461 ggataaggcgcagcggtcgggctgaacggggggttcgtgcacacagcccagcttggagcg 2520
2521 aacgacctacaccgaactgagatacctacagcgtgagcattgagaaagcgccacgcttcc 2580
2581 cgaagggagaaaggcggacaggtatccggtaagcggcagggtcggaacaggagagcgcac 2640
2641 gagggagcttccagggggaaacgcctggtatctttatagtcctgtcgggtttcgccacct 2700
2701 ctgacttgagcgtcgatttttgtgatgctcgtcaggggggcggagcctatggaaaaacgc 2760
2761 cagcaacgcggcctttttacggttcctggccttttgctggccttttgctcacatgttctt 2820
2821 tcctgcgttatcccctgattctgtggataaccgtattaccgcctttgagtgagctgatac 2880
2881 cgctcgccgcagccgaacgaccgagcgcagcgagtcagtgagcgaggaagcggaagagcg 2940
2941 cccaatacgcagggcccccctgca 2963
```

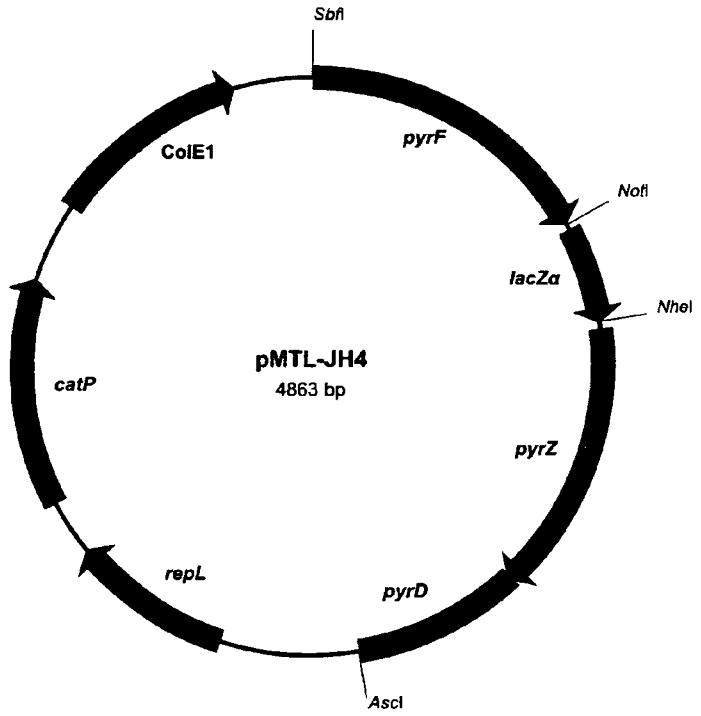

```
   1 gggtgtttaggacttgatactgatattacttatgtaccagaagagttttgtaagaaattt   60
  61 aatagtatagaagatgctatatttaattttaataagaaaataattgatgcgactttagat  120
 121 gttgtttcatgttataaggtgcaaattgcatattatgaagcttatggtttaaaaggactt  180
 181 ttggcctataaaaggacacttgaatatttgagagaaaaaaaggctattgcaattgctgat  240
 241 ataaaaagaggagatatagctaaaacagctgaaatgtatgctaaagctcactttgaaggt  300
 301 gattttgaagcggattttgttacgttaaatccttacatggggttagatggtatagagcct  360
 361 tatatgccttatattgaaaaaatggaaaaaggattatttattttgcttagaacatcgaat  420
 421 aaaggagcctatgatatacaatatataaagactcagggcggaaaaaacgtatatgatgag  480
 481 gttggagaaaaaatatatgatttaggtcaaaaggctacgggaaggagcaagtattcttca  540
 541 ataggagcagtagttggatgtactcacgttgaagaaggcgttgaattagaaataaattt  600
 601 aaaaatatgttttttctaattccaggctatggagcacaaggtggaactgcaaaggaagta  660
 661 agtttgtatttaagagaaggtaatggtggagtggtaaattcctcaagggggaatacttctt  720
 721 gcttataaaaaagaagaaaacggtgaaaaaatatttgatgagtgtgcaaggcttgcagcg  780
 781 attaatatgagagacgagatcagaaaaactttatgagcggccgctgtatccatatgacca  840
 841 tgattacgaattcgagctcggtacccggggatcctctagagtcgacgtcacgcgtccatg  900
 901 gagatctcgaggcctgcagacatgcaagcttggcactggccgtcgttttacaacgtcgtg  960
 961 actgggaaaaccctggcgttacccaacttaatcgccttgcagcacatccccctttcgcca 1020
1021 gctggcgtaatagcgaagaggcccgcaccgatcgcccttcccaacagttgcgcagcctga 1080
1081 atggcgaatggcgctagcattttgggggaattttgatgaaggaaaagtatacagtagaaa 1140
1141 aagtatatgaaaatataaaagttgaagatggtatatacaaacttagtataaagggtgaat 1200
1201 ttgaggtgaggccaggacaattttatcttttaagagcttgggatatagaaccaacacttt 1260
1261 ctagacctattagtatatatgatgcagatgacgaaaaaatatcgttcttatactctgttg 1320
1321 ttggaaaaggaactgaaattttatctaaattaaagagcggcgatgaaataaagataacag 1380
1381 gacctttaggaaatggatttaacgtaaaaaggataagtggaaaagtggctatagtttgtg 1440
1441 gtggtataggtgtagcaccaatggtatatctggctaaaaacttaaaaaattgtaatgttg 1500
1501 attttatgctggcttcaaaactgtgagtaaaactgtggataatgtggaaaaatatgtta 1560
1561 aagagttaaagttgtccacagaagatggaagtattggacataaggggtatgtaacagata 1620
```

1621 actttaagccagaagaatacgattatgttttatgctgcggacctgagataatgatgtata 1680
1681 aagttgttaaaatgtgtgaacaaaagaatgttcctgtatatatttcaatggagaaaaaa 1740
1741 tggcatgtggaataggtgcatgccttgtatgcacttgtaaaactaagggtggaagaagaa 1800
1801 gagcttgtaaagagggcccagtattttaggaagtgagttgatattaaatgactaaagta 1860
1861 aatatttgtggaatagatttaagaaccccgttattgctgcttctggcacctttggattt 1920
1921 ggagaagagtttagtaagtattttgatgtttcaaggcttggtggcatatcttcaaaggga 1980
1981 cttacattgaatcctaaggaaggtaatgatggtgcaagagtttttgaggtcacaggcgga 2040
2041 atgatgaatagtgtaggacttcaaaatcctggagttaaagagtttataaaaaaagaactt 2100
2101 cctaagatgaaaaaaatagatacagtatgtattgttaaccttggtggaagctgtgaggat 2160
2161 gattatttaaggggcatggagcttcttgagaatacagatgctgatatgatagaacttaat 2220
2221 atatcctgtcctaatgtaaagcacggcggcatggcttttggaataaaatcagaagttgct 2280
2281 tataatgttgtatcacaaggcgcgccgcattcacttcttttctatataaatatgagcgaa 2340
2341 gcgaataagcgtcggaaaagcagcaaaaagtttcctttttgctgttggagcatgggggtt 2400
2401 caggggtgcagtatctgacgtcaatgccgagcgaaagcgagccgaagggtagcatttac 2460
2461 gttagataacccccctgatatgctccgacgctttatatagaaaagaagattcaactaggta 2520
2521 aaatcttaatataggttgagatgataaggtttataaggaatttgtttgttctaattttc 2580
2581 actcattttgttctaatttcttttaacaaatgttcttttttttttagaacagttatgata 2640
2641 tagttagaatagtttaaaataaggagtgagaaaaagatgaaagaaagatatggaacagtc 2700
2701 tataaaggctctcagaggctcatagacgaagaaagtggagaagtcatagaggtagacaag 2760
2761 ttataccgtaaacaaacgtctggtaacttcgtaaaggcatatatagtgcaattaataagt 2820
2821 atgttagatatgattggcggaaaaaacttaaaatcgttaactatatcctagataatgtc 2880
2881 cacttaagtaacaatacaatgatagctacaacaagagaaatagcaaaagctacaggaaca 2940
2941 agtctacaaacagtaataacaacacttaaaatcttagaagaaggaaatattataaaaaga 3000
3001 aaaactggagtattaatgttaaaccctgaactactaatgagaggcgacgaccaaaaacaa 3060
3061 aaatacctcttactcgaatttgggaactttgagcaagaggcaaatgaaatagattgacct 3120
3121 cccaataacaccacgtagttattgggaggtcaatctatgaaatgcgattaagggccggcc 3180
3181 agtgggcaagttgaaaaattcacaaaaatgtggtataatatctttgttcattagagcgat 3240
3241 aaacttgaatttgagagggaacttagatggtatttgaaaaaattgataaaaatagttgga 3300
3301 acagaaaagagtattttgaccactactttgcaagtgtaccttgtacctacagcatgaccg 3360
3361 ttaaagtggatatcacacaaataaaggaaaaggaatgaaactatatcctgcaatgcttt 3420
3421 attatattgcaatgattgtaaaccgccattcagagtttaggacggcaatcaatcaagatg 3480
3481 gtgaattggggatatatgatgagatgataccaagctatacaatatttcacaatgatactg 3540
3541 aaacattttccagcctttggactgagtgtaagtctgactttaaatcatttttagcagatt 3600
3601 atgaaagtgatacgcaacggtatggaaacaatcatagaatggaaggaaagccaaatgctc 3660
3661 cggaaaacatttttaatgtatctatgataccgtggtcaaccttcgatggctttaatctga 3720
3721 atttgcagaaaggatatgattatttgattcctatttttactatggggaaatattataaag 3780
3781 aagataacaaaattatacttcctttggcaattcaagttcatcacgcagtatgtgacggat 3840
3841 ttcacatttgccgttttgtaaacgaattgcaggaattgataaatagttaacttcaggttt 3900
3901 gtctgtaactaaaaacaagtatttaagcaaaaacatcgtagaaatacggtgtttttttgtt 3960
3961 accctaagtttaaactcctttttgataatctcatgaccaaaatcccttaacgtgagtttt 4020
4021 cgttccactgagcgtcagaccccgtagaaaagatcaaaggatcttcttgagatcctttttt 4080
4081 ttctgcgcgtaatctgctgcttgcaaacaaaaaaaccaccgctaccagcggtggtttgtt 4140
4141 tgccggatcaagagctaccaactctttttccgaaggtaactggcttcagcagagcgcaga 4200
4201 taccaaatactgtccttctagtgtagccgtagttaggccaccacttcaagaactctgtag 4260
4261 caccgcctacatacctcgctctgctaatcctgttaccagtggctgctgccagtggcgata 4320
4321 agtcgtgtcttaccgggttggactcaagacgatagttaccggataaggcgcagcggtcgg 4380
4381 gctgaacggggggttcgtgcacacagcccagcttggagcgaacgacctacaccgaactga 4440
4441 gatacctacagcgtgagcattgagaaagcgccacgcttcccgaagggagaaaggcggaca 4500
4501 ggtatccggtaagcggcagggtcggaacaggagagcgcacgagggagcttccagggggaa 4560
4561 acgcctggtatctttatagtcctgtcgggtttcgccacctctgacttgagcgtcgatttt 4620
4621 tgtgatgctcgtcaggggggcggagcctatggaaaaacgccagcaacgcggcctttttac 4680
4681 ggttcctggccttttgctggccttttgctcacatgttctttcctgcgttatcccctgatt 4740
4741 ctgtggataaccgtattaccgcctttgagtgagctgataccgctcgccgcagccgaacga 4800
4801 ccgagcgcagcgagtcagtgagcgaggaagcggaagagcgcccaatacgcaggccccct 4860
4861 gca 4863

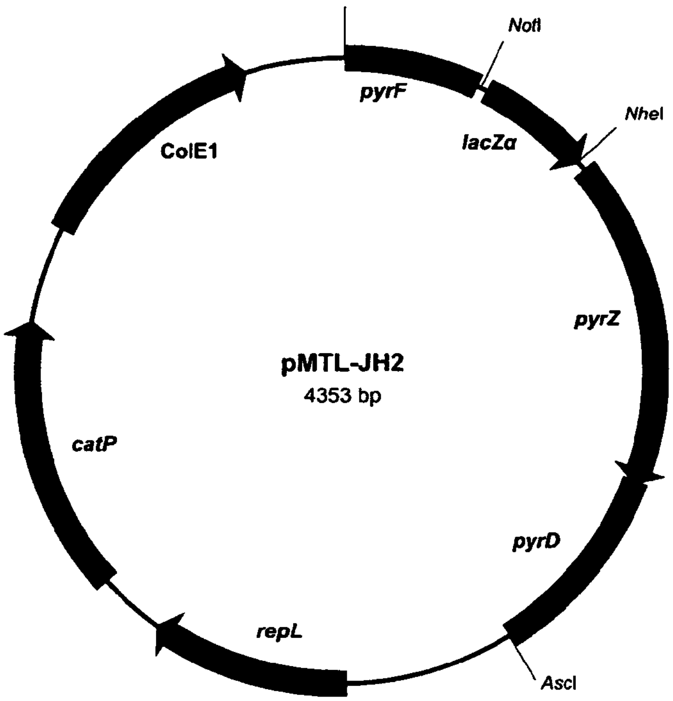

```
   1 gggtgtttaggacttgatactgatattacttatgtaccagaagagttttgtaagaaattt 60
  61 aatagtatagaagatgctatatttaattttaataagaaaataattgatgcgactttagat 120
 121 gttgtttcatgttataaggtgcaaattgcatattatgaagcttatggtttaaaaggactt 180
 181 ttggcctataaaaggacacttgaatatttgagagaaaaaaaggctattgcaattgctgat 240
 241 ataaaaagaggagatatagctaaaacagctgaaatgtatgctaaagctcactttgaaggt 300
 301 taatgagcggccgctgtatccatatgaccatgattacgaattcgagctcggtacccgggg 360
 361 atcctctagagtcgacgtcacgcgtccatggagatctcgaggcctgcagacatgcaagct 420
 421 tggcactggccgtcgttttacaacgtcgtgactgggaaaaccctggcgttacccaactta 480
 481 atcgccttgcagcacatccccctttcgccagctggcgtaatagcgaagaggcccgcaccg 540
 541 atcgcccttcccaacagttgcgcagcctgaatggcgaatggcgctagcatttgggggaa 600
 601 ttttgatgaaggaaaagtatacagtagaaaaagtatatgaaaatataaaagttgaagatg 660
 661 gtatatacaaacttagtataaagggtgaatttgaggtgaggccaggacaattttatcttt 720
 721 taagagcttgggatatagaaccaacactttctagacctattagtatatatgatgcagatg 780
 781 acgaaaaaatatcgttcttatactctgttgttggaaaaggaactgaaattttatctaaat 840
 841 taaagagcggcgatgaaataaagataacaggacctttaggaaatggatttaacgtaaaaa 900
 901 ggataagtggaaaagtggctatagtttgtggtggtataggtgtagcaccaatggtatatc 960
 961 tggctaaaaacttaaaaaattgtaatgttgattttatgctggcttcaaaactgtgagta 1020
1021 aaactgtggataatgtggaaaaatatgttaaagagttaaagttgtccacagaagatggaa 1080
1081 gtattggacataaggggtatgtaacagataactttaagccagaagaatacgattatgttt 1140
1141 tatgctgcggacctgagataatgatgtataaagttgttaaaatgtgtgaacaaaagaatg 1200
1201 ttcctgtatatatttcaatggagaaaaaaatggcatgtggaataggtgcatgccttgtat 1260
1261 gcacttgtaaaactaagggtggaagaagaagagcttgtaaagagggcccagtatttttag 1320
1321 gaagtgagttgatattaaatgactaaagtaaatatttgtggaatagattttaagaacccc 1380
1381 gttattgctgcttctggcacctttggatttggagaagagtttagtaagtattttgatgtt 1440
1441 tcaaggcttggtggcatatcttcaaagggacttacattgaatcctaaggaaggtaatgat 1500
1501 ggtgcaagagtttttgaggtcacaggcggaatgatgaatagtgtaggacttcaaaatcct 1560
1561 ggagttaaagagtttataaaaaaagaacttcctaagatgaaaaaaatagatacagtatgt 1620
1621 attgttaaccttggtggaagctgtgaggatgattatttaaggggcatggagcttcttgag 1680
1681 aatacagatgctgatatgatagaacttaatatatcctgtcctaatgtaaagcacggcggc 1740
1741 atggcttttggaataaaatcagaagttgcttataatgttgtatcacaaggcgcgccgcat 1800
1801 tcacttcttttctatataaatatgagcgaagcgaataagcgtcggaaaagcagcaaaaag 1860
```

```
1861 tttccttttgctgttggagcatggggttcaggggtgcagtatctgacgtcaatgccg 1920
1921 agcgaaagcgagccgaagggtagcatttacgttagataacccctgatatgctccgacgc 1980
1981 tttatatagaaaagaagattcaactaggtaaaatcttaatataggttgagatgataaggt 2040
2041 ttataaggaatttgtttgttctaatttttcactcattttgttctaatttcttttaacaaa 2100
2101 tgttcttttttttttagaacagttatgatatagttagaatagtttaaaataaggagtgag 2160
2161 aaaaagatgaaagaaagatatggaacagtctataaaggctctcagaggctcatagacgaa 2220
2221 gaaagtggagaagtcatagaggtagacaagttataccgtaaacaaacgtctggtaacttc 2280
2281 gtaaaggcatatatagtgcaattaataagtatgttagatatgattggcggaaaaaaactt 2340
2341 aaaatcgttaactatatcctagataatgtccacttaagtaacaatacaatgatagctaca 2400
2401 acaagagaaatagcaaaagctacaggaacaagtctacaaacagtaataacaacacttaaa 2460
2461 atcttagaagaaggaaatattataaaaagaaaaactggagtattaatgttaaaccctgaa 2520
2521 ctactaatgagaggcgacgaccaaaaacaaaaatacctcttactcgaatttgggaacttt 2580
2581 gagcaagaggcaaatgaaatagattgacctcccaataacaccacgtagttattgggaggt 2640
2641 caatctatgaaatgcgattaagggccggccagtgggcaagttgaaaaattcacaaaaatg 2700
2701 tggtataatatctttgttcattagagcgataaacttgaatttgagagggaacttagatgg 2760
2761 tatttgaaaaaattgataaaaatagttggaacagaaaagagtattttgaccactactttg 2820
2821 caagtgtaccttgtacctacagcatgaccgttaaagtggatatcacacaaataaaggaaa 2880
2881 agggaatgaaactatatcctgcaatgctttattatattgcaatgattgtaaaccgccatt 2940
2941 cagagtttaggacggcaatcaatcaagatggtgaattggggatatatgatgagatgatac 3000
3001 caagctatacaatatttcacaatgatactgaaacattttccagcctttggactgagtgta 3060
3061 agtctgactttaaatcattttttagcagattatgaaagtgatacgcaacggtatggaaaca 3120
3121 atcatagaatggaaggaaagccaaatgctccggaaaacatttttaatgtatctatgatac 3180
3181 cgtggtcaaccttcgatggctttaatctgaatttgcagaaaggatatgattatttgattc 3240
3241 ctatttttactatggggaaatattataaagaagataacaaaattatacttcctttggcaa 3300
3301 ttcaagttcatcacgcagtatgtgacggatttcacatttgccgttttgtaaacgaattgc 3360
3361 aggaattgataaatagttaacttcaggtttgtctgtaactaaaaacaagtatttaagcaa 3420
3421 aaacatcgtagaaatacggtgtttttgttaccctaagtttaaactccttttgataatc 3480
3481 tcatgaccaaaatcccttaacgtgagttttcgttccactgagcgtcagaccccgtagaaa 3540
3541 agatcaaaggatcttcttgagatcctttttttctgcgcgtaatctgctgcttgcaaacaa 3600
3601 aaaaaccaccgctaccagcggtggtttgtttgccggatcaagagctaccaactctttttc 3660
3661 cgaaggtaactggcttcagcagagcgcagataccaaatactgtccttctagtgtagccgt 3720
3721 agttaggccaccacttcaagaactctgtagcaccgcctacatacctcgctctgctaatcc 3780
3781 tgttaccagtggctgctgccagtggcgataagtcgtgtcttaccgggttggactcaagac 3840
3841 gatagttaccggataaggcgcagcggtcgggctgaacggggggttcgtgcacacagccca 3900
3901 gcttggagcgaacgacctacaccgaactgagatacctacagcgtgagcattgagaaagcg 3960
3961 ccacgcttcccgaagggagaaaggcggacaggtatccggtaagcggcagggtcggaacag 4020
4021 gagagcgcacgagggagcttccagggggaaacgcctggtatctttatagtcctgtcgggt 4080
4081 ttcgccacctctgacttgagcgtcgatttttgtgatgctcgtcaggggggcggagcctat 4140
4141 ggaaaaacgccagcaacgcggcctttttacggttcctggccttttgctggccttttgctc 4200
4201 acatgttctttcctgcgttatcccctgattctgtggataaccgtattaccgcctttgagt 4260
4261 gagctgataccgctcgccgcagccgaacgaccgagcgcagcgagtcagtgagcgaggaag 4320
4321 cggaagagcgcccaatacgcagggcccctgca 4353
```

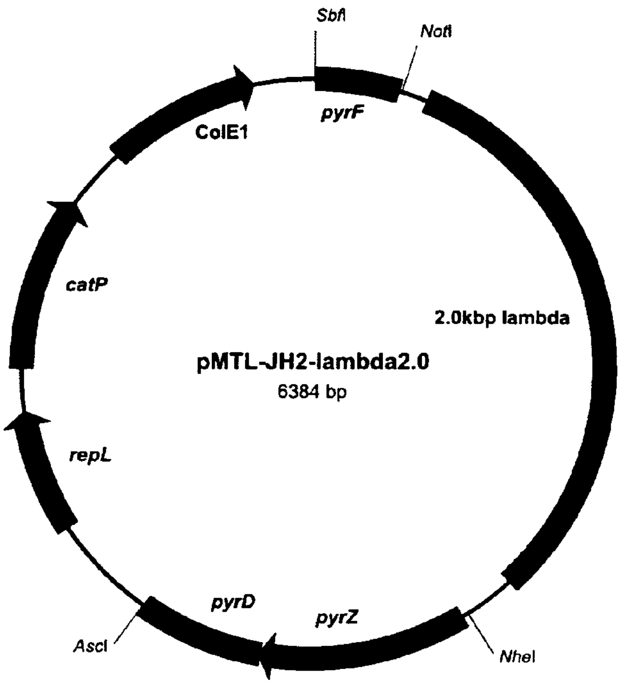

```
   1 gggtgtttaggacttgatactgatattacttatgtaccagaagagttttgtaagaaattt 60
  61 aatagtatagaagatgctatatttaattttaataagaaaataattgatgcgactttagat 120
 121 gttgtttcatgttataaggtgcaaattgcatattatgaagcttatggtttaaaaggactt 180
 181 ttggcctataaaaggacacttgaatatttgagagaaaaaaaggctattgcaattgctgat 240
 241 ataaaaagaggagatatagctaaaacagctgaaatgtatgctaaagctcactttgaaggt 300
 301 taatgagcggccgctgtatccatatgaccatgattacgaattcgagctcggtacccgggg 360
 361 atcctctagagtcgacgtcacgcgtccatggagatctcgaggagcttggctgtatagtca 420
 421 actaactcttctgtcgaagtgatatttttaggcttatctaccagttttagacgctcttta 480
 481 atatcttcaggaattattttattgtcatattgtatcatgctaaatgacaatttgcttatg 540
 541 gagtaatcttttaattttaaataagttattctcctggcttcatcaaataaagagtcgaat 600
 601 gatgttggcgaaatcacatcgtcacccattggattgtttatttgtatgccaagagagtta 660
 661 cagcagttatacattctgccatagattatagctaaggcatgtaataattcgtaatctttt 720
 721 agcgtattagcgacccatcgtctttctgatttaataatagatgattcagttaaatatgaa 780
 781 ggtaatttcttttgtgcaagtctgactaactttttataccaatgtttaacatactttca 840
 841 tttgtaataaactcaatgtcatttcttcaatgtaagatgaaataagagtagcctttgcc 900
 901 tcgctatacatttctaaatcgccttgtttttctatcgtattgcgagaattttagcccaa 960
 961 gccattaatggatcatttttccatttttcaataacattattgttataccaaatgtcatat 1020
1021 cctataatctggttttgtttttttgaataataaatgttactgttcttgcggtttggagg 1080
1081 aattgattcaaattcaagcgaaataattcagggtcaaaatatgtatcaatgcagcatttg 1140
1141 agcaagtgcgataaatctttaagtcttctttcccatggtttttagtcataaaactctcc 1200
1201 attttgataggttgcatgctagatgctgatatattttagaggtgataaaattaactgctt 1260
1261 aactgtcaatgtaatacaagttgtttgatctttgcaatgattcttatcagaaaccatata 1320
1321 gtaaattagttacacaggaaattttaatattattattatcattcattatgtattaaaat 1380
1381 tagagttgtggcttggctctgctaacacgttgctcataggagatatggtagagccgcaga 1440
1441 cacgtcgtatgcaggaacgtgctgcggctggctggtgaacttccgatagtgcgggtgttg 1500
1501 aatgatttccagttgctaccgattttacatatttttttgcatgagagaatttgtaccacct 1560
1561 cccaccgaccatctatgactgtacgccactgtccctaggactgctatgtgccggagcgga 1620
1621 cattacaaacgtccttctcggtgcatgccactgttgccaatgacctgcctaggaattggt 1680
1681 tagcaagttactaccggatttgtaaaaacagccctcctcatataaaagtattcgttca 1740
1741 cttccgataagcgtcgtaatttctatctttcatcatattctagatccctctgaaaaat 1800
```

1801 cttccgagtttgctaggcactgatacataactcttttccaataattggggaagtcattca 1860
1861 aatctataataggtttcagatttgcttcaataaattctgactgtagctgctgaaacgttg 1920
1921 cggttgaactatatttccttataactttacgaaagagtttctttgagtaatcacttcac 1980
1981 tcaagtgcttccctgcctccaaacgatacctgttagcaatatttaatagcttgaaatgat 2040
2041 gaagagctctgtgtttgtcttcctgcctccagttcgccgggcattcaacataaaaactga 2100
2101 tagcacccggagttccggaaacgaaatttgcatatacccattgctcacgaaaaaaatgt 2160
2161 ccttgtcgatatagggatgaatcgcttggtgtacctcatctactgcgaaaacttgacctt 2220
2221 tctctcccatattgcagtcgcggcacgatggaactaaattaataggcatcaccgaaaatt 2280
2281 caggataatgtgcaataggaagaaaatgatctatatttttgtctgtcctatatcaccac 2340
2341 aaaatggacattttcacctgatgaaacaagcatgtcatcgtaatatgttctagcgggtt 2400
2401 tgtttttatctcggagattattttcataaagctcctgcagacatgcaagcttggcactgg 2460
2461 ccgtcgttttacaacgtcgtgactgggaaaaccctggcgttacccaacttaatcgccttg 2520
2521 cagcacatccccctttcgccagctggcgtaatagcgaagaggcccgcaccgatcgccctt 2580
2581 cccaacagttgcgcagcctgaatggcgaatggcgctagcattttggggaattttgatga 2640
2641 aggaaaagtatacagtagaaaaagtatatgaaaatataaaagttgaagatggtatataca 2700
2701 aacttagtataaagggtgaatttgaggtgaggccaggacaattttatcttttaagagctt 2760
2761 gggatatagaaccaacactttctagacctattagtatatatgatgcagatgacgaaaaaa 2820
2821 tatcgttcttatactctgttgttggaaaaggaactgaaattttatctaaattaaagagcg 2880
2881 gcgatgaaataaagataacaggacctttaggaaatggatttaacgtaaaaaggataagtg 2940
2941 gaaaagtggctatagtttgtggtggtataggtgtagcaccaatggtatatctggctaaaa 3000
3001 acttaaaaaattgtaatgttgattttatgctggcttcaaaactgtgagtaaaactgtgg 3060
3061 ataatgtggaaaaatatgttaaagagttaaagttgtccacagaagatggaagtattggac 3120
3121 ataaggggtatgtaacagataactttaagccagaagaatacgattatgttttatgctgcg 3180
3181 gacctgagataatgatgtataaagttgttaaaatgtgtgaacaaaagaatgttcctgtat 3240
3241 atatttcaatggagaaaaaaatggcatgtggaataggtgcatgccttgtatgcacttgta 3300
3301 aaactaagggtggaagaagaagagcttgtaaagagggcccagtattttaggaagtgagt 3360
3361 tgatattaaatgactaaagtaaatatttgtggaatagatttaagaaccccgttattgct 3420
3421 gcttctggcacctttggatttggagaagagtttagtaagtattttgatgtttcaaggctt 3480
3481 ggtggcatatcttcaaagggacttacattgaatcctaaggaaggtaatgatggtgcaaga 3540
3541 gtttttgaggtcacaggcggaatgatgaatagtgtaggacttcaaaatcctggagttaaa 3600
3601 gagtttataaaaaaagaacttcctaagatgaaaaaaatagatacagtatgtattgttaac 3660
3661 cttggtggaagctgtgaggatgattatttaaggggcatggagcttcttgagaatacagat 3720
3721 gctgatatgatagaacttaatatatcctgtcctaatgtaaagcacggcggcatggctttt 3780
3781 ggaataaaatcagaagttgcttataatgttgtatcacaaggcgcgccgcattcacttctt 3840
3841 ttctatataaatatgagcgaagcgaataagcgtcggaaaagcagcaaaaagtttcctttt 3900
3901 tgctgttggagcatgggggttcaggggggtgcagtatctgacgtcaatgccgagcgaaagc 3960
3961 gagccgaagggtagcatttacgttagataacccccctgatatgctccgacgctttatatag 4020
4021 aaaagaagattcaactaggtaaaatcttaatataggttgagatgataaggtttataagga 4080
4081 atttgtttgttctaattttcactcattttgttctaatttcttttaacaaatgttctttt 4140
4141 tttttagaacagttatgatatagttagaatagtttaaaataaggagtgagaaaaagatg 4200
4201 aaagaaagatatggaacagtctataaaggctctcagaggctcatagacgaagaaagtgga 4260
4261 gaagtcatagaggtagacaagttataccgtaaacaaacgtctggtaacttcgtaaaggca 4320
4321 tatatagtgcaattaataagtatgttagatatgattggcggaaaaaaacttaaaatcgtt 4380
4381 aactatatcctagataatgtccacttaagtaacaatacaatgatagctacaacaagagaa 4440
4441 atagcaaaagctacaggaacaagtctacaaacagtaataacaacacttaaaatcttagaa 4500
4501 gaaggaaatattataaaaagaaaaactggagtattaatgttaaaccctgaactactaatg 4560
4561 agaggcgacgaccaaaaacaaaaatacctcttactcgaatttgggaactttgagcaagag 4620
4621 gcaaatgaaatagattgacctcccaataacaccacgtagttattgggaggtcaatctatg 4680
4681 aaatgcgattaagggccggccagtgggcaagttgaaaaattcacaaaaatgtggtataat 4740
4741 atctttgttcattagagcgataaacttgaatttgagagggaacttagatggtatttgaaa 4800
4801 aaattgataaaaatagttggaacagaaaagagtattttgaccactactttgcaagtgtac 4860
4861 cttgtacctacagcatgaccgttaaagtggatatcacacaaataaaggaaaagggaatga 4920
4921 aactatatcctgcaatgctttattatattgcaatgattgtaaaccgccattcagagttta 4980
4981 ggacggcaatcaatcaagatggtgaattggggatatatgatgagatgataccaagctata 5040
5041 caatatttcacaatgatactgaaacattttccagcctttggactgagtgtaagtctgact 5100
5101 ttaaatcattttagcagattatgaaagtgatacgcaacggtatggaaacaatcatagaa 5160
5161 tggaaggaaagccaaatgctccggaaaacattttaatgtatctatgataccgtggtcaa 5220
5221 ccttcgatggctttaatctgaatttgcagaaaggatatgattatttgattcctatttta 5280

Figure 6E (CONT.)

5281 ctatggggaaatattataaagaagataacaaaattatacttcctttggcaattcaagttc 5340
5341 atcacgcagtatgtgacggatttcacatttgccgttttgtaaacgaattgcaggaattga 5400
5401 taaatagttaacttcaggtttgtctgtaactaaaaacaagtatttaagcaaaaacatcgt 5460
5461 agaaatacggtgtttttgttaccctaagtttaaactcctttttgataatctcatgacca 5520
5521 aaatcccttaacgtgagttttcgttccactgagcgtcagaccccgtagaaaagatcaaag 5580
5581 gatcttcttgagatcctttttttctgcgcgtaatctgctgcttgcaaacaaaaaaaccac 5640
5641 cgctaccagcggtggtttgtttgccggatcaagagctaccaactctttttccgaaggtaa 5700
5701 ctggcttcagcagagcgcagataccaaatactgtccttctagtgtagccgtagttaggcc 5760
5761 accacttcaagaactctgtagcaccgcctacatacctcgctctgctaatcctgttaccag 5820
5821 tggctgctgccagtggcgataagtcgtgtcttaccgggttggactcaagacgatagttac 5880
5881 cggataaggcgcagcggtcgggctgaacggggggttcgtgcacacagcccagcttggagc 5940
5941 gaacgacctacaccgaactgagatacctacagcgtgagcattgagaaagcgccacgcttc 6000
6001 ccgaagggagaaaggcggacaggtatccggtaagcggcagggtcggaacaggagagcgca 6060
6061 cgagggagcttccagggggaaacgcctggtatctttatagtcctgtcgggtttcgccacc 6120
6121 tctgacttgagcgtcgatttttgtgatgctcgtcaggggggcggagcctatggaaaaacg 6180
6181 ccagcaacgcggcctttttacggttcctggccttttgctggccttttgctcacatgttct 6240
6241 ttcctgcgttatcccctgattctgtggataaccgtattaccgcctttgagtgagctgata 6300
6301 ccgctcgccgcagccgaacgaccgagcgcagcgagtcagtgagcgaggaagcggaagagc 6360
6361 gcccaatacgcagggccccctgca 6384

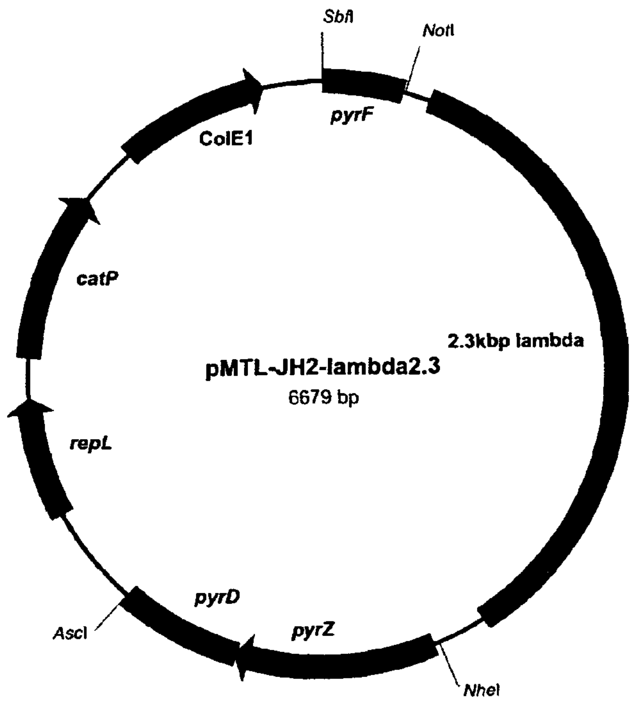

```
   1 gggtgtttaggacttgatactgatattacttatgtaccagaagagttttgtaagaaattt 60
  61 aatagtatagaagatgctatatttaattttaataagaaaataattgatgcgactttagat 120
 121 gttgtttcatgttataaggtgcaaattgcatattatgaagcttatggtttaaaggactt 180
 181 ttggcctataaaggacacttgaatatttgagagaaaaaaaggctattgcaattgctgat 240
 241 ataaaaagaggagatatagctaaaacagctgaaatgtatgctaaagctcactttgaaggt 300
 301 taatgagcggccgctgtatccatatgaccatgattacgaattcgagctcggtacccgggg 360
 361 atcctctagagtcgacgtcacgcgtccatggagatctcgaggagctttgtgtgccaccca 420
 421 ctacgacctgcataaccagtaagaagatagcagtgatgtcaaacgacgcagctgacttct 480
 481 tttctttcacgacttccccacacccagcatgcatacctttccgccataactgtagtgaat 540
 541 gtctgttatgagcgaggagcggaagttaacacttatgaaaaatggctacgaagtccgtgg 600
 601 ctatctatcggcttattagtacttgaaacgcttcttcagaagcctgaagagctaatcgtt 660
 661 cggcgatactatatatgcattaatagactatatcgttggtataaacagtgcaccatgcaa 720
 721 catgaataacagtgggttatccaaaaggaagcagaaagctaaatatggaaaactacaata 780
 781 cgatgccccgttaagttcaatactactaattttagatggaaaacgtatgtaatagagag 840
 841 taacttaaaagagagatcctgtgttgccgccaaataaattgcggttattttaataaaatt 900
 901 aagggttactatatgttggagtttagtgttattgaaagaggcgggtatattcctgcagta 960
 961 gaaaaaaataaggcattcctacgagcagatggttggaatgactattcctttgttacaatg 1020
1021 ttttatcttactgtctttgatgagcatggtgaaaaatgcgatatcggaaatgttaaaatt 1080
1081 ggttttgtaggtcaaaaagaagaagtaagcacttattcattaatagataaaaaattcagt 1140
1141 caactccctgaaatgtttttttccttaggtgaaagcattgactactatgttaatctcagc 1200
1201 aaattaagcgatggttttaaacataaccttcttaaagctattcaggatttagtagtatgg 1260
1261 ccaaatcgattagccgacattgaaaatgaaagcgtccttaacacctcattacttagaggg 1320
1321 gtaactctttcagaaattcatggacagttcgcacgtgtgttaaatggtttgccagaattg 1380
1381 tcagatttccacttttcatttaatagaaaaagtgctcccggattcagtgatttaactata 1440
1441 ccttttgaggtgacggttaattctatgcccagcacgaacattcatgcttttatcgggcgg 1500
1501 aatgggtgtggtaaaacaacaattttgaatggaatgattggtgcaatcaccaacccagaa 1560
1561 aacaatgaatatttttctctgaaaataatagacttatcgagtcaagaatcccaaaggga 1620
1621 tattttcgatcgcttgtttcagtttcgtttagtgcatttgatccttttactcctcctaaa 1680
1681 gaacaacctgacccagcaaaaggtacacaatacttttatattggactcaagaatgctgcc 1740
1741 agcaatagtttaaaatcactaggcgatctccgcttagaattcatttcagcatttattggt 1800
```

1801 tgtatgagagtagatagaaaaagacaactctggcttgaagctatcaaaaaactaagtagt 1860
1861 gatgaaaactttttcaaatatggaactcatcagcctcatttctaaatatgaagagttaaga 1920
1921 cgtaatgaaccacagattcaagtggacgatgataaattcactaaattgttttatgacaat 1980
1981 atccagaaatatctgcttcgaatgagctctggacatgcaattgttttatttactatcaca 2040
2041 agattagtagatgtcgttggcgaaaagtcattagttttattcgatgaaccagaggttcat 2100
2101 ctgcatccacctttgctctctgctttttttacgaacattaagcgacttactcgatgcacgc 2160
2161 aatggtgtagcaataattgcaactcattccccagtagtactgcaagaggttccaaaatcc 2220
2221 tgcatgtggaaagtcctacggtcaagagaagcaataaatattatccgtccggatattgag 2280
2281 acattcggtgagaacttaggtgttttaactcgtgaggtgtttttacttgaagtgacaaat 2340
2341 tctggataccaccacttattatcgcagtccgttgattcagagctttcttatgaaaccatt 2400
2401 ctaaaaaattataatggtcagataggattagaaggtcgaaccgttttaaaagcgatgata 2460
2461 atgaacagagatgaaggtaaagtacaatgaaaaaactacctcttccagcgagaacttata 2520
2521 gcgaaatgcttaataaatgctcggaaggtatgatgcagataaatgttagaaataatttca 2580
2581 ttactcacttccccactttttttgcagaaagaacaacaatatagaatattaagctcgacag 2640
2641 gtcagttatttacctacgacaggacacaccctcttgagcctacaaccttagtagttggta 2700
2701 acctgacaaaggttaaattagaaaagctcctgcagacatgcaagcttggcactggccgtc 2760
2761 gttttacaacgtcgtgactgggaaaaccctggcgttacccaacttaatcgccttgcagca 2820
2821 catccccctttcgccagctggcgtaatagcgaagaggcccgcaccgatcgcccttcccaa 2880
2881 cagttgcgcagcctgaatggcgaatggcgctagcattttggggggaattttgatgaaggaa 2940
2941 aagtatacagtagaaaaagtatatgaaaatataaaagttgaagatggtatatacaaactt 3000
3001 agtataaagggtgaatttgaggtgaggccaggacaattttatcttttaagagcttgggat 3060
3061 atagaaccaacactttctagacctattagtatatatgatgcagatgacgaaaaaatatcg 3120
3121 ttcttatactctgttgttggaaaaggaactgaaattttatctaaattaaagagcggcgat 3180
3181 gaaataaagataacaggacctttaggaaatggatttaacgtaaaaaggataagtggaaaa 3240
3241 gtggctatagtttgtggtggtataggtgtagcaccaatggtatatctggctaaaaactta 3300
3301 aaaaattgtaatgttgatttttatgctggcttcaaaactgtgagtaaaactgtggataat 3360
3361 gtggaaaaatatgttaaagagttaaagttgtccacagaagatggaagtattggacataag 3420
3421 gggtatgtaacagataactttaagccagaagaatacgattatgttttatgctgcggacct 3480
3481 gagataatgatgtataaagttgttaaaatgtgtgaacaaaagaatgttcctgtatatatt 3540
3541 tcaatggagaaaaaaatggcatgtggaataggtgcatgccttgtatgcacttgtaaaact 3600
3601 aagggtggaagaagaagagcttgtaaagagggcccagtatttttaggaagtgagttgata 3660
3661 ttaaatgactaaagtaaatatttgtggaatagattttaagaaccccgttattgctgcttc 3720
3721 tggcacctttggatttggagaagagtttagtaagtattttgatgtttcaaggcttggtgg 3780
3781 catatcttcaaagggacttacattgaatcctaaggaaggtaatgatggtgcaagagtttt 3840
3841 tgaggtcacaggcggaatgatgaatagtgtaggacttcaaaatcctggagttaaagagtt 3900
3901 tataaaaaaagaacttcctaagatgaaaaaaatagatacagtatgtattgttaaccttgg 3960
3961 tggaagctgtgaggatgattatttaaggggcatggagcttcttgagaatacagatgctga 4020
4021 tatgatagaacttaatatatcctgtcctaatgtaaagcacggcggcatggcttttggaat 4080
4081 aaaatcagaagttgcttataatgttgtatcacaaggcgcgccgcattcacttcttttcta 4140
4141 tataaatatgagcgaagcgaataagcgtcggaaaagcagcaaaaagtttcctttttgctg 4200
4201 ttggagcatggggggttcaggggggtgcagtatctgacgtcaatgccgagcgaaagcgagcc 4260
4261 gaagggtagcatttacgttagataacccccctgatatgctccgacgctttatatagaaaag 4320
4321 aagattcaactaggtaaaatcttaatataggttgagatgataaggtttataaggaatttg 4380
4381 tttgttctaattttcactcattttgttctaatttcttttaacaaatgttcttttttttt 4440
4441 tagaacagttatgatatagttagaatagtttaaaataaggagtgagaaaaagatgaaaga 4500
4501 aagatatggaacagtctataaaggctctcagaggctcatagacgaagaaagtggagaagt 4560
4561 catagaggtagacaagttataccgtaaacaaacgtctggtaacttcgtaaaggcatatat 4620
4621 agtgcaattaataagtatgttagatatgattggcggaaaaaaacttaaaatcgttaacta 4680
4681 tatcctagataatgtccacttaagtaacaatacaatgatagctacaacaagagaaatagc 4740
4741 aaaagctacaggaacaagtctacaaacagtaataacaacacttaaaatcttagaagaagg 4800
4801 aaatattataaaaagaaaaactggagtattaatgttaaaccctgaactactaatgagagg 4860
4861 cgacgaccaaaaacaaaatacctcttactcgaatttgggaactttgagcaagaggcaaa 4920
4921 tgaaatagattgacctcccaataacaccacgtagttattgggaggtcaatctatgaaatg 4980
4981 cgattaagggccggccagtgggcaagttgaaaaattcacaaaaatgtggtataatatctt 5040
5041 tgttcattagagcgataaacttgaatttgagagggaacttagatggtatttgaaaaatt 5100
5101 gataaaaatagttggaacagaaaagagtattttgaccactactttgcaagtgtaccttgt 5160
5161 acctacagcatgaccgttaaagtggatatcacacaaataaaggaaaagggaatgaaacta 5220
5221 tatcctgcaatgctttattatattgcaatgattgtaaaccgccattcagagtttaggacg 5280

Figure 6F (CONT.)

```
5281 gcaatcaatcaagatggtgaattggggatatatgatgagatgataccaagctatacaata 5340
5341 tttcacaatgatactgaaacattttccagcctttggactgagtgtaagtctgactttaaa 5400
5401 tcatttttagcagattatgaaagtgatacgcaacggtatggaaacaatcatagaatggaa 5460
5461 ggaaagccaaatgctccggaaaacattttaatgtatctatgataccgtggtcaaccttc 5520
5521 gatggctttaatctgaatttgcagaaaggatatgattatttgattcctatttttactatg 5580
5581 gggaaatattataaagaagataacaaaattatacttcctttggcaattcaagttcatcac 5640
5641 gcagtatgtgacggatttcacatttgccgttttgtaaacgaattgcaggaattgataaat 5700
5701 agttaacttcaggtttgtctgtaactaaaaacaagtatttaagcaaaaacatcgtagaaa 5760
5761 tacggtgtttttgttaccctaagtttaaactcctttttgataatctcatgaccaaaatc 5820
5821 ccttaacgtgagttttcgttccactgagcgtcagaccccgtagaaaagatcaaaggatct 5880
5881 tcttgagatcctttttttctgcgcgtaatctgctgcttgcaaacaaaaaaaccaccgcta 5940
5941 ccagcggtggtttgtttgccggatcaagagctaccaactctttttccgaaggtaactggc 6000
6001 ttcagcagagcgcagataccaaatactgtccttctagtgtagccgtagttaggccaccac 6060
6061 ttcaagaactctgtagcaccgcctacatacctcgctctgctaatcctgttaccagtggct 6120
6121 gctgccagtggcgataagtcgtgtcttaccgggttggactcaagacgatagttaccggat 6180
6181 aaggcgcagcggtcgggctgaacggggggttcgtgcacacagcccagcttggagcgaacg 6240
6241 acctacaccgaactgagatacctacagcgtgagcattgagaaagcgccacgcttcccgaa 6300
6301 gggagaaaggcggacaggtatccggtaagcggcagggtcggaacaggagagcgcacgagg 6360
6361 gagcttccagggggaaacgcctggtatctttatagtcctgtcgggtttcgccacctctga 6420
6421 cttgagcgtcgatttttgtgatgctcgtcaggggggcggagcctatggaaaaacgccagc 6480
6481 aacgcggcctttttacggttcctggccttttgctggccttttgctcacatgttctttcct 6540
6541 gcgttatcccctgattctgtggataaccgtattaccgcctttgagtgagctgataccgct 6600
6601 cgccgcagccgaacgaccgagcgcagcgagtcagtgagcgaggaagcggaagagcgccca 6660
6661 atacgcagggccccctgca 6679
```

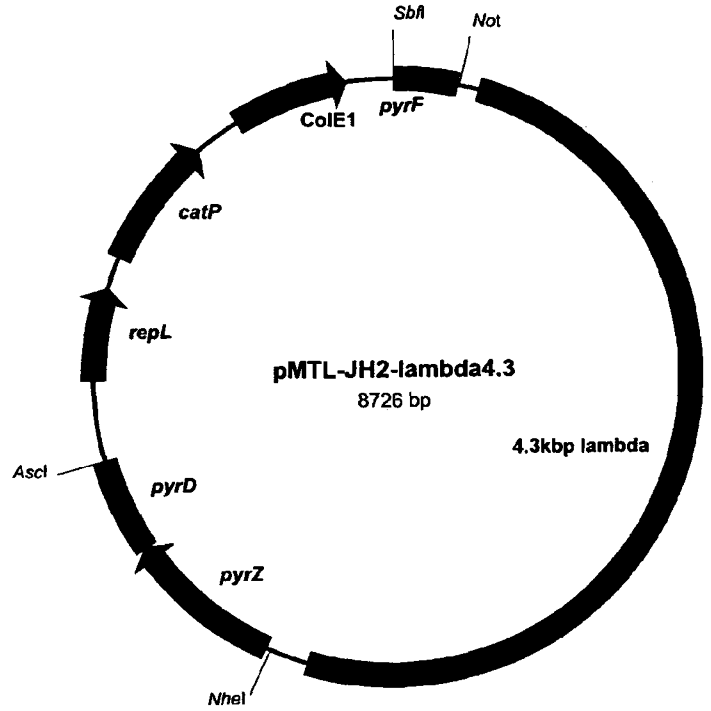

```
   1 gggtgtttaggacttgatactgatattacttatgtaccagaagagttttgtaagaaattt 60
  61 aatagtatagaagatgctatatttaattttaataagaaaataattgatgcgactttagat 120
 121 gttgtttcatgttataaggtgcaaattgcatattatgaagcttatggtttaaaaggactt 180
 181 ttggcctataaaaggacacttgaatatttgagagaaaaaaaggctattgcaattgctgat 240
 241 ataaaaagaggagatatagctaaaacagctgaaatgtatgctaaagctcactttgaaggt 300
 301 taatgagcggccgctgtatccatatgaccatgattacgaattcgagctcggtacccgggg 360
 361 atcctctagagtcgacgtcacgcgtccatggagatctcgaggagcttgaaggaaatacta 420
 421 aggcaaaggtactgcaagtgctcgcaacattcgcttatgcggattattgccgtagtgccg 480
 481 cgacgccgggggcaagatgcagagattgccatggtacaggccgtgcggttgatattgcca 540
 541 aaacagagctgtgggggagagttgtcgagaaagagtgcggaagatgcaaaggcgtcggct 600
 601 attcaaggatgccagcaagcgcagcatatcgcgctgtgacgatgctaatcccaaacctta 660
 661 cccaacccacctggtcacgcactgttaagccgctgtatgacgctctggtggtgcaatgcc 720
 721 acaaagaagagtcaatcgcagacaacattttgaatgcggtcacacgttagcagcatgatt 780
 781 gccacggatggcaacatattaacggcatgatattgacttattgaataaaattgggtaaat 840
 841 ttgactcaacgatgggttaattcgctcgttgtggtagtgagatgaaaagaggcggcgctt 900
 901 actaccgattccgcctagttggtcacttcgacgtatcgtctggaactccaaccatcgcag 960
 961 gcagagaggtctgcaaaatgcaatcccgaaacagttcgcaggtaatagttagagcctgca 1020
1021 taacggtttcgggatttttatatctgcacaacaggtaagagcattgagtcgataatcgt 1080
1081 gaagagtcggcgagcctggttagccagtgctctttccgttgtgctgaattaagcgaatac 1140
1141 cggaagcagaaccggatcaccaaatgcgtacaggcgtcatcgccgcccagcaacagcaca 1200
1201 acccaaactgagccgtagccactgtctgtcctgaattcattagtaatagttacgctgcgg 1260
1261 ccttttacacatgaccttcgtgaaagcgggtggcaggaggtcgcgctaacaacctcctgc 1320
1321 cgttttgcccgtgcatatcggtcacgaacaaatctgattactaaacacagtagcctggat 1380
1381 ttgttctatcagtaatcgaccttattcctaattaaatagagcaaatccccttattgggg 1440
1441 taagacatgaagatgccagaaaaacatgacctgttggccgccattctcgcggcaaaggaa 1500
1501 caaggcatcggggcaatccttgcgtttgcaatggcgtaccttcgcggcagatataatggc 1560
1561 ggtgcgtttacaaaaacagtaatcgacgcaacgatgtgcgccattatcgcctggttcatt 1620
1621 cgtgaccttctcgacttcgccggactaagtagcaatctcgcttatataacgagcgtgttt 1680
1681 atcggctacatcggtactgactcgattggttcgcttatcaaacgcttcgctgctaaaaaa 1740
1741 gccggagtagaagatggtagaaatcaataatcaacgtaaggcgttcctcgatatgctggc 1800
```

1801 gtggtcggagggaactgataacggacgtcagaaaaccagaaatcatggttatgacgtcat 1860
1861 tgtaggcggagagctatttactgattactccgatcaccctcgcaaacttgtcacgctaaa 1920
1921 cccaaaactcaaatcaacaggcgccggacgctaccagcttctttcccgttggtgggatgc 1980
1981 ctaccgcaagcagcttggcctgaaagacttctctccgaaaagtcaggacgctgtggcatt 2040
2041 gcagcagattaaggagcgtggcgctttacctatgattgatcgtggtgatatccgtcaggc 2100
2101 aatcgaccgttgcagcaatatctgggcttcactgccgggcgctggttatggtcagttcga 2160
2161 gcataaggctgacagcctgattgcaaaattcaaagaagcgggcggaacggtcagagagat 2220
2221 tgatgtatgagcagagtcaccgcgattatctccgctctggttatctgcatcatcgtctgc 2280
2281 ctgtcatgggctgttaatcattaccgtgataacgccattacctacaaagcccagcgcgac 2340
2341 aaaaatgccagagaactgaagctggcgaacgcggcaattactgacatgcagatgcgtcag 2400
2401 cgtgatgttgctgcgctcgatgcaaaatacacgaaggagttagctgatgctaaagctgaa 2460
2461 aatgatgctctgcgtgatgatgttgccgctggtcgtcgtcggttgcacatcaaagcagtc 2520
2521 tgtcagtcagtgcgtgaagccaccaccgcctccggcgtggataatgcagcctccccccga 2580
2581 ctggcagacaccgctgaacgggattatttcaccctcagagagaggctgatcactatgcaa 2640
2641 aaacaactggaaggaacccagaagtatattaatgagcagtgcagatagagttgcccatat 2700
2701 cgatgggcaactcatgcaattattgtgagcaatacacacgcgcttccagcggagtataaa 2760
2761 tgcctaaagtaataaaaccgagcaatccatttacgaatgtttgctgggtttctgttttaa 2820
2821 caacatttctgcgccgccacaaattttggctgcatcgacagttttcttctgcccaattc 2880
2881 cagaaacgaagaaatgatgggtgatggtttcctttggtgctactgctgccggtttgtttt 2940
2941 gaacagtaaacgtctgttgagcacatcctgtaataagcagggccagcgcagtagcgagta 3000
3001 gcatttttttcatggtgttattcccgatgctttttgaagttcgcagaatcgtatgtgtag 3060
3061 aaaattaaacaaaccctaaacaatgagttgaaatttcatattgttaatatttattaatgt 3120
3121 atgtcaggtgcgatgaatcgtcattgtattcccggattaactatgtccacagccctgacg 3180
3181 gggaacttctctgcgggagtgtccgggaataattaaaacgatgcacacagggtttagcgc 3240
3241 gtacacgtattgcattatgccaacgccccggtgctgacacggaagaaaccggacgttatg 3300
3301 atttagcgtggaaagatttgtgtagtgttctgaatgctctcagtaaatagtaatgaatta 3360
3361 tcaaaggtatagtaatatcttttatgttcatggatatttgtaacccatcggaaaactcct 3420
3421 gctttagcaagattttccctgtattgctgaaatgtgatttctcttgatttcaacctatca 3480
3481 taggacgtttctataagatgcgtgtttcttgagaatttaacatttacaaccttttaagt 3540
3541 ccttttattaacacggtgttatcgttttctaacacgatgtgaatattatctgtggctaga 3600
3601 tagtaaatataatgtgagacgttgtgacgttttagttcagaataaaacaattcacagtct 3660
3661 aaatcttttcgcacttgatcgaatatttctttaaaaatggcaacctgagccattggtaaa 3720
3721 accttccatgtgatacgagggcgcgtagtttgcattatcgtttttatcgtttcaatctgg 3780
3781 tctgacctccttgtgttttgttgatgatttatgtcaaatattaggaatgttttcacttaa 3840
3841 tagtattggttgcgtaacaaagtgcggtcctgctggcattctggagggaaatacaaccga 3900
3901 cagatgtatgtaaggccaacgtgctcaaatcttcatacagaaagatttgaagtaatattt 3960
3961 taaccgctagatgaagagcaagcgcatggagcgacaaaatgaataaagaacaatctgctg 4020
4021 atgatccctccgtggatctgattcgtgtaaaaaatatgcttaatagcaccatttctatga 4080
4081 gttaccctgatgttgtaattgcatgtatagaacataaggtgtctctggaagcattcagag 4140
4141 caattgaggcagcgttggtgaagcacgataataatatgaaggattattccctggtggttg 4200
4201 actgatcaccataactgctaatcattcaaactatttagtctgtgacagagccaacacgca 4260
4261 gtctgtcactgtcaggaaagtggtaaaactgcaactcaattactgcaatgccctcgtaat 4320
4321 taagtgaatttacaatatcgtcctgttcggagggaagaacgcgggatgttcattcttcat 4380
4381 cacttttaattgatgtatatgctctcttttctgacgttagtctccgacggcaggcttcaa 4440
4441 tgacccaggctgagaaattcccggacccttttgctcaagagcgatgttaatttgttcaa 4500
4501 tcatttggttaggaaagcggatgttgcgggttgttgttctgcgggttctgttcttcgttg 4560
4561 acatgaggttgccccgtattcagtgtcgctgatttgtattgtctgaagttgtttttacgt 4620
4621 taagttgatgcagatcaattaatacgatacctgcgtcataattgattatttgacgtggtt 4680
4681 tgatggcctccacgcacgttgtgatatgtagatgataatcattatcactttacgggtcct 4740
4741 ttccggtgatccgacaggttacggggcggcgacctcctgcagacatgcaagcttggcact 4800
4801 ggccgtcgttttacaacgtcgtgactgggaaaaccctggcgttacccaacttaatcgcct 4860
4861 tgcagcacatccccctttcgccagctggcgtaatagcgaagaggcccgcaccgatcgccc 4920
4921 ttcccaacagttgcgcagcctgaatggcgaatggcgctagcattttggggggaattttgat 4980
4981 gaaggaaaagtatacagtagaaaaagtatatgaaaatataaaagttgaagatggtatata 5040
5041 caaacttagtataaagggtgaatttgaggtgaggccaggacaattttatctttaagagc 5100
5101 ttgggatatagaaccaacactttctagacctattagtatatatgatgcagatgacgaaaa 5160
5161 aatatcgttcttatactctgttgttggaaaaggaactgaaattttatctaaattaaagag 5220
5221 cggcgatgaaataaagataacaggacctttaggaaatggatttaacgtaaaaaggataag 5280

Figure 6G (CONT.)

```
5281 tggaaaagtggctatagtttgtggtggtataggtgtagcaccaatggtatatctggctaa 5340
5341 aaacttaaaaaattgtaatgttgattttatgctggcttcaaaactgtgagtaaaactgt 5400
5401 ggataatgtggaaaaatatgttaaagagttaaagttgtccacagaagatggaagtattgg 5460
5461 acataaggggtatgtaacagataactttaagccagaagaatacgattatgttttatgctg 5520
5521 cggacctgagataatgatgtataaagttgttaaaatgtgtgaacaaaagaatgttcctgt 5580
5581 atatatttcaatggagaaaaaaatggcatgtggaataggtgcatgccttgtatgcacttg 5640
5641 taaaactaagggtggaagaagaagagcttgtaaagagggcccagtatttttaggaagtga 5700
5701 gttgatattaaatgactaaagtaaatatttgtggaatagattttaagaaccccgttattg 5760
5761 ctgcttctggcacctttggatttggagaagagtttagtaagtattttgatgtttcaaggc 5820
5821 ttggtggcatatcttcaaagggacttacattgaatcctaaggaaggtaatgatggtgcaa 5880
5881 gagtttttgaggtcacaggcggaatgatgaatagtgtaggacttcaaaatcctggagtta 5940
5941 aagagtttataaaaaaagaacttcctaagatgaaaaaaatagatacagtatgtattgtta 6000
6001 accttggtggaagctgtgaggatgattatttaaggggcatggagcttcttgagaatacag 6060
6061 atgctgatatgatagaacttaatatatcctgtcctaatgtaaagcacggcggcatggctt 6120
6121 ttggaataaaatcagaagttgcttataatgttgtatcacaaggcgcgccgcattcacttc 6180
6181 ttttctatataaatatgagcgaagcgaataagcgtcggaaaagcagcaaaaagtttcctt 6240
6241 tttgctgttggagcatgggggttcagggggtgcagtatctgacgtcaatgccgagcgaaa 6300
6301 gcgagccgaagggtagcatttacgttagataacccccctgatatgctccgacgctttatat 6360
6361 agaaaagaagattcaactaggtaaaatcttaatataggttgagatgataaggtttataag 6420
6421 gaatttgtttgttctaatttttcactcattttgttctaatttcttttaacaaatgttctt 6480
6481 tttttttagaacagttatgatatagttagaatagtttaaaataaggagtgagaaaaaga 6540
6541 tgaaagaaagatatggaacagtctataaaggctctcagaggctcatagacgaagaaagtg 6600
6601 gagaagtcatagaggtagacaagttataccgtaaacaaacgtctggtaacttcgtaaagg 6660
6661 catatatagtgcaattaataagtatgttagatatgattggcggaaaaaaacttaaaatcg 6720
6721 ttaactatatcctagataatgtccacttaagtaacaatacaatgatagctacaacaagag 6780
6781 aaatagcaaaagctacaggaacaagtctacaaacagtaataacaacacttaaaatcttag 6840
6841 aagaaggaaatattataaaaagaaaaactggagtattaatgttaaaccctgaactactaa 6900
6901 tgagaggcgacgaccaaaaacaaaaatacctcttactcgaatttgggaactttgagcaag 6960
6961 aggcaaatgaaatagattgacctcccaataacaccacgtagttattgggaggtcaatcta 7020
7021 tgaaatgcgattaagggccggccagtgggcaagttgaaaaattcacaaaaatgtggtata 7080
7081 atatctttgttcattagagcgataaacttgaatttgagagggaacttagatggtatttga 7140
7141 aaaaattgataaaaatagttggaacagaaaagagtattttgaccactactttgcaagtgt 7200
7201 accttgtacctacagcatgaccgttaaagtggatatcacacaaataaaggaaaagggaat 7260
7261 gaaactatatcctgcaatgctttattatattgcaatgattgtaaaccgccattcagagtt 7320
7321 taggacggcaatcaatcaagatggtgaattggggatatatgatgagatgataccaagcta 7380
7381 tacaatatttcacaatgatactgaaacattttccagcctttggactgagtgtaagtctga 7440
7441 ctttaaatcattttttagcagattatgaaagtgatacgcaacggtatggaaacaatcatag 7500
7501 aatggaaggaaagccaaatgctccggaaaacattttaatgtatctatgataccgtggtc 7560
7561 aaccttcgatggctttaatctgaatttgcagaaaggatatgattatttgattcctatttt 7620
7621 tactatggggaaatattataaagaagataacaaaattatacttcctttggcaattcaagt 7680
7681 tcatcacgcagtatgtgacggatttcacatttgccgttttgtaaacgaattgcaggaatt 7740
7741 gataaatagttaacttcaggtttgtctgtaactaaaaacaagtatttaagcaaaaacatc 7800
7801 gtagaaatacggtgtttttttgttaccctaagtttaaactcctttttgataatctcatgac 7860
7861 caaaatcccttaacgtgagttttcgttccactgagcgtcagaccccgtagaaaagatcaa 7920
7921 aggatcttcttgagatcctttttttctgcgcgtaatctgctgcttgcaaacaaaaaaacc 7980
7981 accgctaccagcggtggtttgtttgccggatcaagagctaccaactctttttccgaaggt 8040
8041 aactggcttcagcagagcgcagataccaaatactgtccttctagtgtagccgtagttagg 8100
8101 ccaccacttcaagaactctgtagcaccgcctacatacctcgctctgctaatcctgttacc 8160
8161 agtggctgctgccagtggcgataagtcgtgtcttaccgggttggactcaagacgatagtt 8220
8221 accggataaggcgcagcggtcgggctgaacggggggttcgtgcacacagcccagcttgga 8280
8281 gcgaacgacctacaccgaactgagatacctacagcgtgagcattgagaaagcgccacgct 8340
8341 tcccgaagggagaaaggcggacaggtatccggtaagcggcagggtcggaacaggagagcg 8400
8401 cacgagggagcttccagggggaaacgcctggtatctttatagtcctgtcgggtttcgcca 8460
8461 cctctgacttgagcgtcgatttttgtgatgctcgtcaggggggcggagcctatggaaaaa 8520
8521 cgccagcaacgcggcctttttacggttcctggccttttgctggccttttgctcacatgtt 8580
8581 ctttcctgcgttatcccctgattctgtggataaccgtattaccgcctttgagtgagctga 8640
8641 taccgctcgccgcagccgaacgaccgagcgcagcgagtcagtgagcgaggaagcggaaga 8700
8701 gcgcccaatacgcagggcccccctgca 8726
```

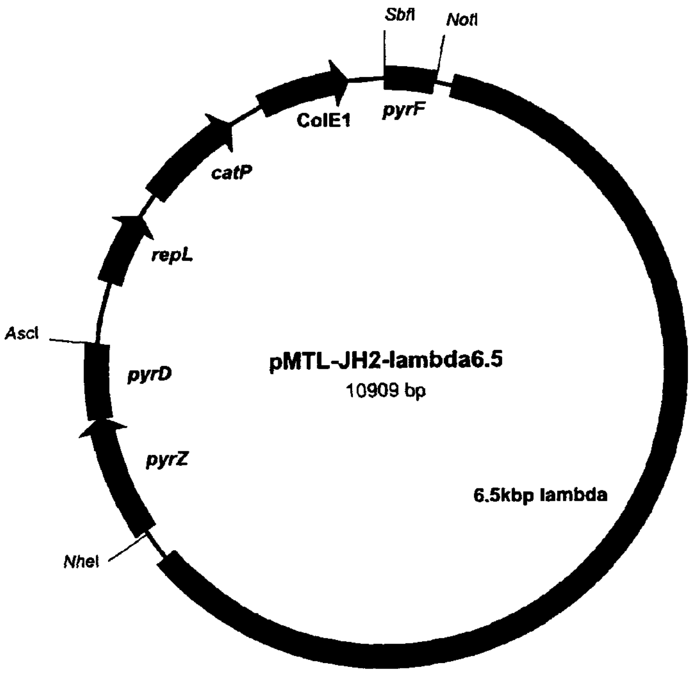

```
   1 gggtgtttaggacttgatactgatattacttatgtaccagaagagttttgtaagaaattt 60
  61 aatagtatagaagatgctatatttaattttaataagaaataattgatgcgactttagat 120
 121 gttgtttcatgttataaggtgcaaattgcatattatgaagcttatggtttaaaaggactt 180
 181 ttggcctataaaggacacttgaatatttgagagaaaaaaaggctattgcaattgctgat 240
 241 ataaaaagaggagatatagctaaaacagctgaaatgtatgctaaagctcactttgaaggt 300
 301 taatgagcggccgctgtatccatatgaccatgattacgaattcgagctcggtacccgggg 360
 361 atcctctagagtcgacgtcacgcgtccatggagatctcgaggagcttaggtgagaacatc 420
 421 cctgcctgaacatgagaaaaaacagggtactcatactcacttctaagtgacggctgcata 480
 481 ctaaccgcttcatacatctcgtagatttctctggcgattgaagggctaaattcttcaacg 540
 541 ctaactttgagaattttgtaagcaatgcggcgttataagcatttaatgcattgatgcca 600
 601 ttaaataaagcaccaacgcctgactgccccatccccatcttgtctgcgacagattcctgg 660
 661 gataagccaagttcatttttctttttttcataaattgctttaaggcgacgtgcgtcctca 720
 721 agctgctcttgtgttaatggtttctttttgtgctcatacgttaaatctatcaccgcaag 780
 781 ggataaatatctaacaccgtgcgtgttgactattttacctctggcggtgataatggttgc 840
 841 atgtactaaggaggttgtatggaacaacgcataaccctgaaagattatgcaatgcgcttt 900
 901 gggcaaaccaagacagctaaagatctcggcgtatatcaaagcgcgatcaacaaggccatt 960
 961 catgcaggccgaaagatttttttaactataaacgctgatggaagcgtttatgcggaagag 1020
1021 gtaaagcccttcccgagtaacaaaaaaacaacagcataaataaccccgctcttacacatt 1080
1081 ccagccctgaaaaagggcatcaaattaaaccacacctatggtgtatgcatttatttgcat 1140
1141 acattcaatcaattgttatctaaggaaatacttacatatggttcgtgcaaacaaacgcaa 1200
1201 cgaggctctacgaatcgagagtgcgttgcttaacaaaatcgcaatgcttggaactgagaa 1260
1261 gacagcggaagctgtgggcgttgataagtcgcagatcagcaggtggaagagggactggat 1320
1321 tccaaagttctcaatgctgcttgctgttcttgaatggggggtcgttgacgacgacatggc 1380
1381 tcgattggcgcgacaagttgctgcgattctcaccaataaaaaacgcccggcggcaaccga 1440
1441 gcgttctgaacaaatccagatggagttctgaggtcattactggatctatcaacaggagtc 1500
1501 attatgacaaatacagcaaaaatactcaacttcggcagaggtaactttgccggacaggag 1560
1561 cgtaatgtggcagatctcgatgatggttacgccagactatcaaatatgctgcttgaggct 1620
1621 tattcgggcgcagatctgaccaagcgacagtttaaagtgctgcttgccattctgcgtaaa 1680
```

```
1681 acctatgggtggaataaaccaatggacagaatcaccgattctcaacttagcgagattaca 1740
1741 aagttacctgtcaaacggtgcaatgaagccaagttagaactcgtcagaatgaatattatc 1800
1801 aagcagcaaggcggcatgtttggaccaaataaaaacatctcagaatggtgcatccctcaa 1860
1861 aacgagggaaaatcccctaaaacgagggataaaacatccctcaaattgggggattgctat 1920
1921 ccctcaaaacaggggacacaaaagacactattacaaaagaaaaagaaaagattattcg 1980
1981 tcagagaattctggcgaatcctctgaccagccagaaaacgacctttctgtggtgaaaccg 2040
2041 gatgctgcaattcagagcggcagcaagtgggggacagcagaagacctgaccgccgcagag 2100
2101 tggatgtttgacatggtgaagactatcgcaccatcagccagaaaaccgaattttgctggg 2160
2161 tgggctaacgatatccgcctgatgcgtgaacgtgacggacgtaaccaccgcgacatgtgt 2220
2221 gtgctgttccgctgggcatgccaggacaacttctggtccggtaacgtgctgagcccggcc 2280
2281 aaactccgcgataagtggacccaactcgaaatcaaccgtaacaagcaacaggcaggcgtg 2340
2341 acagccagcaaaccaaaactcgacctgacaaacacagactggatttacggggtggatcta 2400
2401 tgaaaaacatcgccgcacagatggttaactttgaccgtgagcagatgcgtcggatcgcca 2460
2461 acaacatgccggaacagtacgacgaaaagccgcaggtacagcaggtagcgcagatcatca 2520
2521 acggtgtgttcagccagttactggcaactttcccggcgagcctggctaaccgtgaccaga 2580
2581 acgaagtgaacgaaatccgtcgccagtgggttctggcttttcgggaaaacgggatcacca 2640
2641 cgatggaacaggttaacgcaggaatgcgcgtagcccgtcggcagaatcgaccatttctgc 2700
2701 catcacccgggcagtttgttgcatggtgccgggaagaagcatccgttaccgccggactgc 2760
2761 caaacgtcagcgagctggttgatatggtttacgagtattgccggaagcgaggcctgtatc 2820
2821 cggatgcggagtcttatccgtggaaatcaaacgcgcactactggctggttaccaacctgt 2880
2881 atcagaacatgcgggccaatgcgcttactgatgcggaattacgccgtaaggccgcagatg 2940
2941 agcttgtccatatgactgcgagaattaaccgtggtgaggcgatccctgaaccagtaaaac 3000
3001 aacttcctgtcatgggcggtagacctctaaatcgtgcacaggctctggcgaagatcgcag 3060
3061 aaatcaaagctaagttcggactgaaaggagcaagtgtatgacgggcaaagaggcaattat 3120
3121 tcattacctggggacgcataatagcttctgtgcgccggacgttgccgcgctaacaggcgc 3180
3181 aacagtaaccagcataaatcaggccgcggctaaaatggcacgggcaggtcttctggttat 3240
3241 cgaaggtaaggtctggcgaacggtgtattaccggtttgctaccagggaagaacgggaagg 3300
3301 aaagatgagcacgaacctggttttaaggagtgtcgccagagtgccgcgatgaaacgggt 3360
3361 attggcggtatatggagttaaaagatgaccatctacattactgagctaataacaggcctg 3420
3421 ctggtaatcgcaggcctttttatttgggggagagggaagtcatgaaaaaactaacctttg 3480
3481 aaattcgatctccagcacatcagcaaaacgctattcacgcagtacagcaaatccttccag 3540
3541 acccaaccaaaccaatcgtagtaaccattcaggaacgcaaccgcagcttagaccaaaaca 3600
3601 ggaagctatgggcctgcttaggtgacgtctctcgtcaggttgaatggcatggtcgctggc 3660
3661 tggatgcagaaagctggaagtgtgtgtttaccgcagcattaaagcagcaggatgttgttc 3720
3721 ctaaccttgccgggaatggctttgtggtaataggccagtcaaccagcaggatgcgtgtag 3780
3781 gcgaatttgcggagctattagagcttatacaggcattcggtacagagcgtggcgttaagt 3840
3841 ggtcagacgaagcgagactggctctggagtggaaagcgagatggggagacagggctgcat 3900
3901 gataaatgtcgttagtttctccggtggcaggacgtcagcatatttgctctggctaatgga 3960
3961 gcaaaagcgacgggcaggtaaagacgtgcattacgttttcatggatacaggttgtgaaca 4020
4021 tccaatgacatatcggtttgtcagggaagttgtgaagttctgggatataccgctcaccgt 4080
4081 attgcaggttgatatcaacccggagcttggacagccaaatggttatacggtatgggaacc 4140
4141 aaaggatattcagacgcgaatgcctgttctgaagccatttatcgatatggtaaagaaata 4200
4201 tggcactccatacgtcggcggcgcgttctgcactgacagattaaactcgttcccttcac 4260
4261 caaatactgtgatgaccatttcgggcgagggaattacaccacgtggattggcatcagagc 4320
4321 tgatgaaccgaagcggctaaagccaaagcctggaatcagatatcttgctgaactgtcaga 4380
4381 ctttgagaaggaagatatcctcgcatggtggaagcaacaaccattcgatttgcaaatacc 4440
4441 ggaacatctcggtaactgcatattctgcattaaaaatcaacgcaaaaatcggacttgc 4500
4501 ctgcaaagatgaggagggattgcagcgtgtttttaatgaggtcatcacgggatcccatgt 4560
4561 gcgtgacggacatcgggaaacgccaaaggagattatgtaccgaggaagaatgtcgctgga 4620
4621 cggtatcgcgaaaatgtattcagaaaatgattatcaagccctgtatcaggacatggtacg 4680
4681 agctaaaagattcgataccggctcttgttctgagtcatgcgaaatatttggagggcagct 4740
4741 tgatttcgacttcgggagggaagctgcatgatgcgatgttatcggtgcggtgaatgcaaa 4800
4801 gaagataaccgcttccgaccaaatcaaccttactggaatcgatggtgtctccggtgtgaa 4860
4861 agaacaccaacaggggtgttaccactaccgcaggaaaaggaggacgtgtggcgagacagc 4920
4921 gacgaagtatcaccgacataatctgcgaaaactgcaaataccttccaacgaaacgcacca 4980
4981 gaaataaacccaagccaatcccaaaagaatctgacgtaaaaaccttcaactacacggctc 5040
5041 acctgtgggatatccggtggctaagacgtcgtgcgaggaaaacaaggtgattgaccaaaa 5100
5101 tcgaagttacgaacaagaaagcgtcgagcgagctttaacgtgcgctaactgcggtcagaa 5160
```

Figure 6H (CONT.)

5161 gctgcatgtgctggaagttcacgtgtgtgagcactgctgcgcagaactgatgagcgatcc 5220
5221 gaatagctcgatgcacgaggaagaagatgatggctaaaccagcgcgaagacgatgtaaaa 5280
5281 acgatgaatgccgggaatggtttcaccctgcattcgctaatcagtggtggtgctctccag 5340
5341 agtgtggaaccaagatagcactcgaacgacgaagtaaagaacgcgaaaaagcggaaaaag 5400
5401 cagcagagaagaaacgacgacgagaggagcagaaacagaaagataaacttaagattcgaa 5460
5461 aactcgccttaaagccccgcagttactggattaaacaagcccaacaagccgtaaacgcct 5520
5521 tcatcagagaaagagaccgcgacttaccatgtatctcgtgcggaacgctcacgtctgctc 5580
5581 agtgggatgccggacattaccggacaactgctgcggcacctcaactccgatttaatgaac 5640
5641 gcaatattcacaagcaatgcgtggtgtgcaaccagcacaaaagcggaaatctcgttccgt 5700
5701 atcgcgtcgaactgattagccgcatcgggcaggaagcagtagacgaaatcgaatcaaacc 5760
5761 ataaccgccatcgctggactatcgaagagtgcaaggcgatcaaggcagagtaccaacaga 5820
5821 aactcaaagacctgcgaaatagcagaagtgaggccgcatgacgttctcagtaaaaaccat 5880
5881 tccagacatgctcgttgaagcatacggaaatcagacagaagtagcacgcagactgaaatg 5940
5941 tagtcgcggtacggtcagaaaatacgttgatgataaagacgggaaaatgcacgccatcgt 6000
6001 caacgacgttctcatggttcatcgcggatggagtgaaagagatgcgctattacgaaaaaa 6060
6061 ttgatggcagcaaataccgaaatatttgggtagttggcgatctgcacggatgctacacga 6120
6121 acctgatgaacaaactggatacgattggattcgacaacaaaaaagacctgcttatctcgg 6180
6181 tgggcgatttggttgatcgtggtgcagagaacgttgaatgcctggaattaatcacattcc 6240
6241 cctggttcagagctgtacgtggaaaccatgagcaaatgatgattgatggcttatcagagc 6300
6301 gtggaaacgttaatcactggctgcttaatggcggtggctggttctttaatctcgattacg 6360
6361 acaaagaaattctggctaaagctcttgcccataaagcagatgaacttccgttaatcatcg 6420
6421 aactggtgagcaaagataaaaaatatgttatctgccacgccgattatccctttgacgaat 6480
6481 acgagtttggaaagccagttgatcatcagcaggtaatctggaaccgcgaacgaatcagca 6540
6541 actcacaaaacgggatcgtgaaagaaatcaaaggcgcggacacgttcatctttggtcata 6600
6601 cgccagcagtgaaaccactcaagtttgccaaccaaatgtatatcgataccggcgcagtgt 6660
6661 tctgcggaaacctaacattgattcaggtacagggagaaggcgcatgagactcgaaagcgt 6720
6721 agctaaatttcattcgccaaaaagcccgatgatgagcgactcaccacgggccacggcttc 6780
6781 tgactctctttccggtactgatgtgatggctgctatggggatggcgcaatcacaagccgg 6840
6841 attcggtatggctgcattctgcggtaagcacgaactcagccagaacgacaaacaaaaggc 6900
6901 tatcaactatctgatgcaatttgcacacaaggtatcggggaaataccgtggtgtggcacc 6960
6961 tgcagacatgcaagcttggcactggccgtcgttttacaacgtcgtgactgggaaaaccct 7020
7021 ggcgttacccaacttaatcgccttgcagcacatccccctttcgccagctggcgtaatagc 7080
7081 gaagaggcccgcaccgatcgcccttcccaacagttgcgcagcctgaatggcgaatggcgc 7140
7141 tagcattttggggaattttgatgaaggaaaagtatacagtagaaaaagtatatgaaaat 7200
7201 ataaaagttgaagatggtatatacaaacttagtataaagggtgaatttgaggtgaggcca 7260
7261 ggacaattttatcttttaagagcttgggatatagaaccaacactttctagacctattagt 7320
7321 atatatgatgcagatgacgaaaaaatatcgttcttatactctgttgttggaaaaggaact 7380
7381 gaaattttatctaaattaaagagcggcgatgaaataaagataacaggacctttaggaaat 7440
7441 ggatttaacgtaaaaaggataagtggaaaagtggctatagtttgtggtggtataggtgta 7500
7501 gcaccaatggtatatctggctaaaaacttaaaaaattgtaatgttgattttttatgctggc 7560
7561 ttcaaaactgtgagtaaaactgtggataatgtggaaaaatatgttaaagagttaaagttg 7620
7621 tccacagaagatggaagtattggacataaggggtatgtaacagataactttaagccagaa 7680
7681 gaatacgattatgttttatgctgcggacctgagataatgatgtataaagttgttaaaatg 7740
7741 tgtgaacaaaagaatgttcctgtatatatttcaatggagaaaaaaatggcatgtggaata 7800
7801 ggtgcatgccttgtatgcacttgtaaaactaagggtggaagaagaagagcttgtaaagag 7860
7861 ggcccagtattttaggaagtgagttgatattaaatgactaaagtaaatatttgtggaat 7920
7921 agatttaagaaccccgttattgctgcttctggcacctttggatttggagaagagtttag 7980
7981 taagtattttgatgtttcaaggcttggtggcatatcttcaaagggacttacattgaatcc 8040
8041 taaggaaggtaatgatggtgcaagagtttttgaggtcacaggcggaatgatgaatagtgt 8100
8101 aggacttcaaaatcctggagttaaagagtttataaaaaaagaacttcctaagatgaaaaa 8160
8161 aatagatacagtatgtattgttaaccttggtggaagctgtgaggatgattatttaagggg 8220
8221 catggagcttcttgagaatacagatgctgatatgatagaacttaatatatcctgtcctaa 8280
8281 tgtaaagcacggcggcatggcttttggaataaaatcagaagttgcttataatgttgtatc 8340
8341 acaaggcgcgccgcattcacttcttttctatataaatatgagcgaagcgaataagcgtcg 8400
8401 gaaaagcagcaaaaagtttcctttttgctgttggagcatgggggttcagggggtgcagta 8460
8461 tctgacgtcaatgccgagcgaaagcgagccgaagggtagcatttacgttagataaccccc 8520
8521 tgatatgctccgacgctttatatagaaaagaagattcaactaggtaaaatcttaatatag 8580
8581 gttgagatgataaggtttataaggaatttgtttgttctaattttcactcattttgttct 8640

Figure 6H (CONT.)

8641 aatttcttttaacaaatgttcttttttttttagaacagttatgatatagttagaatagtt 8700
8701 taaaataaggagtgagaaaaagatgaaagaaagatatggaacagtctataaaggctctca 8760
8761 gaggctcatagacgaagaaagtggagaagtcatagaggtagacaagttataccgtaaaca 8820
8821 aacgtctggtaacttcgtaaaggcatatatagtgcaattaataagtatgttagatatgat 8880
8881 tggcggaaaaaaacttaaaatcgttaactatatcctagataatgtccacttaagtaacaa 8940
8941 tacaatgatagctacaacaagagaaatagcaaaagctacaggaacaagtctacaaacagt 9000
9001 aataacaacacttaaaatcttagaagaaggaaatattataaaaagaaaaactggagtatt 9060
9061 aatgttaaaccctgaactactaatgagaggcgacgaccaaaaacaaaaatacctcttact 9120
9121 cgaatttgggaactttgagcaagaggcaaatgaaatagattgacctcccaataacaccac 9180
9181 gtagttattgggaggtcaatctatgaaatgcgattaagggccggccagtgggcaagttga 9240
9241 aaaattcacaaaaatgtggtataatatctttgttcattagagcgataaacttgaatttga 9300
9301 gagggaacttagatggtatttgaaaaaattgataaaaatagttggaacagaaaagagtat 9360
9361 tttgaccactactttgcaagtgtaccttgtacctacagcatgaccgttaaagtggatatc 9420
9421 acacaaataaaggaaaagggaatgaaactatatcctgcaatgctttattatattgcaatg 9480
9481 attgtaaaccgccattcagagtttaggacggcaatcaatcaagatggtgaattggggata 9540
9541 tatgatgagatgataccaagctatacaatatttcacaatgatactgaaacattttccagc 9600
9601 ctttggactgagtgtaagtctgactttaaatcattttagcagattatgaaagtgatacg 9660
9661 caacggtatggaaacaatcatagaatggaaggaaagccaaatgctccggaaaacattttt 9720
9721 aatgtatctatgataccgtggtcaaccttcgatggctttaatctgaatttgcagaaagga 9780
9781 tatgattatttgattcctattttactatggggaaatattataaagaagataacaaaatt 9840
9841 atacttcctttggcaattcaagttcatcacgcagtatgtgacggatttcacatttgccgt 9900
9901 tttgtaaacgaattgcaggaattgataaatagttaacttcaggtttgtctgtaactaaaa 9960
9961 acaagtatttaagcaaaaacatcgtagaaatacggtgtttttgttaccctaagtttaaa 10020
10021 ctccttttgataatctcatgaccaaaatcccttaacgtgagttttcgttccactgagcg 10080
10081 tcagaccccgtagaaaagatcaaaggatcttcttgagatcctttttttctgcgcgtaatc 10140
10141 tgctgcttgcaaacaaaaaaaccaccgctaccagcggtggtttgtttgccggatcaagag 10200
10201 ctaccaactctttttccgaaggtaactggcttcagcagagcgcagataccaaatactgtc 10260
10261 cttctagtgtagccgtagttaggccaccacttcaagaactctgtagcaccgcctacatac 10320
10321 ctcgctctgctaatcctgttaccagtggctgctgccagtggcgataagtcgtgtcttacc 10380
10381 gggttggactcaagacgatagttaccggataaggcgcagcggtcgggctgaacggggggt 10440
10441 tcgtgcacacagcccagcttggagcgaacgacctacaccgaactgagatacctacagcgt 10500
10501 gagcattgagaaagcgccacgcttcccgaagggagaaaggcggacaggtatccggtaagc 10560
10561 ggcagggtcggaacaggagagcgcacgagggagcttccagggggaaacgcctggtatctt 10620
10621 tatagtcctgtcgggtttcgccacctctgacttgagcgtcgatttttgtgatgctcgtca 10680
10681 ggggggcggagcctatggaaaaacgccagcaacgcggcctttttacggttcctggccttt 10740
10741 tgctggccttttgctcacatgttctttcctgcgttatcccctgattctgtggataaccgt 10800
10801 attaccgcctttgagtgagctgataccgctcgccgcagccgaacgaccgagcgcagcgag 10860
10861 tcagtgagcgaggaagcggaagagcgcccaatacgcagggcccccctgca 10909

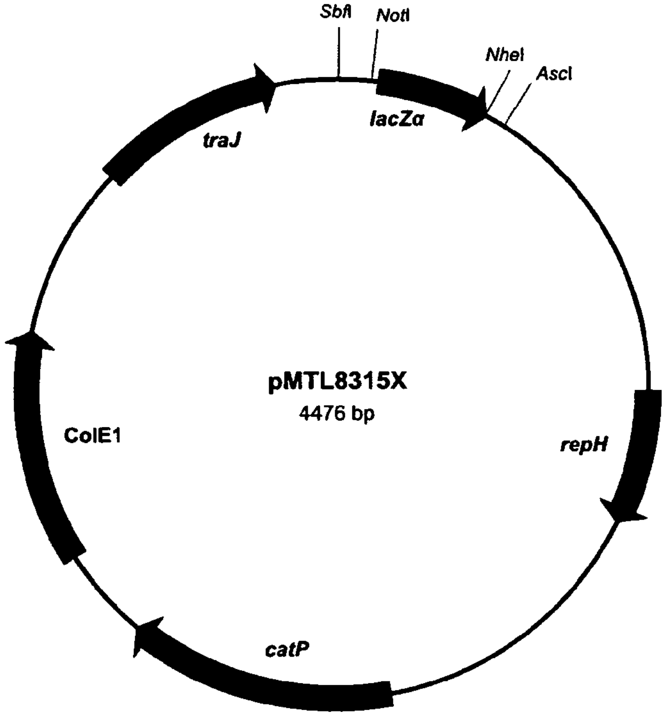

```
   1 ggataaaaaaattgtagataaattttataaaatagttttatctacaattttttttatcagg   60
  61 aaacagctatgaccgcggccgctgtatccatatgaccatgattacgaattcgagctcggt  120
 121 acccggggatcctctagagtcgacgtcacgcgtccatggagatctcgaggcctgcagaca  180
 181 tgcaagcttggcactggccgtcgttttacaacgtcgtgactgggaaaaccctggcgttac  240
 241 ccaacttaatcgccttgcagcacatccccctttcgccagctggcgtaatagcgaagaggc  300
 301 ccgcaccgatcgcccttcccaacagttgcgcagcctgaatggcgaatggcgctagcataa  360
 361 aaataagaagcctgcatttgcaggcttcttattttttatggcgcgccgccattattttttt  420
 421 gaacaattgacaattcatttcttattttttattaagtgatagtcaaaaggcataacagtg  480
 481 ctgaatagaaagaaatttacagaaaagaaaattatagaatttagtatgattaattatact  540
 541 catttatgaatgtttaattgaatacaaaaaaaaatacttgttatgtattcaattacgggt  600
 601 taaaatatagacaagttgaaaaatttaataaaaaaataagtcctcagctcttatatatta  660
 661 agctaccaacttagtatataagccaaaacttaaatgtgctaccaacacatcaagccgtta  720
 721 gagaactctatctatagcaatatttcaaatgtaccgacatacaagagaaacattaactat  780
 781 atatattcaatttatgagattatcttaacagatataaatgtaaattgcaataagtaagat  840
 841 ttagaagtttatagcctttgtgtattggaagcagtacgcaaaggcttttttatttgataa  900
 901 aaattagaagtatatttattttttcataattaatttatgaaaatgaaaggggggtgagcaa  960
 961 agtgacagaggaaagcagtatcttatcaaataacaaggtattagcaatatcattattgac 1020
1021 tttagcagtaaacattatgacttttatagtgcttgtagctaagtagtacgaaaggggggag 1080
1081 ctttaaaaagctccttggaatacatagaattcataaattaatttatgaaaagaagggcgt 1140
1141 atatgaaaacttgtaaaaattgcaaagagtttattaaagatactgaaatatgcaaaatac 1200
1201 attcgttgatgattcatgataaaacagtagcaacctattgcagtaaatacaatgagtcaa 1260
1261 gatgtttacataaagggaaagtccaatgtattaattgttcaaagatgaaccgatatggat 1320
1321 ggtgtgccataaaaatgagatgttttacagaggaagaacagaaaaaagaacgtacatgca 1380
1381 ttaaatattatgcaaggagctttaaaaaagctcatgtaaagaagagtaaaagaaaaaat 1440
1441 aatttatttattaatttaatattgagagtgccgacacagtatgcactaaaaaatatatct 1500
1501 gtggtgtagtgagccgatacaaaaggatagtcactcgcattttcataatacatcttatgt 1560
1561 tatgattatgtgtcggtgggacttcacgacgaaaacccacaataaaaaaagagttcgggg 1620
```

```
1621 tagggttaagcatagttgaggcaactaaacaatcaagctaggatatgcagtagcagaccg 1680
1681 taaggtcgttgtttaggtgtgttgtaatacatacgctattaagatgtaaaaatacggata 1740
1741 ccaatgaagggaaaagtataattttggatgtagtttgtttgttcatctatgggcaaact 1800
1801 acgtccaaagccgtttccaaatctgctaaaaagtatatcctttctaaaatcaaagtcaag 1860
1861 tatgaaatcataaataaagtttaattttgaagttattatgatattatgtttttctattaa 1920
1921 aataaattaagtatatagaatagtttaataatagtatatacttaatgtgataagtgtctg 1980
1981 acagtgtcacagaaaggatgattgttatggattataagcggccggccagtgggcaagttg 2040
2041 aaaaattcacaaaaatgtggtataatatctttgttcattagagcgataaacttgaatttg 2100
2101 agagggaacttagatggtatttgaaaaaattgataaaaatagttggaacagaaaagagta 2160
2161 ttttgaccactactttgcaagtgtaccttgtacctacagcatgaccgttaaagtggatat 2220
2221 cacacaaataaaggaaaagggaatgaaactatatcctgcaatgctttattatattgcaat 2280
2281 gattgtaaaccgccattcagagtttaggacggcaatcaatcaagatggtgaattggggat 2340
2341 atatgatgagatgataccaagctatacaatatttcacaatgatactgaaacattttccag 2400
2401 cctttggactgagtgtaagtctgactttaaatcatttttagcagattatgaaagtgatac 2460
2461 gcaacggtatggaaacaatcatagaatggaaggaaagccaaatgctccggaaaacatttt 2520
2521 taatgtatctatgataccgtggtcaaccttcgatggctttaatctgaatttgcagaaagg 2580
2581 atatgattatttgattcctatttttactatggggaaatattataaagaagataacaaaat 2640
2641 tatacttcctttggcaattcaagttcatcacgcagtatgtgacggatttcacatttgccg 2700
2701 ttttgtaaacgaattgcaggaattgataaatagttaacttcaggtttgtctgtaactaaa 2760
2761 aacaagtatttaagcaaaaacatcgtagaaatacggtgtttttttgttaccctaagtttaa 2820
2821 actcctttttgataatctcatgaccaaaatcccttaacgtgagttttcgttccactgagc 2880
2881 gtcagaccccgtagaaaagatcaaaggatcttcttgagatcctttttttctgcgcgtaat 2940
2941 ctgctgcttgcaaacaaaaaaaccaccgctaccagcggtggtttgtttgccggatcaaga 3000
3001 gctaccaactctttttccgaaggtaactggcttcagcagagcgcagataccaaatactgt 3060
3061 ccttctagtgtagccgtagttaggccaccacttcaagaactctgtagcaccgcctacata 3120
3121 cctcgctctgctaatcctgttaccagtggctgctgccagtggcgataagtcgtgtcttac 3180
3181 cgggttggactcaagacgatagttaccggataaggcgcagcggtcgggctgaacgggggg 3240
3241 ttcgtgcacacagcccagcttggagcgaacgacctacaccgaactgagatacctacagcg 3300
3301 tgagcattgagaaagcgccacgcttcccgaagggagaaaggcggacaggtatccggtaag 3360
3361 cggcagggtcggaacaggagagcgcacgagggagcttccagggggaaacgcctggtatct 3420
3421 ttatagtcctgtcgggtttcgccacctctgacttgagcgtcgatttttgtgatgctcgtc 3480
3481 aggggggcggagcctatggaaaaacgccagcaacgcggcctttttacggttcctggcctt 3540
3541 ttgctggccttttgctcacatgttctttcctgcgttatcccctgattctgtggataaccg 3600
3601 tattaccgcctttgagtgagctgataccgctcgccgcagccgaacgaccgagcgcagcga 3660
3661 gtcagtgagcgaggaagcggaagagcgcccaatacgcagggccccctgcttcggggtcat 3720
3721 tatagcgatttttttcggtatatccatcctttttcgcacgatatacaggattttgccaaag 3780
3781 ggttcgtgtagactttccttggtgtatccaacggcgtcagccgggcaggataggtgaagt 3840
3841 aggcccacccgcgagcgggtgttccttcttcactgtcccttattcgcacctggcggtgct 3900
3901 caacgggaatcctgctctgcgaggctggccggctaccgccggcgtaacagatgagggcaa 3960
3961 gcggatggctgatgaaaccaagccaaccaggaagggcagcccacctatcaaggtgtactg 4020
4021 ccttccagacgaacgaagagcgattgaggaaaaggcggcggcggccggcatgagcctgtc 4080
4081 ggcctacctgctggccgtcggccagggctacaaaatcacgggcgtcgtggactatgagca 4140
4141 cgtccgcgagctggcccgcatcaatggcgacctgggccgcctgggcggcctgctgaaact 4200
4201 ctggctcaccgacgacccgcgcacggcgcggttcggtgatgccacgatcctcgccctgct 4260
4261 ggcgaagatcgaagagaagcaggacgagcttggcaaggtcatgatgggcgtggtccgccc 4320
4321 gagggcagagccatgactttttagccgctaaaacggccggggggtgcgcgtgattgcca 4380
4381 agcacgtccccatgcgctccatcaagaagagcgacttcgcggagctggtgaagtacatca 4440
4441 ccgacgagcaaggcaagaccgatcgggccccctgca 4476
```

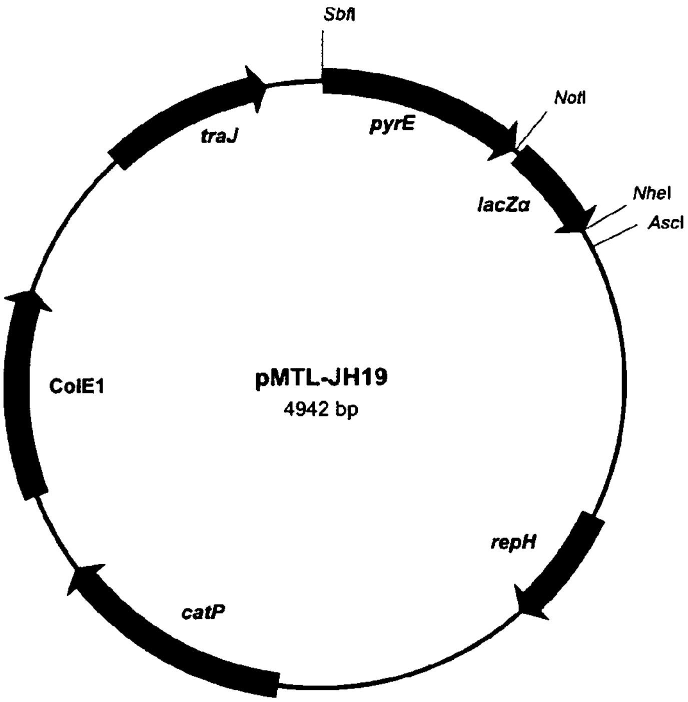

1 ggggagggacatttttattatcttcaggaaaacacagtaatagatacgtacaatgtgca 60
61 aaagtattaagattcccagaatatgctgctgaggtattaagtacagttgttgaacaaata 120
121 aaagacttagatatagacttagtagtaggaccagctatgggtggagtaatagtttcttat 180
181 gagttaggaagacaattaggaaaagaagctgtatttactgagagaaaagacaatacaatg 240
241 gagttaagaagaggatttgaagttaaaaaaggagcaaagataataattgctgaagacgtt 300
301 gtaactactggtaaatcaactatggagacaaaaagagtattagaagccttaggtggagaa 360
361 gttgtaggtgttgcatgtatagcagatagaactaatcatgatataggtatgcctatatat 420
421 agtgctataaaacttgatattcaagtttatgaatctgatgagtgtcctttatgtaaggaa 480
481 ggaaaattaccagttgttaagcctggaagtagagagttcaaggaattagggatgtaataa 540
541 gcggccgctgtatccatatgaccatgattacgaattcgagctcggtacccggggatcctc 600
601 tagagtcgacgtcacgcgtccatggagatctcgaggcctgcagacatgcaagcttggcac 660
661 tggccgtcgttttacaacgtcgtgactgggaaaaccctggcgttacccaacttaatcgcc 720
721 ttgcagcacatccccctttcgccagctggcgtaatagcgaagaggcccgcaccgatcgcc 780
781 cttcccaacagttgcgcagcctgaatggcgaatggcgctagcataaaaataagaagcctg 840
841 catttgcaggcttcttatttttatggcgcgccgccattatttttttgaacaattgacaat 900
901 tcatttcttatttttattaagtgatagtcaaaaggcataacagtgctgaatagaaagaa 960
961 atttacagaaaagaaaattatagaatttagtatgattaattatactcatttatgaatgtt 1020
1021 taattgaatacaaaaaaaaatacttgttatgtattcaattacgggttaaaatatagacaa 1080
1081 gttgaaaaatttaataaaaaaataagtcctcagctcttatatattaagctaccaacttag 1140
1141 tatataagccaaaacttaaatgtgctaccaacacatcaagccgttagagaactctatcta 1200
1201 tagcaatatttcaaatgtaccgacatacaagagaaacattaactatatatattcaattta 1260
1261 tgagattatcttaacagatataaatgtaaattgcaataagtaagatttagaagtttatag 1320
1321 cctttgtgtattggaagcagtacgcaaaggctttttatttgataaaaattagaagtata 1380
1381 tttatttttcataattaatttatgaaaatgaaagggggtgagcaaagtgacagaggaaa 1440
1441 gcagtatcttatcaaataacaaggtattagcaatatcattattgactttagcagtaaaca 1500
1501 ttatgacttttatagtgcttgtagctaagtagtacgaaaggggggagctttaaaaagctcc 1560
1561 ttggaatacatagaattcataaattaatttatgaaaagaagggcgtatatgaaaacttgt 1620
1621 aaaaattgcaaagagtttattaaagatactgaaatatgcaaaatacattcgttgatgatt 1680
1681 catgataaaacagtagcaacctattgcagtaaatacaatgagtcaagatgtttacataaa 1740

```
1741 gggaaagtccaatgtattaattgttcaaagatgaaccgatatggatggtgtgccataaaa 1800
1801 atgagatgttttacagaggaagaacagaaaaagaacgtacatgcattaaatattatgca 1860
1861 aggagctttaaaaagctcatgtaaagaagagtaaaagaaaaaataatttatttattaa 1920
1921 tttaatattgagagtgccgacacagtatgcactaaaaatatatctgtggtgtagtgagc 1980
1981 cgatacaaaggatagtcactcgcattttcataatacatcttatgttatgattatgtgtc 2040
2041 ggtgggacttcacgacgaaaacccacaataaaaaaagagttcggggtagggttaagcata 2100
2101 gttgaggcaactaaacaatcaagctaggatatgcagtagcagaccgtaaggtcgttgttt 2160
2161 aggtgtgttgtaatacatacgctattaagatgtaaaaatacggataccaatgaagggaaa 2220
2221 agtataattttggatgtagtttgtttgttcatctatgggcaaactacgtccaaagccgt 2280
2281 ttccaaatctgctaaaaagtatatcctttctaaaatcaaagtcaagtatgaaatcataaa 2340
2341 taaagtttaattttgaagttattatgatattatgtttttctattaaaataaattaagtat 2400
2401 atagaatagtttaataatagtatatacttaatgtgataagtgtctgacagtgtcacagaa 2460
2461 aggatgattgttatggattataagcggccggccagtgggcaagttgaaaaattcacaaaa 2520
2521 atgtggtataatatctttgttcattagagcgataaacttgaatttgagagggaacttaga 2580
2581 tggtatttgaaaaaattgataaaaatagttggaacagaaaagagtattttgaccactact 2640
2641 ttgcaagtgtaccttgtacctacagcatgaccgttaaagtggatatcacacaaataaagg 2700
2701 aaaagggaatgaaactatatcctgcaatgctttattatattgcaatgattgtaaaccgcc 2760
2761 attcagagtttaggacggcaatcaatcaagatggtgaattggggatatatgatgagatga 2820
2821 taccaagctatacaatatttcacaatgatactgaaacattttccagcctttggactgagt 2880
2881 gtaagtctgactttaaatcattttagcagattatgaaagtgatacgcaacggtatggaa 2940
2941 acaatcatagaatggaaggaaagccaaatgctccggaaaacattttaatgtatctatga 3000
3001 taccgtggtcaaccttcgatggctttaatctgaatttgcagaaaggatatgattatttga 3060
3061 ttcctatttttactatggggaaatattataaagaagataacaaaattatacttcctttgg 3120
3121 caattcaagttcatcacgcagtatgtgacggatttcacatttgccgttttgtaaacgaat 3180
3181 tgcaggaattgataaatagttaacttcaggtttgtctgtaactaaaaacaagtatttaag 3240
3241 caaaaacatcgtagaaatacggtgtttttgttaccctaagtttaaactcctttttgata 3300
3301 atctcatgaccaaaatcccttaacgtgagttttcgttccactgagcgtcagaccccgtag 3360
3361 aaaagatcaaaggatcttcttgagatcctttttttctgcgcgtaatctgctgcttgcaaa 3420
3421 caaaaaaaccaccgctaccagcggtggtttgtttgccggatcaagagctaccaactcttt 3480
3481 ttccgaaggtaactggcttcagcagagcgcagataccaaatactgtccttctagtgtagc 3540
3541 cgtagttaggccaccacttcaagaactctgtagcaccgcctacatacctcgctctgctaa 3600
3601 tcctgttaccagtggctgctgccagtggcgataagtcgtgtcttaccgggttggactcaa 3660
3661 gacgatagttaccggataaggcgcagcggtcgggctgaacggggggttcgtgcacacagc 3720
3721 ccagcttggagcgaacgacctacaccgaactgagatacctacagcgtgagcattgagaaa 3780
3781 gcgccacgcttcccgaagggagaaaggcggacaggtatccggtaagcggcagggtcggaa 3840
3841 caggagagcgcacgagggagcttccagggggaaacgcctggtatctttatagtcctgtcg 3900
3901 ggtttcgccacctctgacttgagcgtcgatttttgtgatgctcgtcaggggggcggagcc 3960
3961 tatggaaaaacgccagcaacgcggcctttttacggttcctggccttttgctggccttttg 4020
4021 ctcacatgttctttcctgcgttatcccctgattctgtggataaccgtattaccgcctttg 4080
4081 agtgagctgataccgctcgccgcagccgaacgaccgagcgcagcgagtcagtgagcgagg 4140
4141 aagcggaagagcgcccaatacgcagggcccccctgcttcggggtcattatagcgattttt 4200
4201 cggtatatccatcctttttcgcacgatatacaggattttgccaaagggttcgtgtagact 4260
4261 ttccttggtgtatccaacggcgtcagccgggcaggataggtgaagtaggcccacccgcga 4320
4321 gcgggtgttccttcttcactgtcccttattcgcacctggcggtgctcaacgggaatcctg 4380
4381 ctctgcgaggctggccggctaccgccggcgtaacagatgagggcaagcggatggctgatg 4440
4441 aaaccaagccaaccaggaagggcagcccacctatcaaggtgtactgccttccagacgaac 4500
4501 gaagagcgattgaggaaaaggcggcggcggccggcatgagcctgtcggcctacctgctgg 4560
4561 ccgtcggccagggctacaaaatcacgggcgtcgtggactatgagcacgtccgcgagctgg 4620
4621 cccgcatcaatggcgacctgggccgcctgggcggcctgctgaaactctggctcaccgacg 4680
4681 acccgcgcacggcgcggttcggtgatgccacgatcctcgccctgctggcgaagatcgaag 4740
4741 agaagcaggacgagcttggcaaggtcatgatgggcgtggtccgcccgagggcagagccat 4800
4801 gactttttagccgctaaaacggccgggggtgcgcgtgattgccaagcacgtccccatg 4860
4861 cgctccatcaagaagagcgacttcgcggagctggtgaagtacatcaccgacgagcaaggc 4920
4921 aagaccgatcgggccccctgca 4942
```

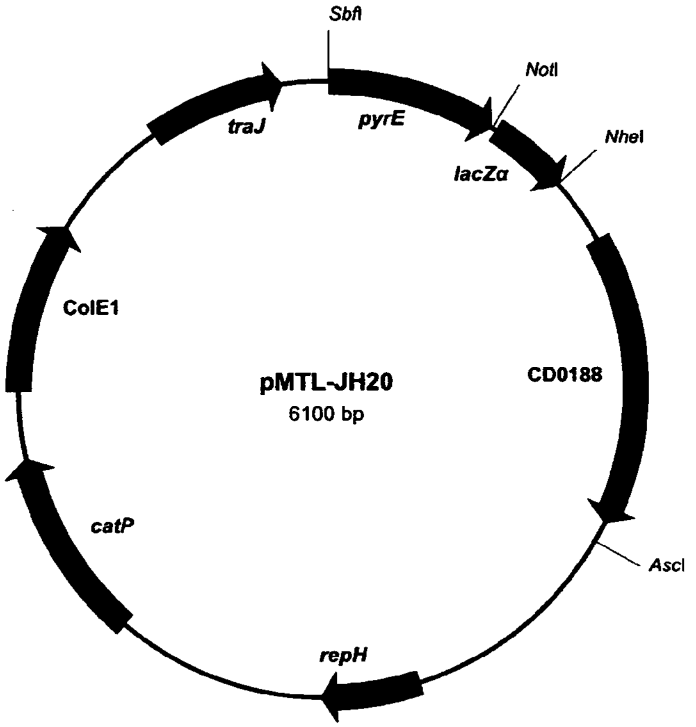

```
   1 ggggagggacattttttattatcttcaggaaaacacagtaatagatacgtacaatgtgca   60
  61 aaagtattaagattcccagaatatgctgctgaggtattaagtacagttgttgaacaaata  120
 121 aaagacttagatatagacttagtagtaggaccagctatgggtggagtaatagtttcttat  180
 181 gagttaggaagacaattaggaaaagaagctgtatttactgagagaaaagacaatacaatg  240
 241 gagttaagaagaggatttgaagttaaaaaaggagcaaagataataattgctgaagacgtt  300
 301 gtaactactggtaaatcaactatggagacaaaaagagtattagaagccttaggtggagaa  360
 361 gttgtaggtgttgcatgtatagcagatagaactaatcatgatataggtatgcctatatat  420
 421 agtgctataaaacttgatattcaagtttatgaatctgatgagtgtcctttatgtaaggaa  480
 481 ggaaaattaccagttgttaagcctggaagtagagagttcaaggaattagggatgtaataa  540
 541 gcggccgctgtatccatatgaccatgattacgaattcgagctcggtacccggggatcctc  600
 601 tagagtcgacgtcacgcgtccatggagatctcgaggcctgcagacatgcaagcttggcac  660
 661 tggccgtcgttttacaacgtcgtgactgggaaaaccctggcgttacccaacttaatcgcc  720
 721 ttgcagcacatccccctttcgccagctggcgtaatagcgaagaggcccgcaccgatcgcc  780
 781 cttcccaacagttgcgcagcctgaatggcgaatggcgctagcaaacttaattatttatag  840
 841 tgttacttaaaaaatgtaaatttttttagagtaaaaatttgtaatataacatataacttaa  900
 901 aaataaaaagcagttagccttataaatgaaggttagctgttttttttgttaaaaatatat  960
 961 ttacaaaataagagatagtagcagtacaatataagtataaggtaaaagtattatatatta 1020
1021 gggaggggtaagtatgaaaaatcaattaaatgaaaataataaaaaggttgtattttttgg 1080
1081 agtaggtgctgtaggagctacttttgcagaacaattttttaactctaaatatgatttta 1140
1141 aattctttgtgataatgaaagaaagaaaagatatttagaagaaggatttataataaatgg 1200
1201 aaaaaggtatgattttgattatgtaactaaagatgagtataaacaagaggctgatttat 1260
1261 aattataggtctaaaatataataatttaaaagaaaatataaaagaattagatggattagt 1320
1321 tggaaaaaatacagttataatgtctctgctaaatggagttgatagcgaagagataatagg 1380
1381 agaaagatttggaattgaaaaaatggtatattcatatgttaccaatatagatgcaaagaa 1440
1441 aatcaataataatattatacacactactaatgggataattgtatttggtaacaaagataa 1500
1501 tagtgaagatagaaaaactaatataataaccgaagtctttgatgatgtaaatatagaata 1560
1561 tactttatcaaaagatattcaacgagatatgtggtggaagtacatggttaatattggtgt 1620
1621 aaatcaaacttcagctatacttggtgcaccttatggagttttttcagagttctgagcattt 1680
1681 aagagaattagcaaaatctgcaatgagggaagttgttgctatagcacaagcaaaagacat 1740
1741 atctcttacagaagatgatgtggaacattcattacatagaatactagaacattcaaaaga 1800
```

```
1801 aggaagaacatcaatgcttcaagatgtggaagctcatagacttacagaagtagatatgtt 1860
1861 ttctaagaatatctgtaaacttggaaaaaatataacatacctactcctataaatcagac 1920
1921 tttcttttatatgataaaagtaattgaaagtagattttaaaggggctttgtaagaaatat 1980
1981 tgataattattgattttaaattttattaatgttatatactatggcgcgccgccattattt 2040
2041 ttttgaacaattgacaattcatttcttatttttattaagtgatagtcaaaaggcataac 2100
2101 agtgctgaatagaaagaaatttacagaaaagaaaattatagaatttagtatgattaatta 2160
2161 tactcatttatgaatgtttaattgaatacaaaaaaaatacttgttatgtattcaattac 2220
2221 gggttaaaatatagacaagttgaaaaatttaataaaaaaataagtcctcagctcttatat 2280
2281 attaagctaccaacttagtatataagccaaaacttaaatgtgctaccaacacatcaagcc 2340
2341 gttagagaactctatctatagcaatatttcaaatgtaccgacatacaagagaaacattaa 2400
2401 ctatatatattcaatttatgagattatcttaacagatataaatgtaaattgcaataagta 2460
2461 agatttagaagtttatagcctttgtgtattggaagcagtacgcaaaggctttttttatttg 2520
2521 ataaaaattagaagtatatttatttttttcataattaatttatgaaaatgaaaggggtga 2580
2581 gcaaagtgacagaggaaagcagtatcttatcaaataacaaggtattagcaatatcattat 2640
2641 tgactttagcagtaaacattatgactttttatagtgcttgtagctaagtagtacgaaaggg 2700
2701 ggagctttaaaaagctccttggaatacatagaattcataaattaatttatgaaaagaagg 2760
2761 gcgtatatgaaaacttgtaaaaattgcaaagagtttattaaagatactgaaatatgcaaa 2820
2821 atacattcgttgatgattcatgataaaacagtagcaacctattgcagtaaatacaatgag 2880
2881 tcaagatgtttacataaagggaaagtccaatgtattaattgttcaaagatgaaccgatat 2940
2941 ggatggtgtgccataaaaatgagatgttttacagaggaagaacagaaaaaagaacgtaca 3000
3001 tgcattaaatattatgcaaggagctttaaaaaagctcatgtaaagaagagtaaaaagaaa 3060
3061 aaataatttatttattaatttaatattgagagtgccgacacagtatgcactaaaaaatat 3120
3121 atctgtggtgtagtgagccgatacaaaaggatagtcactcgcattttcataatacatctt 3180
3181 atgttatgattatgtgtcggtgggacttcacgacgaaaacccacaataaaaaaagagttc 3240
3241 ggggtagggttaagcatagttgaggcaactaaacaatcaagctaggatatgcagtagcag 3300
3301 accgtaaggtcgttgtttaggtgtgttgtaatacatacgctattaagatgtaaaaatacg 3360
3361 gataccaatgaagggaaaagtataattttggatgtagtttgtttgttcatctatgggca 3420
3421 aactacgtccaaagccgtttccaaatctgctaaaaagtatatcctttctaaaatcaaagt 3480
3481 caagtatgaaatcataaataaagtttaatttgaagttattatgatattatgtttttcta 3540
3541 ttaaaataaattaagtatatagaatagtttaataatagtatatacttaatgtgataagtg 3600
3601 tctgacagtgtcacagaaaggatgattgttatggattataagcggccggccagtgggcaa 3660
3661 gttgaaaaattcacaaaaatgtggtataatatctttgttcattagagcgataaacttgaa 3720
3721 tttgagagggaacttagatggtatttgaaaaaattgataaaaatagttggaacagaaaag 3780
3781 agtattttgaccactactttgcaagtgtaccttgtacctacagcatgaccgttaaagtgg 3840
3841 atatcacacaaataaaggaaaagggaatgaaactatatcctgcaatgctttattatattg 3900
3901 caatgattgtaaaccgccattcagagtttaggacggcaatcaatcaagatggtgaattgg 3960
3961 ggatatatgatgagatgataccaagctatacaatatttcacaatgatactgaaacatttt 4020
4021 ccagcctttggactgagtgtaagtctgactttaaatcatttttagcagattatgaaagtg 4080
4081 atacgcaacggtatggaaacaatcatagaatggaaggaaagccaaatgctccggaaaaca 4140
4141 tttttaatgtatctatgataccgtggtcaaccttcgatggctttaatctgaatttgcaga 4200
4201 aaggatatgattatttgattcctatttttactatggggaaatattataaagaagataaca 4260
4261 aaattatacttcctttggcaattcaagttcatcacgcagtatgtgacggatttcacattt 4320
4321 gccgttttgtaaacgaattgcaggaattgataaatagttaacttcaggtttgtctgtaac 4380
4381 taaaaacaagtatttaagcaaaaacatcgtagaaatacggtgtttttttgttaccctaagt 4440
4441 ttaaactcctttttgataatctcatgaccaaaatcccttaacgtgagttttcgttccact 4500
4501 gagcgtcagaccccgtagaaaagatcaaaggatcttcttgagatcctttttttctgcgcg 4560
4561 taatctgctgcttgcaaacaaaaaaaccaccgctaccagcggtggtttgtttgccggatc 4620
4621 aagagctaccaactctttttccgaaggtaactggcttcagcagagcgcagataccaaata 4680
4681 ctgtccttctagtgtagccgtagttaggccaccacttcaagaactctgtagcaccgccta 4740
4741 catacctcgctctgctaatcctgttaccagtggctgctgccagtggcgataagtcgtgtc 4800
4801 ttaccgggttggactcaagacgatagttaccggataaggcgcagcggtcgggctgaacgg 4860
4861 ggggttcgtgcacacagcccagcttggagcgaacgacctacaccgaactgagatacctac 4920
4921 agcgtgagcattgagaaagcgccacgcttcccgaagggagaaaggcggacaggtatccgg 4980
4981 taagcggcagggtcggaacaggagagcgcacgagggagcttccagggggaaacgcctggt 5040
5041 atctttatagtcctgtcgggtttcgccacctctgacttgagcgtcgatttttgtgatgct 5100
5101 cgtcaggggggcggagcctatggaaaaacgccagcaacgcggcctttttacggttcctgg 5160
5161 ccttttgctggccttttgctcacatgttctttcctgcgttatcccctgattctgtggata 5220
5221 accgtattaccgcctttgagtgagctgataccgctcgccgcagccgaacgaccgagcgca 5280
```

Figure 6K (CONT.)

```
5281 gcgagtcagtgagcgaggaagcggaagagcgcccaatacgcagggccccctgcttcgggg 5340
5341 tcattatagcgatttttcggtatatccatcctttttcgcacgatatacaggattttgcc 5400
5401 aaagggttcgtgtagactttccttggtgtatccaacggcgtcagccgggcaggataggtg 5460
5461 aagtaggcccacccgcgagcgggtgttccttcttcactgtcccttattcgcacctggcgg 5520
5521 tgctcaacgggaatcctgctctgcgaggctggccggctaccgccggcgtaacagatgagg 5580
5581 gcaagcggatggctgatgaaaccaagccaaccaggaagggcagcccacctatcaaggtgt 5640
5641 actgccttccagacgaacgaagagcgattgaggaaaaggcggcggcggccggcatgagcc 5700
5701 tgtcggcctacctgctggccgtcggccagggctacaaaatcacgggcgtcgtggactatg 5760
5761 agcacgtccgcgagctggcccgcatcaatggcgacctgggccgcctgggcggcctgctga 5820
5821 aactctggctcaccgacgacccgcgcacggcgcggttcggtgatgccacgatcctcgccc 5880
5881 tgctggcgaagatcgaagagaagcaggacgagcttggcaaggtcatgatgggcgtggtcc 5940
5941 gcccgagggcagagccatgactttttagccgctaaaacggccgggggtgcgcgtgatt 6000
6001 gccaagcacgtccccatgcgctccatcaagaagagcgacttcgcggagctggtgaagtac 6060
6061 atcaccgacgagcaaggcaagaccgatcgggccccctgca 6100
```

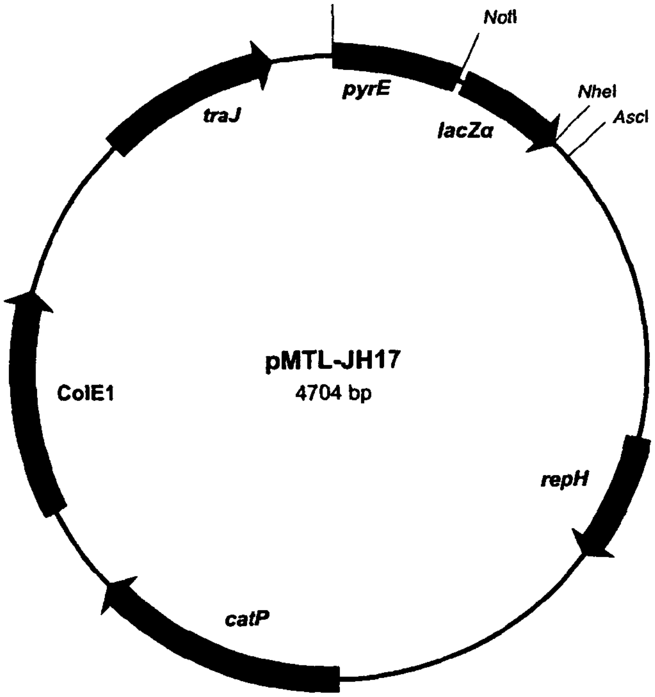

```
   1 ggggagggacatttttttattatcttcaggaaaacacagtaatagatacgtacaatgtgca 60
  61 aaagtattaagattcccagaatatgctgctgaggtattaagtacagttgttgaacaaata 120
 121 aaagacttagatatagacttagtagtaggaccagctatgggtggagtaatagtttcttat 180
 181 gagttaggaagacaattaggaaaagaagctgtatttactgagagaaaagacaatacaatg 240
 241 gagttaagaagaggatttgaagttaaaaaaggagcaaagataataattgctgaagacgtt 300
 301 gtgcggccgctgtatccatatgaccatgattacgaattcgagctcggtacccggggatcc 360
 361 tctagagtcgacgtcacgcgtccatggagatctcgaggcctgcagacatgcaagcttggc 420
 421 actggccgtcgttttacaacgtcgtgactgggaaaaccctggcgttacccaacttaatcg 480
 481 ccttgcagcacatccccctttcgccagctggcgtaatagcgaagaggcccgcaccgatcg 540
 541 cccttcccaacagttgcgcagcctgaatggcgaatggcgctagcataaaaataagaagcc 600
 601 tgcatttgcaggcttcttattttatggcgcgccgccattattttttgaacaattgaca 660
 661 attcatttcttattttttattaagtgatagtcaaaaggcataacagtgctgaatagaaag 720
 721 aaatttacagaaaagaaaattatagaatttagtatgattaattatactcatttatgaatg 780
 781 tttaattgaatacaaaaaaaaatacttgttatgtattcaattacgggttaaaatatagac 840
 841 aagttgaaaaatttaataaaaaaataagtcctcagctcttatatattaagctaccaactt 900
 901 agtatataagccaaaacttaaatgtgctaccaacacatcaagccgttagagaactctatc 960
 961 tatagcaatatttcaaatgtaccgacatacaagagaaacattaactatatatattcaatt 1020
1021 tatgagattatcttaacagatataaatgtaaattgcaataagtaagatttagaagtttat 1080
1081 agcctttgtgtattggaagcagtacgcaaaggcttttttatttgataaaaattagaagta 1140
1141 tatttattttttcataattaatttatgaaaatgaaaggggggtgagcaaagtgacagagga 1200
1201 aagcagtatcttatcaaataacaaggtattagcaatatcattattgactttagcagtaaa 1260
1261 cattatgacttttatagtgcttgtagctaagtagtacgaaaggggggagctttaaaaagct 1320
1321 ccttggaatacatagaattcataaattaatttatgaaaagaagggcgtatatgaaaactt 1380
1381 gtaaaaattgcaaagagtttattaaagatactgaaatatgcaaaatacattcgttgatga 1440
1441 ttcatgataaaacagtagcaacctattgcagtaaatacaatgagtcaagatgttcacata 150
1501 aagggaaagtccaatgtattaattgttcaaagatgaaccgatatggatggtgtgccataa 1560
1561 aaatgagatgttttacagaggaagaacagaaaaagaacgtacatgcattaaatattatg 1620
1621 caaggagctttaaaaaagctcatgtaaagaagagtaaaaagaaaaaataatttatttatt 1680
1681 aatttaatattgagagtgccgacacagtatgcactaaaaaatatatctgtggtgtagtga 1740
1741 gccgatacaaaaggatagtcactcgcatttcataatacatcttatgttatgattatgtg 1800
```

```
1801 tcggtgggacttcacgacgaaaacccacaataaaaaaagagttcggggtagggttaagca 1860
1861 tagttgaggcaactaaacaatcaagctaggatatgcagtagcagaccgtaaggtcgttgt 1920
1921 ttaggtgtgttgtaatacatacgctattaagatgtaaaaatacggataccaatgaaggga 1980
1981 aaagtataattttggatgtagtttgtttgttcatctatgggcaaactacgtccaaagcc 2040
2041 gtttccaaatctgctaaaaagtatatcctttctaaaatcaaagtcaagtatgaaatcata 2100
2101 aataaagtttaattttgaagttattatgatattatgtttttctattaaaataaattaagt 2160
2161 atatagaatagtttaataatagtatatacttaatgtgataagtgtctgacagtgtcacag 2220
2221 aaaggatgattgttatggattataagcggccggccagtgggcaagttgaaaaattcacaa 2280
2281 aaatgtggtataatatctttgttcattagagcgataaacttgaatttgagagggaactta 2340
2341 gatggtatttgaaaaaattgataaaaatagttggaacagaaaagagtattttgaccacta 2400
2401 ctttgcaagtgtaccttgtacctacagcatgaccgttaaagtggatatcacacaaataaa 2460
2461 ggaaaagggaatgaaactatatcctgcaatgctttattatattgcaatgattgtaaaccg 2520
2521 ccattcagagtttaggacggcaatcaatcaagatggtgaattggggatatatgatgagat 2580
2581 gataccaagctatacaatatttcacaatgatactgaaacattttccagcctttggactga 2640
2641 gtgtaagtctgactttaaatcattttagcagattatgaaagtgatacgcaacggtatgg 2700
2701 aaacaatcatagaatggaaggaaagccaaatgctccggaaaacattttaatgtatctat 2760
2761 gataccgtggtcaaccttcgatggctttaatctgaatttgcagaaaggatatgattattt 2820
2821 gattcctatttttactatggggaaatattataaagaagataacaaaattatacttccttt 2880
2881 ggcaattcaagttcatcacgcagtatgtgacggatttcacatttgccgttttgtaaacga 2940
2941 attgcaggaattgataaatagttaacttcaggtttgtctgtaactaaaaacaagtattta 3000
3001 agcaaaaacatcgtagaaatacggtgtttttgttaccctaagtttaaactccttttga 3060
3061 taatctcatgaccaaaatcccttaacgtgagttttcgttccactgagcgtcagaccccgt 3120
3121 agaaaagatcaaaggatcttcttgagatcctttttttctgcgcgtaatctgctgcttgca 318
3181 aacaaaaaaaccaccgctaccagcggtggtttgtttgccggatcaagagctaccaactct 3240
3241 ttttccgaaggtaactggcttcagcagagcgcagataccaaatactgtccttctagtgta 3300
3301 gccgtagttaggccaccacttcaagaactctgtagcaccgcctacatacctcgctctgct 3360
3361 aatcctgttaccagtggctgctgccagtggcgataagtcgtgtcttaccgggttggactc 3420
3421 aagacgatagttaccggataaggcgcagcggtcgggctgaacggggggttcgtgcacaca 3480
3481 gcccagcttggagcgaacgacctacaccgaactgagatacctacagcgtgagcattgaga 3540
3541 aagcgccacgcttcccgaagggagaaaggcggacaggtatccggtaagcggcagggtcgg 3600
3601 aacaggagagcgcacgagggagcttccagggggaaacgcctggtatctttatagtcctgt 3660
3661 cgggtttcgccacctctgacttgagcgtcgatttttgtgatgctcgtcaggggggcggag 3720
3721 cctatggaaaaacgccagcaacgcggcctttttacggttcctggccttttgctggcctttt 3780
3781 tgctcacatgttctttcctgcgttatcccctgattctgtggataaccgtattaccgcctt 3840
3841 tgagtgagctgataccgctcgccgcagccgaacgaccgagcgcagcgagtcagtgagcga 3900
3901 ggaagcggaagagcgcccaatacgcagggcccccctgcttcggggtcattatagcgatttt 3960
3961 ttcggtatatccatcctttttcgcacgatatacaggattttgccaaagggttcgtgtaga 4020
4021 ctttccttggtgtatccaacggcgtcagccgggcaggataggtgaagtaggcccacccgc 4080
4081 gagcgggtgttccttcttcactgtcccttattcgcacctggcggtgctcaacgggaatcc 4140
4141 tgctctgcgaggctggccggctaccgccggcgtaacagatgagggcaagcggatggctga 4200
4201 tgaaaccaagccaaccaggaagggcagcccacctatcaaggtgtactgccttccagacga 4260
4261 acgaagagcgattgaggaaaaggcggcggcggccggcatgagcctgtcggcctacctgct 4320
4321 ggccgtcggccagggctacaaaatcacgggcgtcgtggactatgagcacgtccgcgagct 4380
4381 ggcccgcatcaatggcgacctgggccgcctgggcggcctgctgaaactctggctcaccga 4440
4441 cgacccgcgcacggcgcggttcggtgatgccacgatcctcgccctgctggcgaagatcga 4500
4501 agagaagcaggacgagcttggcaaggtcatgatgggcgtggtccgcccgagggcagagcc 4560
4561 atgactttttttagccgctaaaacggccgggggtgcgcgtgattgccaagcacgtcccca 4620
4621 tgcgctccatcaagaagagcgacttcgcggagctggtgaagtacatcaccgacgagcaag 4680
4681 gcaagaccgatcgggcccccctgca 4704
```

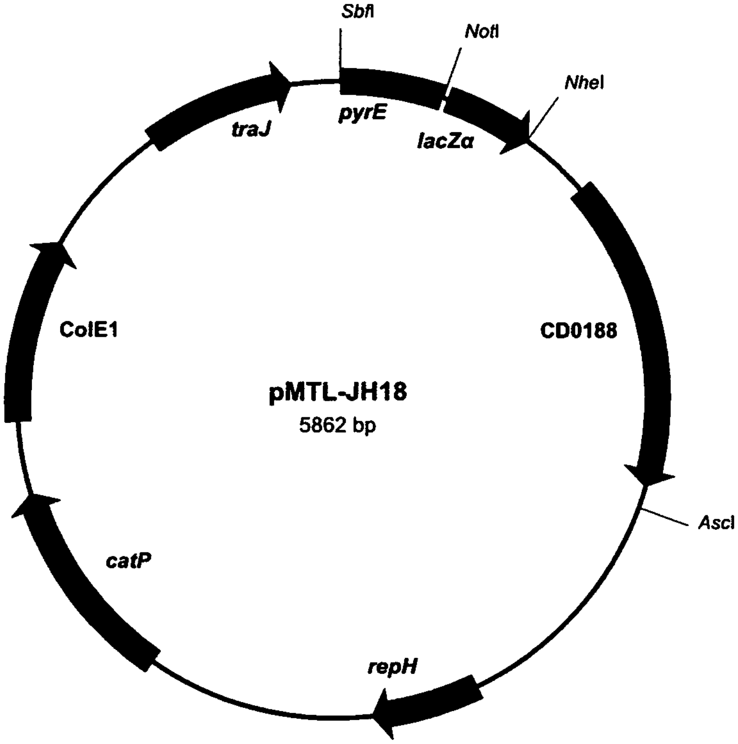

```
   1 ggggagggacatttttattatcttcaggaaaacacagtaatagatacgtacaatgtgca 60
  61 aaagtattaagattcccagaatatgctgctgaggtattaagtacagttgttgaacaaata 120
 121 aaagacttagatatagacttagtagtaggaccagctatgggtggagtaatagtttcttat 180
 181 gagttaggaagacaattaggaaaagaagctgtatttactgagagaaaagacaatacaatg 240
 241 gagttaagaagaggatttgaagttaaaaaggagcaaagataataattgctgaagacgtt 300
 301 gtgcggccgctgtatccatatgaccatgattacgaattcgagctcggtacccggggatcc 360
 361 tctagagtcgacgtcacgcgtccatggagatctcgaggcctgcagacatgcaagcttggc 420
 421 actggccgtcgttttacaacgtcgtgactgggaaaaccctggcgttacccaacttaatcg 480
 481 ccttgcagcacatccccctttcgccagctggcgtaatagcgaagaggcccgcaccgatcg 540
 541 cccttcccaacagttgcgcagcctgaatggcgaatggcgctagcaaacttaattatttat 600
 601 agtgttacttaaaaaatgtaaatttttagagtaaaaatttgtaatataacatataactt 660
 661 aaaaataaaaagcagttagccttataaatgaaggttagctgtttttttgttaaaaatat 720
 721 atttacaaaataagagatagtagcagtacaatataagtataaggtaaaagtattatatat 780
 781 tagggaggggtaagtatgaaaaatcaattaaatgaaaataataaaaaggttgtattttt 840
 841 ggagtaggtgctgtaggagctactttgcagaacaatttttaactctaaatatgatttt 900
 901 aaaattctttgtgataatgaaagaaagaaaagatatttagaagaaggatttataataaat 960
 961 ggaaaaaggtatgatttgattatgtaactaaagatgagtataaacaagaggctgatttt 1020
1021 ataattataggtctaaaatataataatttaaaagaaaatataaaagaattagatggatta 1080
1081 gttggaaaaaatacagttataatgtctctgctaaatggagttgatagcgaagagataata 1140
1141 ggagaaagatttggaattgaaaaaatggtatattcatatgttaccaatatagatgcaaag 1200
1201 aaaatcaataataatattatacacactactaatgggataattgtatttggtaacaaagat 1260
1261 aatagtgaagatagaaaaactaatataataaccgaagtctttgatgatgtaaatatagaa 1320
1321 tatactttatcaaaagatattcaacgagatatgtggtggaagtacatggttaatattggt 1380
1381 gtaaatcaaacttcagctatacttggtgcaccttatggagtttttcagagttctgagcat 1440
1441 ttaagagaattagcaaaatctgcaatgagggaagttgttgctatagcacaagcaaaagac 1500
1501 atatctcttacagaagatgatgtggaacattcattacatagaatactagaacattcaaaa 1560
1561 gaaggaagaacatcaatgcttcaagatgtggaagctcatagacttacagaagtagatatg 1620
1621 ttttctaagaatatctgtaaacttggaaaaaaatataacatacctactcctataaatcag 1680
```

1681 actttcttttatatgataaaagtaattgaaagtagattttaaaggggctttgtaagaaat 1740
1741 attgataattattgattttaaattttattaatgttatatactatggcgcgccgccattat 1800
1801 tttttgaacaattgacaattcatttcttatttttattaagtgatagtcaaaaggcata 1860
1861 acagtgctgaatagaaagaaatttacagaaaagaaaattatagaatttagtatgattaat 1920
1921 tatactcatttatgaatgtttaattgaatacaaaaaaaaatacttgttatgtattcaatt 1980
1981 acgggttaaaatatagacaagttgaaaaatttaataaaaaaataagtcctcagctcttat 2040
2041 atattaagctaccaacttagtatataagccaaaacttaaatgtgctaccaacacatcaag 2100
2101 ccgttagagaactctatctatagcaatatttcaaatgtaccgacatacaagagaaacatt 2160
2161 aactatatatattcaatttatgagattatcttaacagatataaatgtaaattgcaataag 2220
2221 taagatttagaagtttatagcctttgtgtattggaagcagtacgcaaaggctttttatt 2280
2281 tgataaaaattagaagtatatttatttttcataattaatttatgaaaatgaaaggggt 2340
2341 gagcaaagtgacagaggaaagcagtatcttatcaaataacaaggtattagcaatatcatt 2400
2401 attgactttagcagtaaacattatgacttttatagtgcttgtagctaagtagtacgaaag 2460
2461 ggggagctttaaaaagctccttggaatacatagaattcataaattaatttatgaaaagaa 2520
2521 gggcgtatatgaaaacttgtaaaaattgcaaagagtttattaaagatactgaaatatgca 2580
2581 aaatacattcgttgatgattcatgataaaacagtagcaacctattgcagtaaatacaatg 2640
2641 agtcaagatgtttacataaagggaaagtccaatgtattaattgttcaaagatgaaccgat 2700
2701 atggatggtgtgccataaaaatgagatgttttacagaggaagaacagaaaaaagaacgta 2760
2761 catgcattaaatattatgcaaggagctttaaaaaagctcatgtaaagaagagtaaaaaga 2820
2821 aaaaataatttatttattaatttaatattgagagtgccgacacagtatgcactaaaaaat 2880
2881 atatctgtggtgtagtgagccgatacaaaggatagtcactcgcattttcataatacatc 2940
2941 ttatgttatgattatgtgtcggtgggacttcacgacgaaaacccacaataaaaaaagagt 3000
3001 tcggggtagggttaagcatagttgaggcaactaaacaatcaagctaggatatgcagtagc 3060
3061 agaccgtaaggtcgttgtttaggtgtgttgtaatacatacgctattaagatgtaaaaata 3120
3121 cggataccaatgaagggaaaagtataattttggatgtagtttgtttgttcatctatggg 3180
3181 caaactacgtccaaagccgtttccaaatctgctaaaaagtatatcctttctaaaatcaaa 3240
3241 gtcaagtatgaaatcataaataaagtttaattttgaagttattatgatattatgtttttc 3300
3301 tattaaaataaattaagtatatagaatagtttaataatagtatatacttaatgtgataag 3360
3361 tgtctgacagtgtcacagaaaggatgattgttatggattataagcggccggccagtgggc 3420
3421 aagttgaaaaattcacaaaaatgtggtataatatctttgttcattagagcgataaacttg 3480
3481 aatttgagagggaacttagatggtatttgaaaaaattgataaaaatagttggaacagaaa 3540
3541 agagtattttgaccactactttgcaagtgtaccttgtacctacagcatgaccgttaaagt 3600
3601 ggatatcacacaaataaaggaaaagggaatgaaactatatcctgcaatgctttattatat 3660
3661 tgcaatgattgtaaaccgccattcagagtttaggacggcaatcaatcaagatggtgaatt 3720
3721 ggggatatatgatgagatgataccaagctatacaatatttcacaatgatactgaaacatt 3780
3781 ttccagcctttggactgagtgtaagtctgactttaaatcatttttagcagattatgaaag 3840
3841 tgatacgcaacggtatggaaacaatcatagaatggaaggaaagccaaatgctccggaaaa 3900
3901 catttttaatgtatctatgataccgtggtcaaccttcgatggctttaatctgaatttgca 3960
3961 gaaaggatatgattatttgattcctatttttactatggggaaatattataaagaagataa 4020
4021 caaaattatacttcctttggcaattcaagttcatcacgcagtatgtgacggatttcacat 4080
4081 ttgccgttttgtaaacgaattgcaggaattgataaatagttaacttcaggtttgtctgta 4140
4141 actaaaaacaagtatttaagcaaaaacatcgtagaaatacggtgtttttttgttaccctaa 4200
4201 gtttaaactcctttttgataatctcatgaccaaaatcccttaacgtgagttttcgttcca 4260
4261 ctgagcgtcagaccccgtagaaaagatcaaaggatcttcttgagatcctttttttctgcg 4320
4321 cgtaatctgctgcttgcaaacaaaaaaaccaccgctaccagcggtggtttgtttgccgga 4380
4381 tcaagagctaccaactctttttccgaaggtaactggcttcagcagagcgcagataccaaa 4440
4441 tactgtccttctagtgtagccgtagttaggccaccacttcaagaactctgtagcaccgcc 4500
4501 tacatacctcgctctgctaatcctgttaccagtggctgctgccagtggcgataagtcgtg 4560
4561 tcttaccgggttggactcaagacgatagttaccggataaggcgcagcggtcgggctgaac 4620
4621 ggggggttcgtgcacacagcccagcttggagcgaacgacctacaccgaactgagatacct 4680
4681 acagcgtgagcattgagaaagcgccacgcttcccgaagggagaaaggcggacaggtatcc 4740
4741 ggtaagcggcagggtcggaacaggagagcgcacgagggagcttccagggggaaacgcctg 4800
4801 gtatctttatagtcctgtcgggtttcgccacctctgacttgagcgtcgatttttgtgatg 4860
4861 ctcgtcaggggggcggagcctatggaaaaacgccagcaacgcggcctttttacggttcct 4920
4921 ggccttttgctggccttttgctcacatgttctttcctgcgttatcccctgattctgtgga 4980
4981 taaccgtattaccgcctttgagtgagctgataccgctcgccgcagccgaacgaccgagcg 5040
5041 cagcgagtcagtgagcgaggaagcggaagagcgcccaatacgcagggccccctgcttcgg 5100
5101 ggtcattatagcgatttttttcggtatatccatcctttttcgcacgatatacaggattttg 5160

Figure 6M (CONT.)

```
5161 ccaaagggttcgtgtagactttccttggtgtatccaacggcgtcagccgggcaggatagg 5220
5221 tgaagtaggcccacccgcgagcgggtgttccttcttcactgtcccttattcgcacctggc 5280
5281 ggtgctcaacgggaatcctgctctgcgaggctggccggctaccgccggcgtaacagatga 5340
5341 gggcaagcggatggctgatgaaaccaagccaaccaggaagggcagcccacctatcaaggt 5400
5401 gtactgccttccagacgaacgaagagcgattgaggaaaaggcggcggcggccggcatgag 5460
5461 cctgtcggcctacctgctggccgtcggccagggctacaaaatcacgggcgtcgtggacta 5520
5521 tgagcacgtccgcgagctggcccgcatcaatggcgacctgggccgcctgggcggcctgct 5580
5581 gaaactctggctcaccgacgacccgcgcacggcgcggttcggtgatgccacgatcctcgc 5640
5641 cctgctggcgaagatcgaagagaagcaggacgagcttggcaaggtcatgatgggcgtggt 5700
5701 ccgcccgagggcagagccatgactttttagccgctaaaacggccggggggtgcgcgtga 5760
5761 ttgccaagcacgtccccatgcgctccatcaagaagagcgacttcgcggagctggtgaagt 5820
5821 acatcaccgacgagcaaggcaagaccgatcgggccccctgca 5862
```

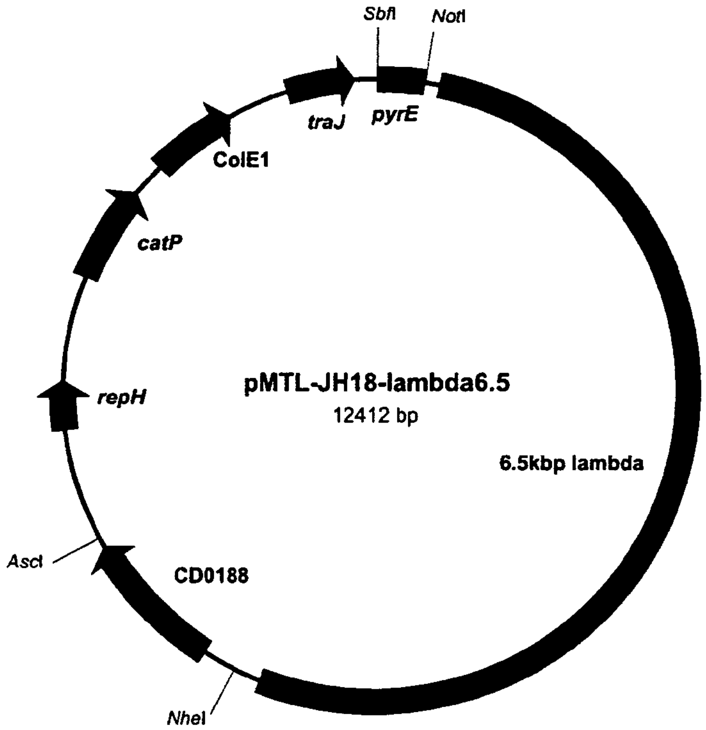

```
   1 ggggagggacatttttattatcttcaggaaaacacagtaatagatacgtacaatgtgca 60
  61 aaagtattaagattcccagaatatgctgctgaggtattaagtacagttgttgaacaaata 120
 121 aaagacttagatatagacttagtagtaggaccagctatgggtggagtaatagtttcttat 180
 181 gagttaggaagacaattaggaaaagaagctgtatttactgagagaaaagacaatacaatg 240
 241 gagttaagaagaggatttgaagttaaaaaggagcaaagataataattgctgaagacgtt 300
 301 gtgcggccgctgtatccatatgaccatgattacgaattcgagctcggtacccggggatcc 360
 361 tctagagtcgacgtcacgcgtccatggagatctcgaggggtgagaacatccctgcctgaa 420
 421 catgagaaaaaacagggtactcatactcacttctaagtgacggctgcatactaaccgctt 480
 481 catacatctcgtagatttctctggcgattgaagggctaaattcttcaacgctaactttga 540
 541 gaatttttgtaagcaatgcggcgttataagcatttaatgcattgatgccattaaataaag 600
 601 caccaacgcctgactgccccatccccatcttgtctgcgacagattcctgggataagccaa 660
 661 gttcatttttctttttttcataaattgctttaaggcgacgtgcgtcctcaagctgctctt 720
 721 gtgttaatggtttctttttttgtgctcatacgttaaatctatcaccgcaagggataaatat 780
 781 ctaacaccgtgcgtgttgactattttacctctggcggtgataatggttgcatgtactaag 840
 841 gaggttgtatggaacaacgcataaccctgaaagattatgcaatgcgctttgggcaaacca 900
 901 agacagctaaagatctcggcgtatatcaaagcgcgatcaacaaggccattcatgcaggcc 960
 961 gaaagatttttttaactataaacgctgatggaagcgtttatgcggaagaggtaaagccct 1020
1021 tcccgagtaacaaaaaaacaacagcataaataaccccgctcttacacattccagccctga 1080
1081 aaaagggcatcaaattaaaccacacctatggtgtatgcatttatttgcatacattcaatc 1140
1141 aattgttatctaaggaaatacttacatatggttcgtgcaaacaaacgcaacgaggctcta 1200
1201 cgaatcgagagtgcgttgcttaacaaaatcgcaatgcttggaactgagaagacagcggaa 1260
1261 gctgtgggcgttgataagtcgcagatcagcaggtggaagagggactggattccaaagttc 1320
1321 tcaatgctgcttgctgttcttgaatggggggtcgttgacgacgacatggctcgattggcg 1380
1381 cgacaagttgctgcgattctcaccaataaaaaacgcccggcggcaaccgagcgttctgaa 1440
1441 caaatccagatggagttctgaggtcattactggatctatcaacaggagtcattatgacaa 1500
1501 atacagcaaaaatactcaacttcggcagaggtaactttgccggacaggagcgtaatgtgg 1560
1561 cagatctcgatgatggttacgccagactatcaaatatgctgcttgaggcttattcggcg 1620
1621 cagatctgaccaagcgacagtttaaagtgctgcttgccattctgcgtaaaacctatgggt 1680
```

1681 ggaataaaccaatggacagaatcaccgattctcaacttagcgagattacaaagttacctg 1740
1741 tcaaacggtgcaatgaagccaagttagaactcgtcagaatgaatattatcaagcagcaag 1800
1801 gcggcatgtttggaccaaataaaaacatctcagaatggtgcatccctcaaaacgagggaa 1860
1861 aatcccctaaaacgagggataaaacatccctcaaattggggggattgctatccctcaaaac 1920
1921 agggggacacaaaagacactattacaaaagaaaaaagaaaagattattcgtcagagaatt 1980
1981 ctggcgaatcctctgaccagccagaaaacgacctttctgtggtgaaaccggatgctgcaa 2040
2041 ttcagagcggcagcaagtgggggacagcagaagacctgaccgccgcagagtggatgtttg 2100
2101 acatggtgaagactatcgcaccatcagccagaaaaccgaattttgctgggtgggctaacg 2160
2161 atatccgcctgatgcgtgaacgtgacggacgtaaccaccgcgacatgtgtgtgctgttcc 2220
2221 gctgggcatgccaggacaacttctggtccggtaacgtgctgagcccggccaaactccgcg 2280
2281 ataagtggacccaactcgaaatcaaccgtaacaagcaacaggcaggcgtgacagccagca 2340
2341 aaccaaaactcgacctgacaaacacagactggatttacggggtggatctatgaaaaacat 2400
2401 cgccgcacagatggttaactttgaccgtgagcagatgcgtcggatcgccaacaacatgcc 2460
2461 ggaacagtacgacgaaaagccgcaggtacagcaggtagcgcagatcatcaacggtgtgtt 2520
2521 cagccagttactggcaactttcccggcgagcctggctaaccgtgaccagaacgaagtgaa 2580
2581 cgaaatccgtcgccagtgggttctggctttcgggaaaacgggatcaccacgatggaaca 2640
2641 ggttaacgcaggaatgcgcgtagcccgtcggcagaatcgaccatttctgccatcacccgg 2700
2701 gcagtttgttgcatggtgccgggaagaagcatccgttaccgccggactgccaaacgtcag 2760
2761 cgagctggttgatatggtttacgagtattgccggaagcgaggcctgtatccggatgcgga 2820
2821 gtcttatccgtggaaatcaaacgcgcactactggctggttaccaacctgtatcagaacat 2880
2881 gcgggccaatgcgcttactgatgcggaattacgccgtaaggccgcagatgagcttgtcca 2940
2941 tatgactgcgagaattaaccgtggtgaggcgatccctgaaccagtaaaacaacttcctgt 3000
3001 catgggcggtagacctctaaatcgtgcacaggctctggcgaagatcgcagaaatcaaagc 3060
3061 taagttcggactgaaaggagcaagtgtatgacgggcaaagaggcaattattcattacctg 3120
3121 gggacgcataatagcttctgtgcgccggacgttgccgcgctaacaggcgcaacagtaacc 3180
3181 agcataaatcaggccgcggctaaaatggcacgggcaggtcttctggttatcgaaggtaag 324
3241 gtctggcgaacggtgtattaccggtttgctaccagggaagaacgggaaggaaagatgagc 3300
3301 acgaacctggtttttaaggagtgtcgccagagtgccgcgatgaaacgggtattggcggta 3360
3361 tatggagttaaaagatgaccatctacattactgagctaataacaggcctgctggtaatcg 3420
3421 caggcctttttatttggggggagagggaagtcatgaaaaaactaacctttgaaattcgatc 3480
3481 tccagcacatcagcaaaacgctattcacgcagtacagcaaatccttccagacccaaccaa 3540
3541 accaatcgtagtaaccattcaggaacgcaaccgcagcttagaccaaaacaggaagctatg 3600
3601 ggcctgcttaggtgacgtctctcgtcaggttgaatggcatggtcgctggctggatgcaga 3660
3661 aagctggaagtgtgtgtttaccgcagcattaaagcagcaggatgttgttcctaaccttgc 3720
3721 cgggaatggctttgtggtaataggccagtcaaccagcaggatgcgtgtaggcgaatttgc 3780
3781 ggagctattagagcttatacaggcattcggtacagagcgtggcgttaagtggtcagacga 3840
3841 agcgagactggctctggagtggaaagcgagatggggagacagggctgcatgataaatgtc 3900
3901 gttagtttctccggtggcaggacgtcagcatatttgctctggctaatggagcaaaagcga 3960
3961 cgggcaggtaaagacgtgcattacgttttcatggatacaggttgtgaacatccaatgaca 4020
4021 tatcggtttgtcagggaagttgtgaagttctgggatataccgctcaccgtattgcaggtt 4080
4081 gatatcaacccggagcttggacagccaaatggttatacggtatgggaaccaaaggatatt 4140
4141 cagacgcgaatgcctgttctgaagccatttatcgatatggtaaagaaatatggcactcca 4200
4201 tacgtcggcggcgcgttctgcactgacagattaaaactcgttcccttcaccaaatactgt 4260
4261 gatgaccatttcgggcgagggaattacaccacgtggattggcatcagagctgatgaaccg 4320
4321 aagcggctaaagccaaagcctggaatcagatatcttgctgaactgtcagactttgagaag 4380
4381 gaagatatcctcgcatggtggaagcaacaaccattcgatttgcaaataccggaacatctc 4440
4441 ggtaactgcatattctgcattaaaaatcaacgcaaaaaatcggacttgcctgcaaagat 4500
4501 gaggagggattgcagcgtgtttttaatgaggtcatcacgggatcccatgtgcgtgacgga 4560
4561 catcgggaaacgccaaaggagattatgtaccgaggaagaatgtcgctggacggtatcgcg 4620
4621 aaaatgtattcagaaaatgattatcaagccctgtatcaggacatggtacgagctaaaaga 4680
4681 ttcgataccggctcttgttctgagtcatgcgaaatatttggagggcagcttgatttcgac 4740
4741 ttcgggagggaagctgcatgatgcgatgttatcggtgcggtgaatgcaaagaagataacc 4800
4801 gcttccgaccaaatcaaccttactggaatcgatggtgtctccggtgtgaaagaacaccaa 4860
4861 caggggtgttaccactaccgcaggaaaaggaggacgtgtggcgagacagcgacgaagtat 4920
4921 caccgacataatctgcgaaaactgcaaatacct tccaacgaaacgcaccagaaataaacc 4980
4981 caagccaatcccaaaagaatctgacgtaaaaaccttcaactacacggctcacctgtggga 5040
5041 tatccggtggctaagacgtcgtgcgaggaaaacaaggtgattgaccaaaatcgaagttac 5100
5101 gaacaagaaagcgtcgagcgagctttaacgtgcgctaactgcggtcagaagctgcatgtg 5160

Figure 6N (CONT.)

5161 ctggaagttcacgtgtgtgagcactgctgcgcagaactgatgagcgatccgaatagctcg 5220
5221 atgcacgaggaagaagatgatggctaaaccagcgcgaagacgatgtaaaaacgatgaatg 5280
5281 ccgggaatggtttcaccctgcattcgctaatcagtggtggtgctctccagagtgtggaac 5340
5341 caagatagcactcgaacgacgaagtaaagaacgcgaaaaagcggaaaaagcagcagagaa 5400
5401 gaaacgacgacgagaggagcagaaacagaaagataaacttaagattcgaaaactcgcctt 5460
5461 aaagccccgcagttactggattaaacaagcccaacaagccgtaaacgccttcatcagaga 5520
5521 aagagaccgcgacttaccatgtatctcgtgcggaacgctcacgtctgctcagtgggatgc 5580
5581 cggacattaccggacaactgctgcggcacctcaactccgatttaatgaacgcaatattca 5640
5641 caagcaatgcgtggtgtgcaaccagcacaaaagcggaaatctcgttccgtatcgcgtcga 5700
5701 actgattagccgcatcgggcaggaagcagtagacgaaatcgaatcaaaccataaccgcca 5760
5761 tcgctggactatcgaagagtgcaaggcgatcaaggcagagtaccaacagaaactcaaaga 5820
5821 cctgcgaaatagcagaagtgaggccgcatgacgttctcagtaaaaaccattccagacatg 5880
5881 ctcgttgaagcatacggaaatcagacagaagtagcacgcagactgaaatgtagtcgcggt 5940
5941 acggtcagaaaatacgttgatgataaagacgggaaaatgcacgccatcgtcaacgacgtt 6000
6001 ctcatggttcatcgcggatggagtgaaagagatgcgctattacgaaaaaattgatggcag 6060
6061 caaataccgaaatatttgggtagttggcgatctgcacggatgctacacgaacctgatgaa 6120
6121 caaactggatacgattggattcgacaacaaaaaagacctgcttatctcggtgggcgattt 6180
6181 ggttgatcgtggtgcagagaacgttgaatgcctggaattaatcacattcccctggttcag 6240
6241 agctgtacgtggaaaccatgagcaaatgatgattgatggcttatcagagcgtggaaacgt 6300
6301 taatcactggctgcttaatggcggtggctggttctttaatctcgattacgacaaagaaat 6360
6361 tctggctaaagctcttgcccataaagcagatgaacttccgttaatcatcgaactggtgag 6420
6421 caaagataaaaaatatgttatctgccacgccgattatccctttgacgaatacgagtttgg 6480
6481 aaagccagttgatcatcagcaggtaatctggaaccgcgaacgaatcagcaactcacaaaa 6540
6541 cgggatcgtgaaagaaatcaaaggcgcggacacgttcatctttggtcatacgccagcagt 6600
6601 gaaaccactcaagtttgccaaccaaatgtatatcgataccggcgcagtgttctgcggaaa 6660
6661 cctaacattgattcaggtacagggagaaggcgcatgagactcgaaagcgtagctaaattt 6720
6721 cattcgccaaaaagcccgatgatgagcgactcaccacgggccacggcttctgactctctt 6780
6781 tccggtactgatgtgatggctgctatggggatggcgcaatcacaagccggattcggtatg 6840
6841 gctgcattctgcggtaagcacgaactcagccagaacgacaaacaaaaggctatcaactat 6900
6901 ctgatgcaatttgcacacaaggtatcggggaaataccgtggtgtggcacctgcagacatg 6960
6961 caagcttggcactggccgtcgttttacaacgtcgtgactgggaaaaccctggcgttaccc 7020
7021 aacttaatcgccttgcagcacatccccctttcgccagctggcgtaatagcgaagaggccc 7080
7081 gcaccgatcgcccttcccaacagttgcgcagcctgaatggcgaatggcgctagcaaactt 7140
7141 aattatttatagtgttacttaaaaaatgtaaatttttagagtaaaaatttgtaatataa 7200
7201 catataacttaaaaataaaaagcagttagccttataaatgaaggttagctgtttttttg 7260
7261 ttaaaaatatatttacaaaataagagatagtagcagtacaatataagtataaggtaaaag 7320
7321 tattatatattagggaggggtaagtatgaaaaatcaattaaatgaaaataataaaaaggt 7380
7381 tgtatttttggagtaggtgctgtaggagctacttttgcagaacaatttttaactctaa 7440
7441 atatgattttaaaattctttgtgataatgaaagaaagaaaagatatttagaagaaggatt 7500
7501 tataataaatggaaaaaggtatgattttgattatgtaactaaagatgagtataaacaaga 7560
7561 ggctgatttataattataggtctaaaatataataatttaaaagaaaatataaaagaatt 7620
7621 agatggattagttggaaaaaatacagttataatgtctctgctaaatggagttgatagcga 7680
7681 agagataataggagaaagatttggaattgaaaaaatggtatattcatatgttaccaatat 7740
7741 agatgcaaagaaaatcaataataatattatacacactactaatgggataattgtatttgg 7800
7801 taacaaagataatagtgaagatagaaaaactaatataataaccgaagtctttgatgatgt 7860
7861 aaatatagaatatactttatcaaaagatattcaacgagatatgtggtggaagtacatggt 7920
7921 taatattggtgtaaatcaaacttcagctatacttggtgcaccttatggagtttttcagag 7980
7981 ttctgagcatttaagagaattagcaaaatctgcaatgagggaagttgttgctatagcaca 8040
8041 agcaaaagacatatctcttacagaagatgatgtggaacattcattacatagaatactaga 8100
8101 acattcaaaagaaggaagaacatcaatgcttcaagatgtggaagctcatagacttacaga 8160
8161 agtagatatgttttctaagaatatctgtaaacttggaaaaaaatataacatacctactcc 8220
8221 tataaatcagactttcttttatatgataaaagtaattgaaagtagatttaaaggggctt 8280
8281 tgtaagaaatattgataattattgattttaaattttattaatgttatatactatggcgcg 8340
8341 ccgccattattttttgaacaattgacaattcatttcttatttttttattaagtgatagtc 8400
8401 aaaaggcataacagtgctgaatagaaagaaatttacagaaagaaaattatagaatttag 8460
8461 tatgattaattatactcatttatgaatgtttaattgaatacaaaaaaaatacttgttat 8520
8521 gtattcaattacgggttaaaatatagacaagttgaaaaatttaataaaaaataagtcct 8580
8581 cagctcttatatattaagctaccaacttagtatataagccaaaacttaaatgtgctacca 8640

Figure 6N (CONT.)

```
8641 acacatcaagccgttagagaactctatctatagcaatatttcaaatgtaccgacatacaa 8700
8701 gagaaacattaactatatatattcaatttatgagattatcttaacagatataaatgtaaa 8760
8761 ttgcaataagtaagatttagaagtttatagcctttgtgtattggaagcagtacgcaaagg 8820
8821 ctttttatttgataaaaattagaagtatatttatttttcataattaatttatgaaaat 8880
8881 gaaaggggtgagcaaagtgacagaggaaagcagtatcttatcaaataacaaggtattag 8940
8941 caatatcattattgactttagcagtaaacattatgacttttatagtgcttgtagctaagt 9000
9001 agtacgaaaggggagctttaaaagctccttggaatacatagaattcataaattaattt 9060
9061 atgaaaagaagggcgtatatgaaacttgtaaaattgcaaagagtttattaaagatact 9120
9121 gaaatatgcaaaatacattcgttgatgattcatgataaaacagtagcaacctattgcagt 9180
9181 aaatacaatgagtcaagatgtttacataaagggaaagtccaatgtattaattgttcaaag 9240
9241 atgaaccgatatggatggtgtgccataaaaatgagatgttttacagaggaagaacagaaa 9300
9301 aaagaacgtacatgcattaaatattatgcaaggagctttaaaaaagctcatgtaaagaag 9360
9361 agtaaaaagaaaaaataatttatttattaatttaatattgagagtgccgacacagtatgc 9420
9421 actaaaaaatatatctgtggtgtagtgagccgatacaaaaggatagtcactcgcattttc 9480
9481 ataatacatcttatgttatgattatgtgtcggtgggacttcacgacgaaaacccacaata 9540
9541 aaaaaagagttcggggtagggttaagcatagttgaggcaactaaacaatcaagctaggat 9600
9601 atgcagtagcagaccgtaaggtcgttgtttaggtgtgttgtaatacatacgctattaaga 9660
9661 tgtaaaaatacggataccaatgaagggaaaagtataatttttggatgtagtttgtttgtt 9720
9721 catctatgggcaaactacgtccaaagccgtttccaaatctgctaaaaagtatatcctttc 9780
9781 taaaatcaaagtcaagtatgaaatcataaataaagtttaattttgaagttattatgatat 9840
9841 tatgtttttctattaaaataaattaagtatatagaatagtttaataatagtatatactta 9900
9901 atgtgataagtgtctgacagtgtcacagaaaggatgattgttatggattataagcggccg 9960
9961 gccagtgggcaagttgaaaaattcacaaaaatgtggtataatatctttgttcattagagc 10020
10021 gataaacttgaatttgagagggaacttagatggtatttgaaaaaattgataaaaatagtt 10080
10081 ggaacagaaaagagtattttgaccactactttgcaagtgtaccttgtacctacagcatga 10140
10141 ccgttaaagtggatatcacacaaataaaggaaaagggaatgaaactatatcctgcaatgc 10200
10201 tttattatattgcaatgattgtaaaccgccattcagagtttaggacggcaatcaatcaag 10260
10261 atggtgaattggggatatatgatgagatgataccaagctatacaatatttcacaatgata 10320
10321 ctgaaacattttccagcctttggactgagtgtaagtctgactttaaatcatttttagcag 10380
10381 attatgaaagtgatacgcaacggtatggaaacaatcatagaatggaaggaaagccaaatg 10440
10441 ctccggaaaacattttaatgtatctatgataccgtggtcaaccttcgatggctttaatc 10500
10501 tgaatttgcagaaaggatatgattatttgattcctatttttactatggggaaatattata 10560
10561 aagaagataacaaaattatacttcctttggcaattcaagttcatcacgcagtatgtgacg 10620
10621 gatttcacatttgccgttttgtaaacgaattgcaggaattgataaatagttaacttcagg 10680
10681 tttgtctgtaactaaaaacaagtatttaagcaaaaacatcgtagaaatacggtgttttt 10740
10741 gttaccctaagtttaaactccttttgataatctcatgaccaaaatcccttaacgtgagt 10800
10801 tttcgttccactgagcgtcagaccccgtagaaaagatcaaaggatcttcttgagatcctt 10860
10861 tttttctgcgcgtaatctgctgcttgcaaacaaaaaaaccaccgctaccagcggtggttt 10920
10921 gtttgccggatcaagagctaccaactctttttccgaaggtaactggcttcagcagagcgc 10980
10981 agataccaaatactgtccttctagtgtagccgtagttaggccaccacttcaagaactctg 11040
11041 tagcaccgcctacatacctcgctctgctaatcctgttaccagtggctgctgccagtggcg 11100
11101 ataagtcgtgtcttaccgggttggactcaagacgatagttaccggataaggcgcagcggt 11160
11161 cgggctgaacggggggttcgtgcacacagcccagcttggagcgaacgacctacaccgaac 11220
11221 tgagatacctacagcgtgagcattgagaaagcgccacgcttcccgaagggagaaaggcgg 11280
11281 acaggtatccggtaagcggcagggtcggaacaggagagcgcacgagggagcttccagggg 11340
11341 gaaacgcctggtatctttatagtcctgtcgggtttcgccacctctgacttgagcgtcgat 11400
11401 ttttgtgatgctcgtcaggggggcggagcctatggaaaaacgccagcaacgcggcctttt 11460
11461 tacggttcctggccttttgctggccttttgctcacatgttctttcctgcgttatcccctg 11520
11521 attctgtggataaccgtattaccgcctttgagtgagctgataccgctcgccgcagccgaa 11580
11581 cgaccgagcgcagcgagtcagtgagcgaggaagcggaagagcgcccaatacgcagggccc 11640
11641 cctgcttcggggtcattatagcgatttttcggtatatccatcctttttcgcacgatata 11700
11701 caggattttgccaaagggttcgtgtagactttccttggtgtatccaacggcgtcagccgg 11760
11761 gcaggataggtgaagtaggcccacccgcgagcgggtgttccttcttcactgtcccttatt 11820
11821 cgcacctggcggtgctcaacgggaatcctgctctgcgaggctggccggctaccgccggcg 11880
11881 taacagatgagggcaagcggatggctgatgaaaccaagccaaccaggaagggcagcccac 11940
11941 ctatcaaggtgtactgccttccagacgaacgaagagcgattgaggaaaaggcggcggcgg 12000
12001 ccggcatgagcctgtcggcctacctgctggccgtcggccagggctacaaaatcacgggcg 12060
12061 tcgtggactatgagcacgtccgcgagctggcccgcatcaatggcgacctgggccgcctgg 12120
```

Figure 6N (CONT.)

```
12121 gcggcctgctgaaactctggctcaccgacgacccgcgcacggcgcggttcggtgatgcca 12180
12181 cgatcctcgccctgctggcgaagatcgaagagaagcaggacgagcttggcaaggtcatga 12240
12241 tgggcgtggtccgcccgagggcagagccatgactttttagccgctaaaacggccggggg 12300
12301 gtgcgcgtgattgccaagcacgtccccatgcgctccatcaagaagagcgacttcgcggag 12360
12361 ctggtgaagtacatcaccgacgagcaaggcaagaccgatcgggccccctgca 12412
```

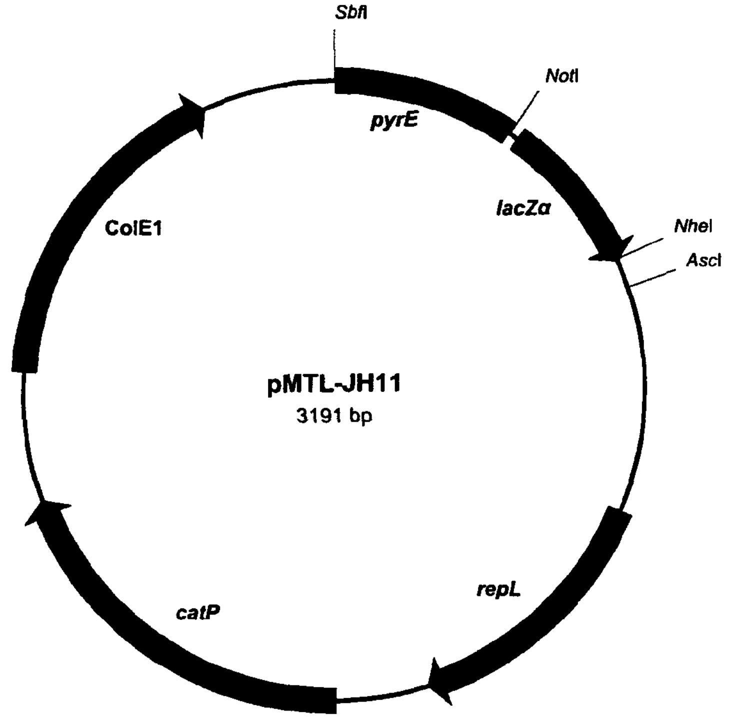

```
   1 ggagagtaatgtacttacctttggggatttcataactaaaagcggcagaagaacaccatt 60
  61 ttttataaatacaggtaactacaagacaggtaatcaattaaataagttggctaagtttta 120
 121 tgctaaagcaatatatgataattttggagatgattttgatattttatttgggcctgcata 180
 181 taaaggaatacctttaagtgtttcagtagctatggcacttgataatatttatggaattaa 240
 241 tgcagcttattgttcaaatagaaaagaagttaaagatcacggtgataagggaatacttct 300
 301 tggcggccgctgtatccatatgaccatgattacgaattcgagctcggtacccggggatcc 360
 361 tctagagtcgacgtcacgcgtccatggagatctcgaggcctgcagacatgcaagcttggc 420
 421 actggccgtcgttttacaacgtcgtgactgggaaaaccctggcgttacccaacttaatcg 480
 481 ccttgcagcacatccccctttcgccagctggcgtaatagcgaagaggcccgcaccgatcg 540
 541 cccttcccaacagttgcgcagcctgaatggcgaatggcgctagcataaaaataagaagcc 600
 601 tgcatttgcaggcttcttatttttatggcgcgccgcattcacttcttttctatataaata 660
 661 tgagcgaagcgaataagcgtcggaaaagcagcaaaaagtttcctttttgctgttggagca 720
 721 tggggttcagggggtgcagtatctgacgtcaatgccgagcgaaagcgagccgaagggta 780
 781 gcatttacgttagataacccctgatatgctccgacgctttatatagaaaagaagattca 840
 841 actaggtaaaatcttaatataggttgagatgataaggtttataaggaatttgtttgttct 900
 901 aattttcactcattttgttctaatttcttttaacaaatgttcttttttttttagaacag 960
 961 ttatgatatagttagaatagtttaaaataaggagtgagaaaaagatgaaagaaagatatg 1020
1021 gaacagtctataaaggctctcagaggctcatagacgaagaaagtggagaagtcatagagg 1080
1081 tagacaagttataccgtaaacaaacgtctggtaacttcgtaaaggcatatatagtgcaat 1140
1141 taataagtatgttagatatgattggcggaaaaaaacttaaaatcgttaactatatcctag 1200
1201 ataatgtccacttaagtaacaatacaatgatagctacaacaagagaaatagcaaaagcta 1260
1261 caggaacaagtctacaaacagtaataacaacacttaaaatcttagaagaaggaaatatta 1320
1321 taaaaagaaaaactggagtattaatgttaaaccctgaactactaatgagaggcgacgacc 1380
1381 aaaaacaaaaatacctcttactcgaatttgggaactttgagcaagaggcaaatgaaatag 1440
1441 attgacctcccaataacaccacgtagttattgggaggtcaatctatgaaatgcgattaag 1500
1501 ggccggccagtgggcaagttgaaaaattcacaaaaatgtggtataatatctttgttcatt 1560
1561 agagcgataaacttgaatttgagagggaacttagatggtatttgaaaaaattgataaaaa 1620
1621 tagttggaacagaaaagagtattttgaccactactttgcaagtgtaccttgtacctacag 1680
```

1681 catgaccgttaaagtggatatcacacaaataaaggaaaagggaatgaaactatatcctgc 1740
1741 aatgctttattatattgcaatgattgtaaaccgccattcagagtttaggacggcaatcaa 1800
1801 tcaagatggtgaattggggatatatgatgagatgataccaagctatacaatatttcacaa 1860
1861 tgatactgaaacattttccagcctttggactgagtgtaagtctgactttaaatcattttt 1920
1921 agcagattatgaaagtgatacgcaacggtatggaaacaatcatagaatggaaggaaagcc 1980
1981 aaatgctccggaaaacattttaatgtatctatgataccgtggtcaaccttcgatggctt 2040
2041 taatctgaatttgcagaaaggatatgattatttgattcctatttttactatggggaaata 2100
2101 ttataaagaagataacaaaattatacttcctttggcaattcaagttcatcacgcagtatg 2160
2161 tgacggatttcacatttgccgttttgtaaacgaattgcaggaattgataaatagttaact 2220
2221 tcaggtttgtctgtaactaaaaacaagtatttaagcaaaaacatcgtagaaatacggtgt 2280
2281 tttttgttaccctaagtttaaactcctttttgataatctcatgaccaaaatcccttaacg 2340
2341 tgagttttcgttccactgagcgtcagaccccgtagaaaagatcaaaggatcttcttgaga 2400
2401 tcctttttttctgcgcgtaatctgctgcttgcaaacaaaaaaaccaccgctaccagcggt 2460
2461 ggtttgtttgccggatcaagagctaccaactctttttccgaaggtaactggcttcagcag 2520
2521 agcgcagataccaaatactgtccttctagtgtagccgtagttaggccaccacttcaagaa 2580
2581 ctctgtagcaccgcctacatacctcgctctgctaatcctgttaccagtggctgctgccag 2640
2641 tggcgataagtcgtgtcttaccgggttggactcaagacgatagttaccggataaggcgca 2700
2701 gcggtcgggctgaacggggggttcgtgcacacagcccagcttggagcgaacgacctacac 2760
2761 cgaactgagatacctacagcgtgagcattgagaaagcgccacgcttcccgaagggagaaa 2820
2821 ggcggacaggtatccggtaagcggcagggtcggaacaggagagcgcacgagggagcttcc 2880
2881 agggggaaacgcctggtatctttatagtcctgtcgggtttcgccacctctgacttgagcg 2940
2941 tcgatttttgtgatgctcgtcaggggggcggagcctatggaaaaacgccagcaacgcggc 3000
3001 ctttttacggttcctggccttttgctggccttttgctcacatgttctttcctgcgttatc 3060
3061 ccctgattctgtggataaccgtattaccgcctttgagtgagctgataccgctcgccgcag 3120
3121 ccgaacgaccgagcgcagcgagtcagtgagcgaggaagcggaagagcgcccaatacgcag 3180
3181 ggccccctgca 3191

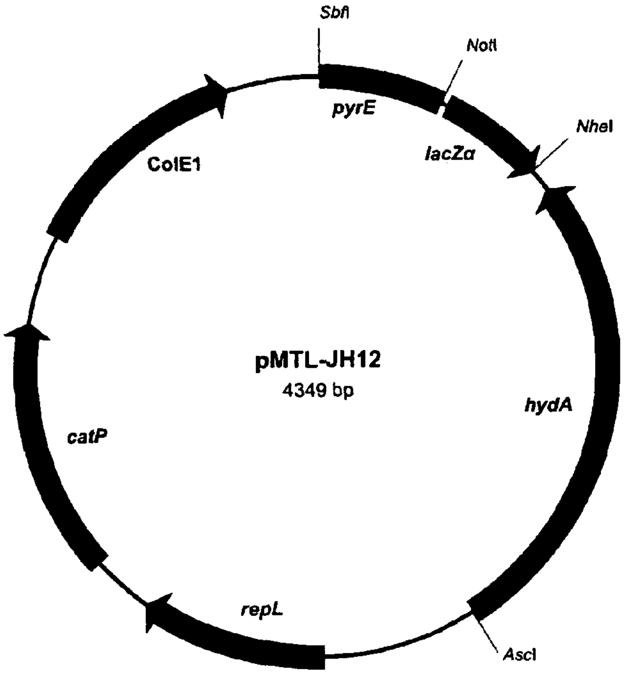

```
   1 ggagagtaatgtacttacctttggggatttcataactaaaagcggcagaagaacaccatt 60
  61 ttttataaatacaggtaactacaagacaggtaatcaattaaataagttggctaagtttta 120
 121 tgctaaagcaatatatgataattttggagatgattttgatattttatttgggcctgcata 180
 181 taaaggaatacctttaagtgtttcagtagctatggcacttgataatatttatggaattaa 240
 241 tgcagcttattgttcaaatagaaaagaagttaaagatcacggtgataagggaatacttct 300
 301 tggcggccgctgtatccatatgaccatgattacgaattcgagctcggtacccggggatcc 360
 361 tctagagtcgacgtcacgcgtccatggagatctcgaggcctgcagacatgcaagcttggc 420
 421 actggccgtcgttttacaacgtcgtgactgggaaaaccctggcgttacccaacttaatcg 480
 481 ccttgcagcacatccccctttcgccagctggcgtaatagcgaagaggcccgcaccgatcg 540
 541 cccttcccaacagttgcgcagcctgaatggcgaatggcgctagctaaaataaatgtgcct 600
 601 caacttagatgttaaggcacatttattttatatattattcatgttttgaaacatttttat 660
 661 cttttgtgtattttacgtgtagtaatttgtgagcaagtccttcacctggttttccaaagt 720
 721 agctatcatacattttaataatagctggattatcatgtgactttctctttgaaagaacat 780
 781 ttttatcttggttgtataatactgatgctcttagttttctgtaatcaacattttctctat 840
 841 caagagcatttacgtgaggttgacctccaccatttatacatccaccagggcaagccatta 900
 901 cttctataaagtgatattgtttttcgttcatttttccagatttcataaactcgaagaagt 960
 961 tagaagcaccatttataacagcaacgtttagtttatttccagcaatttcaacttccgctt 1020
1021 cttttatgcctttaaagcctcttacttcagtgtaatcaacattttcaagttctttatttt 1080
1081 cagcaaagtctttagctgatcttattgcagcttccataacgccaccggttgcaccaaaga 1140
1141 tagctccagcaccactgtaagtacccatagcaggatcaacttcaccatcttcaagatctg 1200
1201 caaatttaatttttgcatctttaatcattttgcaagctctcttgtagttaaggatgcat 1260
1261 caatatctcttaagctgttagtttccatgaaaggaatatctgcttcatatttttatcat 1320
1321 tacaaggcatgatagtaactgtataaacatcttctggagctattcctgaaattgaaggat 1380
1381 agtaagtttttgatgcagtaccaaatatttgttgtggtgattttgctgatgaaagattat 1440
1441 ctaataattcaggatgataattttgagctaatcttacccatgcaggacagcaagatgtaa 1500
1501 acatagggaatgggccattatttttaactctgcctaaaagttcagtagcttcttccatta 1560
1561 tagtcatatctgcaccaaagtttatatcaaatactttatcaaagcctaacattctaagtg 1620
1621 cagtatatagttttcctgttacatcttttccatatcccattttgaataattcgcccatag 1680
```

```
1681 cagttcttactgatggagccattgcaacaatgacatgtttttagggtcattaagagctt 1740
1741 cttgaacttttctatatgggatttttcttttaaagcagcaacaggcgcgccgcattcac 1800
1801 ttcttttctatataaatatgagcgaagcgaataagcgtcggaaaagcagcaaaaagtttc 1860
1861 ctttttgctgttggagcatgggggttcagggggtgcagtatctgacgtcaatgccgagcg 1920
1921 aaagcgagccgaagggtagcatttacgttagataacccccctgatatgctccgacgcttta 1980
1981 tatagaaaagaagattcaactaggtaaaatcttaatataggttgagatgataaggtttat 2040
2041 aaggaatttgtttgttctaatttttcactcattttgttctaatttcttttaacaaatgtt 2100
2101 cttttttttttagaacagttatgatatagttagaatagtttaaaataaggagtgagaaaa 2160
2161 agatgaaagaaagatatggaacagtctataaaggctctcagaggctcatagacgaagaaa 2220
2221 gtggagaagtcatagaggtagacaagttataccgtaaacaaacgtctggtaacttcgtaa 2280
2281 aggcatatatagtgcaattaataagtatgttagatatgattggcggaaaaaaacttaaaa 2340
2341 tcgttaactatatcctagataatgtccacttaagtaacaatacaatgatagctacaacaa 2400
2401 gagaaatagcaaaagctacaggaacaagtctacaaacagtaataacaacacttaaaatct 2460
2461 tagaagaaggaaatattataaaaagaaaaactggagtattaatgttaaaccctgaactac 2520
2521 taatgagaggcgacgaccaaaaacaaaaatacctcttactcgaatttgggaactttgagc 2580
2581 aagaggcaaatgaaatagattgacctcccaataacaccacgtagttattgggaggtcaat 2640
2641 ctatgaaatgcgattaagggccggccagtgggcaagttgaaaaattcacaaaaatgtggt 2700
2701 ataatatctttgttcattagagcgataaacttgaatttgagagggaacttagatggtatt 2760
2761 tgaaaaaattgataaaaatagttggaacagaaaagagtattttgaccactactttgcaag 2820
2821 tgtaccttgtacctacagcatgaccgttaaagtggatatcacacaaataaaggaaaaggg 2880
2881 aatgaaactatatcctgcaatgctttattatattgcaatgattgtaaaccgccattcaga 2940
2941 gtttaggacggcaatcaatcaagatggtgaattggggatatatgatgagatgataccaag 3000
3001 ctatacaatatttcacaatgatactgaaacattttccagcctttggactgagtgtaagtc 3060
3061 tgactttaaatcattttagcagattatgaaagtgatacgcaacggtatggaaacaatca 3120
3121 tagaatggaaggaaagccaaatgctccggaaaacatttttaatgtatctatgataccgtg 3180
3181 gtcaaccttcgatggctttaatctgaatttgcagaaaggatatgattatttgattcctat 3240
3241 ttttactatggggaaatattataaagaagataacaaaattatacttcctttggcaattca 3300
3301 agttcatcacgcagtatgtgacggatttcacatttgccgttttgtaaacgaattgcagga 3360
3361 attgataaatagttaacttcaggtttgtctgtaactaaaaacaagtatttaagcaaaaac 3420
3421 atcgtagaaatacggtgtttttgttaccctaagtttaaactcctttttgataatctcat 3480
3481 gaccaaaatcccttaacgtgagttttcgttccactgagcgtcagaccccgtagaaaagat 3540
3541 caaaggatcttcttgagatcctttttttctgcgcgtaatctgctgcttgcaaacaaaaaa 3600
3601 accaccgctaccagcggtggtttgtttgccggatcaagagctaccaactctttttccgaa 3660
3661 ggtaactggcttcagcagagcgcagataccaaatactgtccttctagtgtagccgtagtt 3720
3721 aggccaccacttcaagaactctgtagcaccgcctacatacctcgctctgctaatcctgtt 3780
3781 accagtggctgctgccagtggcgataagtcgtgtcttaccgggttggactcaagacgata 3840
3841 gttaccggataaggcgcagcggtcgggctgaacggggggttcgtgcacacagcccagctt 3900
3901 ggagcgaacgacctacaccgaactgagatacctacagcgtgagcattgagaaagcgccac 3960
3961 gcttcccgaagggagaaaggcggacaggtatccggtaagcggcagggtcggaacaggaga 4020
4021 gcgcacgagggagcttccagggggaaacgcctggtatctttatagtcctgtcgggtttcg 4080
4081 ccacctctgacttgagcgtcgatttttgtgatgctcgtcaggggggcggagcctatggaa 4140
4141 aaacgccagcaacgcggcctttttacggttcctggccttttgctggccttttgctcacat 4200
4201 gttctttcctgcgttatcccctgattctgtggataaccgtattaccgcctttgagtgagc 4260
4261 tgataccgctcgccgcagccgaacgaccgagcgcagcgagtcagtgagcgaggaagcgga 4320
4321 agagcgcccaatacgcagggccccctgca 4349
```

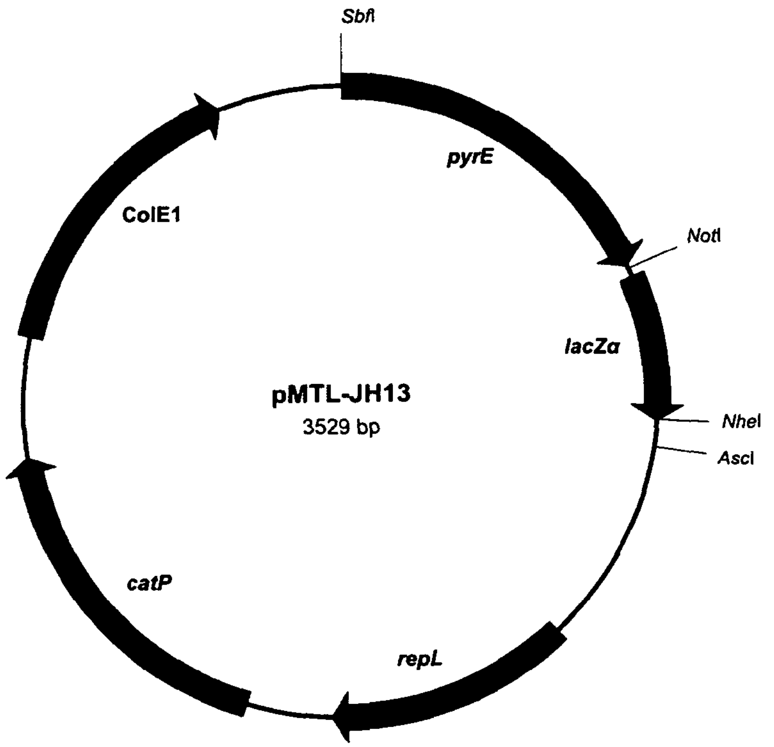

```
   1 ggagagtaatgtacttacctttggggatttcataactaaaagcggcagaagaacaccatt 60
  61 ttttataaatacaggtaactacaagacaggtaatcaattaaataagttggctaagtttta 120
 121 tgctaaagcaatatatgataattttggagatgattttgatattttatttgggcctgcata 180
 181 taaaggaatacctttaagtgtttcagtagctatggcacttgataatatttatggaattaa 240
 241 tgcagcttattgttcaaatagaaaagaagttaaagatcacggtgataagggaatacttct 300
 301 tggagcaaagcttgaagaaggagacagagttataattgtagaagatgtcacaacagctgg 360
 361 tacatcagtatacgaaacaatgcctatacttaaatcacaggctgaggttgatgtaaaggg 420
 421 aatcataatatcagtggatagaatggaaagaggtaagggagataagagtgccttaactga 480
 481 acttaaagaaaagtttggatttaaaacatgttctattgttactatggaagaggtagtaga 540
 541 atatttgtataagaaaaatatcaatggcaaagtaatcatagatgataaaatgaaagatag 600
 601 aattaatgagtactataaagagtatggagtaaaatagtaagcggccgctgtatccatatg 660
 661 accatgattacgaattcgagctcggtacccggggatcctctagagtcgacgtcacgcgtc 720
 721 catggagatctcgaggcctgcagacatgcaagcttggcactggccgtcgttttacaacgt 780
 781 cgtgactgggaaaaccctggcgttacccaacttaatcgccttgcagcacatccccctttc 840
 841 gccagctggcgtaatagcgaagaggcccgcaccgatcgcccttcccaacagttgcgcagc 900
 901 ctgaatggcgaatggcgctagcataaaaataagaagcctgcatttgcaggcttcttattt 960
 961 ttatggcgcgccgcattcacttcttttctatataaatatgagcgaagcgaataagcgtcg 1020
1021 gaaaagcagcaaaaagtttcctttttgctgttggagcatgggggttcagggggtgcagta 1080
1081 tctgacgtcaatgccgagcgaaagcgagccgaagggtagcatttacgttagataaccccc 1140
1141 tgatatgctccgacgctttatatagaaaagaagattcaactaggtaaaatcttaatatag 1200
1201 gttgagatgataaggtttataaggaatttgtttgttctaatttttcactcattttgttct 1260
1261 aatttcttttaacaaatgttcttttttttttagaacagttatgatatagttagaatagtt 1320
1321 taaaataaggagtgagaaaaagatgaaagaaagatatggaacagtctataaaggctctca 1380
1381 gaggctcatagacgaagaaagtggagaagtcatagaggtagacaagttataccgtaaaca 1440
1441 aacgtctggtaacttcgtaaaggcatatatagtgcaattaataagtatgttagatatgat 1500
1501 tggcggaaaaaaacttaaaatcgttaactatatcctagataatgtccacttaagtaacaa 1560
1561 tacaatgatagctacaacaagagaaatagcaaaagctacaggaacaagtctacaaacagt 1620
1621 aataacaacacttaaaatcttagaagaaggaaatattataaaaagaaaaactggagtatt 1680
```

```
1681 aatgttaaaccctgaactactaatgagaggcgacgaccaaaaacaaaaataccTcttact 1740
1741 cgaatttgggaactttgagcaagaggcaaatgaaatagattgacctcccaataacaccac 1800
1801 gtagttattgggaggtcaatctatgaaatgcgattaagggccggccagtgggcaagttga 1860
1861 aaaattcacaaaaatgtggtataatatctttgttcattagagcgataaacttgaatttga 1920
1921 gagggaacttagatggtatttgaaaaaattgataaaaatagttggaacagaaaagagtat 1980
1981 tttgaccactactttgcaagtgtaccttgtacctacagcatgaccgttaaagtggatatc 2040
2041 acacaaataaaggaaaagggaatgaaactatatcctgcaatgctttattatattgcaatg 2100
2101 attgtaaaccgccattcagagtttaggacggcaatcaatcaagatggtgaattggggata 2160
2161 tatgatgagatgataccaagctatacaatatttcacaatgatactgaaacattttccagc 2220
2221 ctttggactgagtgtaagtctgactttaaatcattttt agcagattatgaaagtgatacg 2280
2281 caacggtatggaaacaatcatagaatggaaggaaagccaaatgctccggaaaacattttt 2340
2341 aatgtatctatgataccgtggtcaaccttcgatggctttaatctgaatttgcagaaagga 2400
2401 tatgattatttgattcctatttttactatggggaaatattataaagaagataacaaaatt 2460
2461 atacttcctttggcaattcaagttcatcacgcagtatgtgacggatttcacatttgccgt 2520
2521 tttgtaaacgaattgcaggaattgataaatagttaacttcaggtttgtctgtaactaaaa 2580
2581 acaagtatttaagcaaaaacatcgtagaaatacggtgttttttgttaccctaagtttaaa 2640
2641 ctccttttt gataatctcatgaccaaaatcccttaacgtgagttttcgttccactgagcg 2700
2701 tcagaccccgtagaaaagatcaaaggatcttcttgagatcctttttttctgcgcgtaatc 2760
2761 tgctgcttgcaaacaaaaaaaccaccgctaccagcggtggtttgtttgccggatcaagag 2820
2821 ctaccaactctttttccgaaggtaactggcttcagcagagcgcagataccaaatactgtc 2880
2881 cttctagtgtagccgtagttaggccaccacttcaagaactctgtagcaccgcctacatac 2940
2941 ctcgctctgctaatcctgttaccagtggctgctgccagtggcgataagtcgtgtcttacc 3000
3001 gggttggactcaagacgatagttaccggataaggcgcagcggtcgggctgaacggggggt 3060
3061 tcgtgcacacagcccagcttggagcgaacgacctacaccgaactgagatacctacagcgt 3120
3121 gagcattgagaaagcgccacgcttcccgaagggagaaaggcggacaggtatccggtaagc 3180
3181 ggcagggtcggaacaggagagcgcacgagggagcttccaggggaaacgcctggtatctt 3240
3241 tatagtcctgtcgggtttcgccacctctgacttgagcgtcgatttttgtgatgctcgtca 3300
3301 ggggggcggagcctatgaaaaacgccagcaacgcggcctttttacggttcctggccttt 3360
3361 tgctggccttttgctcacatgttctttcctgcgttatcccctgattctgtggataaccgt 3420
3421 attaccgcctttgagtgagctgataccgctcgccgcagccgaacgaccgagcgcagcgag 3480
3481 tcagtgagcgaggaagcggaagagcgcccaatacgcagggccccctgca 3529
```

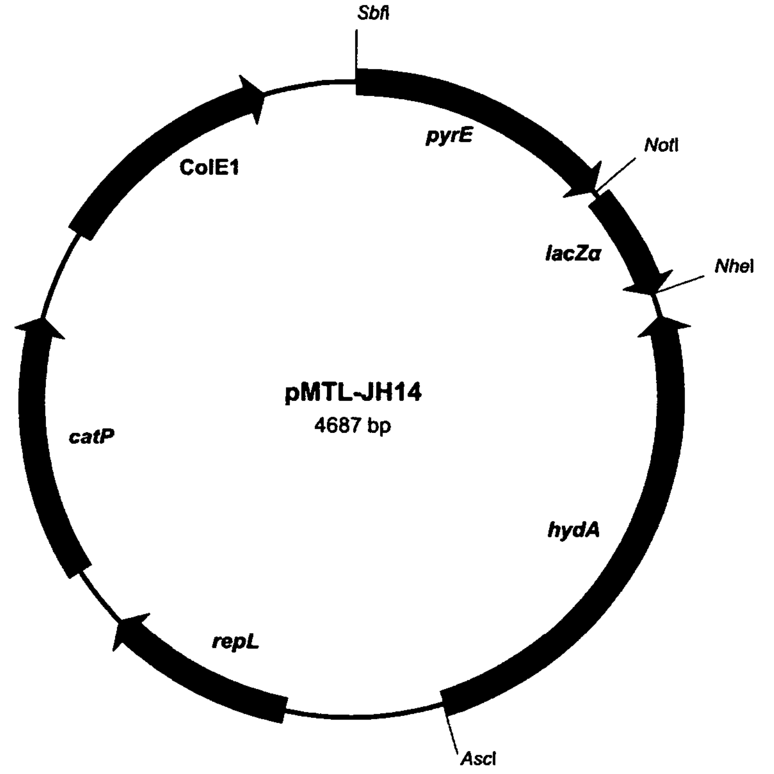

```
   1 ggagagtaatgtacttacctttggggatttcataactaaaagcggcagaagaacaccatt   60
  61 ttttataaatacaggtaactacaagacaggtaatcaattaaataagttggctaagtttta  120
 121 tgctaaagcaatatatgataattttggagatgattttgatattttatttgggcctgcata  180
 181 taaaggaatacctttaagtgtttcagtagctatggcacttgataatatttatggaattaa  240
 241 tgcagcttattgttcaaatagaaaagaagttaaagatcacggtgataagggaatacttct  300
 301 tggagcaaagcttgaagaaggagacagagttataattgtagaagatgtcacaacagctgg  360
 361 tacatcagtatacgaaacaatgcctatacttaaatcacaggctgaggttgatgtaaaggg  420
 421 aatcataatatcagtggatagaatggaaagaggtaagggagataagagtgccttaactga  480
 481 acttaaagaaaagtttggatttaaaacatgttctattgttactatggaagaggtagtaga  540
 541 atatttgtataagaaaaatatcaatggcaaagtaatcatagatgataaaatgaaagatag  600
 601 aattaatgagtactataaagagtatggagtaaaatagtaagcggccgctgtatccatatg  660
 661 accatgattacgaattcgagctcggtacccggggatcctctagagtcgacgtcacgcgtc  720
 721 catggagatctcgaggcctgcagacatgcaagcttggcactggccgtcgttttacaacgt  780
 781 cgtgactgggaaaaccctggcgttacccaacttaatcgccttgcagcacatccccctttc  840
 841 gccagctggcgtaatagcgaagaggcccgcaccgatcgcccttcccaacagttgcgcagc  900
 901 ctgaatggcgaatggcgctagctaaaataaatgtgcctcaacttagatgttaaggcacat  960
 961 ttattttatatattattcatgttttgaaacattttatcttttgtgtattttacgtgtag 1020
1021 taatttgtgagcaagtccttcacctggttttccaaagtagctatcatacattttaataat 1080
1081 agctggattatcatgtgactttctctttgaaagaacattttatcttggttgtataatac 1140
1141 tgatgctcttagttttctgtaatcaacatttctctatcaagagcatttacgtgaggttg 1200
1201 acctccaccatttatacatccaccagggcaagccattacttctataaagtgatattgttt 1260
1261 ttcgttcatttttccagatttcataaactcgaagaagttagaagcaccatttataacagc 1320
1321 aacgtttagtttatttccagcaatttcaacttccgcttcttttatgcctttaaagcctct 1380
1381 tacttcagtgtaatcaacattttcaagttctttattttcagcaaagtctttagctgatct 1440
1441 tattgcagcttccataacgccaccggttgcaccaaagatagctccagcaccactgtaagt 1500
1501 acccatagcaggatcaacttcaccatcttcaagatctgcaaatttaatttttgcatcttt 1560
1561 aatcattttgcaagctctcttgtagttaaggatgcatcaatatctcttaagctgttagt 1620
1621 ttccatgaaaggaatatctgcttcatatttttatcattacaaggcatgatagtaactgt 1680
1681 ataaacatcttctggagctattcctgaaattgaaggatagtaagttttgatgcagtacc 1740
```

1741 aaatatttgttgtggtgatttgctgatgaaagattatctaataattcaggatgataatt 1800
1801 ttgagctaatcttacccatgcaggacagcaagatgtaaacatagggaatgggccattatt 1860
1861 tttaactctgcctaaaagttcagtagcttcttccattatagtcatatctgcaccaaagtt 1920
1921 tatatcaaatactttatcaaagcctaacattctaagtgcagtatatagttttcctgttac 1980
1981 atcttttccatatcccatttgaataattcgcccatagcagttcttactgatggagccat 2040
2041 tgcaacaatgacatgtttttagggtcattaagagcttcttgaacttttctatatggga 2100
2101 tttttcttttaaagcagcaacaggcgcgccgcattcacttcttttctatataaatatgag 2160
2161 cgaagcgaataagcgtcggaaaagcagcaaaaagtttcctttttgctgttggagcatggg 2220
2221 ggttcagggggtgcagtatctgacgtcaatgccgagcgaaagcgagccgaagggtagcat 2280
2281 ttacgttagataacccccctgatatgctccgacgctttatatagaaaagaagattcaacta 2340
2341 ggtaaaatcttaatataggttgagatgataaggtttataaggaatttgtttgttctaatt 2400
2401 tttcactcattttgttctaatttctttaacaaatgttcttttttttttagaacagttat 2460
2461 gatatagttagaatagtttaaaataaggagtgagaaaaagatgaaagaaagatatggaac 2520
2521 agtctataaaggctctcagaggctcatagacgaagaaagtggagaagtcatagaggtaga 2580
2581 caagttataccgtaaacaaacgtctggtaacttcgtaaaggcatatatagtgcaattaat 2640
2641 aagtatgttagatatgattggcggaaaaaaacttaaaatcgttaactatatcctagataa 2700
2701 tgtccacttaagtaacaatacaatgatagctacaacaagagaaatagcaaaagctacagg 2760
2761 aacaagtctacaaacagtaataacaacacttaaaatcttagaagaaggaaatattataaa 2820
2821 aagaaaaactggagtattaatgttaaaccctgaactactaatgagaggcgacgaccaaaa 2880
2881 acaaaaatacctcttactcgaatttgggaactttgagcaagaggcaaatgaaatagattg 2940
2941 acctcccaataacaccacgtagttattgggaggtcaatctatgaaatgcgattaagggcc 3000
3001 ggccagtgggcaagttgaaaaattcacaaaaatgtggtataatatctttgttcattagag 3060
3061 cgataaacttgaatttgagagggaacttagatggtatttgaaaaaattgataaaaatagt 3120
3121 tggaacagaaaagagtatttgaccactactttgcaagtgtaccttgtacctacagcatg 3180
3181 accgttaaagtggatatcacacaaataaaggaaaagggaatgaaactatatcctgcaatg 3240
3241 ctttattatattgcaatgattgtaaaccgccattcagagtttaggacggcaatcaatcaa 3300
3301 gatggtgaattggggatatatgatgagatgataccaagctatacaatatttcacaatgat 3360
3361 actgaaacattttccagcctttggactgagtgtaagtctgactttaaatcatttttagca 3420
3421 gattatgaaagtgatacgcaacggtatggaaacaatcatagaatggaaggaaagccaaat 3480
3481 gctccggaaaacatttttaatgtatctatgataccgtggtcaaccttcgatggctttaat 3540
3541 ctgaatttgcagaaaggatatgattatttgattcctatttttactatggggaaatattat 3600
3601 aaagaagataacaaaattatacttcctttggcaattcaagttcatcacgcagtatgtgac 3660
3661 ggatttcacatttgccgttttgtaaacgaattgcaggaattgataaatagttaacttcag 3720
3721 gtttgtctgtaactaaaaacaagtatttaagcaaaaacatcgtagaaatacggtgttttt 3780
3781 tgttaccctaagtttaaactcctttttgataatctcatgaccaaaatcccttaacgtgag 3840
3841 ttttcgttccactgagcgtcagaccccgtagaaaagatcaaaggatcttcttgagatcct 3900
3901 ttttttctgcgcgtaatctgctgcttgcaaacaaaaaaaccaccgctaccagcggtggtt 3960
3961 tgtttgccggatcaagagctaccaactctttttccgaaggtaactggcttcagcagagcg 4020
4021 cagataccaaatactgtccttctagtgtagccgtagttaggccaccacttcaagaactct 4080
4081 gtagcaccgcctacatacctcgctctgctaatcctgttaccagtggctgctgccagtggc 4140
4141 gataagtcgtgtcttaccgggttggactcaagacgatagttaccggataaggcgcagcgg 4200
4201 tcgggctgaacggggggttcgtgcacacagcccagcttggagcgaacgacctacaccgaa 4260
4261 ctgagatacctacagcgtgagcattgagaaagcgccacgcttcccgaagggagaaaggcg 4320
4321 gacaggtatccggtaagcggcagggtcggaacaggagagcgcacgagggagcttccaggg 4380
4381 ggaaacgcctggtatctttatagtcctgtcgggtttcgccacctctgacttgagcgtcga 4440
4441 tttttgtgatgctcgtcaggggggcggagcctatggaaaaacgccagcaacgcggccttt 4500
4501 ttacggttcctggccttttgctggccttttgctcacatgttctttcctgcgttatcccct 4560
4561 gattctgtggataaccgtattaccgcctttgagtgagctgataccgctcgccgcagccga 4620
4621 acgaccgagcgcagcgagtcagtgagcgaggaagcggaagagcgcccaatacgcagggcc 4680
4681 ccctgca 4687

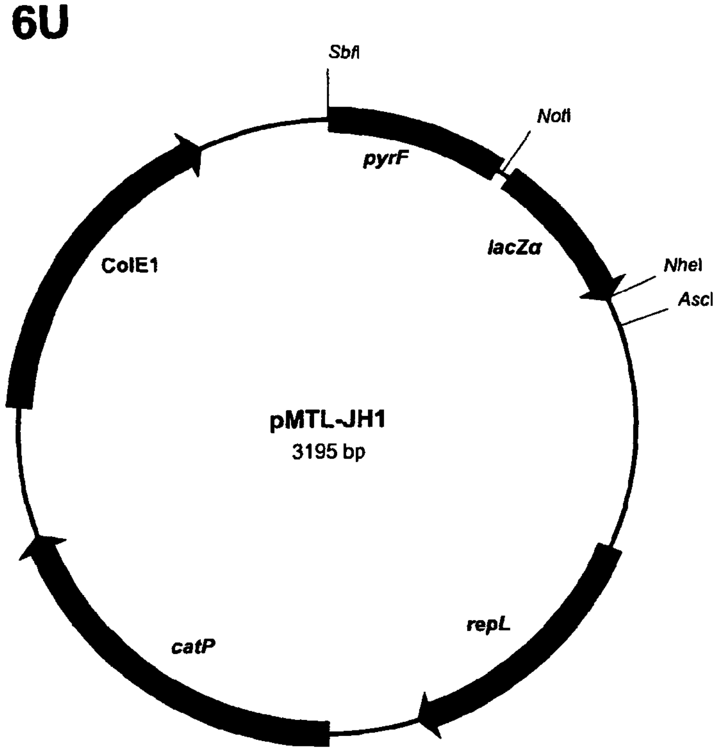

pMTL-JH1
3195 bp

```
   1 gggtgtttaggacttgatactgatattacttatgtaccagaagagttttgtaagaaattt   60
  61 aatagtatagaagatgctatatttaattttaataagaaaataattgatgcgactttagat  120
 121 gttgtttcatgttataaggtgcaaattgcatattatgaagcttatggtttaaaaggactt  180
 181 ttggcctataaaaggacacttgaatatttgagagaaaaaaaggctattgcaattgctgat  240
 241 ataaaaagaggagatatagctaaaacagctgaaatgtatgctaaagctcactttgaaggt  300
 301 taatgagcggccgctgtatccatatgaccatgattacgaattcgagctcggtacccgggg  360
 361 atcctctagagtcgacgtcacgcgtccatggagatctcgaggcctgcagacatgcaagct  420
 421 tggcactggccgtcgttttacaacgtcgtgactgggaaaaccctggcgttacccaactta  480
 481 atcgccttgcagcacatcccccttttcgccagctggcgtaatagcgaagaggcccgcaccg  540
 541 atcgcccttcccaacagttgcgcagcctgaatggcgaatggcgctagcataaaaataaga  600
 601 agcctgcatttgcaggcttcttatttttatggcgcgccgcattcacttcttttctatata  660
 661 aatatgagcgaagcgaataagcgtcggaaaagcagcaaaaagtttccttttttgctgttgg  720
 721 agcatgggggttcaggggggtgcagtatctgacgtcaatgccgagcgaaagcgagccgaag  780
 781 ggtagcatttacgttagataaccccctgatatgctccgacgctttatatagaaaagaaga  840
 841 ttcaactaggtaaaatcttaatataggttgagatgataaggtttataaggaatttgtttg  900
 901 ttctaattttttcactcattttgttctaatttcttttaacaaatgttctttttttttaga  960
 961 acagttatgatatagttagaatagtttaaaataaggagtgagaaaaagatgaaagaaaga 1020
1021 tatggaacagtctataaaggctctcagaggctcatagacgaagaaagtggagaagtcata 1080
1081 gaggtagacaagttataccgtaaacaaacgtctggtaacttcgtaaaggcatatatagtg 1140
1141 caattaataagtatgttagatatgattggcggaaaaaaacttaaaatcgttaactatatc 1200
1201 ctagataatgtccacttaagtaacaatacaatgatagctacaacaagagaaatagcaaaa 1260
1261 gctacaggaacaagtctacaaacagtaataacaacacttaaaatcttagaagaaggaaat 1320
1321 attataaaagaaaaactggagtattaatgttaaaccctgaactactaatgagaggcgac 1380
1381 gaccaaaaacaaaaatacctcttactcgaatttgggaactttgagcaagaggcaaatgaa 1440
1441 atagattgacctcccaataacaccacgtagttattgggaggtcaatctatgaaatgcgat 1500
1501 taagggccggccagtgggcaagttgaaaaattcacaaaaatgtggtataatatctttgtt 1560
1561 cattagagcgataaacttgaatttgagagggaacttagatggtatttgaaaaaattgata 1620
1621 aaaatagttggaacagaaaagagtattttgaccactactttgcaagtgtaccttgtacct 1680
1681 acagcatgaccgttaaagtggatatcacacaaataaaggaaaagggaatgaaactatatc 1740
1741 ctgcaatgctttattatattgcaatgattgtaaaccgccattcagagtttaggacggcaa 1800
1801 tcaatcaagatggtgaattggggatatatgatgagatgataccaagctatacaatatttc 1860
```

```
1861 acaatgatactgaaacattttccagcctttggactgagtgtaagtctgactttaaatcat 1920
1921 ttttagcagattatgaaagtgatacgcaacggtatggaaacaatcatagaatggaaggaa 1980
1981 agccaaatgctccggaaaacattttaatgtatctatgataccgtggtcaaccttcgatg 2040
2041 gctttaatctgaatttgcagaaaggatatgattatttgattcctattttactatggga 2100
2101 aatattataaagaagataacaaaattatacttcctttggcaattcaagttcatcacgcag 2160
2161 tatgtgacggatttcacatttgccgttttgtaaacgaattgcaggaattgataaatagtt 2220
2221 aacttcaggtttgtctgtaactaaaaacaagtatttaagcaaaaacatcgtagaaatacg 2280
2281 gtgtttttgttaccctaagtttaaactcctttttgataatctcatgaccaaaatccctt 2340
2341 aacgtgagttttcgttccactgagcgtcagaccccgtagaaaagatcaaaggatcttctt 2400
2401 gagatcctttttttctgcgcgtaatctgctgcttgcaaacaaaaaaaccaccgctaccag 2460
2461 cggtggtttgtttgccggatcaagagctaccaactctttttccgaaggtaactggcttca 2520
2521 gcagagcgcagataccaaatactgtccttctagtgtagccgtagttaggccaccacttca 2580
2581 agaactctgtagcaccgcctacatacctcgctctgctaatcctgttaccagtggctgctg 2640
2641 ccagtggcgataagtcgtgtcttaccgggttggactcaagacgatagttaccggataagg 2700
2701 cgcagcggtcgggctgaacggggggttcgtgcacacagcccagcttggagcgaacgacct 2760
2761 acaccgaactgagatacctacagcgtgagcattgagaaagcgccacgcttcccgaaggga 2820
2821 gaaaggcggacaggtatccggtaagcggcagggtcggaacaggagagcgcacgagggagc 2880
2881 ttccagggggaaacgcctggtatctttatagtcctgtcgggtttcgccacctctgacttg 2940
2941 agcgtcgatttttgtgatgctcgtcaggggggcggagcctatggaaaaacgccagcaacg 3000
3001 cggcctttttacggttcctggccttttgctggccttttgctcacatgttctttcctgcgt 3060
3061 tatcccctgattctgtggataaccgtattaccgcctttgagtgagctgataccgctcgcc 3120
3121 gcagccgaacgaccgagcgcagcgagtcagtgagcgaggaagcggaagagcgcccaatac 3180
3181 gcagggcccccctgca 3195
```

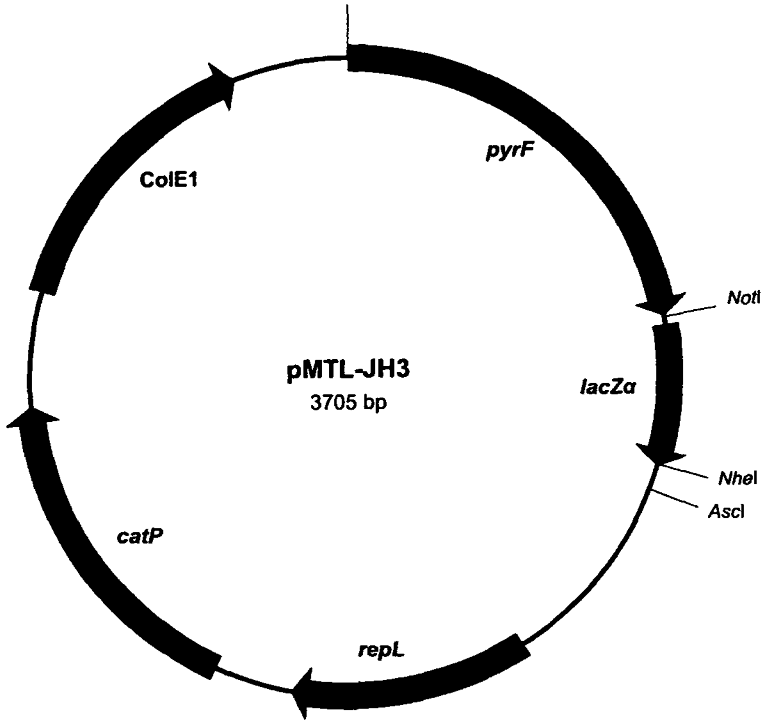

```
   1 gggtgtttaggacttgatactgatattacttatgtaccagaagagttttgtaagaaattt   60
  61 aatagtatagaagatgctatatttaattttaataagaaaataattgatgcgactttagat  120
 121 gttgtttcatgttataaggtgcaaattgcatattatgaagcttatggtttaaaaggactt  180
 181 ttggcctataaaaggacacttgaatatttgagagaaaaaaggctattgcaattgctgat   240
 241 ataaaaagaggagatatagctaaaacagctgaaatgtatgctaaagctcactttgaaggt  300
 301 gattttgaagcggattttgttacgttaaatccttacatggggttagatggtatagagcct  360
 361 tatatgccttatattgaaaaaatggaaaaaggattatttattttgcttagaacatcgaat  420
 421 aaaggagcctatgatatacaatatataaagactcagggcggaaaaaacgtatatgatgag  480
 481 gttggagaaaaaatatatgatttaggtcaaaaggctacgggaaggagcaagtattcttca  540
 541 ataggagcagtagttggatgtactcacgttgaagaaggcgttgaaattagaaataaattt  600
 601 aaaaatatgttttttctaattccaggctatggagcacaaggtggaactgcaaaggaagta  660
 661 agtttgtatttaagagaaggtaatggtggagtggtaaattcctcaaggggaatacttctt  720
 721 gcttataaaaaagaagaaaacggtgaaaaaatatttgatgagtgtgcaaggcttgcagcg  780
 781 attaatatgagagacgagatcagaaaaactttatgagcggccgctgtatccatatgacca  840
 841 tgattacgaattcgagctcggtacccggggatcctctagagtcgacgtcacgcgtccatg  900
 901 gagatctcgaggcctgcagacatgcaagcttggcactggccgtcgttttacaacgtcgtg  960
 961 actgggaaaaccctggcgttacccaacttaatcgccttgcagcacatcccccttcgcca  1020
1021 gctggcgtaatagcgaagaggcccgcaccgatcgcccttcccaacagttgcgcagcctga  1080
1081 atggcgaatggcgctagcataaaaataagaagcctgcatttgcaggcttcttatttttat  1140
1141 ggcgcgccgcattcacttcttttctatataaatatgagcgaagcgaataagcgtcggaaa  1200
1201 agcagcaaaaagtttccttttttgctgttggagcatgggggttcagggggtgcagtatctg  1260
1261 acgtcaatgccgagcgaaagcgagccgaagggtagcatttacgttagataaccccctgat  1320
1321 atgctccgacgctttatatagaaaagaagattcaactaggtaaaatcttaatataggttg  1380
1381 agatgataaggtttataaggaatttgtttgttctaattttcactcattttgttctaatt   1440
1441 tcttttaacaaatgttcttttttttagaacagttatgatatagttagaatagtttaaa   1500
1501 ataaggagtgagaaaagatgaaagaaagatatggaacagtctataaaggctctcagagg  1560
1561 ctcatagacgaagaaagtggagaagtcatagaggtagacaagttataccgtaaacaaacg  1620
1621 tctggtaacttcgtaaaggcatatatagtgcaattaataagtatgttagatatgattggc  1680
1681 ggaaaaaaacttaaaatcgttaactatatcctagataatgtccacttaagtaacaataca  1740
1741 atgatagctacaacaagagaaatagcaaaagctacaggaacaagtctacaaacagtaata  1800
```

```
1801 acaacacttaaaatcttagaagaaggaaatattataaaagaaaaactggagtattaatg 1860
1861 ttaaaccctgaactactaatgagaggcgacgaccaaaaacaaaaatacctcttactcgaa 1920
1921 tttgggaactttgagcaagaggcaaatgaaatagattgacctcccaataacaccacgtag 1980
1981 ttattgggaggtcaatctatgaaatgcgattaagggccggccagtgggcaagttgaaaaa 2040
2041 ttcacaaaaatgtggtataatatctttgttcattagagcgataaacttgaatttgagagg 2100
2101 gaacttagatggtatttgaaaaaattgataaaaatagttggaacagaaaagagtattttg 2160
2161 accactactttgcaagtgtaccttgtacctacagcatgaccgttaaagtggatatcacac 2220
2221 aaataaaggaaaagggaatgaaactatatcctgcaatgctttattatattgcaatgattg 2280
2281 taaaccgccattcagagtttaggacggcaatcaatcaagatggtgaattggggatatatg 2340
2341 atgagatgataccaagctatacaatatttcacaatgatactgaaacattttccagccttt 2400
2401 ggactgagtgtaagtctgactttaaatcatttttagcagattatgaaagtgatacgcaac 2460
2461 ggtatggaaacaatcatagaatggaaggaaagccaaatgctccggaaaacattttttaatg 2520
2521 tatctatgataccgtggtcaaccttcgatggctttaatctgaatttgcagaaaggatatg 2580
2581 attatttgattcctatttttactatggggaaatattataaagaagataacaaaattatac 2640
2641 ttcctttggcaattcaagttcatcacgcagtatgtgacggatttcacatttgccgttttg 2700
2701 taaacgaattgcaggaattgataaatagttaacttcaggtttgtctgtaactaaaaacaa 2760
2761 gtatttaagcaaaaacatcgtagaaatacggtgtttttgttaccctaagtttaaactcc 2820
2821 tttttgataatctcatgaccaaaatcccttaacgtgagttttcgttccactgagcgtcag 2880
2881 accccgtagaaaagatcaaaggatcttcttgagatcctttttttctgcgcgtaatctgct 2940
2941 gcttgcaaacaaaaaaaccaccgctaccagcggtggtttgtttgccggatcaagagctac 3000
3001 caactctttttccgaaggtaactggcttcagcagagcgcagataccaaatactgtccttc 3060
3061 tagtgtagccgtagttaggccaccacttcaagaactctgtagcaccgcctacatacctcg 3120
3121 ctctgctaatcctgttaccagtggctgctgccagtggcgataagtcgtgtcttaccgggt 3180
3181 tggactcaagacgatagttaccggataaggcgcagcggtcgggctgaacggggggttcgt 3240
3241 gcacacagcccagcttggagcgaacgacctacaccgaactgagatacctacagcgtgagc 3300
3301 attgagaaagcgccacgcttcccgaagggagaaaggcggacaggtatccggtaagcggca 3360
3361 gggtcggaacaggagagcgcacgagggagcttccagggggaaacgcctggtatctttata 3420
3421 gtcctgtcgggtttcgccacctctgacttgagcgtcgatttttgtgatgctcgtcagggg 3480
3481 ggcggagcctatggaaaaacgccagcaacgcggcctttttacggttcctggccttttgct 3540
3541 ggccttttgctcacatgttctttcctgcgttatcccctgattctgtggataaccgtatta 3600
3601 ccgcctttgagtgagctgataccgctcgccgcagccgaacgaccgagcgcagcgagtcag 3660
3661 tgagcgaggaagcggaagagcgcccaatacgcagggcccccctgca 3705
```

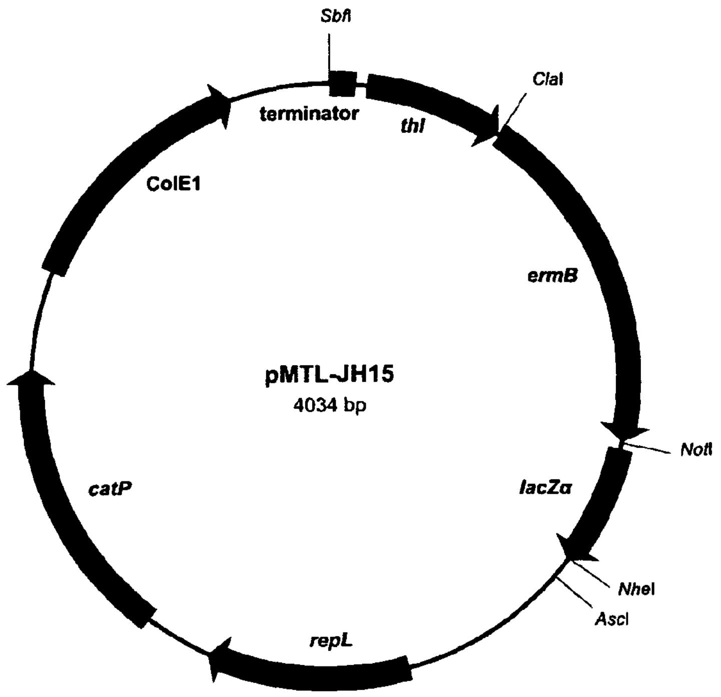

```
   1 ggataaaaaaattgtagataaatttataaaatagttttatctacaatttttttatcagg 60
  61 aaacagctatgaccgcggccatctatgcaacaaaagcagctattgaaaaagcaggttgga 120
 121 cagttgatgaattagatttaatagaatcaaatgaagcttttgcagctcaaagtttagcag 180
 181 tagcaaaagatttaaatttgatatgaataaagtaaatgtaaatggaggagctattgccc 240
 241 ttggtcatccaattggagcatcaggtgcaagaatactcgttactcttgtacacgcaatgc 300
 301 aaaaaagagatgcaaaaaaaggcttagcaactttatgtataggtggcggacaaggaacag 360
 361 caatattgctagaaaagtgctagatcgattaagaaggagtgattacatgaacaaaaatat 420
 421 aaaatattctcaaaactttttaacgagtgaaaaagtactcaaccaaataataaaacaatt 480
 481 gaatttaaaagaaaccgataccgtttacgaaattggaacaggtaaagggcatttaacgac 540
 541 gaaactggctaaaataagtaaacaggtaacgtctattgaattagacagtcatctattcaa 600
 601 cttatcgtcagaaaaattaaaactgaatactcgtgtcactttaattcaccaagatattct 660
 661 acagtttcaattccctaacaaacagaggtataaaattgttgggagtattccttaccattt 720
 721 aagcacacaaattattaaaaaagtggtttttgaaagccatgcgtctgacatctatctgat 780
 781 tgttgaagaaggattctacaagcgtaccttggatattcaccgaacactagggttgctctt 840
 841 gcacactcaagtctcgattcagcaattgcttaagctgccagcggaatgctttcatcctaa 900
 901 accaaaagtaaacagtgtcttaataaacttacccgccataccacagatgttccagataa 960
 961 atattggaagctatatacgtactttgtttcaaaatgggtcaatcgagaatatcgtcaact 1020
1021 gtttactaaaaatcagtttcatcaagcaatgaaacacgccaaagtaaacaatttaagtac 1080
1081 cgttacttatgagcaagtattgtctatttttaatagttatctattatttaacgggaggaa 1140
1141 ataaagcggccgctgtatccatatgaccatgattacgaattcgagctcggtacccgggga 1200
1201 tcctctagagtcgacgtcacgcgtccatggagatctcgaggcctgcagacatgcaagctt 1260
1261 ggcactggccgtcgttttacaacgtcgtgactgggaaaaccctggcgttacccaacttaa 1320
1321 tcgccttgcagcacatccccctttcgccagctggcgtaatagcgaagaggcccgcaccga 1380
1381 tcgcccttcccaacagttgcgcagcctgaatggcgaatggcgctagcataaaaataagaa 1440
1441 gcctgcatttgcaggcttcttatttttatggcgcgccgcattcacttcttttctatataa 1500
1501 atatgagcgaagcgaataagcgtcggaaaagcagcaaaaagtttcctttttgctgttgga 1560
1561 gcatgggggttcagggggtgcagtatctgacgtcaatgccgagcgaaagcgagccgaagg 1620
1621 gtagcatttacgttagataacccccctgatatgctccgacgctttatatagaaaagaagat 1680
```

1681 tcaactaggtaaaatcttaatataggttgagatgataaggtttataaggaatttgtttgt 1740
1741 tctaatttttcactcattttgttctaatttcttttaacaaatgttctttttttttttagaa 1800
1801 cagttatgatatagttagaatagtttaaaataaggagtgagaaaaagatgaaagaaagat 1860
1861 atggaacagtctataaaggctctcagaggctcatagacgaagaaagtggagaagtcatag 1920
1921 aggtagacaagttataccgtaaacaaacgtctggtaacttcgtaaaggcatatatagtgc 1980
1981 aattaataagtatgttagatatgattggcggaaaaaaacttaaaatcgttaactatatcc 2040
2041 tagataatgtccacttaagtaacaatacaatgatagctacaacaagagaaatagcaaaag 2100
2101 ctacaggaacaagtctacaaacagtaataacaacacttaaaatcttagaagaaggaaata 2160
2161 ttataaaaagaaaaactggagtattaatgttaaaccctgaactactaatgagaggcgacg 2220
2221 accaaaaacaaaaatacctcttactcgaatttgggaactttgagcaagaggcaaatgaaa 2280
2281 tagattgacctcccaataacaccacgtagttattgggaggtcaatctatgaaatgcgatt 2340
2341 aagggccggccagtgggcaagttgaaaattcacaaaaatgtggtataatatctttgttc 2400
2401 attagagcgataaacttgaatttgagagggaacttagatggtatttgaaaaaattgataa 2460
2461 aaatagttggaacagaaaagagtattttgaccactactttgcaagtgtaccttgtaccta 2520
2521 cagcatgaccgttaaagtggatatcacacaaataaaggaaaagggaatgaaactatatcc 2580
2581 tgcaatgctttattatattgcaatgattgtaaaccgccattcagagtttaggacggcaat 2640
2641 caatcaagatggtgaattggggatatatgatgagatgataccaagctatacaatatttca 2700
2701 caatgatactgaaacattttccagcctttggactgagtgtaagtctgactttaaatcatt 2760
2761 tttagcagattatgaaagtgatacgcaacggtatggaaacaatcatagaatggaaggaaa 2820
2821 gccaaatgctccggaaaacattttaatgtatctatgataccgtggtcaaccttcgatgg 2880
2881 ctttaatctgaatttgcagaaaggatatgattatttgattcctatttttactatggggaa 2940
2941 atattataaagaagataacaaaattatacttcctttggcaattcaagttcatcacgcagt 3000
3001 atgtgacggatttcacatttgccgttttgtaaacgaattgcaggaattgataaatagtta 3060
3061 acttcaggtttgtctgtaactaaaaacaagtatttaagcaaaaacatcgtagaaatacgg 3120
3121 tgtttttgttaccctaagtttaaactccttttgataatctcatgaccaaaatccctta 3180
3181 acgtgagttttcgttccactgagcgtcagaccccgtagaaaagatcaaaggatcttcttg 3240
3241 agatcctttttttctgcgcgtaatctgctgcttgcaaacaaaaaaaccaccgctaccagc 3300
3301 ggtggtttgtttgccggatcaagagctaccaactctttttccgaaggtaactggcttcag 3360
3361 cagagcgcagataccaaatactgtccttctagtgtagccgtagttaggccaccacttcaa 3420
3421 gaactctgtagcaccgcctacatacctcgctctgctaatcctgttaccagtggctgctgc 3480
3481 cagtggcgataagtcgtgtcttaccgggttggactcaagacgatagttaccggataaggc 3540
3541 gcagcggtcgggctgaacggggggttcgtgcacacagcccagcttggagcgaacgaccta 3600
3601 caccgaactgagatacctacagcgtgagcattgagaaagcgccacgcttcccgaagggag 3660
3661 aaaggcggacaggtatccggtaagcggcagggtcggaacaggagagcgcacgagggagct 3720
3721 tccagggggaaacgcctggtatctttatagtcctgtcgggtttcgccacctctgacttga 3780
3781 gcgtcgatttttgtgatgctcgtcaggggggcggagcctatggaaaaacgccagcaacgc 3840
3841 ggcctttttacggttcctggccttttgctggccttttgctcacatgttctttcctgcgtt 3900
3901 atcccctgattctgtggataaccgtattaccgcctttgagtgagctgataccgctcgccg 3960
3961 cagccgaacgaccgagcgcagcgagtcagtgagcgaggaagcggaagagcgcccaatacg 4020
4021 cagggcccccctgca 4034

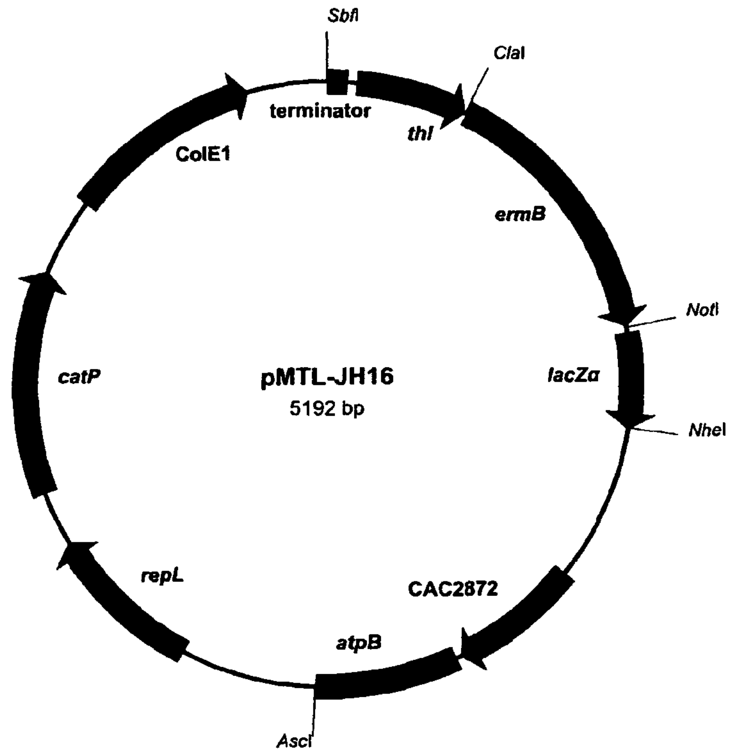

```
   1 ggataaaaaaattgtagataaattttataaaatagttttatctacaatttttttatcagg 60
  61 aaacagctatgaccgcggccatctatgcaacaaaagcagctattgaaaaagcaggttgga 120
 121 cagttgatgaattagatttaatagaatcaaatgaagcttttgcagctcaaagtttagcag 180
 181 tagcaaaagatttaaatttgatatgaataaagtaaatgtaaatggaggagctattgccc 240
 241 ttggtcatccaattggagcatcaggtgcaagaatactcgttactcttgtacacgcaatgc 300
 301 aaaaaagagatgcaaaaaaaggcttagcaactttatgtataggtggcggacaaggaacag 360
 361 caatattgctagaaaagtgctagatcgattaagaaggagtgattacatgaacaaaaatat 420
 421 aaaatattctcaaaacttttaacgagtgaaaaagtactcaaccaaataataaaacaatt 480
 481 gaatttaaaagaaaccgataccgtttacgaaattggaacaggtaaagggcatttaacgac 540
 541 gaaactggctaaaataagtaaacaggtaacgtctattgaattagacagtcatctattcaa 600
 601 cttatcgtcagaaaaattaaaactgaatactcgtgtcactttaattcaccaagatattct 660
 661 acagtttcaattccctaacaaacagaggtataaaattgttgggagtattccttaccattt 720
 721 aagcacacaaattattaaaaaagtggtttttgaaagccatgcgtctgacatctatctgat 780
 781 tgttgaagaaggattctacaagcgtaccttggatattcaccgaacactagggttgctctt 840
 841 gcacactcaagtctcgattcagcaattgcttaagctgccagcggaatgctttcatcctaa 900
 901 accaaaagtaaacagtgtcttaataaacttacccgccataccacagatgttccagataa 960
 961 atattggaagctatatacgtactttgtttcaaaatgggtcaatcgagaatatcgtcaact 1020
1021 gtttactaaaaatcagtttcatcaagcaatgaaacacgccaaagtaaacaatttaagtac 1080
1081 cgttacttatgagcaagtattgtctatttttaatagttatctattatttaacgggaggaa 1140
1141 ataaagcggccgctgtatccatatgaccatgattacgaattcgagctcggtacccgggga 1200
1201 tcctctagagtcgacgtcacgcgtccatggagatctcgaggcctgcagacatgcaagctt 1260
1261 ggcactggccgtcgttttacaacgtcgtgactgggaaaaccctggcgttacccaacttaa 1320
1321 tcgccttgcagcacatccccctttcgccagctggcgtaatagcgaagaggcccgcaccga 1380
1381 tcgcccttcccaacagttgcgcagcctgaatggcgaatggcgctagcaaagtattgttaa 1440
1441 aaataactctgtagaattataaattagttctacagagttatttttttaaaaaaattctaaa 1500
1501 cttatgtataaaaaaatacgataagaatgtagaattaaaactaaagacagttcaatttctt 1560
1561 ttagaataatttagttagtgtggtaaaaaaatgtcataatgatatttatgttgaaatttg 1620
1621 tataaaattcagaaaatgaatatattttatcaattttcagtcatttgaaagattatgagg 1680
1681 ctaatgcagtactaggcgtaaattgaatttataattactatagcgataagaaatggccta 1740
```

```
1741 aaaacgtttgcagtaatgaaagaaccgtaaatattataaaaaaaatcttaaaacagagtt 1800
1801 ttatttataaaatttaagatatataatttaaataacgtgttaaaatagtggaggaagta 1860
1861 atttgaatctgaatattaaaagaatgttaaaggttgtaactctttatgatgcaattattg 1920
1921 ctgcaatagtttcagtaatactttttgtttgctgctaattataagatttcgttaatagtga 1980
1981 ttatagggatttttcagcaatatttaattttatttaagtaatttaacagctgatttcg 2040
2041 ttttgtaaaaaaaatgggaaatacgtcacttatatttcttagttcaatttttagagtaa 2100
2101 tacttgtttttttataggtattattctttataaaatatataaatattatttaatagcct 2160
2161 acttaggaggatatagtgctcattttatagcccttataatttatgggtcactagtaaata 2220
2221 aacgatgaaaggaagtgattgaatggagctaggtgcaaagacagtattttcgatgaagct 2280
2281 tggaagttacaactttgctataacagaaactgtagtattacagtggattatcatggcagt 2340
2341 tataatattacttgcaatatttcttactaaaaatcttaagaaagtaccaaataggaaaca 2400
2401 aagcgtaatagaaatgattgttaacttaataaatggattggtaaaagaaaatatgggaga 2460
2461 gaaattcatgaatttcgttccaattatcggtactatggcagtgtttatactttcttaaa 2520
2521 tttaacagggctagtaggtatcgaaccagcaacaaaggatattagtgttacagcaggctt 2580
2581 tgctttagtaagtgcattttaataaatgcaactgcaataaaaagaaggcgcgccgcatt 2640
2641 cacttcttttctatataaatatgagcgaagcgaataagcgtcggaaaagcagcaaaaagt 2700
2701 ttcctttttgctgttggagcatgggggttcagggggtgcagtatctgacgtcaatgccga 2760
2761 gcgaaagcgagccgaagggtagcatttacgttagataacccccctgatatgctccgacgct 2820
2821 ttatatagaaaagaagattcaactaggtaaaatcttaatataggttgagatgataaggtt 2880
2881 tataaggaatttgtttgttctaatttttcactcattttgttctaatttcttttaacaaat 2940
2941 gttcttttttttttagaacagttatgatatagttagaatagtttaaaataaggagtgaga 3000
3001 aaaagatgaaagaaagatatggaacagtctataaaggctctcagaggctcatagacgaag 3060
3061 aaagtggagaagtcatagaggtagacaagttataccgtaaacaaacgtctggtaacttcg 3120
3121 taaaggcatatatagtgcaattaataagtatgttagatatgattggcggaaaaaaactta 3180
3181 aaatcgttaactatatcctagataatgtccacttaagtaacaatacaatgatagctacaa 3240
3241 caagagaaatagcaaaagctacaggaacaagtctacaaacagtaataacaacacttaaaa 3300
3301 tcttagaagaaggaaatattataaaaagaaaaactggagtattaatgttaaaccctgaac 3360
3361 tactaatgagaggcgacgaccaaaaacaaaaatacctcttactcgaatttgggaactttg 3420
3421 agcaagaggcaaatgaaatagattgacctcccaataacaccacgtagttattgggaggtc 3480
3481 aatctatgaaatgcgattaagggccggccagtgggcaagttgaaaaattcacaaaaatgt 3540
3541 ggtataatatctttgttcattagagcgataaacttgaatttgagagggaacttagatggt 3600
3601 atttgaaaaaattgataaaaatagttggaacagaaaagagtattttgaccactactttgc 3660
3661 aagtgtaccttgtacctacagcatgaccgttaaagtggatatcacacaaataaaggaaaa 3720
3721 gggaatgaaactatatcctgcaatgctttattatattgcaatgattgtaaaccgccattc 3780
3781 agagtttaggacggcaatcaatcaagatggtgaattggggatatatgatgagatgatacc 3840
3841 aagctatacaatatttcacaatgatactgaaacattttccagcctttggactgagtgtaa 3900
3901 gtctgactttaaatcattttttagcagattatgaaagtgatacgcaacggtatggaaacaa 3960
3961 tcatagaatggaaggaaagccaaatgctccggaaaacattttttaatgtatctatgatacc 4020
4021 gtggtcaaccttcgatggcttaatctgaatttgcagaaaggatatgattatttgattcc 4080
4081 tatttttactatggggaaatattataaagaagataacaaaattatacttcctttggcaat 4140
4141 tcaagttcatcacgcagtatgtgacggatttcacatttgccgttttgtaaacgaattgca 4200
4201 ggaattgataaatagttaacttcaggtttgtctgtaactaaaaacaagtatttaagcaaa 4260
4261 aacatcgtagaaatacggtgtttttttgttaccctaagtttaaactcctttttgataatct 4320
4321 catgaccaaaatcccttaacgtgagttttcgttccactgagcgtcagaccccgtagaaaa 4380
4381 gatcaaaggatcttcttgagatcctttttttctgcgcgtaatctgctgcttgcaaacaaa 4440
4441 aaaaccaccgctaccagcggtggtttgtttgccggatcaagagctaccaactctttttcc 4500
4501 gaaggtaactggcttcagcagagcgcagataccaaatactgtccttctagtgtagccgta 4560
4561 gttaggccaccacttcaagaactctgtagcaccgcctacatacctcgctctgctaatcct 4620
4621 gttaccagtggctgctgccagtggcgataagtcgtgtcttaccgggttggactcaagacg 4680
4681 atagttaccggataaggcgcagcggtcgggctgaacggggggttcgtgcacacagcccag 4740
4741 cttggagcgaacgacctacaccgaactgagatacctacagcgtgagcattgagaaagcgc 4800
4801 cacgcttcccgaagggagaaaggcggacaggtatccggtaagcggcagggtcggaacagg 4860
4861 agagcgcacgagggagcttccagggggaaacgcctggtatctttatagtcctgtcgggtt 4920
4921 tcgccacctctgacttgagcgtcgatttttgtgatgctcgtcaggggggcggagcctatg 4980
4981 gaaaaacgccagcaacgcggcctttttacggttcctggccttttgctggccttttgctca 5040
5041 catgttctttcctgcgttatcccctgattctgtggataaccgtattaccgcctttgagtg 5100
5101 agctgataccgctcgccgcagccgaacgaccgagcgcagcgagtcagtgagcgaggaagc 5160
5161 ggaagagcgcccaatacgcagggccccctgca 5192
```

Figure 8C (CONT.)

METHODS OF MODIFYING NUCLEIC ACIDS IN HOST CELLS

The present invention relates to methods of modifying nucleic acids in host cells, particularly by double crossover homologous recombination. Such methods are useful in inserting DNA and/or deleting DNA from a DNA molecule in a host cell, or otherwise altering a DNA molecule in a host cell.

Stable genetic modification of the genome of cells is desirable for many applications, including methods for the production of recombinant proteins, medical applications and research applications. The ability to rationally integrate DNA into the genome of microbial species in particular can act as a springboard for the generation of strains with improved properties. Such technology may be employed: (i) to generate specific mutants as a means of ascribing function to individual genes, and gene sets, as an essential first step towards understanding physiology and/or pathogenesis; (ii) to insertionally inactivate regulatory or structural genes as a means of enhancing the production of desirable commercial commodities, and; (iii) to stably introduce genetic information encoding adventitious factors.

Various means of rationally integrating DNA into the genome are known. Methods relying upon homologous recombination mediated by introduced enzymes, such as lambda red 'recombineering' and analogous approaches are useful in a limited number of bacterial classes, particularly *Escherichia* (Datsenko and Wanner (2000) *Proc Natl Acad Sci USA.* 97: 6640-5) and *Salmonella*. Methods relying upon site-specific recombination mediated by introduced enzymes, such as phage integrases, FLP/FRT or Cre/loxP may also be used, but are reliant on the presence of pre-existing sites within the target DNA (Wirth et al (2007) *Current Opinions in Biotechnology* 18, 411-419). Alternative methods exploit viruses or mobile elements, or their components e.g. phage, transposons or mobile introns. However, methods relying upon host-mediated homologous recombination are by far the most commonly-used type of chromosomal DNA modifications.

In a typical microbial application of host-mediated homologous recombination, a plasmid with a single region of sequence identity with the chromosome is integrated into the chromosome by single-crossover integration, sometimes referred to as 'Campbell-like integration'. After such an event, genes on the introduced plasmid are replicated as part of the chromosome, which may be more rapid than the plasmid replication. Accordingly, growth in medium with selection for a plasmid-borne selectable marker gene may provide a selective pressure for integration. Campbell-like integration can be used to inactivate a chromosomal gene by placing an internal fragment of a gene of interest on the plasmid, so that after integration, the chromosome will not contain a full-length copy of the gene. The chromosome of a Campbell-like integrant cell is not stable, because the integrated plasmid is flanked by the homologous sequences that directed the integration. A further homologous recombination event between these sequences leads to excision of the plasmid, and reversion of the chromosome to wild-type. For this reason, it may be necessary to maintain selection for the plasmid-borne selectable marker gene to maintain the integrant clone.

An improvement on the basic single-crossover integration method of chromosomal modification is double crossover homologous recombination, also referred to as allelic exchange, which involves two recombination events. The desired modified allele is placed on a plasmid flanked by regions of homology to the regions flanking the target allele in the chromosome ('homology arms'). A first integration event can occur in either pair of homology arms, leading to integration of the plasmid into the chromosome in the same manner as Campbell-like integration. After the first crossover event, the chromosome contains two alternative sets of homologous sequences that can direct a second recombination event. If the same sequences that directed the first event recombine, the plasmid will be excised, and the cell will revert to wild-type. If the second recombination event is directed by the other homology arm, a plasmid will be excised, but the original chromosomal allele will have been exchanged for the modified allele introduced on the plasmid; the desired chromosomal modification will have been achieved. As with Campbell-like integration, the first recombination event is typically detected and integrants isolated using selective advantage conferred by integration of a plasmid-borne selectable marker gene.

To allow the second recombination event to occur in allelic exchange without detriment to the cell, selection for the plasmid-borne selectable marker gene is typically removed. In the absence of a suitable selection strategy to distinguish cells in which a second recombination event has occurred from cells in which only the first recombination event has occurred, large numbers of clones must typically be isolated and screened for the desired second recombination event, which can be very laborious, even prohibitively so. Such direct selection of double crossovers is routinely practical only in very few organisms, such as the naturally-competent *Bacillus subtilis.*

In certain organisms, the second recombination event can be selected using a counter selection marker. The counter selection marker gene is placed on the plasmid, and is localised to the chromosome by the first recombination event. After removal of selection for the plasmid-borne (positive) selectable marker gene, second recombination events can occur without conferring a selective disadvantage to the cell. A suitable experimental condition which causes a selective disadvantage to cells containing the counter selection marker is then applied. Cells in which the second recombination event has occurred have lost the counter selection marker from their chromosome, and since the plasmid replicates more slowly than the chromosome, some cells will also have lost all copies of the plasmid and therefore all plasmid-borne copies of the counter selection marker. Such cells will have a selective advantage under the counter-selection conditions, and can be isolated in this way. The most widely used counter selection marker in Gram negative bacteria is the sacB gene of *Bacillis subtilis*, the product of which, levan sucrase, confers sucrose sensitivity on a large number of gram negative species (Gay et al (1985) *J Bacteriol* 164:918-921; Simon et al (1991) *J Bacteriol* 173: 1502-1508).

An alternative counter selection marker is the oritidine-5'-monophosphate decarboxylase gene pyrF, which is a homolog of the *Saccharomyces cerevisiae* ura3 gene. Both genes confer sensitivity to fluoroorotic acid. Allelic exchange has been used to replace the pyrF gene in *Mycobacterium smegmatis* by selecting for loss of pyrF from the chromosome in the second recombination event by application of fluoroorotic acid (Knipfer, Seth and Shrader (1997) *Plasmid* 37: 129-140). Where it has been possible to prepare a pyrF− strain, pyrF has been used in the allelic exchange vector in methods of mutating the pyrF− strain (Peck, DasSarma and Krebs (2000) *Mol Microbiol* 35: 667-676; Galvao and de Lorenzo (2005) *Appl Env Microbiol* 71:883-892). As the product of the latter methods is pyrF−, a further mutation could be made in the product strain by the same method. However, such methods are clearly only applicable in pyrF− strains.

In organisms in which no counter-selection marker has been available to select for the second recombination event in allelic exchange, and in which direct selection for the second recombination event has been impracticable, the opportunities for applying double crossover homologous recombination have been very limited. For example, double crossover homologous recombination has hitherto found only very limited application in genetic modification of bacteria of the class Clostridia, although single crossover integration has proved more widely feasible.

The class Clostridia includes the orders Clostridiales, Halanaerobiales and Thermoanaerobacteriales. The order Clostridiales includes the family Clostridiaceae, which includes the genus *Clostridium*. *Clostridium* is one of the largest bacterial genera. It is composed of obligately anaerobic, Gram-positive, spore formers. In recent years, the complete genome sequences of all of the major species of *Clostridium* have been determined from at least one representative strain, including *C. acetobutylicum, C. difficile, C. botulinum* and *C. perfringens*. *C. acetobutylicum*, together with other benign representatives, has demonstrable potential as a delivery vehicle for therapeutic agents directed against cancer. However, the genus has achieved greatest notoriety as a consequence of those members that cause disease in humans and domestic animals, eg, *C. difficile, C. botulinum* and *C. perfringens*. Despite the tremendous commercial and medical importance of the genus, progress either towards their effective exploitation, or on the development of rational approaches to counter the diseases they cause, has been severely hindered by the lack of a basic understanding of the organisms' biology at the molecular level. This is largely a consequence of an absence of effective genetic tools.

Directed gene knock-out using homologous recombination was first demonstrated in the clostridial strain *C. perfringens* strain 13 using replication-deficient suicide vectors carrying a copy of the gene to be inactivated into which was centrally inserted either a tet (Shimizu at al (1994) *Journal of Bacteriology* 176, 1616-23) or an ermBP (Awad at al (1995) *Molecular Microbiology* 15, 191-202) selectable marker. In both cases, the vectors were designed with the intention of achieving reciprocal exchange, however, as only a single selectable marker was used (tet or ermBP), the antibiotic resistance transformants obtained were comprised of both single cross-over (non-mutagenic) and double cross-over integrants (mutagenic). It proved possible to distinguish between the two classes of integrant through the use of a simple phenotypic plate test capable of measuring the activities of the toxin genes being affected by inactivation. The frequency with which virR mutants were obtained was not stated (Shimizu et al (1994) *Journal of Bacteriology* 176, 1616-1623). The number of pfoA mutants isolated represented between 1.9% and 2.8% of the total erythromycin resistant colonies obtained in 3 of 4 experiments, while an unstated number of plc mutants were obtained in only two of ten independent transformation experiments (Awad et al (1995) *Molecular Microbiology* 15, 191-202). These experiments served to illustrate that following transformation with suicide vector constructs, single cross-over, non-mutagenic events are in the majority, but that rarer double cross-over, mutant integrants may be detected through appropriate screening.

In subsequent studies, where a simple phenotypic test for gene inactivation was not available, the plasmid backbone was endowed with a second antibiotic resistance marker (R2), in addition to the antibiotic resistance gene (R1) inserted into the plasmid-borne copy of the gene being targeted. In this instance, single crossover mutants could first be obtained by selecting for acquisition of R1, and then screening for cells in which the plasmid has excised, through homologous recombination, causing loss of R2. Such an excision event can generate both a wild type chromosome and the desired double crossover mutant. This type of strategy was taken to isolate a double crossover mutant of colA in *C. perfringens* strain 13 (Awad et al (2000) *Microbial Pathogenesis* 28, 107-17), cpe mutants of *C. perfringens* strains SM101 and FM4969 (Sarker et al (1999) *Molecular Microbiology* 33, 946-958), a plc mutant of the *C. perfringens* strain EHE-NE18 (Keyburn et al (2006) *Infection and Immunity* 74, 6496-500) and a csa mutant in *C. septicum* (Kennedy et al (2005) *Molecular Microbiology* 57, 1357-66. The frequency of mutant isolation by this method is low, i.e., just 2 cpe mutants were obtained from a total of 360 erythromycin-resistant transformants, which were themselves derived from 30 independent transformations (Sarker et al (1999) *Molecular Microbiology* 33, 946-958).

In perhaps a reflection of the low frequency with which double crossover mutants can be directly selected, other workers have chosen strategies which are designed to specifically create single crossover mutants, e.g., in pfoA (Awad et al (2001) Infection and Immunity 69, 7904-7910), in pfoR (Awad and Rood (2002) *Journal of Bacteriology* 184, 2034-8), luxS and virX (Ohtani et al (2002) FEMS Microbiology Letters 209, 113-8). pfoA and plc mutants in *C. perfringens* strain 13 (O'Brien and Melville (2004) Infection and Immunity 72, 5204-15), pilT and pilC mutants in *C. perfringens* strain 13 (Varga et al (2006) Molecular Microbiology 62, 680-94). In *C. difficile*, the generation of only a handful of single cross-over mutants have been reported. These include the use of a replication-defective suicide vector to generate a gldA mutant in *C. difficile* strain 37 (Liyanage et al (2001) *Molecular Microbiology and Biotechnology* 2, 87-93), and the use of a replication-deficient plasmid to create mutants in two putative response regulators rgaR and rgbR (O'Connor et al (2006) *Molecular Microbiology* 61, 1335-51) and codY (Dineen et al (2007) *Molecular Microbiology* 66, 206-219) of *C. difficile* strain 13. Whilst single crossover mutants can be generated more efficiently than double crossover mutants, they are disadvantaged by being inherently unstable. Thus, Southern blotting of the *C. difficile* rgaR mutant revealed the presence of "looped out", independently replicating plasmid in some cells in the population (O'Connor et al (2006) *Molecular Microbiology* 61, 1335-51), whilst in the absence of antibiotic selection, culture of the codY mutant became dominated by wild-type cells in which excision of the integrated plasmid apparently restored the wild-type gene (Dineen et al (2007) *Molecular Microbiology* 66, 206-219).

The meager number of mutants generated in solventogenic bacteria are similarly confined to single cross-over knockouts. These include the generation of gutD, spo0A, scrB and scrR mutants of *C. beijerinckii* (Wilkinson and Young (1994). Microbiology 140, 89-95; Reid et al (1999) Microbiology 145, 1461-1472) using replication-defective suicide vectors. In *C. acetobutylicum*, essentially five published mutations have been made by homologous recombination. Four (butK, CAC3075; pta, CAC1742; aad, CACP0162, and; solR, CACP061) were made by single cross-over integration of a replication deficient plasmid introduced by electroporation (Green et al (1996) *Microbiology* 142, 2079-86; Green and Bennett (1996) *Appl. Biochem. Biotechnol.* 213, 57-58; Nair et al (1999) *J. Bacteriol.* 181, 319-330), and generally arose at frequencies of 0.8 to 0.9 'colonies' per μg of DNA (Green at al (1996) *Microbiology* 142, 2079-86). As single crossover integrants, these mutants were segregationally unstable, e.g., losses per 30 generations of between 1.8 to $3.0\times10^{-3}$ for buk and pta in *C. acetobutylicum* (Green at al (1996) *Microbiology* 142, 2079-86). This compares to between 0.37 to $1.3\times10^{-3}$ for *C. beijerinckii* (Wilkinson and Young (1994). Microbiology 140, 89-95).

In a more recent study, Harris and coworkers (Harris et al (2002) *J. Bacteriol.* 184, 3586-3597) attempted a similar strategy to the double cross-over strategy of Sarker and coworkers (Sarker at al (1999). Mol. Microbiol. 33, 946-581999). The pIM13-based plasmid used (pETSPO) carried a chloramphenciol resistance gene and a knock-out cassette in which ermB interrupted the spo0A gene. Following successive subculturing of a transformant in media lacking thiamphenicol, an erythromycin resistant spo0A mutant was isolated. However, the expected double crossover event had not occurred, rather, a crossover event had occurred between two 10-nt homologous sequences (5'-ACGACCAAAA-3' (SEQ ID NO:1)) that were present in the 3' end of the pIM13 repL structural gene and upstream of ermB. Loss of the 3-kb fragment between these homologous sequences resulted in inactivation of spo0A through insertion of a 2.1-kb fragment containing ermB.

The listing or discussion of a prior-published document in this specification should not necessarily be taken as an acknowledgement that the document is part of the state of the art or is common general knowledge.

The inventors have devised a method of double crossover homologous recombination in a host cell in which the second homologous recombination event itself generates a selectable allele. This allows for a wider application of double crossover homologous recombination than has hitherto been possible. For example, the method can be employed without the use of counter selection. It can be employed without the need to first create a mutant host cell. In a particular embodiment, neither initial mutation of the host cell nor counter selection are required.

A first aspect of the invention provides a method of double crossover homologous recombination in a host cell comprising:

a first homologous recombination event between a donor DNA molecule comprising a first element of a selectable allele and an acceptor DNA molecule comprising a second element of the selectable allele in the host cell, thereby to form a product of the first homologous recombination event in the host cell; and a second homologous recombination event within the product of the first homologous recombination event, thereby to form a product of the second homologous recombination event in the host cell which confers a selectable phenotype on the host cell, wherein the selectable phenotype arises following and in dependency on the formation of a selectable allele from the first and second elements of the selectable allele.

The donor DNA molecule may be any DNA molecule suitable for use in double crossover homologous recombination. Typically, the acceptor DNA molecule is a chromosome of the host cell, although it may be some other DNA molecule, for example episomal DNA such as a plasmid, or artificial chromosome. The product of the first homologous recombination event is a single crossover integrant of the donor DNA molecule into the acceptor DNA molecule. The product of the first crossover event may not be uniform, but may comprise different molecular species depending on the location at which the donor DNA molecule integrated into the acceptor DNA molecule. Nevertheless, it may not be necessary to select between different first recombination products. It may be that the different molecular species in the product of the first recombination event can give rise to the desired product of the second recombination event. This possibility is illustrated in Example 4 and FIG. 6A. Even in situations in which not all possible molecular species in the product of the first recombination event can give rise to the desired product of the second recombination event, it may be that undesired products occur so rarely that it is not necessary to select against them. This possibility is illustrated in Example 1 and FIG. 2.

A selectable allele is formed from the first and second elements of the selectable allele, which confers a selectable phenotype on the host cell in which the product of the second homologous recombination event is formed. The first element of the selectable allele is initially located on the donor DNA molecule and the second element on the acceptor DNA molecule. Prior to the second recombination event, the host cell has not acquired the selectable phenotype. The selectable phenotype arises following and in dependency on the formation of the selectable allele from its first and second elements. In other words, the formation of the selectable allele is necessary for the selectable phenotype to arise. However, the formation of the selectable allele may not be sufficient for the selectable phenotype to arise. An additional condition fulfilled by the second recombination event may also be required.

Typically, the method comprises a second homologous recombination event within the product of the first homologous recombination event which forms a selectable allele from the first and second elements of the selectable allele, thereby to form a product of the second homologous recombination event in the host cell, wherein the selectable allele confers a selectable phenotype on the host cell. Typically, the cell has not acquired the selectable phenotype prior to the second recombination event because the first and second elements do not confer the selectable phenotype until they are operably linked by the second recombination event. Such operable linkage may be achieved by the bringing together of two parts of a gene so as to form a complete gene. The two parts may be made contiguous when operably linked. This possibility is illustrated in Example 1 and FIG. 2. Alternatively, for example if one element is a regulatory region of a gene, and the other element is in the coding region of the gene, the two parts may not be contiguous, but are nevertheless operably linked. This possibility is illustrated in Example 6 and FIGS. 8 and 9.

Alternatively, the two elements of the selectable allele may become operably linked in the first recombination event, but the cell has not acquired the selectable phenotype because of the dominant effect of an element present in the product of the first recombination event, which is lost in the second recombination event. This dominant effect suppresses the phenotype that would be conferred by the selectable allele. The cell then acquires the selectable phenotype in the second recombination event, due to the loss of the dominant element. This may occur, for example, where the selectable allele is a partial version of a gene, and its effect is recessive to the full version of the gene. The selectable allele may be formed in the first recombination event, but the presence of the full version of the gene prevents the selectable allele from conferring the selectable phenotype. In such an embodiment of the invention, the elements of the selectable allele may be arranged in the product of the first recombination event such that, were it not for the presence of a functional gene in the product of the first recombination event, the elements of the selectable allele would confer the selectable phenotype. However, only in the second homologous recombination event is this functional gene removed or disrupted, and so only in the second homologous recombination event does the selectable allele confer the selectable phenotype. This possibility is illustrated in Example 4 and FIG. 6A.

The selectable allele may be any suitable selectable allele which can be used to select a host cell. A selectable allele may provide for positive selection by being expressed in the host cell and conferring a selective advantage on the host cell in which the selectable allele is expressed, compared to the host cell in which it is not expressed. Such a selectable allele allows for expression of a selectable marker. Suitable selectable markers include enzymes that detoxify a toxin, such as certain antibiotic resistance enzymes or prodrug-converting enzymes. Selectable markers also include a prototrophic gene (for use in a corresponding auxotrophic mutant).

Preferably, the selectable marker is one which gives a growth advantage to the host cell in which it is expressed. Thus, typically, under a given growth condition the host cell which expresses the selectable marker is able to grow (or grow more quickly) compared to an equivalent cell that does not express the selectable marker. The person of skill in this art can readily choose a selectable marker for use with a given host cell.

The selectable allele may alternatively provide for counter selection. In this situation, its presence in the host cell is linked to the loss of a counter selection marker in the host cell, as a consequence of the second recombination event. Preferably, under a given growth condition, the host cell which expresses the counter selection marker dies, whereas the host cell which does not express the counter selection marker survives. Alternatively, the host cell which expresses the counter selection marker may grow more slowly than the host cell which does not.

As an alternative to using differential growth or survival of a host cell as an indicator of the presence or absence of the selectable allele, a change in a different aspect of phenotype may be used. For example, a selectable allele may cause expression (or lack of expression) of a marker which changes the visual properties of the host cell. Suitably, a change in colour may arise in the presence of a chromogenic substrate.

Preferably, in the method of the first aspect of the invention, the donor DNA molecule comprises at least two homology arms, one homology arm providing for homologous recombination with the acceptor DNA molecule at a first site upstream of the first element of the selectable marker allele, and one homology arm providing for homologous recombination with the acceptor DNA molecule at a second site downstream of the first element of the selectable marker allele; and the acceptor DNA molecule comprises homology arms corresponding to the homology arms of the donor DNA molecule and the second element of the selectable marker allele is located upstream of the first site or downstream of the second site.

Homology arms provide for homologous recombination between the donor DNA molecule and the acceptor DNA molecule in the first recombination event, and within the product of the first recombination event in the second recombination event. The extent of homology between corresponding homology arms must be sufficient to allow homologous recombination to occur. Factors affecting whether homologous recombination can occur are the sequence identity between the corresponding homology arms and the base-pair size of the homology arms. Typically, at least 85% sequence identity is required between corresponding homology arms for homologous recombination to occur. Preferably, the sequence identity is at least 90%, more preferably at least 95%, still more preferably at least 98% and most preferably 100%. Typically, the size of each homology arm is at least 10 bp, more typically at least 20 bp, at least 40 bp, at least 75 bp, at least 100 bp, at least 200 bp, or at least 300 bp. There is no particular upper limit for the size of the homology arm although in practice this may be governed by the size of the donor DNA molecule, which must have at least two homology arms. A homology arm could be as large as 1 kb, or up to 2 kb, up to 5 kb, up to 10 kb, even up to 50 kb, 100 kb, 1 Mb, 5 Mb or 10 Mb.

As noted above, the product of the first recombination event may not be uniform, but may comprise different molecular species depending on the location at which the donor DNA molecule integrated into the acceptor DNA molecule. Each homology arm in the donor DNA molecule has a corresponding homology arm in the acceptor DNA molecule. The homology arm in the donor DNA molecule and the corresponding homology arm in the acceptor DNA molecule can be considered to be a pair.

The first recombination event may occur by homologous recombination in either the first pair of homology arms, or the second pair of homology arms. Thus, typically, in some host cells the homologous recombination occurs at the first pair of homology arms and in others homologous recombination occurs at the second pair of homology arms, such that different molecular species of DNA are formed by the first recombination event. Both pairs of homology arms are present in the product of the first recombination event.

If a second recombination event occurs between the same pair of homology arms in which the first recombination event occurred, the donor DNA molecule will be recombined out, and the acceptor DNA molecule will be restored to its original form. In contrast, the desired product of the second recombination event is formed by homologous recombination between the pair of homology arms that did not recombine in the first recombination event. Thus, although both homology arms of the donor DNA molecule can provide for homologous recombination with the acceptor DNA molecule, it is to be understood that, for any particular donor DNA molecule, only one homology arm will homologously recombine with the acceptor DNA molecule, and the other homology arm will homologously recombine intramolecularly in the product of the first recombination event.

In particular embodiments, there may be more than two pairs of homology arm, for example there may be three pairs of homology arms. As in the case where there are two pairs of homology arms, only one homology arm will homologously recombine with the acceptor DNA molecule, and another homology arm will homologously recombine intramolecularly in the product of the first recombination event.

One homology arm of the donor DNA molecule provides for homologous recombination with the acceptor DNA molecule at a first site upstream of the first element of the selectable allele, and one homology arm provides for homologous recombination with the acceptor DNA molecule at a second site downstream of the first element of the selectable allele. By stating that a region is upstream of another region we mean that it appears earlier in 5' to 3' order relative to a given strand (leading or trailing) of the DNA molecule.

It will be understood that when a pair of homology arms undergo homologous recombination, the exact site of homologous recombination is unpredictable. If the pair are identical in DNA sequence, the products of homologous recombination are also identical in sequence, even though the exact site at which the integration occurs is unknown.

If a homology arm is completely upstream (or downstream) of the first element of the selectable allele, then homologous recombination at that homology arm does not cause recombination within the first element of the selectable allele. However, the first element of the selectable allele may alternatively overlap with the homology arm. In that case, the recombination event itself will define the limit of the first element of the selectable allele. For example, where the homology arm provides for homologous recombination at a first site upstream of the first element of the selectable allele, and the first element is overlapping with the homology arm, the site of recombination defines the 5' end of the first element. In such a case, the same recombination event also defines the 3' end of the second element of the selectable allele, when the two elements are brought together. In this instance, the second element of the selectable allele also overlaps with a homology arm. Whether or not there is an overlap, the second element of the selectable allele is located upstream of the first site at which homologous recombination may occur with the donor DNA molecule or downstream of the second site at which homologous recombination may occur with the donor DNA molecule. The formation of a selectable allele from first and second elements located in homology arms is illustrated in FIG. 1.

As discussed above, the acceptor DNA molecule of the host cell is modified by the method of the first aspect of the invention by the generation therein of a selectable allele. This aspect may provide for additional modification to the acceptor DNA molecule. Preferably, the donor DNA molecule comprises cargo DNA, and the cargo DNA is included in the product of the first recombination event and retained in the product of the second recombination event. In this way, cargo DNA may be stably introduced into the acceptor DNA molecule. Preferably, the cargo DNA is located in the donor DNA molecule downstream of the first site and upstream of the second site. In this arrangement, the donor DNA can be inserted between the homology arms of the acceptor DNA molecule. Cargo DNA may be selected to confer a desirable phenotype on the host cell, such as ability to express a particular protein. There is no particular limitation on the selection of the cargo DNA. Where the cargo DNA is included in the product of the first recombination event and retained in the product of the second recombination event, the second recombination event occurs either completely upstream or completely downstream of the cargo DNA. Therefore, the region of DNA excised during the second recombination event is independent of the cargo DNA. Thus, the size of the cargo DNA will have no effect on the size of the region of DNA excised during the second recombination event. However large the cargo DNA, the efficiency of the second recombination event should be unaffected. There is no particular limit to the size of the cargo DNA although, in practice, this will be limited by the size of the donor DNA molecule. Depending on the host cell, there may be a practical limit to the size of the donor DNA molecule that can be introduced. For example, in certain Clostridia, transformation of plasmids is poorly efficient and efficiency is reduced when the size of the plasmid is increased. The skilled person can readily determine experimentally an upper limit for the size of the cargo DNA, which may vary depending on the host cell and the donor DNA molecule. Suitably, cargo DNA of at least 1 bp may be introduced, preferably at least 1, 2, 3, 4, 5, 10, 15, 20, 50, 100, 1000, 10,000, 100,000 or 1,000,000 kb.

Cargo DNA may comprise genes or other genetic material from the same genus as the host cell, or from a different genus. Cargo DNA may also be entirely synthetic, or any combination of synthetic and natural genetic material. Genes may function in, for example, a catabolic pathway or a biosynthetic pathway.

Preferably, in the method of the first aspect of the invention, the donor DNA molecule comprises a selectable marker gene and the first recombination event confers a selectable phenotype on the host cell, based on the incorporation of the selectable marker gene into the product of the first homologous recombination event. The use of a selectable marker to select for the first recombination event is typical in methods of allelic exchange and the skilled person can readily identify a suitable marker. Suitable selectable marker genes encode resistance to antibiotics (eg., to tetracycline, erythromycin, neomycin, lincomycin, spectinomycin, ampicillin, penicillin, chloramphenciol, thiamphenicol, streptinomycin, kanamycin, etc), chemicals (eg., herbicides), heavy metals (eg., cadmium, mercury, selenium, etc.) and other agents (eg., UV, radiation), as well as genes that complement chromosomal defects in the recipient organism (eg., leuD, murA, manA). Typically the selectable marker gene confers a growth or survival advantage on the host cell in which the first recombination event has occurred. Preferably, the selectable marker gene is not retained in the product of the second recombination event. Suitably, this may be achieved by locating the selectable marker gene in the donor DNA molecule upstream of the homology arm providing the first site, or downstream of the homology arm providing the second site.

Preferably, in the method of the first aspect of the invention, the selectable allele is either:

(i) a gene which can confer either a selective advantage or a selective disadvantage on the host cell as compared to a host cell lacking the selectable allele, depending on the conditions in which the host cell is maintained; or (ii) a disrupted or partial form of such a gene, which does not confer the selective advantage or the selective disadvantage conferred by the gene.

Where the selectable allele is a gene as defined above, an experimental condition can be applied in order to positively select for the presence of the selectable allele in the host cell. Disrupted or partial forms of the gene do not confer the selective advantage, and so host cells carrying such forms are not selected. Alternatively, where the selectable allele is a disrupted or partial form of the gene as defined above, and a different experimental condition is applied, host cells carrying the full gene are counter selected because they have a selective disadvantage in the experimental condition. As yet, few genes are known which can act as both positive selection and counter selection markers. However, certain genes involved in pyrimidine biosynthesis may be used. Suitably, the selective advantage conferred by a gene is uracil prototrophy and the selective disadvantage is sensitivity to fluoroorotic acid. A preferred gene is the highly conserved (Radford and Dix (1988) *Genome* 30, 501-505) pyrF gene (encoding orotidine 5'-monophosphate decarboxylase) or a homologue thereof, e.g., ura3. The pyrE (encoding orotate phosphoribosyltransferase), or other genes involved in the same metabolic pathway, even if not yet known, might also be used. Indeed, the steps involved in pyrimidine biosynthesis occur nearly universally in all organisms, e.g., mammals (Evans and Guy (2004) *Journal of Biological Chemistry* 279, 33035-33038), plants (Boldt and Zrenner (2003) *Physiologia Plantarum* 117, 297-304), yeast (Denis-Duphil (1989) *Biochemistry and Cell Biology* 67, 612-631), filamentous fungi (Aleksenko et al (2003) *Physiologia Plantarum* 117, 297-304), Gram-positive bacteria (Kilstrup et al (2005) *FEMS Microbiology Reviews* 29, 555-590), Gram-negative bacteria (West (1997) *Antonie van Leeuwenhoek,* 72, 175-181) and Archeae (Toshiaki et al (2005) *Genome Research* 15, 352-363).

Positive selection and counter selection may alternatively be based on the thymidylate synthase A (thyA) gene, which is involved in the de novo synthesis of dTTP from dUMP (Wong et al (2005) *Nucleic Acids Res* 33: e59). A thyA mutant cell is unable to grow in growth media in the absence of thymine. Thus, the presence of the thyA gene can be positively selected for by culture in growth medium in the absence of thymine. A thyA mutant cell is, however, able to grow in growth media containing thymine and trimethoprim, whereas a cell expressing thyA is unable to grow in such conditions. Thus, thyA acts as a counter selection marker in growth media containing thymine and trimethoprim. Such a selective system may be used in any organism, provided it is sensitive to trimethoprim, eg., in Gram-positive bacteria (Kiel et al (1995) *Applied and Environmental Microbiology* 61, 4244-4250) or Gram-negative bacteria (Wong et al (2005) *Nucleic Acids Research* 33: e59).

In an alternative preferred embodiment, the selectable allele confers a selective advantage on the host cell, and may be, for example, an antibiotic resistance gene. A skilled person in this field can readily select an appropriate selectable allele. Where a selectable marker is to select for the first recombination event, clearly a selectable allele which confers a different phenotype on the host cell than does that selectable marker is required.

Optionally, the method of the first aspect of the invention comprises a step following the first recombination event, of selecting the host cell in which the selectable phenotype has not been conferred by the product of the first recombination event. As discussed above, the product of the first recombination event may comprise different molecular species depending on the location at which the donor DNA molecule integrated into the acceptor DNA molecule. In order to select for the second recombination event, the selectable phenotype should be conferred by the second recombination event. Where the selectable phenotype is conferred by the first recombination event, it is not feasible to select for the second recombination event by virtue of the phenotype conferred by the selectable marker. Accordingly, it may be desirable to select only host cells in which the selectable phenotype has not been conferred by the first recombination event. Typically, clones derived from individual host cells are tested under selective and non-selective conditions. Where a clone is able to grow under selective conditions, the selectable phenotype has already been conferred. Such a clone is rejected. Where a clone is unable to grow under selective conditions, the selectable phenotype has not yet been conferred. The same clone grown under non-selective conditions may therefore be chosen for the second recombination step. Typically, the donor DNA molecule comprises a selectable marker gene which is not retained in the second recombination event. Under such circumstances, it is convenient to test clones of host cells for the selectable phenotype under conditions which select for the presence of the selectable marker gene.

As noted above, even if the first recombination event can produce different products depending on where the donor DNA molecule integrated into the acceptor DNA molecule, and not all such products can lead to the generation of the selectable phenotype in the second recombination event, it may be not be necessary to select against host cells in which the selectable phenotype has been conferred in the first recombination event. Instead it may be possible to favour the first recombination event occurring at a desired pair of homology arms, such that the selectable phenotype is not conferred by the first recombination event. This can be achieved by making the desired homology arm in the donor DNA molecule longer than the other homology arm or arms in the donor DNA molecule. For example, in Example 1, the length of the homology arm at which the first recombination event was sought was 1200 bp. Other homology arms in the donor DNA molecule were 300 bp and 500 bp. The first recombination event occurred more prevalently at the 1200 bp pair of homology arms.

Preferably, the method of the first aspect of the invention comprises the further step of isolating the host cell comprising the product of the second homologous recombination event by virtue of the altered phenotype conferred by the selectable allele, so as to provide an altered isolated host cell. Thus, the invention provides a method of producing an altered host cell, the method comprising providing a host cell and carrying out the aforesaid method.

The invention therefore includes an altered host cell obtained by the method.

Preferably, following isolation of the host cell comprising the product of the second homologous recombination event, the product is modified in the host cell so as to generate a new first element of a selectable allele in the altered isolated host cell. The method of the first aspect of the invention may be applied to the altered isolated host cell comprising such a modified DNA product, using an appropriate donor DNA molecule so as to generate a selectable phenotype in the second recombination step. This further application of the method can be considered a further iteration. Thus, the method of the first aspect of the invention may further comprise subjecting the altered isolated host cell to a method of double cross over homologous recombination of the first aspect of the invention. The selectable phenotype and allele may be the same or different to the selectable phenotype and allele used in the first iteration. Where it is the same, the first and second elements may nonetheless be different in the second iteration than in the first. Such iterative use of the method of the first aspect can be used, for example, to iteratively add cargo DNA to the acceptor DNA molecule of the host cell.

A second aspect of the invention provides a method of iteratively inserting cargo DNA into an acceptor DNA molecule in a host cell comprising:

(i) inserting a first cargo DNA into the acceptor DNA molecule by the method of double crossover homologous recombination between a first donor DNA molecule and an acceptor molecule of the first aspect of the invention, thereby forming in the host cell a product of the second homologous recombination event comprising a selectable allele and the first cargo DNA, wherein the selectable allele can confer a selective advantage on the host cell;

(ii) isolating the host cell by virtue of the altered phenotype conferred by the selectable allele;

(iii) disrupting the selectable allele so that it does not confer the selective advantage on the host cell, so as to form in the host cell a modified acceptor DNA molecule;

(iv) inserting a second cargo DNA into the modified acceptor DNA molecule by the method of double crossover homologous recombination between a second donor DNA molecule and the modified acceptor molecule of the first aspect of the invention, thereby forming in the host cell a further modified acceptor DNA molecule comprising the selectable allele, the first cargo DNA and the second cargo DNA. This aspect of the invention is illustrated in Example 2.

The second aspect of the invention comprises the iterative use of the method of the first aspect of the invention, in which the first iteration is performed as step (i) and the second iteration is performed as step (iv). Preferably, the method further comprises isolating the host cell comprising the further modified acceptor DNA molecule by virtue of the altered phenotype conferred by the selectable allele. It will be apparent to the skilled person that, as the DNA product of the second iteration comprises the same selectable allele as the DNA product of the first iteration, the host cell comprising the DNA product of the second iteration may be selected as in step (ii), the selectable allele disrupted as in step (iii), and a further iteration of the method applied. A third, fourth, fifth or sixth iteration may be applied. There is no particular limit to the number of iterations that may be applied. With each iteration, further cargo DNA is added to the DNA product of the preceding iteration. The advantage of iterative use is that the quantity of cargo DNA that can be inserted is limited only by the capacity of the acceptor DNA molecule, typically a chromosome, which must be replicated in order for the host cell to be propagated. Thus, if in a particular combination of host cell and donor DNA molecule, it is feasible to introduce 100 kb of DNA in a single iteration, but it is impracticable to introduce 200 kb, the method may be used iteratively to introduce 200 kb. In the first iteration, 100 kb is introduced and in the second iteration, a further 100 kb is introduced. In this way, it may be possible to build up larger quantities of DNA in iterative use of the method than can be done in a single use of the method. This may be of importance when introducing large numbers of genes into the host organisms, for example to allow for new biosynthetic activities.

In the method of the first aspect of the invention, disruption of the selectable allele in step (iii) may be achieved by any method appropriate for the particular host cell. The selectable allele may be disrupted by partial deletion or by insertional disruption, with the proviso that a second element of the selectable allele remains intact, so as to allow for the re-formation of the selectable allele in the host cell during the second iteration of the method. Targeted insertional disruption may be more convenient. For example, a method which relies on the insertion of a mobile genetic element may be used. The Group II intron Ll.LtrB of *Lactococcus lactis* is an element that mediates its own mobility through the action of an intron-encoded reverse transcriptase (LtrA) and the excised lariat RNA, which may be re-targeted to virtually any desired DNA sequence through modification of the intron RNA (Guo of al (2000) *Science* 289: 452-457; Mohr et al (2000) *Genes Dev.* 14: 559-573). A kit for performing gene knockouts (principally in *E. coli*) in which retrotransposition of the Ll.LtrB element is selected for based on acquisition of kanamycin resistance is marketed as "TargeTron™ Gene Knockout System" by Sigma-Aldrich. Methods in which there is no selection for retrotransposition, or in which selection is achieved by acquisition of a different resistance phenotype may also be used (Yao et al (2006) *RNA* 12: 1-11; WO 2007/148091 to Morvus Technology Limited). A mutant may also be derived using a random approach, through the use of a genetic element (eg., a transposon such as Tn5 or Tn10), a chemical mutagen (nitrosoguanidine or ethyl methanesulfonate) or other agent, eg., Ultra Violet Light.

Preferred or optional features of each iteration of the method of the first aspect of the invention are as described above in relation to the first aspect of the invention.

A third aspect of the invention provides a method of iteratively inserting cargo DNA into an acceptor DNA molecule in a host cell comprising:

(i) inserting a first cargo DNA into the acceptor DNA molecule by the method of double crossover homologous recombination between a first donor DNA molecule and an acceptor molecule of the first aspect of the invention, thereby forming in the host cell a modified acceptor DNA molecule comprising a first selectable allele and the first cargo DNA;

(ii) isolating the host cell by virtue of the altered phenotype conferred by the first selectable allele;

(iii) inserting a second cargo DNA into the modified acceptor DNA molecule by the method of double crossover homologous recombination between a second donor DNA molecule and the modified acceptor molecule of the first aspect of the invention, thereby forming in the host cell a further modified acceptor DNA molecule comprising a second selectable allele, the first cargo DNA and the second cargo DNA, wherein the second selectable allele confers a different altered phenotype on the host cell than the first selectable allele. This aspect of the invention is illustrated by Examples 3, 4, 5 and 6, and FIGS. 5, 6, 7, 8 and 9.

As in the method of the second aspect of the invention, the method of the third aspect allows iterative insertion of cargo DNA into the acceptor DNA molecule in the host cell, by repeated use of the method of the first aspect. The preferred or optional features of each iteration of the method of the first aspect of the invention are as described above in relation to the first aspect of the invention. However, preferred features of the selectable alleles are as described below.

The method of the third aspect of the invention comprises two iterations of the method of the first aspect. The product of the first iteration is selected for by a first selectable allele and the product of the second iteration is selected for by a second selectable allele.

In a preferred scheme, one of the first or second selectable alleles is a gene which can confer either a selective advantage or a selective disadvantage on the host cell as compared to a host cell lacking the selectable allele, depending on the conditions in which the host cell is maintained; and the other of the first or second selectable alleles is a disrupted or partial form of such a gene, which does not confer the selective advantage or the selective disadvantage conferred by the gene. This aspect of the invention is illustrated by Examples 3, 4, and 5 and FIGS. 5, 6, and 7.

Where the first selectable allele is such a gene as described above, the acquisition of the first selectable allele can be positively selected for in the first iteration. In the second iteration, the first selectable allele is lost or disrupted and the second selectable allele is formed in the second homologous recombination event, so as to confer a selectable phenotype on the host cell. Counter selection conditions are applied to select for this second selectable allele. If the host cell has retained the first selectable allele (but does not have the second selectable allele) it is at a selective disadvantage compared to the cell that has lost the first selectable allele (and acquired the second selectable allele).

Alternatively, the first selectable allele is the partial or disrupted form of the gene as described above. In this situation, counter selection is applied in the first iteration to select for the loss of the gene in the second recombination event and the acquisition of the first selectable phenotype. In the second iteration, the second selectable marker is the gene and its acquisition is positively selected for in the second recombination event.

Preferably, in this mode of the third aspect of the invention, the selective advantage is uracil prototrophy and the selective disadvantage is sensitivity to fluoroorotic acid. Suitably, the gene is pyrF or a homologous gene. Other suitable genes and conditions for use in positive and counter selection are as described above.

In this scheme, where positive selection is applied in the first iteration, counter selection is applied in the second iteration. Conversely, where counter selection is applied in the first iteration, positive selection is applied in the second iteration. It will be apparent that the method can be applied in more than two iterations. Thus the selection applied in the first iteration can be applied in a third, fifth and seventh iteration and so on. The selection applied in the second iteration can be applied in a fourth, sixth and eighth iteration and so on. Accordingly, in a preferred embodiment, the method further comprises isolating the host cell comprising the further modified acceptor DNA molecule by virtue of the altered phenotype conferred by the second selectable allele. The host cell, thus isolated, may be used in further iterations of the method. In particular, the method may further comprise inserting a third cargo DNA into the further modified acceptor DNA molecule by the method of double crossover homologous recombination between a third donor DNA molecule and the further modified acceptor DNA molecule of the first aspect of the invention, thereby forming in the host cell a modified acceptor DNA molecule comprising the first selectable allele, the first cargo DNA, the second cargo DNA and the third cargo DNA.

In another preferred scheme, the first and second selectable alleles do not undergo homologous recombination. In other words, the first and second elements of these alleles are not located on homology arms. Typically, they each confer a different selective advantage on the host cell. Preferably, they each confer resistance to a different antibiotic on the host cell.

In the first iteration, selection is applied to select for the first selectable allele. In the second iteration, selection is applied to select for the second selectable allele. In a particularly preferred embodiment, the first selectable allele is not retained in the product of the second recombination event in step (iii) i.e. of the second iteration. This may be achieved by locating the homology arms in the modified acceptor DNA molecule at either side of the first selectable allele. In other words, the homology arms of the donor DNA molecule are chosen to correspond to a region upstream and a region downstream of the first selectable allele. Preferably, the method further comprises isolating the host cell comprising the further modified acceptor DNA molecule by virtue of the altered phenotype conferred by the second selectable allele, so as to provide an altered isolated host cell. Thus, the invention provides a method of producing an altered host cell containing cargo DNA, the method comprising providing an isolated altered host cell according to the aforesaid method.

It will be apparent that where the DNA product of the second iteration does not retain the first selectable allele, a further iteration may be performed and the second recombination event selected for by acquisition of the first selectable marker. Accordingly, the method preferably further comprises inserting a third cargo DNA into the further modified acceptor DNA molecule by the method of double crossover homologous recombination between a third donor DNA molecule and the further modified acceptor DNA molecule of the first aspect of the invention, thereby forming in the host cell a modified acceptor DNA molecule comprising the first selectable allele, the first cargo DNA, the second cargo DNA and the third cargo DNA. In this third iteration, the donor DNA molecule can be designed such that the second selectable allele is not retained in the product of the second recombination event. Thus the DNA product of the third iteration may be used as the substrate of a fourth iteration. There is no particular limit to the number of iterations that may be performed. Where the first selectable allele is used as the basis of selection in the first iteration, it may be used in a third, fifth and seventh iteration and so on. The second selectable allele may be used as the basis of selection in a second, fourth, sixth and eighth iteration and so on.

Preferably, in the method of each of the first, second and third aspects of the invention, the host cell is a prokaryote. The method is equally applicable in Gram positive and Gram negative bacteria. Suitably, the host cell is a Gram positive bacterium, such as a bacterium of the class Clostridia and preferably of the genus *Clostridium*. Suitable species of the genus *Clostridium* include *C. acetobutylicum, C. cellulolyticum, C. phytofermentans, C. thermocellum, C. beijerinckii, C. saccharobutylicum* and *C. saccharoperbutylacetonicum, C. difficile, C. botulinum, C. sporogenes, C. butyricum*, and *perfringens*. Another preferred species of the class Clostridia is *Thermoanaerobacterium saccharolyticum*. The host cell may alternatively be a bacterium of the class Bacilli, particularly of the order Bacillales, more particularly of the family Bacillaceae, still more particularly of the genus *Bacillus*. A suitable host cell of the genus *Bacillus* is *B. stearothermophilus*.

Alternatively, the host cell is a eukaryote, and particularly a yeast or filamentous fungus. The eukaryotic host cell may be haploid or diploid. *Saccharomyces cerevisiae* and *Schizosaccharomyces pombe* are particularly preferred yeasts. Alternative preferred host cells are plant cells or mammalian cells.

Preferably, in the method of each of the first, second and third aspects of the invention, the acceptor DNA molecule is a chromosome.

A fourth aspect of the invention provides a method of designing and making a donor DNA molecule for inserting a cargo DNA into an acceptor DNA molecule of a host cell by the method of the first aspect of the invention comprising:

(i) selecting a region of the acceptor DNA molecule into which the cargo DNA is to be inserted, wherein the acceptor DNA molecule comprises a second element of a selectable allele, downstream of or overlapping with the second element of the selectable allele a first acceptor homology arm and downstream of the first acceptor homology arm a second acceptor homology arm;

(iii) constructing the donor DNA molecule so as to comprise a first donor homology arm which is homologous to the first acceptor homology arm, a first element of the selectable allele overlapping with or downstream of the first donor homology arm, the cargo DNA downstream of the first element of the selectable allele, a second homology arm which is homologous to the second acceptor homology arm downstream of the cargo DNA, and a selectable marker gene upstream of the first donor homology arm or downstream of the second donor homology arm;

wherein when appropriately combined in a single DNA molecule, the first and second elements of the selectable allele are able to confer a selectable phenotype on the host cell.

Any convenient region of the acceptor DNA molecule may be selected for insertion of the cargo DNA, provided that the region contains an element which can act as the second element of the selectable allele. Such an element may be a promoter, for example where the coding region forms the first element of the selectable marker. Typically, the promoter is already present in the acceptor DNA molecule. Alternatively, the second element may comprise part of a coding region of a gene. A suitable acceptor DNA molecule may have been engineered using the methods of molecular biology. For example, where the second element is a part of a coding region of a gene, the gene may have been disrupted in order that it does not confer the selectable phenotype within the host cell. Typically, the DNA sequence of the region of acceptor DNA molecule is known.

Methods of constructing donor DNA molecules are well known in the art. DNA molecules of the invention may be made using standard molecular biological techniques as described in Sambrook et al, "Molecular cloning: A laboratory manual", 2001, 3rd edition, Cold Spring Harbor Laboratory Press, Cold Spring Harbor, N.Y. Components of the donor DNA molecule may be pieced together by standard restriction enzyme cloning or SOEing PCR. Where large regions of DNA are required as cargo DNA, gene synthesis may be used. Gene synthesis has the added advantage of allowing codons to be optimised for expression in the desired host cell, such as *C. acetobutylicum*, while at the same time enabling elements to be designed which are devoid of restriction enzyme sites important in component construction. A suitable general strategy of gene synthesis is 'BioBrick assembly' (http://openwetware.org/wiki/Synthetic_Biology:BioBricks).

Preferably, in the method of the fourth aspect of the invention, the first or second donor homology arm is of sufficient extent and comprises sufficient homology with a pyrF gene or homologue thereof that the donor DNA molecule is capable of undergoing homologous recombination with a DNA molecule comprising the pyrF gene or homologue thereof. Preferably, the pyrF gene is a pyrF gene of a *Clostridium.*

Preferably, in the method of any of the first, second, third or fourth aspects of the invention, the donor DNA molecule is a plasmid, particularly a non-replicative plasmid, a replication-defective plasmid or a conditional plasmid. Alternatively, the DNA may be linear or it may be filamentous phage like M13. The skilled person can readily select a donor DNA molecule, such as a plasmid, which is suitable for use with a given host cell.

A non-replicative plasmid would include those plasmids which do not carry 'machinery' able to support the autonomous replication of the plasmid in the intended recipient host. Such suicide vectors designed for use in a Gram-positive host would include, for instance, plasmids based on the ColE1 replicon, but which lack replication functions derived from Gram-positive plasmids (eg., pMTL30, Wilkinson and Young (1994). Microbiology 140, 89-95).

A replication-defective plasmid would carry replication functions that function only inefficiently in the intended recipient host. Such plasmids would be characterised by their segregational instability in the intended host in the absence of any form of selective pressure. For instance, where such a plasmid carries a gene encoding antibiotic resistance, and cells are grown in media lacking that antibiotic, daughter cells would arise which have not received a replicative copy of that plasmid. Moreover, in the presence of the antibiotic, the growth rate of the cell population as a whole will be reduced, due to ineffective segregation of the antibiotic resistance gene. Many Gram-positive/*E. coli* shuttle vectors replicate poorly in their intended host. For instance, the majority of clostridial plasmids are segregationally unstable (Minton of al (1993) In "The Clostridia and Biotechnology", ed. D R Woods, pp. 119-150, Butterworths-Heinemann), including plasmids based on the pIM13 replicon (Hams et al (2002) *J. Bacteriol.* 184, 3586-3597) and pIP404 and pCB102 (Purdy et al (2002) *Molecular Microbiology* 46, 439-52). Plasmids that replicate via a single-stranded deoxyribonucleic acid (ssDNA) intermediate by a rolling-circle mechanism are the most common family of Gram-positive plasmid. Vectors based on such plasmids are frequently segregationally unstable (Gruss and Ehrlich (1989) *Microbiol Mol Biol Rev* 53, 231-241). Other plasmids may be deliberately engineered to possess the required instability, such as the frame shift introduced into the repH gene of the pCB102 replicon (Davis (1998) "Regulation of botulinum toxin complex formation in *Clostridium botulinum", PhD Thesis Open University*).

Conditional vectors represent those plasmids that cannot replicate under defined, non-permissive conditions. Examples of such vectors for *E. coli* include ColE1-derived plasmids, which do not replicate in polA mutants (Gutterson and Koshland (1983) *Proc Natl Acad Sci USA.* 80, 4894-4898; Saarilahti and Palva (1985) *FEMS Microbiol Lett.* 26, 27-33), a temperature-sensitive pSC101 replicon (Hamilton et al (1989) *J Bacteriol* 171, 4617-4622), and a phagemid-based vector (Slater et al (1993) *J Bacteriol* 175, 260-4262.), Thermosensitive, pir-dependent, and repA-dependent broad-host-range plasmids for use in Gram-positive bacteria have been described (Biswas of al (1993) *J Bacteriol.* 175, 3628-3635, Leenhouts et al (1996) *Mol Gen Genet* 253, 217-224; Miller and Mekalanos (1988) *J Bacteriol* 170, 2575-2583).

Typically, a 'suicide'/non-replicative plasmid requires high frequencies of DNA transfer in order for the rare recombination events to be detected; an 'unstable'/replication-defective plasmid does not require high frequencies of DNA transfer, but instead rely upon the growth rate differential between plasmid replication and chromosome replication; a conditional plasmid does not require high frequencies of DNA transfer, and its replication rate can be decreased by a user-controlled variable such as temperature. Alternatively, the effective rate of replication of many plasmids in microorganisms can be decreased by culturing cells under conditions which promote plasmid loss, e.g, in phosphate- or sulphate-limited media in the case of *E. coli* (Jones et al (1980) *Gen Genet* 180, 579-584; Caulcott et al (1987) *J Gen Microbiol* 133, 1881-1889) or magnesium-limited media in the case of *Saccharomyces cerevisiae* (O'Kennedy and Patching (1997) *J Ind Microbiol Biotechnol* 8, 319-325).

Where the host cell is a bacterium that is difficult to transform, it is convenient that the donor DNA molecule is a shuttle vector which allows for replication and propagation in a bacterial cell such as *Escherichia coli* and in the host cell. Additionally or alternatively, the donor DNA molecule may contain a region which permits conjugative transfer from one bacterial cell such as *E. coli* to a bacterial host cell. Methods of transformation and conjugation in Clostridia are provided in Davis, I, Carter, G, Young, M and Minton, N P (2005) "Gene Cloning in Clostridia", In: Handbook on Clostridia (Durre P, ed) pages 37-52, CRC Press, Boca Raton, USA.

The invention will now be described with reference to the following non-limiting Examples and Figures.

Figure 1:
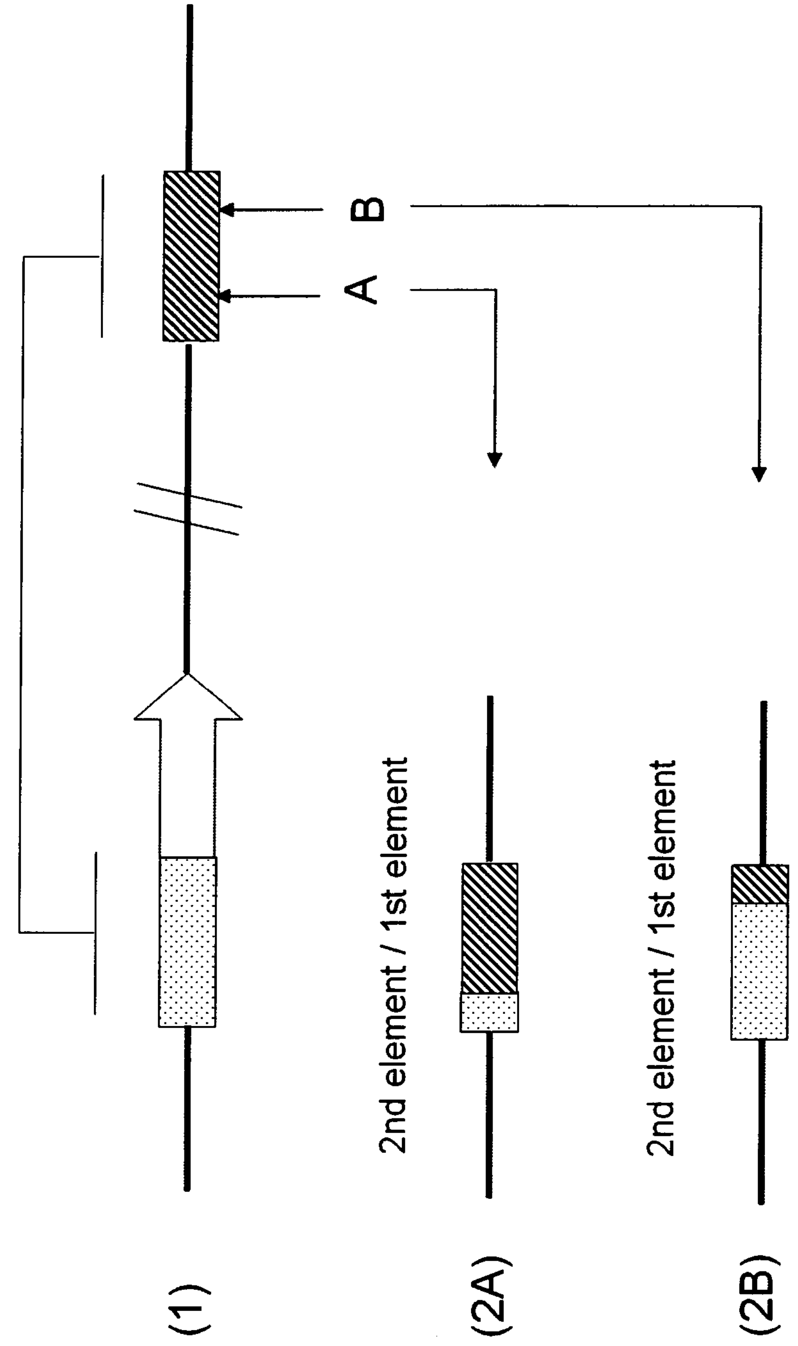
FIG. 1. Schematic diagram illustrating generation of selectable allele in second recombination event. A product of a first recombination event between a donor DNA and an acceptor DNA molecule is shown in (1). The product contains a part of a gene (hatched) from the donor DNA molecule and a complete gene (plain) from the acceptor DNA molecule. The part of the gene and the corresponding part within the complete gene are a pair of homology arms. In the second recombination event, homologous recombination occurs between this pair of homology arms. Two of many possible sites of crossover A and B are illustrated in the product of the first recombination event. Corresponding outcomes are illustrated as (2A) and (2B). Irrespective of where the crossover occurs between the pair of homology arms, the selectable allele formed is the same. The region originating from the donor DNA is the first element of the selectable allele and the region originating from the acceptor DNA molecule is the second element of the selectable allele. As illustrated, the internal limit of these elements is determined by the site of the second recombination event.

A plasmid based on the plasmid of Example 1, together with the relevant region of the chromosome of the pyrF mutant of *C. acetobutylicum* host cell of Example 1, are illustrated. Recombination may occur at any of the homology arms (A), (B) and (C) of the plasmid and the corresponding homology arms of the chromosome. Whereas in Example 1, the actual cargo DNA was lacZ' gene, here the cargo DNA is represented as Bio-Bricks 1-4. The cargo sequence may include an appropriate promoter to direct transcription of the pyrZ and pyrD ORFs in the desired final recombinant cell, as illustrated. The phenotype of the host cell is indicated in a box. The phenotype that the plasmid confers on the host cell is also indicated in a box. In step 1 indicated by the first arrow, a first homologous recombination event occurs between the plasmid and the chromosome. Possible products of the first recombination event resulting from homologous recombination at either one of the three pairs of homology arms (A), (B) or (C) are illustrated, together with the phenotype conferred on the host cell. For each first recombination product, pairs of homology arms which are able to mediate a second recombination event are indicated by thin dashed lines. Adjacent to each dotted line is a circle containing a "+" or a "−" sign. The "+" sign indicates that the product of homologous recombination at the relevant homology arms confers uracil prototrophy. The "−" sign indicates that the host cell containing the relevant product is a uracil auxotroph. The desired product of the second recombination event can be obtained from the type (C) first recombination product, by homologous recombination at the pair of homology arms indicated with thick dashed lines. In the second step indicated by the arrow, this desired product is formed as illustrated. The phenotype of the cell containing this product is indicated in the box. Key: "uracil −ve" means uracil auxotroph; "uracil +ve" means uracil prototroph; "Tm" means thiamphenicol; "FOA" means fluoroorotic acid; "R" means resistance phenotype; "S" means sensitive phenotype; "ori" is the origin of replication of the plasmid.

FIG. 3. Map and sequence (SEQ ID NO: 50) of pMTL85141—Plasmid pMTL85141 is an *E. coli-Clostridium* shuttle plasmid containing a lacZα multiple-cloning site; a replication function from *Bacillus* plasmid pIM13, including an origin of replication and replication gene repL; the chloramphenicol/thiamphenicol antibiotic resistance marker gene catP; and the ColE1/pUC19 origin of replication. The plasmid can replicate in *E. coli* and in *Clostridium* strains including *C. acetobutylicum* ATCC 824.

FIG. 4. Map and sequence (SEQ ID NO: 51) of pMTL-JH4—Plasmid pMTL-JH4 is an *E. coli-Clostridium* shuttle plasmid derived from pMTL-JH3. Between the indicated SbfI and NotI sites is almost the entire pyrF ORF of *C. acetobutylicum* ATCC 824, foreshortened to omit the first 47 bp, which can serve as a homology region in an allelic exchange procedure. Between the indicated NheI and AscI sites is the 1200 bp region of the *C. acetobutylicum* ATCC 824 chromosome immediately downstream of the pyrF ORF, which can serve as a homology region in an allelic exchange procedure.

Figure 5:
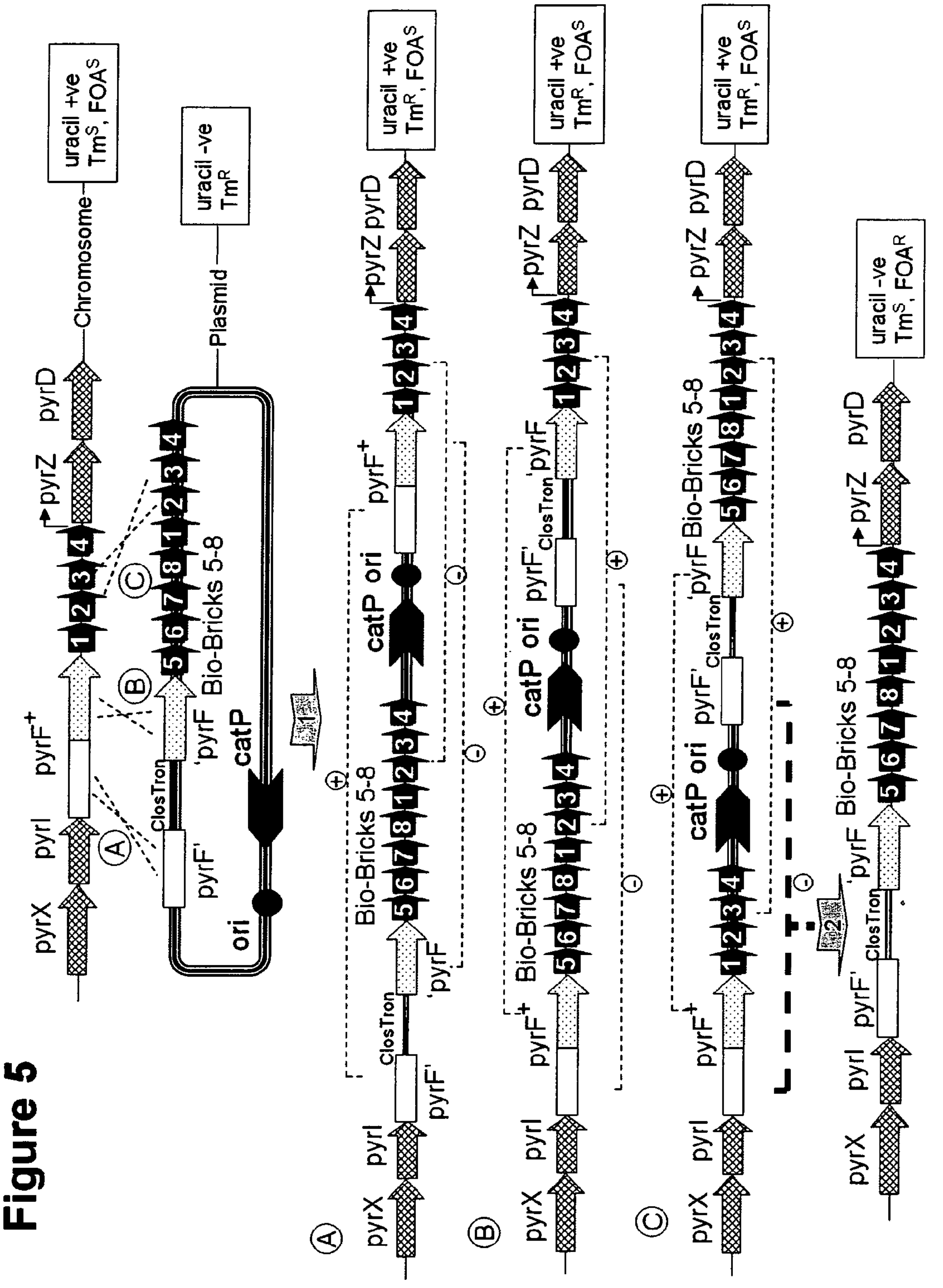

FIG. 5. Schematic diagram illustrating method of Example 3.

Figure 2:
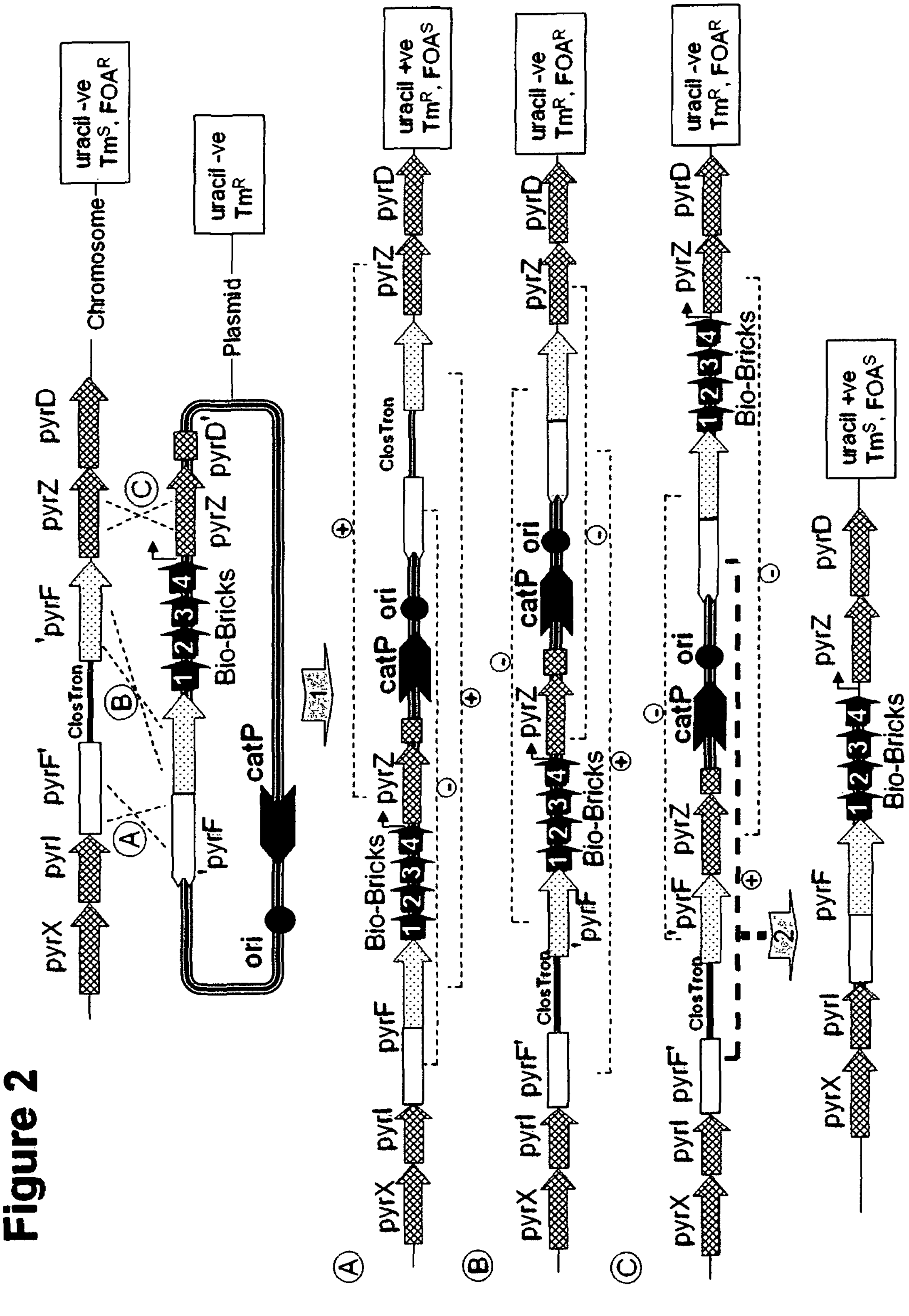
FIG. 2. Schematic diagram illustrating method of Example 1

A plasmid suitable for use in the method described in Example 3, together with the relevant region of the chromosome of the pyrF+ *C. acetobutylicum* host cell generated in the method illustrated in FIG. 2, are illustrated. The illustrated plasmid has Bio-Bricks 5-8 as cargo DNA. Recombination may occur at any of the homology arms (A), (B) and (C) of the plasmid and the corresponding homology arms of the chromosome. The phenotype of the host cell is indicated in box. The phenotype that the plasmid would confer on a neutral host cell is also indicated in a box. The plasmid is indicated as confering "uracil −ve" ie uracil auxotrophy although in the context of the pyrF+ *C. acetobutylicum* host cell, "uracil +ve" is dominant and so that host cell remains a uracil prototroph when transformed with the plasmid. In step 1 indicated by the first arrow, a first homologous recombination event occurs between the plasmid and the chromosome. Possible products of the first recombination event resulting from homologous recombination at either one of the three pairs of homology arms (A), (B) or (C) are illustrated, together with the phenotype conferred on the host cell. For each first recombination product, pairs of homology arms which are able to mediate a second recombination event are indicated by thin dashed lines. Adjacent to each dotted line is a circle containing a "+" or a "−" sign. The "+" sign indicates that the product of homologous recombination at the relevant homology arms confers uracil prototrophy. The "−" sign indicates that the host cell containing the relevant product is a uracil auxotroph. The desired product of the second recombination event can be obtained from the type (C) first recombination product, by homologous recombination at the pair of homology arms indicated with thick dashed lines. In the second step indicated by the arrow, this desired product is formed as illustrated. The phenotype of the cell containing this product is indicated in the box. Key: "uracil −ve" means uracil auxotroph; "uracil +ve" means uracil prototroph; "Tm" means thiamphenicol; "FOA" means fluoroorotic acid; "R" means resistance phenotype; "S" means sensitive phenotype; "ori" is the origin of replication of the plasmid.

Figure 6A:
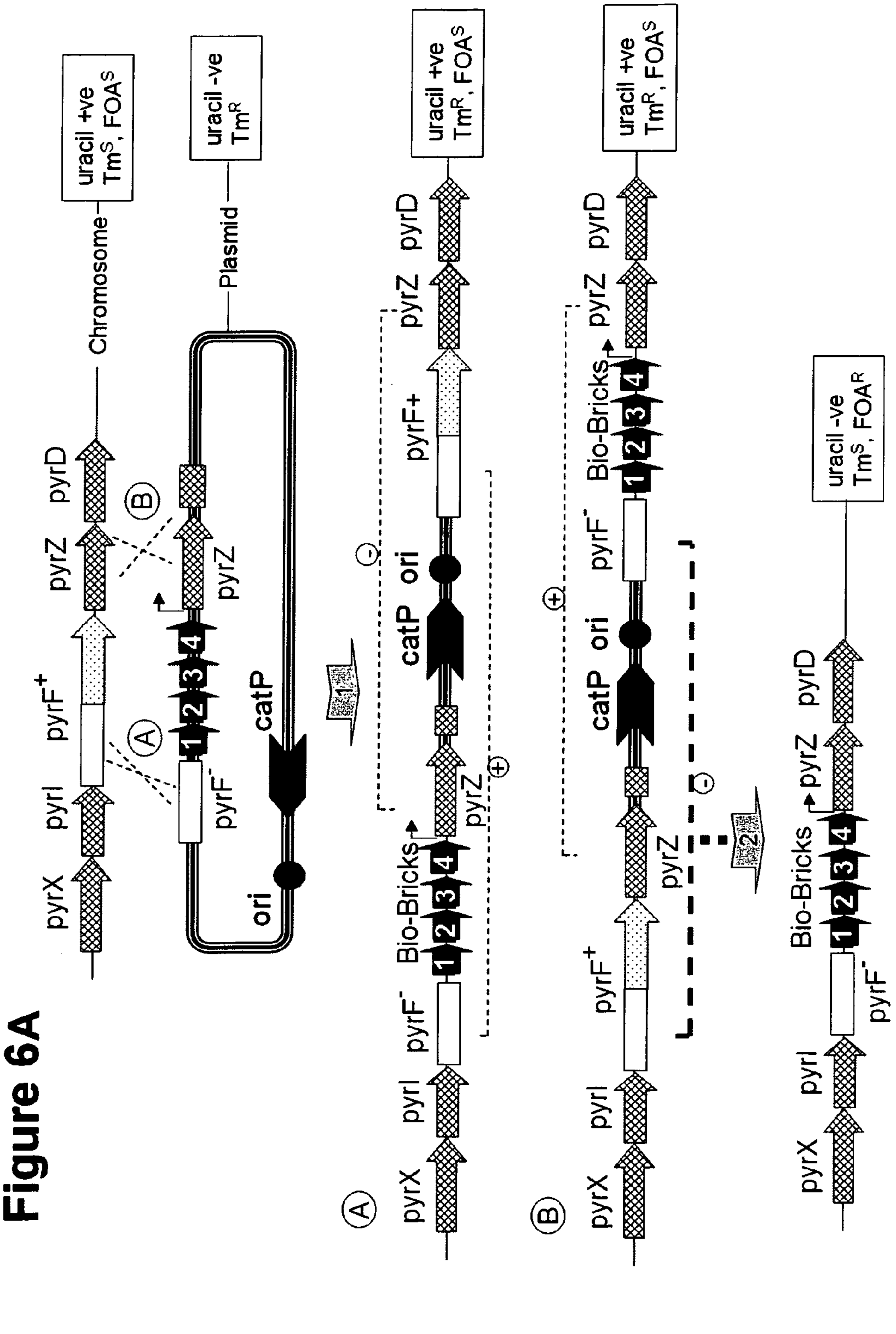

FIG. 6A. Schematic diagram illustrating method of Example 4

A plasmid suitable for use in the method described in Example 4, together with the relevant region of the chromosome of the wild-type pyrF+ *C. acetobutylicum* host cell, are illustrated. The illustrated plasmid has Bio-Bricks 1-4 as cargo DNA. Recombination may occur at either of the homology arms (A) or (B) of the plasmid and the corresponding homology arms of the chromosome. The phenotype of the host cell is indicated in box. The phenotype that the plasmid would confer on a neutral host cell is also indicated in a box. The plasmid is indicated as confering "uracil −ve" ie uracil auxotrophy although in the context of the pyrF+ *C. acetobutylicum* host cell, "uracil +ve" is dominant and so that host cell remains a uracil prototroph when transformed with the plasmid. In step 1 indicated by the first arrow, a first homologous recombination event occurs between the plasmid and the chromosome. Possible products of the first recombination event resulting from homologous recombination at either one of the two pairs of homology arms (A) or (B) are illustrated, together with the phenotype conferred on the host cell. For each first recombination product, pairs of homology arms which are able to mediate a second recombination event are indicated by thin dashed lines. Adjacent to each dotted line is a circle containing a "+" or a "−" sign. The "+" sign indicates that the product of homologous recombination at the relevant homology arms confers uracil prototrophy. The "−" sign indicates that the host cell containing the relevant product is a uracil auxotroph. The desired product of the second recombination event can be obtained from the type (B) first recombination product, by homologous recombination at the pair of homology arms indicated with thick dashed lines. In the second step indicated by the arrow, this desired product is formed as illustrated. The phenotype of the cell containing this product is indicated in the box. Key: "uracil −ve" means uracil auxotroph; "uracil +ve" means uracil prototroph; "Tm" means thiamphenicol; "FOA" means fluoroorotic acid; "R" means resistance phenotype; "S" means sensitive phenotype; "ori" is the origin of replication of the plasmid.

FIG. 6B. Map and sequence (SEQ ID NO: 52) of pMTL-JH2 Plasmid pMTL-JH2 is an *E. coli-Clostridium* shuttle plasmid derived from pMTL-JH1. Between the indicated SbfI and NotI sites is an internal portion of the pyrF ORF of

*C. acetobutylicum* ATCC 824 which can serve as a homology region in an allelic exchange procedure. Between the indicated NheI and AscI sites is the 1200 bp region of the *C. acetobutylicum* ATCC 824 chromosome immediately downstream of the pyrF ORF, which can serve as a homology region in an allelic exchange procedure.

Figure 6C:
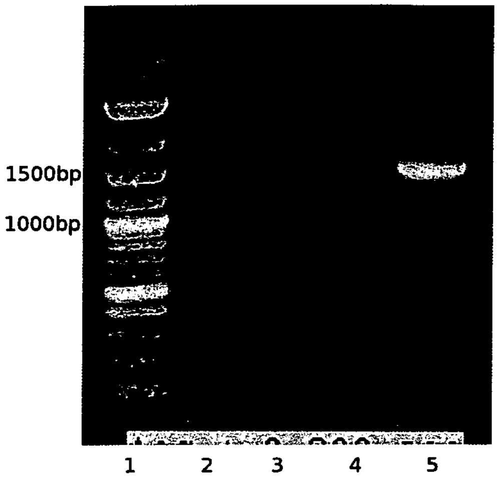

FIG. 6C shows an agarose gel of a right-hand crossover PCR experiment to screen a candidate double-crossover clone obtained using pMTL-JH2. Lane 1, NEB 2-log DNA ladder with 1500 bp and bright 1000 bp markers indicated; lane 2, PCR using water template; lane 3, PCR using pMTL-JH2 plasmid template; lane 4, PCR using wild-type *C. acetobutylicum* ATCC824 genomic DNA template; lane 5, PCR using candidate double crossover clone genomic DNA template. The specific ~1400 bp PCR product, indicative of the right-hand homologous recombination event, is visible in lane 5. A smaller, non-specific amplification product is visible in lane 3. No PCR products are visible in lanes 2 or 4.

Figure 6D:
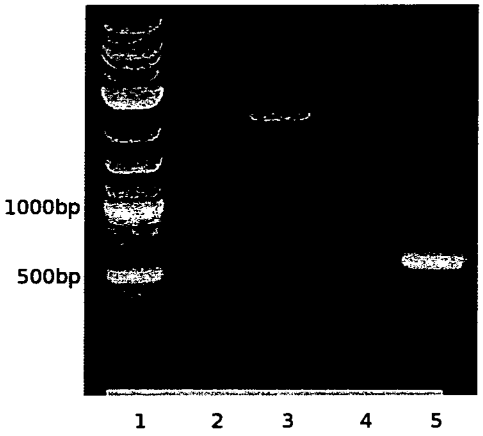

FIG. 6D shows an agarose gel of a left-hand crossover PCR experiment to screen a candidate double-crossover clone obtained using pMTL-JH2. Lane 1, NEB 2-log DNA ladder with bright 500 bp and 1000 bp markers indicated; lane 2, PCR using water template; lane 3, PCR using pMTL-JH2 plasmid template; lane 4, PCR using wild-type *C. acetobutylicum* ATCC824 genomic DNA template; lane 5, PCR using candidate double crossover clone genomic DNA template. The specific ~500 bp PCR product, indicative of the left-hand homologous recombination event, is visible in lane 5. Non-specific amplification products are visible in lane 3. No PCR products are visible in lanes 2 or 4.

FIG. 6E. Map and sequence (SEQ ID NO: 53) of pMTL-JH2-lambda2.0 Plasmid pMTL-JH2-lambda2.0 is an *E. coli-Clostridium* shuttle plasmid derived from pMTL-JH2 by the insertion of approximately 2.0 kbp of phage lambda (cl857ind1 Sam 7) DNA into the StuI site of lacZα. This positioned the phage lambda DNA between the homology arms, such that it would be delivered to the chromosome in an allelic exchange procedure.

FIG. 6F. Map and sequence (SEQ ID NO: 54) of pMTL-JH2-lambda2.3 Plasmid pMTL-JH2-lambda2.3 is an *E. coli-Clostridium* shuttle plasmid derived from pMTL-JH2 by the insertion of approximately 2.3 kbp of phage lambda (cl857ind1 Sam 7) DNA into the StuI site of lacZα. This positioned the phage lambda DNA between the homology arms, such that it would be delivered to the chromosome in an allelic exchange procedure.

FIG. 6G. Map and sequence (SEQ ID NO: 55) of pMTL-JH2-lambda4.3 Plasmid pMTL-JH2-lambda4.3 is an *E. coli-Clostridium* shuttle plasmid derived from pMTL-JH2 by the insertion of approximately 4.3 kbp of phage lambda (cl857ind1 Sam 7) DNA into the StuI site of lacZα. This positioned the phage lambda DNA between the homology arms, such that it would be delivered to the chromosome in an allelic exchange procedure.

FIG. 6H. Map and sequence (SEQ ID NO: 56) of pMTL-JH2-lambda6.5 Plasmid pMTL-JH2-lambda6.5 is an *E. coli-Clostridium* shuttle plasmid derived from pMTL-JH2 by the insertion of approximately 6.5 kbp of phage lambda (cl857ind1 Sam 7) DNA into the StuI site of lacZα. This positioned the phage lambda DNA between the homology arms, such that it would be delivered to the chromosome in an allelic exchange procedure.

FIG. 6I. Map and sequence (SEQ ID NO: 57) of pMTL83151 Plasmid pMTL83151 is an *E. coli-Clostridium* shuttle plasmid containing a lacZα multiple-cloning site; a replication function from *Clostridium butyricum* plasmid pCB102, including an origin of replication and putative replication gene repH; the chloramphenicol/thiamphenicol antibiotic resistance marker gene catP; the ColE1/pUC19 origin of replication; and part of the transfer function of plasmid RK2, including an origin of transfer (oriT) and transfer gene traJ. The plasmid can replicate in *E. coli* and in *Clostridium* strains including *C. difficile* 630.

FIG. 6J. Map and sequence (SEQ ID NO: 58) of pMTL-JH19 Plasmid pMTL-JH19 is an *E. coli-Clostridium* shuttle plasmid derived from pMTL83151. Between the indicated SbfI and NotI sites is almost the entire pyrE ORF of *C. difficile* 630, foreshortened to omit the first 50 bp, which can serve as a homology region in an allelic exchange procedure.

FIG. 6K. Map and sequence (SEQ ID NO: 59) of pMTL-JH20 Plasmid pMTL-JH20 is an *E. coli-Clostridium* shuttle plasmid derived from pMTL-JH19. Between the indicated SbfI and NotI sites is almost the entire pyrE ORF of *C. difficile* 630, foreshortened to omit the first 50 bp, which can serve as a homology region in an allelic exchange procedure. Between the indicated NheI and AscI sites is the 1200 bp region of the *C. difficile* 630 chromosome immediately downstream of the pyrE ORF, which can serve as a homology region in an allelic exchange procedure.

FIG. 6L. Map and sequence (SEQ ID NO: 60) of pMTL-JH17 Plasmid pMTL-JH17 is an *E. coli-Clostridium* shuttle plasmid derived from pMTL83151. Between the indicated SbfI and NotI sites is an internal portion of the pyrE ORF of *C. difficile* 630 which can serve as a homology region in an allelic exchange procedure.

FIG. 6M. Map and sequence (SEQ ID NO: 61) of pMTL-JH18 Plasmid pMTL-JH18 is an *E. coli-Clostridium* shuttle plasmid derived from pMTL-JH17. Between the indicated SbfI and NotI sites is an internal portion of the pyrE ORF of *C. difficile* 630 which can serve as a homology region in an allelic exchange procedure. Between the indicated NheI and AscI sites is the 1200 bp region of the *C. difficile* 630 chromosome immediately downstream of the pyrE ORF, which can serve as a homology region in an allelic exchange procedure.

FIG. 6N. Map and sequence (SEQ ID NO: 62) of pMTL-JH18-lambda6.5 Plasmid pMTL-JH18-lambda6.5 is an *E. coli-Clostridium* shuttle plasmid derived from pMTL-JH18 by the insertion of approximately 6.5 kbp of phage lambda (cl857ind1 Sam 7) DNA into the StuI site of lacZα. This positioned the phage lambda DNA between the homology arms, such that it would be delivered to the chromosome in an allelic exchange procedure.

Figure 6O:
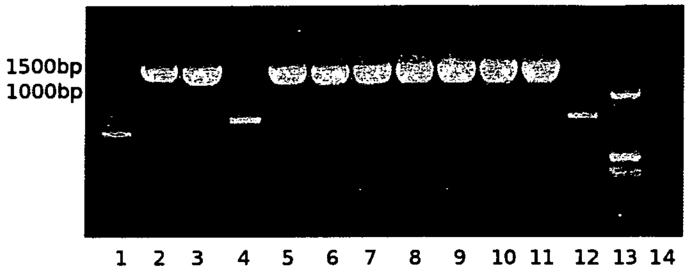

FIG. 6O shows an agarose gel of a right-hand crossover PCR experiment to screen candidate double-crossover clones obtained using pMTL-JH18-lambda6.5. Lane 1, Promega 100 bp DNA ladder with 1000 bp and 1500 bp markers indicated; lanes 2-6, PCR using genomic DNA templates from five putative single crossover clones picked from the P2 plate; lanes 7-11, PCR using genomic DNA templates from candidate double crossover clones picked from the P4 plate; lane 12, PCR using wild-type *C. difficile* 630Δerm genomic DNA template; lane 13, PCR using pMTL-JH18-lambda6.5 plasmid template; lane 14, PCR using water template. The specific ~1500 bp PCR product, indicative of the right-hand homologous recombination event, is visible in lanes 1,2,5-11. Non-specific amplification products are visible in lanes 2-13. No PCR products are visible in lane 14.

Figure 6P:
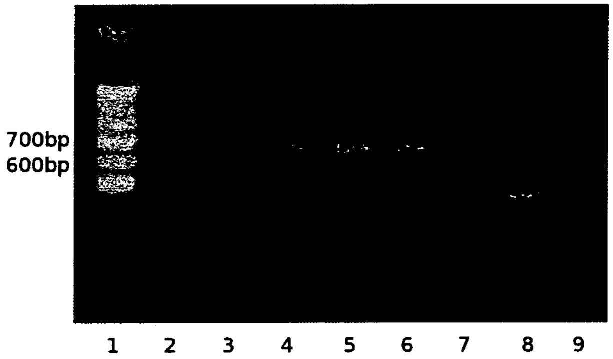

FIG. 6P shows an agarose gel of a left-hand crossover PCR experiment to screen candidate double-crossover clones obtained using pMTL-JH18-lambda6.5. Lane 1, Promega 100 bp DNA ladder with 600 bp and 700 bp markers indicated; lanes 2-6, PCR using genomic DNA templates from candidate double crossover clones picked from the P4 plate;

lane 7, PCR using wild-type *C. difficile* 630Δerm genomic DNA template; lane 13, PCR using pMTL-JH18-lambda6.5 plasmid template; lane 14, PCR using water template. The specific ~600 bp PCR product, indicative of the left-hand homologous recombination event, is visible in lanes 2-6. A non-specific amplification product is visible in lane 8. No PCR products are visible in lanes 7 or 9.

FIG. 6Q. Map and sequence (SEQ ID NO: 63) of pMTL-JH11 Plasmid pMTL-JH11 is an *E. coli-Clostridium* shuttle plasmid derived from pMTL85141. Between the indicated SbfI and NotI sites is an internal portion of the pyrE ORF of *C. acetobutylicum* ATCC 824 which can serve as a homology region in an allelic exchange procedure.

FIG. 6R. Map and sequence (SEQ ID NO: 64) of pMTL-JH12 Plasmid pMTL-JH12 is an *E. coli-Clostridium* shuttle plasmid derived from pMTL-JH11. Between the indicated SbfI and NotI sites is an internal portion of the pyrE ORF of *C. acetobutylicum* ATCC 824 which can serve as a homology region in an allelic exchange procedure. Between the indicated NheI and AscI sites is the 1200 bp region of the *C. acetobutylicum* ATCC 824 chromosome immediately downstream of the pyrE ORF, which can serve as a homology region in an allelic exchange procedure.

FIG. 6S. Map and sequence (SEQ ID NO: 65) of pMTL-JH13 Plasmid pMTL-JH13 is an *E. coli-Clostridium* shuttle plasmid derived from pMTL85141. Between the indicated SbfI and NotI sites is almost the entire pyrE ORF of *C. acetobutylicum* ATCC 824, foreshortened to omit the first 40 bp, which can serve as a homology region in an allelic exchange procedure.

FIG. 6T. Map and sequence (SEQ ID NO: 66) of pMTL-JH14 Plasmid pMTL-JH14 is an *E. coli-Clostridium* shuttle plasmid derived from pMTL-JH13. Between the indicated SbfI and NotI sites is almost the entire pyrE ORF of *C. acetobutylicum* ATCC 824, foreshortened to omit the first 40 bp, which can serve as a homology region in an allelic exchange procedure. Between the indicated NheI and AscI sites is the 1200 bp region of the *C. acetobutylicum* ATCC 824 chromosome immediately downstream of the pyrE ORF, which can serve as a homology region in an allelic exchange procedure.

FIG. 6U. Map and sequence (SEQ ID NO: 67) of pMTL-JH1 Plasmid pMTL-JH1 is an *E. coli-Clostridium* shuttle plasmid derived from pMTL85141. Between the indicated SbfI and NotI sites is an internal portion of the pyrF ORF of *C. acetobutylicum* ATCC 824 which can serve as a homology region in an allelic exchange procedure.

FIG. 6V. Map and sequence (SEQ ID NO: 68) of pMTL-JH3 Plasmid pMTL-JH3 is an *E. coli-Clostridium* shuttle plasmid derived from pMTL85141. Between the indicated SbfI and NotI sites is almost the entire pyrF ORF of *C. acetobutylicum* ATCC 824, foreshortened to omit the first 47 bp, which can serve as a homology region in an allelic exchange procedure FIG. 7. Schematic diagram illustrating method of Example 5.

A plasmid suitable for use in the method described in Example 5, together with the relevant region of the chromosome of the pyrF− *C. acetobutylicum* host cell obtained in Example 4, are illustrated. The illustrated plasmid has Bio-Bricks 5-8 as cargo DNA. Recombination may occur at either of the homology arms (A) or (B) of the plasmid and the corresponding homology arms of the chromosome. The phenotype of the host cell is indicated in box. The phenotype that the plasmid would confer on a neutral host cell is also indicated in a box. In step 1 indicated by the first arrow, a first homologous recombination event occurs between the plasmid and the chromosome. Possible products of the first recombination event resulting from homologous recombination at either one of the two pairs of homology arms (A) or (B) are illustrated, together with the phenotype conferred on the host cell. For each first recombination product, pairs of homology arms which are able to mediate a second recombination event are indicated by thin dashed lines. Adjacent to each dotted line is a circle containing a "+" or a "−" sign. The "+" sign indicates that the product of homologous recombination at the relevant homology arms confers uracil prototrophy. The "−" sign indicates that the host cell containing the relevant product is a uracil auxotroph. The desired product of the second recombination event can be obtained from the type (B) first recombination product, by homologous recombination at the pair of homology arms indicated with thick dashed lines. In the second step indicated by the arrow, this desired product is formed as illustrated. The phenotype of the cell containing this product is indicated in the box. Key: "uracil −ve" means uracil auxotroph; "uracil +ve" means uracil prototroph; "Tm" means thiamphenicol; "FOA" means fluoroorotic acid; "R" means resistance phenotype; "S" means sensitive phenotype; "ori" is the origin of replication of the plasmid.

Figure 8A:
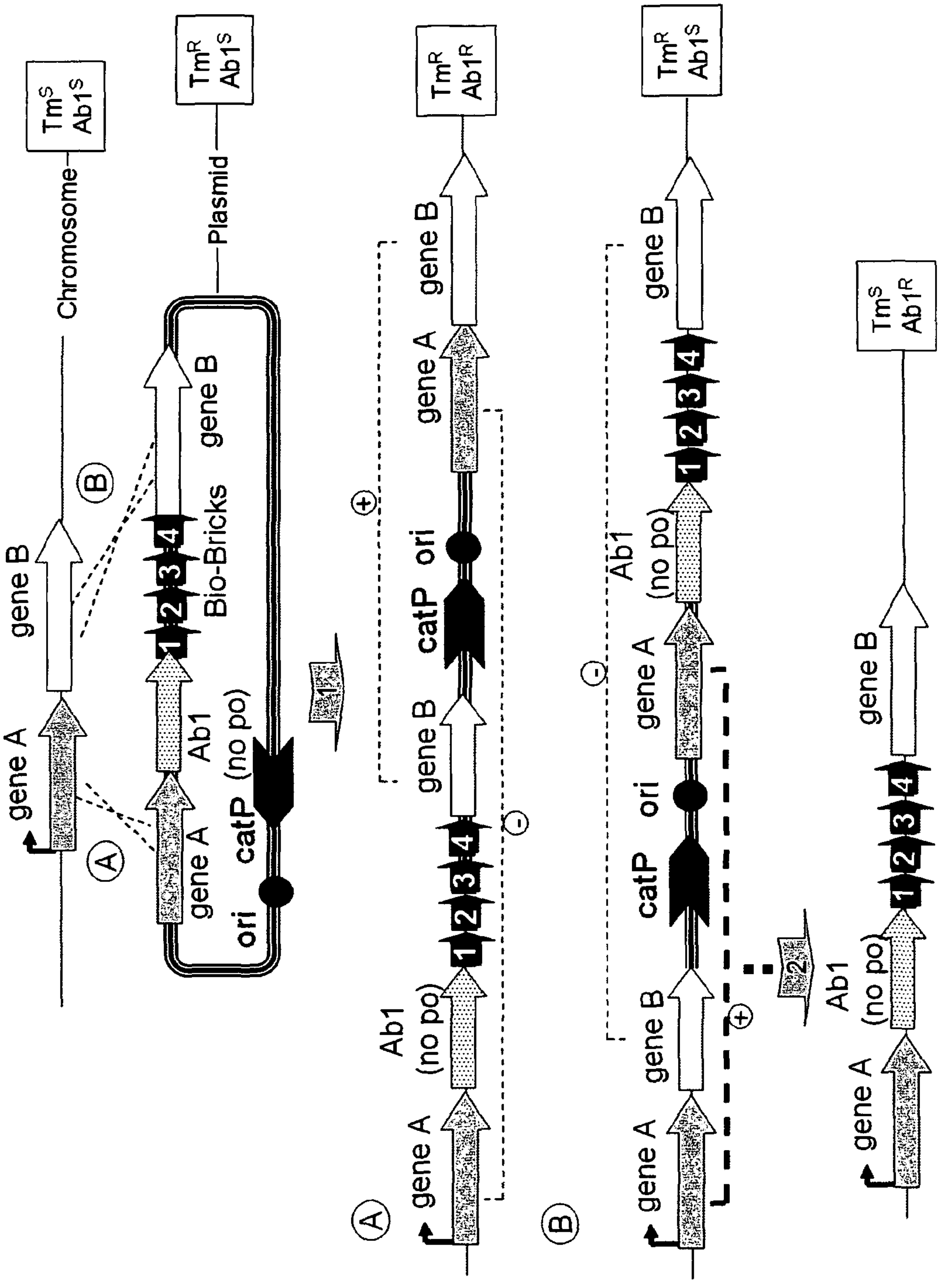

FIG. 8A. Schematic diagram illustrating method of Example 6.

A plasmid suitable for use in the method described in Example 6, together with the relevant region of the chromosome of a host cell, are illustrated. A promoter preceding gene A in the chromosome is the second element of the selectable allele. Ab1 in the plasmid is the coding region of a gene conferring resistance on an antibiotic Ab1. The illustrated plasmid has Bio-Bricks 1-4 as cargo DNA. Recombination may occur at either of the homology arms (A) or (B) of the plasmid and the corresponding homology arms of the chromosome. The phenotype of the host cell is indicated in box. The phenotype that the plasmid would confer on a neutral host cell is also indicated in a box. In step 1 indicated by the first arrow, a first homologous recombination event occurs between the plasmid and the chromosome. Possible products of the first recombination event resulting from homologous recombination at either one of the two pairs of homology arms (A) or (B) are illustrated, together with the phenotype conferred on the host cell. For each first recombination product, pairs of homology arms which are able to mediate a second recombination event are indicated by thin dashed lines. Adjacent to each dotted line is a circle containing a "+" or a "−" sign. The "+" sign indicates that the product of homologous recombination at the relevant homology arms confers resistance to Ab1. The "−" sign indicates that the host cell containing the relevant product is sensitive to Ab1. The desired product of the second recombination event can be obtained from the type (B) first recombination product, by homologous recombination at the pair of homology arms indicated with thick dashed lines. In the second step indicated by the arrow, this desired product is formed as illustrated. The phenotype of the cell containing this product is indicated in the box. Key: "Tm" means thiamphenicol; "R" means resistance phenotype; "S" means sensitive phenotype; "ori" is the origin of replication of the plasmid; "no po" means the Ab1 coding region has no promoter.

FIG. 8B. Map and sequence (SEQ ID NO: 69) of pMTL-JH15 Plasmid pMTL-JH15 is an *E. coli-Clostridium* shuttle plasmid derived from pMTL85141. Between the indicated SbfI and ClaI sites is a transcriptional terminator inherited from pMTL85141; followed by the last 300 bp (the 300 bp at the extreme 3' end) of the thl ORF of *C. acetobutylicum* ATCC 824, including the stop codon. This thl sequence can serve as a homology region in an allelic exchange procedure. Between the indicated ClaI and NotI sites is the ribosome-binding site (RBS) and ORF, but not the promoter, of an ermB gene. In this arrangement, the ermB ORF is not transcribed from plasmid pMTL-JH15, and so does not confer macrolide-lincosamide-streptogramin (MLS) resistance. However, recombination between the plasmid's thl homology region and the corresponding region of the chromosome would place the ermB ORF under the control of the strong chromosomal thl promoter, leading to transcription and translation of the ermB ORF, and in turn MLS resistance.

Figure 8D:
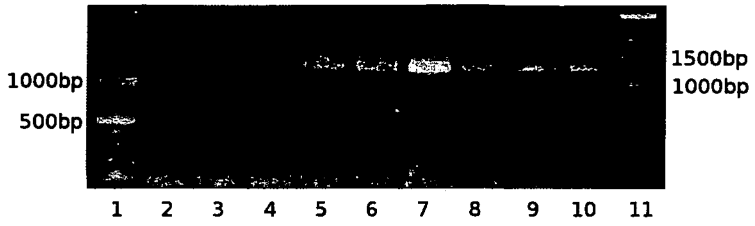

FIG. 8C. Map and sequence (SEQ ID NO: 70) of pMTL-JH16 Plasmid pMTL-JH16 is an *E. coli-Clostridium* shuttle plasmid derived from pMTL-JH15. Between the indicated SbfI and ClaI sites is a transcriptional terminator inherited from pMTL85141; followed by the last 300 bp (the 300 bp at the extreme 3' end) of the thl ORF of *C. acetobutylicum* ATCC 824, including the stop codon. This thl sequence can serve as a homology region in an allelic exchange procedure. Between the indicated ClaI and NotI sites is the ribosome-binding site (RBS) and ORF, but not the promoter, of an ermB gene. In this arrangement, the ermB ORF is not transcribed from plasmid pMTL-JH15, and so does not confer macrolide-lincosamide-streptogramin (MLS) resistance. However, recombination between the plasmid's thl homology region and the corresponding region of the chromosome would place the ermB ORF under the control of the strong chromosomal thl promoter, leading to transcription and translation of the ermB ORF, and in turn MLS resistance. Between the indicated NheI and AscI sites is the 1200 bp region of the *C. acetobutylicum* ATCC 824 chromosome immediately downstream of the thl ORF, which can serve as a homology region in an allelic exchange procedure FIG. 8D shows an agarose gel of a right-hand crossover PCR experiment to screen candidate double-crossover clones obtained using pMTL-JH16. Lane 1, NEB 2-log DNA ladder with bright 500 bp and 1000 bp markers indicated; lane 2, PCR using water template; lane 3, PCR using pMTL-JH16 plasmid template; lane 4, PCR using wild-type *C. acetobutylicum* ATCC824 genomic DNA template; lanes 5-10, PCR using genomic DNA templates from candidate double crossover clones 1-6; lane 11 NEB 1 kb DNA ladder with 1500 bp and 1000 bp markers indicated. The specific ~1450 bp PCR product, indicative of the right-hand homologous recombination event, is visible in lanes 5-10. No PCR products are visible in lanes 2, 3 or 4.

Figure 8E:

FIG. 8E shows an agarose gel of a left-hand crossover PCR experiment to screen candidate double-crossover clones obtained using pMTL-JH16. Lane 1, PCR using water template; lane 2, PCR using pMTL-JH16 plasmid template; lane 3, PCR using wild-type *C. acetobutylicum* ATCC824 genomic DNA template; lanes 4-9, PCR using genomic DNA templates from candidate double crossover clones 1-6; lane 10 NEB 1 kb DNA ladder with 1500 bp and 1000 bp markers indicated. The specific ~1250 bp PCR product, indicative of the right-hand homologous recombination event, is visible in lanes 4-9. Non-specific amplification products are visible in lanes 2 and 3. No PCR products are visible in lane 1.

Figure 9:
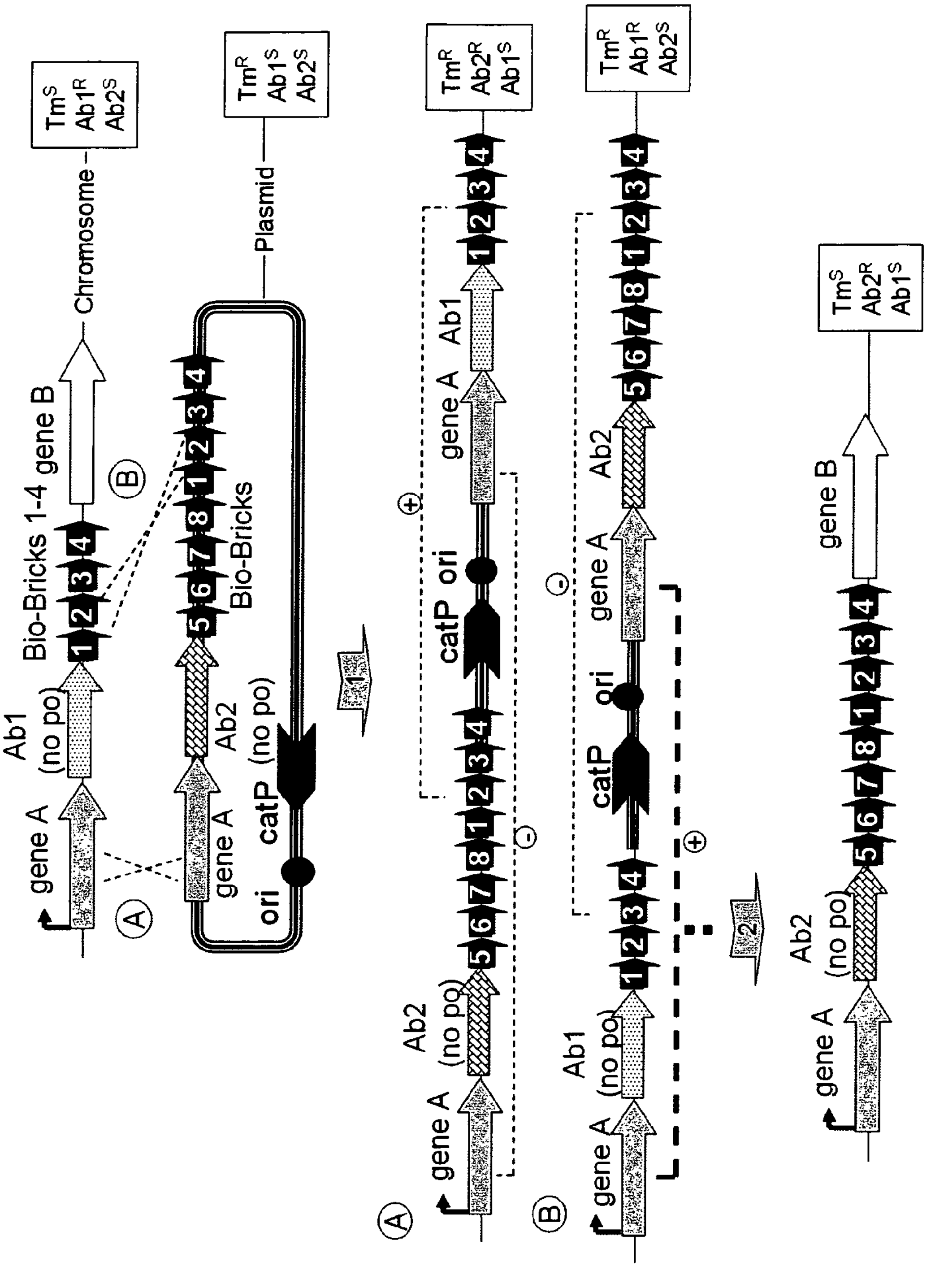

FIG. 9. Schematic diagram illustrating method of Example 6

A plasmid suitable for use in the method described in the second iteration of Example 6, together with the relevant region of the chromosome of the host cell, are illustrated. A promoter preceding gene A in the chromosome is the second element of the selectable allele. Ab2 in the plasmid is the coding region of a gene conferring resistance on an antibiotic Ab2. The illustrated plasmid has Bio-Bricks 5-8 as cargo DNA. Recombination may occur at either of the homology arms (A) or (B) of the plasmid and the corresponding homology arms of the chromosome. The phenotype of the host cell is indicated in box. The phenotype that the plasmid would confer on a neutral host cell is also indicated in a box. The plasmid is indicated as confering "Ab1$^{S}$" ie sensitivity to Ab1, although in the context of the Ab1 resistant host cell, "Ab1$^{R}$" is dominant and so that host cell remains resistant of Ab1 when transformed with the plasmid. In step 1 indicated by the first arrow, a first homologous recombination event occurs between the plasmid and the chromosome. Possible products of the first recombination event resulting from homologous recombination at either one of the two pairs of homology arms (A) or (B) are illustrated, together with the phenotype conferred on the host cell. For each first recombination product, pairs of homology arms which are able to mediate a second recombination event are indicated by thin dashed lines. Adjacent to each dotted line is a circle containing a "+" or a "−" sign. The "+" sign indicates that the product of homologous recombination at the relevant homology arms confers resistance to Ab2. The "−" sign indicates that the host cell containing the relevant product is sensitive to Ab2. The desired product of the second recombination event can be obtained from the type (B) first recombination product, by homologous recombination at the pair of homology arms indicated with thick dashed lines. In the second step indicated by the arrow, this desired product is formed as illustrated. The phenotype of the cell containing this product is indicated in the box. Key: "Tm" means thiamphenicol; "R" means resistance phenotype; "S" means sensitive phenotype; "ori" is the origin of replication of the plasmid; "no po" means the Ab1 or Ab2 coding region has no promoter.

Figure 10A:
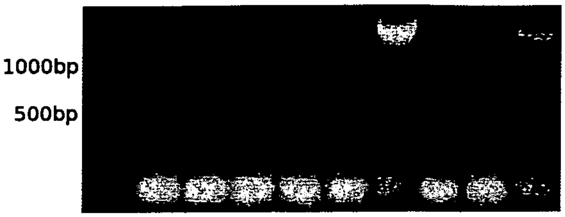

FIG. 10A shows an agarose gel of a right-hand crossover PCR experiment to screen candidate double-crossover clones obtained using pMTL-JH2-lambda2.0. Lane 1, NEB 2-log DNA ladder with bright 500 bp and 1000 bp markers indicated; lane 2, PCR using water template; lane 3, PCR using pMTL-JH2-lambda2.0 plasmid template; lane 4, PCR using wild-type *C. acetobutylicum* ATCC824 genomic DNA template; lanes 5-10, PCR using genomic DNA templates from candidate double crossover clones 1-6. The specific ~1600 bp PCR product, indicative of the right-hand homologous recombination event, is visible in lanes 7 and 10. A smaller non-specific amplification product is visible in lane 3. No PCR products are visible in lanes 2 or 4.

Figure 10B:

FIG. 10B shows an agarose gel of a left-hand crossover PCR experiment to screen candidate double-crossover clones obtained using pMTL-JH2-lambda2.0. Lane 1, PCR using water template; lane 2, PCR using pMTL-JH2-lambda2.0 plasmid template; lane 3, PCR using wild-type *C. acetobutylicum* ATCC824 genomic DNA template; lanes 4-9, PCR using genomic DNA templates from candidate double crossover clones 1-6; lane 10, NEB 2-log DNA ladder with bright 500 bp and 1000 bp markers indicated. The specific ~600 bp PCR product, indicative of the left-hand homologous recombination event, is visible in lane 6. No PCR products are visible in lanes 1, 2 or 3.

Figure 10C:
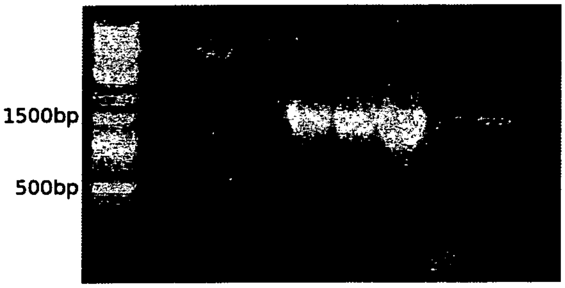

FIG. 10C shows an agarose gel of a right-hand crossover PCR experiment to screen candidate double-crossover clones obtained using pMTL-JH2-lambda2.3. Lane 1, NEB 2-log DNA ladder with 1500 bp and bright 500 bp markers indicated; lane 2, PCR using water template; lane 3, PCR using pMTL-JH2-lambda2.3 plasmid template; lane 4, PCR using wild-type *C. acetobutylicum* ATCC824 genomic DNA template; lanes 5-10, PCR using genomic DNA templates from candidate double crossover clones 1-6. The specific ~1550 bp PCR product, indicative of the right-hand homologous recombination event, is clearly visible in lanes 5-7, and more faintly visible in lanes 8-10. Non-specific amplification products are visible in lane 3. No PCR products are visible in lanes 2 or 4.

Figure 10D:
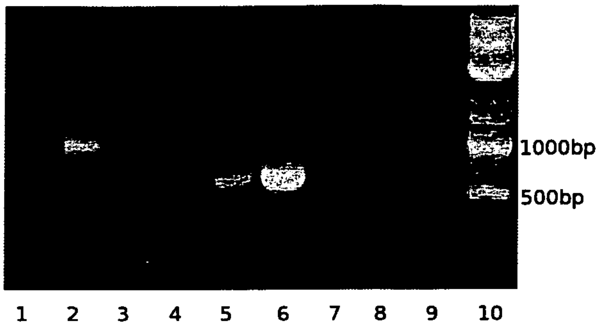

FIG. 10D shows an agarose gel of a left-hand crossover PCR experiment to screen candidate double-crossover clones obtained using pMTL-JH2-lambda2.3. Lane 1, PCR using water template; lane 2, PCR using pMTL-JH2-lambda2.3 plasmid template; lane 3, PCR using wild-type *C. acetobutylicum* ATCC824 genomic DNA template; lanes 4-9, PCR using genomic DNA templates from candidate double crossover clones 1-6; lane 10, NEB 2-log DNA ladder with bright 500 bp and 1000 bp markers indicated. The specific ~600 bp PCR product, indicative of the left-hand homologous recombination event, is visible in lanes 5 and 6. A smaller non-specific amplification product may be very faintly visible in lane 3. Non-specific amplification products are visible in lane 2. No PCR products are visible in lane 1.

Figure 10E:
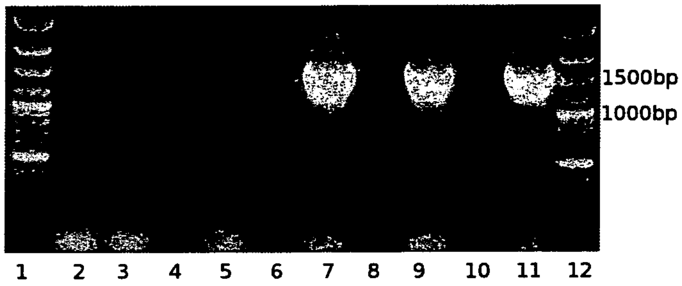

FIG. 10E shows an agarose gel of a right-hand crossover PCR experiment to screen candidate double-crossover clones obtained using pMTL-JH2-lambda4.3. Lane 1, NEB 2-log DNA ladder; lane 2, PCR using water template; lane 3, PCR using pMTL-JH2-lambda4.3 plasmid template; lane 5 PCR using wild-type *C. acetobutylicum* ATCC824 genomic DNA template; lanes 7, 9 and 11, PCR using genomic DNA templates from three candidate double crossover clones; lane 12, NEB 2-log DNA ladder with 1500 bp and bright 1000 bp markers indicated; lanes 4, 6, 8 and 10, empty. The specific ~1600 bp PCR product, indicative of the right-hand homologous recombination event, is clearly visible in lanes 7, 9 and 11. A non-specific amplification product is visible in lane 5. No PCR products are visible in lanes 2 or 3.

Figure 10F:
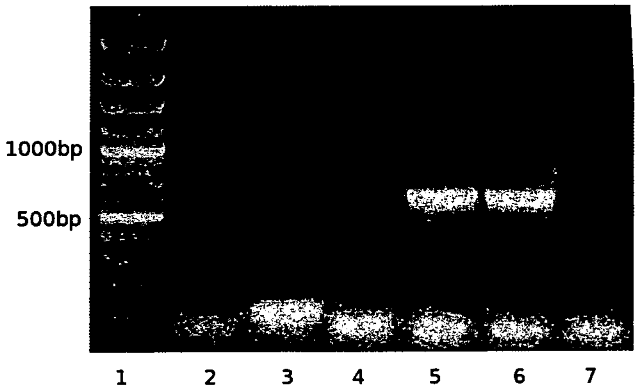

FIG. 10F shows an agarose gel of a left-hand crossover PCR experiment to screen candidate double-crossover clones obtained using pMTL-JH2-lambda4.3. Lane 1, NEB 2-log DNA ladder with bright 500 bp and 1000 bp markers indicated; lane 2, PCR using water template; lane 3, PCR using pMTL-JH2-lambda4.3 plasmid template; lane 4, PCR using wild-type *C. acetobutylicum* ATCC824 genomic DNA template; lanes 5-7, PCR using genomic DNA templates from three candidate double crossover clones. The specific ~600 bp PCR product, indicative of the left-hand homologous recombination event, is visible in lanes 5, 6 and 7. A very small non-specific amplification product may be visible in lane 3. No PCR products are visible in lanes 1 or 4.

Figure 10G:
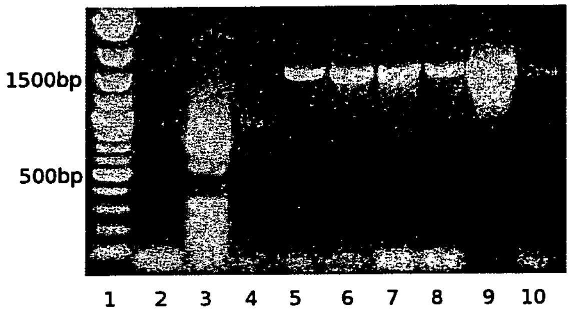

FIG. 10G shows an agarose gel of a right-hand crossover PCR experiment to screen candidate double-crossover clones obtained using pMTL-JH2-lambda6.5. Lane 1, NEB 2-log DNA ladder with bright 500 bp and 1500 bp markers indicated; lane 2, PCR using water template; lane 3, PCR using pMTL-JH2-lambda6.5 plasmid template; lane 4 PCR using wild-type *C. acetobutylicum* ATCC824 genomic DNA template; lanes 5-10, PCR using genomic DNA templates from candidate double crossover clones 1-6. The specific ~1550 bp PCR product, indicative of the right-hand homologous recombination event, is clearly visible in lanes 5-10. No PCR products are visible in lane 2. Non-specific amplification products are visible in lanes 3 and 4.

Figure 10H:
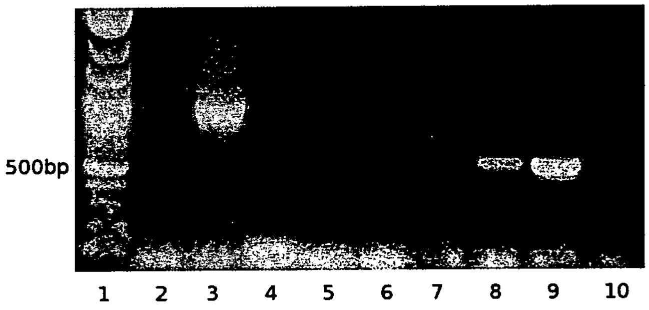

FIG. 10H shows an agarose gel of a left-hand crossover PCR experiment to screen candidate double-crossover clones obtained using pMTL-JH2-lambda6.5. Lane 1, NEB 2-log DNA ladder with bright 500 bp marker indicated; lane 2, PCR using water template; lane 3, PCR using pMTL-JH2-lambda6.5 plasmid template; lane 4, PCR using wild-type *C. acetobutylicum* ATCC824 genomic DNA template; lanes 5-10, PCR using genomic DNA templates from candidate double crossover clones 1-6. The specific ~550 bp PCR product, indicative of the left-hand homologous recombination event, is visible in lanes 5, 8 and 9. A non-specific amplification product is visible in lane 3. No PCR products are visible in lanes 1 or 4.

EXAMPLE 1

Stable Introduction of DNA into the *Clostridium acetobutylicum* Chromosome

The stable introduction of DNA into the *Clostridium acetobutylicum* chromosome via recombination requires a means of achieving double cross-over homologous recombination. The ability to generate mutants in Clostridia by single cross-over integration has demonstrated that the impediment to introducing DNA is not recombination per se, rather it is the inability to detect the rare second recombination event following single cross-over insertion. A strategy for highly efficient and rapid introduction of DNA cargo through positive selection of this second recombination event was developed in *C. acetobutylicum*, as illustrated in FIG. 2.

A previously constructed *C. acetobutylicum* pyrF mutant was utilised as host cell, which requires exogenous uracil for growth (pyrF 345s: Heap et al (2007) J Microbiol Methods. 70: 452-64). The pyrF mutant was generated by insertional disruption using a method which relies on insertion of a mobile group II intron from the ItrB gene of *Lactococcus lactis* (Ll.ItrB) and selection of integrants on the basis of acquisition of resistance to erythromycin. The homologous recombination strategy required that a 5' part of the disrupted pyrF gene could combine with a 3' part of pyrF to be provided on a donor plasmid pMTL-JH4. Downstream of the 5' part of the pyrF gene on the host chromosome in 5'-3' order was the disruption insertion comprising the Ll.ItrB intron and ermB gene, a 3' part of the pyrF gene, the pyrZ gene and the pyrD gene.

Construction of pMTL-JH4

An allelic exchange cassette was constructed to permit double homologous recombination with the host cell genome, such that the second homologous recombination event could be selected for by acquisition of uracil prototrophy due to the generation of a functional pyrF gene in the genome. The cassette contains three homology arms, two of which are contiguous. A left-hand homology region comprising two upstream homology arms corresponding to almost the entire pyrF ORF was PCR-amplified from *Clostridium acetobutylicum* ATCC 824 genomic DNA template using primers SbfI-Cac-pyrF-iF1 (of 5' to 3' sequence taataCCTGCAGGgtgtttaggacttgata-ctgatattacTtatgtaccagaagag (SEQ ID NO: 2)) and Cac-pyrF-NotI-R1 (of 5' to 3' sequence ataaGCGGCCGCTCATAAAGTTTTTCT-GATCTCGTCTCTCATATTAATCGC (SEQ ID NO: 3)). These primers were designed to omit the first 47 bp of the pyrF ORF, thereby ensuring that both the start codon and a possible secondary start codon were not present in the portion of the pyrF ORF used in the left-hand homology region, and therefore that this left-hand homology region alone could not confer a pyrF+ phenotype. The PCR product was cloned into plasmid pCR2.1-TA and its sequence verified. The left-hand homology arm was then sub-cloned using the restriction endonucleases SbfI and NotI into the shuttle vector pMTL85141 yielding plasmid pMTL-JH3. pMTL85141 confers resistance to thiamphenicol, and contains the origin of replication from *Bacillus subtilis* plasmid pIM13, which is commonly used in studies in *C. acetobutylicum*, in which it is replication-defective. The DNA sequence and structure of pMTL85141 are illustrated in FIG. 3.

A right-hand homology region corresponding to the entire pyrZ ORF and part of the pyrD ORF was PCR-amplified from *Clostridium acetobutylicum* ATCC 824 genomic DNA template using primers NheI-Cac-pyrZ-F1 (of 5' to 3' sequence ataaaGCTAGCatttt-gggggaattttgatgaaggaaaagtatacag (SEQ ID NO: 4)) and AscI-Cac-pyrD-iR1 (of 5' to 3' sequence attGGCGCGCCTTGTGATACAACAT-TATAAGCAACTTCTGATTTTATTCCA-AAAGCC (SEQ ID NO: 5)). The PCR product was cloned into plasmid pCR2.1-TA and its sequence verified. The right-hand homology arm was then sub-cloned using the restriction endonucleases NheI and AscI into the plasmid pMTL-JH3 yielding plasmid pMTL-JH4.

pMTL-JH4 is a replication-defective shuttle plasmid conferring resistance to thiamphenicol and containing a complete allelic exchange cassette: The left-hand homology region corresponds to the 5' and 3' parts of pyrF in the genome that are separated by the disruption insertion. The lacZ' gene serves as cargo DNA and is situated immediately downstream of the left-hand homology region. Immediately downstream of the lacZ' gene is the right-hand homology region, consisting of the pyrZ gene and part of the pyrD gene, which corresponds to the equivalent region of the genome. Since the pyrF gene in the cassette does not include a start codon, the cassette itself cannot confer uracil prototrophy on the host cell prior to homologous recombination. To favour integration at the desired position, the extent of the right-hand homology region was deliberately designed to considerably exceed the regions of homology of the left-hand homology region. The right-hand homology region encompassed 1200 bp whereas the homology arms of the left-hand homology region were of approximately 300 bp and 500 bp. The DNA sequence and structure of pMTL-JH4 are illustrated in FIG. 4.

Scheme for Obtaining Double Crossover Homologous Recombination Integrants

Vector pMTL-JH4 was designed such that integrants in the previously constructed *C. acetobutylicum* pyrF mutant host (pyrF 345s: Heap et al (2007) J Microbiol Methods. 70: 452-64 are of three possible types (A, B or C; FIG. 2), depending upon which homology arm directs the first recombination event. Cells in which a first recombination event has occurred, although initially relatively rare, may be readily enriched and selected by re-streaking on plates containing thiamphenicol, because the integration of the catP gene into the chromosome confers a growth advantage on the host cell, compared to a host cell in which the plasmid has not integrated. A suitable scheme for distinguishing between the different outcomes of the first recombination event, and selecting the desired outcome in which the cargo DNA is stably inserted, is as follows. Replica streaking of integrants onto media with and without uracil will allow the identification of cells in which integration occurred at either position 'A' or at positions 'B' or 'C'. Only integrants at position 'A' are uracil prototrophs, through restoration of a functional pyrF gene, and may be discarded. They may in any case be expected to be in the minority due to the relatively smaller extent of DNA available for homologous recombination, compared to 'B' and 'C'. Integration at positions 'B' and 'C' will generate cells that remain uracil auxotrophs. Such clones are streaked onto media lacking this supplement, to select for the second recombination event. In both types, three classes of recombination event can occur, but in each case only one will result in restoration of the pyrF gene, and, therefore, enable growth on media lacking uracil. As in every case the catP gene is lost, the media does not contain thiamphenicol. Having obtained prototrophic colonies, a simple PCR screen can distinguish between those cells derived from the original type 'B' integration event (which has lost the delivered cargo DNA) and the desired type 'C' integration event (which retains the delivered cargo DNA).

Experimental Results

A proof of concept experiment, demonstrating how the above scheme can be applied in practice, was performed as follows. A table summarising four steps of the procedure, and their results, is included below. [1] pMTL-JH4 was transformed into *C. acetobutylicum* pyrF 345s and transformants were selected on CGM media supplemented with 50 ng/ml uracil and 15 μg/ml thiamphenicol. The control plasmid pMTL85141 was transformed into the host cell and transformants selected in the same way. [2] When single colonies from the two types of transformant were subcultured onto fresh media it became apparent that the single colonies that appeared in the 'streaks' derived from pMTL-JH4 colonies were larger than the equivalent colonies of cells carrying the parental plasmid pMTL85141. These results are consistent with the observation that plasmid pIMP1 and its derivatives replicate relatively inefficiently in *C. acetobutylicum*, and that cells in which the plasmid integrates by single cross-over into the genome (i.e., those derived from pMTL-JH4 transformants) have a growth advantage in the presence of thiamphenicol. [3] To allow the isolation of cells in which integrated plasmid, and its associated catP gene, is excised, several colonies from each type of transformant were restreaked onto CGM media supplemented with uracil, but lacking thiamphenicol, and then [4] onto CBM minimal media lacking any supplementation. Both types of transformant were able to grow in the presence of uracil, as expected. Six pMTL-JH4 transformants were still able to grow in the absence of uracil, but the cells that had received the parental plasmid did not grow, illustrating the selectivity of the procedure. Using appropriate primers, PCR demonstrated that of the six clones derived from the pMTL-JH4 transformants capable of growth on CBM lacking uracil, two were derived from a type 'C' recombination event and hence retained the cargo DNA, and four were derived from a type 'B' event. No examples of a type 'A' event were evident. (See above for a description of type A, B and C events.)

Using genomic DNA as PCR template and PCR primers Cac-pyrI-sF1 (of 5' to 3' sequence tgtgatgaaatatataagggag-caaaggcgc (SEQ ID NO: 6)) and Cac-pyrD-sR1 (of 5' to 3' sequence AGCCATATCCACTATATCCTCTGCATTAGG (SEQ ID NO: 7)) single PCR products of diagnostic sizes were obtained. PCR products of 2195 bp were amplified from clones derived from initial type 'B' events, which are wild-type at the pyrF locus, while PCR products of 2477 bp were amplified from clones derived from initial type 'C' events, which contain a chromosomal insertion of the lacZ' cargo sequence between the pyrF and pyrZ ORFs. The equivalent PCR product from the pyrF mutant host strain (in which the pyrF gene is interrupted by an intron insertion of 1781 bp) would be 3976 bp.

At this stage it became apparent that in many instances, cells from within the colonies on the pMTL-JH4 plates at stage [2] had continued to grow, resulting in the formation of large dome-like outgrowths to the colony. Upon restreaking onto minimal media these all proved to be uracil prototrophs. PCR screening of six randomly selected examples demonstrated that in all cases a second recombination event had occurred, and that five of the six were of the desired type 'C' recombinant class, and one was of a type 'B' recombinant class. Thus, it would appear that the original colony growth of the pyrF minus cells had been curtailed by exhaustion of the exogenous supply of uracil, but cells from within the colony that had undergone a second recombination event were able to continue to grow. This finding demonstrated that the required double cross-over integrants may be selected in a single step. The experiment also showed that it was practically unnecessary to detect and discard single crossover pyrF prototrophs that arise through a class ‘A’ recombination event, as they apparently arose at an undetectable frequency, presumably as a consequence of the small region of DNA (300 bp) included in the first homology arm in the left-hand homology region, compared to the right-hand homology region (1200 bp).

TABLE 1

Summary of results of proof of concept experiment

| Manipulation/media | pMTL85141 [parental plasmid control] | pMTL-JH4 [pyrF locus integration plasmid] |
|---|---|---|
| [1] Transformation Rich medium [CGM + uracil + Tm] | Primary transformants | Primary transformants |
| [2] Streak to single colonies Rich medium [CGM + uracil + Tm] Allows first recombination event (integration) to occur | Single colonies significantly smaller than equivalent colonies derived from pMTL-JH4 | Single colonies significantly larger Outgrowth due to double crossover evident after 3 days → Six outgrowth clones screened: 5 were derived from type ‘C’ events and 1 from a type ‘B’ event |
| [3] Streak to single colonies Rich medium [CGM + uracil] Allows second recombination event to occur | With removal of Tm selection, colony size/growth rate increased to equal equivalent colonies derived from pMTL-JH4 | No change in colony growth rate from fastest colonies of previous step |
| [3] Streak to single colonies Minimal medium [CBM lacking uracil] Selects uracil prototrophs | No growth Host pyrF mutant cannot revert, and plasmid lacks pyrF cassette | Many uracil prototrophic colonies obtained → Six clones screened: 2 were derived from type ‘C’ events and 4 from type ‘B’ events |

The strategy has proven remarkably effective. Following isolation of the primary transformant, when restreaked onto uracil-supplemented media containing antibiotic, all of the well isolated single colonies appear to be single cross-over integrants. Moreover, double crossover events can be selected without further restreaking.

EXAMPLE 2

Scheme for Inserting Cargo DNA by Regenerating the pyrF Disruption

The *C. acetobutylicum* strain obtained in Example 1 is a uracil prototroph because the pyrF gene has been restored by the combination of elements of the gene present in the original pyrF mutant genome, and the allelic exchange cassette. The pyrF wild-type strain can be subjected to insertional disruption in pyrF using the same method that was used to generate the original pyrF mutant (Heap et al (2007) supra). An equivalent cargo delivery vector to pMTL-JH4 can then be constructed, but in this instance the right-hand homology region (DNA encoding pyrZ, pyrD') is modified to match whatever sequence (i.e. the previously inserted cargo DNA) is located downstream of pyrF in the new host strain. Desired double recombination integrants containing the further cargo DNA can be obtained as described in Example 1. Further rounds of the method may be applied to iteratively insert cargo DNA.

EXAMPLE 3

Scheme for Inserting Cargo DNA by Counter Selection for Inactivation of Wild-Type pyrF The pyrF+ *C. acetobutylicum* strain obtained in Example 1 could be used in a further round of double homologous recombination with a differently designed vector, and the second recombination event counter selected for by inactivation of the pyrF gene, as illustrated in FIG. 5. In this scheme, a sister plasmid to pMTL-JH4 is constructed which carries the mutant pyrF gene carrying the disruption insertion. The 5' and 3' parts of pyrF are each upstream homology arms. An appropriate downstream i.e. right-hand homology arm is selected to correspond to the region downstream of pyrF in the chromosome. In the case of the strain obtained in Example 1, this is the lacZ' gene and pyrZ, although if the cargo DNA had been larger, the homology arm could correspond to the cargo DNA, or upstream part of the cargo DNA.

pyrF+ *C. acetobutylicum* would be transformed with the plasmid and transformants plated on uracil supplemented media containing thiamphenicol to select for fast growing cells due to the growth advantage conferred by insertion of catP into the genome by single cross-over recombination. There are three possible outcomes of the first recombination event, depending on which of the three pairs of homology arms recombine. All possible outcomes are pyrF+. The selection for the double cross-over event is for a pyrF-minus, uracil requiring recombinant. Such clones may be positively selected using fluoroorotic acid. This is because cells can only grow in the presence of this chemical if they have defective pyrF or pyrE genes. Depending on which pair of homology arms directed the first recombination event, a cell acquiring pyrF+ in the second recombination event may or may not retain the cargo DNA. Desired cells retaining the cargo DNA may be identified by PCR of their chromosomal DNA. If, in the scheme illustrated in FIG. 5 the downstream i.e. right-hand homology arm is designed to have a greater extent of homology than the other homology arms, for example, if it is at least double, typically 3-4 fold the size, a type (C) event would be expected to predominate. The desired product retaining the cargo DNA is the only product that confers resistance to fluoroorotic acid that can arise from the type (C) first recombination product. Thus, increasing the propensity of the first recombination event to occur at (C) increases the proportion of cells selected following the second recombination event retaining the cargo DNA.

The desired product strain would be a uracil auxotroph because it contains the pyrF gene disrupted by the insertion disruption. It could therefore be used in a further round of double crossover homologous recombination as described in Example 1. Of course, one could first apply the method described above to a wild type *C. acetobutylicum* and then apply the method of Example 1 to its product. One could cycle between each method, iteratively adding cargo DNA.

This strategy negates the need to recreate a new pyrF− mutant between each iteration of the method, thereby reducing the overall time required to build complex operons. We have established the feasibility of this option through the demonstration that whilst the wild-type *C. acetobutylicum* ATCC 824 strain is unable to grow on media supplemented with 0.4 mg/mL fluoroorotic acid and 50 ng/mL uracil, our previously constructed pyrF mutant (strain *C. acetobutylicum* pyrF 345s; Heap et al., 2007) is able to grow.

EXAMPLE 4

Alternative Scheme for Inserting Cargo DNA by Counter Selection for Inactivation of Wild-Type pyrF A wild-type pyrF+ *C. acetobutylicum* strain could be used in a method of double homologous recombination with a vector as illustrated in FIG. 6A, and the second recombination event counter selected for by inactivation of the pyrF gene. Alternatively, with a differently designed plasmid, the method could be used in a further round of double homologous recombination to add further cargo DNA to the host cell product obtained as described in Example 3. In either case, the 5' part of pyrF is the upstream homology arm. It is 3' truncated, rendering the gene non-functional. The downstream homology arm corresponds to the region downstream of pyrF in the chromosome. In the plasmid illustrated in FIG. 6A, this is pyrZ and the first part of pyrD. However, if the chromosome contained cargo DNA downstream of pyrF, the downstream homology arm would correspond to the cargo DNA, or upstream part of the cargo DNA. In either case, cargo DNA is located between the upstream and downstream homology arms. It may contain a promoter to direct transcription of pyrZ in the final desired product. The plasmid also contains a catP gene located outside of the allelic exchange cassette.

Either homology arm may direct the first recombination event, leading to two possible products, illustrated as (A) and (B) in FIG. 6A. Either of these events confers a growth advantage to the host cell in the presence of thiamphenicol, since the catP gene is now linked to the efficient replication of the chromosome. Cells in which a type (A) or (B) recombination event has occurred, although initially relatively rare, are readily enriched and selected by re-streaking one or more times.

Products of either type (A) or (B) recombination events contain both a truncated, non-functional pyrF allele and a full-length pyrF allele. A full-length pyrF allele confers dominant uracil prototrophy and FOA-sensitivity in cells containing the product of type (B) events, but may or may not confer these phenotypes in cells containing the product of type (A) events, dependent upon whether the full-length pyrF allele is efficiently expressed. In FIG. 6A, it is assumed that the pyrF gene is expressed in the type (A) product. To ensure that only cells containing a dominant pyrF+ phenotype are obtained, the enrichment and selection for cells in which an integration event has occurred would be performed using minimal medium containing thiamphenicol but un-supplemented with uracil. Cells containing the products of type (A) integration events only if they possess the pyrF+ phenotype and cells containing the products of type (B) integration events would be re-streaked onto rich media containing uracil, but lacking thiamphenicol. This process should allow second recombination events to occur without selection for thiamphenicol-resistance.

Depending upon which pair of homology arms directs the second recombination event, different chromosomal arrangements would result. In a final step, cells would be re-streaked onto rich medium supplemented with uracil and FOA. FOA-resistant cells growing after this final step will be the desired double-crossover integrants containing the cargo sequence. These could be derived from cells in which a type (B) event directed the initial plasmid integration, or may be derived from cells in which a type (A) event directed the initial plasmid integration, as long as the cells containing the product of the first type (A) recombination event possessed a pyrF+ phenotype.

In an alternative arrangement, the 5' region of pyrF present on the donor DNA molecule has a 5' truncation. In this case, of the two possible products of the first recombination event, only product (B) is a uracil prototroph. Product (A) is a uracil auxotroph. It is not possible to select for a second recombination event in which the cargo DNA is retained starting from product (A). Thus, product (A) would be discarded. The desired second recombination event would be selected from product B, by acquisition of resistance to fluoroorotic acid in the presence of uracil.

In either arrangement of this method, a pyrF− strain is produced, which could be subjected to a further round of double homologous recombination according to the method described in Example 1, or the method described below in Example 5.

A Set of Four Plasmids for the pyrF Locus of *Clostridium acetobutylicum*

To exemplify the scheme described in Example 4a set of four plasmids was designed and constructed to facilitate allelic exchange at the pyrF locus of *C. acetobutylicum* ATCC 824 and derivatives thereof. In typical use, but not necessarily, 'cargo' sequence will be inserted between the left-hand homology arm and right-hand homology arm of a plasmid, such that after the allelic exchange procedure is complete, the cargo sequence will be stably localised to the chromosome.

A long left-hand homology region corresponding to almost the entire pyrF ORF was PCR-amplified from *C. acetobutylicum* ATCC 824 genomic DNA template using primers SbfI-Cac-pyrF-iF1 (5' to 3' sequence taataCCTGCAGGgtgtttaggacttgatactgatattacTtatgtaccagaagag (SEQ ID NO: 8)) and Cac-pyrF-NotI-R1 (5' to 3' sequence ataaGCGGCCGCTCATAAAGTTTTTCTGATCTCGTCTCTCATATTAATCGC (SEQ ID NO: 9)). These primers were designed to omit the first 47 bp of the pyrF ORF, thereby ensuring that both the start codon and a possible secondary start codon were not present in the portion of the pyrF ORF used in the left-hand homology region, and therefore that this left-hand homology region alone could not confer a pyrF+ phenotype. (For convenience in possible future cloning strategies, primer SbfI-Cac-pyrF-iF1 also silences an NdeI site early in the pyrF ORF without altering the sequence of the encoded protein). The PCR product was cloned into plasmid pCR2.1-TA and its sequence verified. The long left-hand homology arm was then sub-cloned using the restriction endonucleases SbfI and NotI into the shuttle vector pMTL85141 (FIG. 3) yielding plasmid pMTL-JH3 (FIG. 6V). A right-hand homology region corresponding to the 1200 bp immediately downstream of the pyrF ORF, including the entire pyrZ ORF and part of the pyrD ORF, was PCR-amplified from *C. acetobutylicum* ATCC 824 genomic DNA template using primers NheI-Cac-pyrZ-F1 (5' to 3' sequence ataaaGCTAGCattttgggggaattttgatgaaggaaaagtatacag (SEQ ID NO: 10)) and AscI-Cac-pyrD-iR1 (5' to 3' sequence attGGCGCGCCTTGTGATACAACATTATAAGCAACTTCTGATTTTATTCCAAAAGCC (SEQ ID NO: 11)). The PCR product was cloned into plasmid pCR2.1-TA and its sequence verified. The right-hand homology arm was then sub-cloned using the restriction endonucleases NheI and AscI into the plasmid pMTL-JH3 yielding plasmid pMTL-JH4 (FIG. 4).

A short left-hand homology region corresponding to an internal portion of the pyrF ORF near the 5' end was PCR-amplified from *C. acetobutylicum* ATCC 824 genomic DNA template using primer SbfI-Cac-pyrF-iF1 described above and primer Cac824-pyrF-NotI-iR1 (5' to 3' sequence tGCGGCCGCTCATTAACCTTCAAAGTGAGCTTTAGCATACATTTCAGC (SEQ ID NO: 12)). These primers were designed to omit both the first 47 bp of the pyrF ORF and a substantial 3' portion of the pyrF ORF. This design ensures that a homologous recombination event between this internal portion of the pyrF ORF and the full-length pyrF ORF would lead to two non-functional derivatives of the pyrF ORF: one foreshortened derivative lacking the first 47 bp of the pyrF ORF, which includes both the start codon and a possible secondary start codon; and the other derivative truncated, lacking a substantial 3' portion of the pyrF ORF. The PCR product was cloned into plasmid pCR2.1-TA and its sequence verified. The short left-hand homology arm was then sub-cloned using the restriction endonucleases SbfI and NotI into the shuttle vector pMTL85141 yielding plasmid pMTL-JH1 (FIG. 6U). The same right-hand homology region described above, corresponding to the 1200 bp immediately downstream of the pyrF ORF, was sub-cloned using the restriction endonucleases NheI and AscI into the plasmid pMTL-JH1 yielding plasmid pMTL-JH2 (FIG. 6B).

Each of the four plasmids is designed for use in an allelic exchange procedure at the pyrF locus in which the first of two homologous recombination events is directed by a long right-hand homology arm. Plasmids pMTL-JH2 and pMTL-JH4 already contain such a long right-hand homology arm, whereas plasmids pMTL-JH1 and pMTL-JH3 serve as precursors to plasmids for use in derivatives of *C. acetobutylicum* ATCC 824 in which the chromosome has previously been modified such that the sequence immediately downstream of the pyrF ORF differs from the wild-type. In such cases, a right-hand homology arm would be constructed corresponding to the region immediately downstream of the pyrF ORF in the modified derivative of *C. acetobutylicum* ATCC 824, and inserted into pMTL-JH1 or pMTL-JH3 as appropriate. Whenever possible, the right-hand homology arm is designed to be longer than the left-hand homology arm so that the right-hand homology arm is more likely to direct the first of the two homologous recombination events.

During a first phase of the allelic exchange procedure, cells in which a first homologous recombination event has occurred are enriched relative to cells containing free plasmid by culture on growth medium supplemented with the antibiotic thiamphenicol. Thiamphenicol-resistance is encoded by the plasmid-borne catP gene, but the plasmids have a replication defect which limits the growth rate of cells containing free plasmid under these conditions. Those cells in which a first homologous recombination event has occurred are not under this growth rate limitation, as the catP gene is localised to the chromosome. This growth rate difference provides the basis for enrichment of cells in which a first homologous recombination event has occurred.

During a second phase of the allelic exchange procedure, cells in which a second homologous recombination event has occurred are selected. The second homologous recombination event is directed by the left-hand homology arm.

In the case of pMTL-JH2 or a suitable derivative of pMTL-JH1, the second recombination event is between the internal portion of pyrF originating from the plasmid and the equivalent region of the full-length, functional pyrF ORF originating from the host cell chromosome. Such a host strain may be the wild-type, or may have been previously constructed using pMTL-JH4 or a suitable derivative of pMTL-JH3. After this recombination event, the cell contains no functional copies of the pyrF ORF, in contrast to the cell prior to this event, and develops a pyrF− phenotype. Such cells are selected by sub-culturing onto growth medium supplemented with appropriate concentrations of fluoroorotic acid (FOA) and uracil. Under these conditions, cells with a pyrF+ phenotype convert FOA into a more toxic substance and grow very poorly if at all; while cells with a pyrF− phenotype do not catalyze this conversion, and their growth is selected.

In the case of pMTL-JH4 or a suitable derivative of pMTL-JH3, the second recombination event is between some or all of the foreshortened pyrF ORF originating from the plasmid, lacking both the start codon and a possible secondary start codon, and the equivalent region of the truncated pyrF ORF originating from the host cell chromosome. Such a host strain may have been previously constructed using pMTL-JH2 or a suitable derivative of pMTL-JH1. After this recombination event, the cell contains a functional copy of the pyrF ORF, in contrast to the cell prior to this event, and develops a pyrF+ phenotype. Such cells are selected by sub-culturing onto minimal growth medium containing no or low levels of uracil. Under these conditions, cells with a pyrF− phenotype, which cannot synthesize uracil de novo, grow very poorly if at all; while cells with a pyrF+ phenotype can synthesize uracil de novo, and their growth is selected.

Allelic Exchange Using pMTL-JH2 in *C. acetobutylicum* ATCC824

To exemplify the scheme described in Example 4 an allelic exchange procedure was performed using pMTL-JH2 (FIG. 6B) in *C. acetobutylicum* ATCC824. In this example the lacZ-alpha gene serves as the cargo DNA and pMTL-JH2 is the plasmid schematically illustrated in FIG. 6A. Allelic exchange requires two homologous recombination events; one between each of two pairs of homology arms. In a first phase of the procedure cells in which a first recombination event had occurred were enriched for, and in a second phase of the procedure cells in which a second recombination event had occurred were selected. Finally, PCR, sequencing and a thiamphenicol-sensitivity phenotype was used to identify and verify the clones of cells in which the allelic exchange had occurred.

Plasmid pMTL-JH2 was transformed by electroporation into *E. coli* TOP10 cells already harbouring plasmid pAN2, thereby protectively methylating it against the *C. acetobutylicum* ATCC824 Cac8241 DNA restriction system which would otherwise hinder the next step (Mermelstein and Papoutsakis (1993) Applied and Environmental Microbiology 59 (4):1077-1081; Heap et al (2007) Journal of Microbiological Methods 70 (3):452-464). Methylated pMTL-JH2 plasmid DNA was re-isolated from these transformed *E. coli* cells and used to transform *C. acetobutylicum* ATCC824 by electroporation, in accordance with the procedure described by Mermelstein and Papoutsakis (1993) Applied and Environmental Microbiology 59 (4):1077-1081. Cells transformed by pMTL-JH2, which includes the thiamphenicol-resistance gene catP, were selected by plating the transformation mixture onto CGM agar supplemented with 15 μg/ml thiamphenicol and 20 μg/ml uracil, and several transformant colonies were obtained.

It was anticipated that if sub-cultured on the same medium, the growth rate of these transformants would be limited by the replication defect of the plasmid; while cells in which the catP gene was localised to the chromosome by a first recombination event would not be under this growth rate limitation. This growth rate differential provides a potential basis for the enrichment of the desired cells in which the first recombination event has occurred. Accordingly, the largest colonies on each plate, especially those obviously larger than neighbouring colonies, would be indicative of clones of cells able to grow faster due to the localisation of the catP gene to the chromosome by a first recombination event. Therefore transformants were subcultured on the same medium, and fast growing colonies were preferentially sub-cultured.

Forty-eight hours after the transformation, six of the largest colonies were sub-cultured onto fresh plates of the same growth medium (passage 1; P1). These clones and their derivatives were treated independently in all subsequent steps of the procedure. Twenty-four hours later, colonies on the P1 plates were large enough to be picked, and were sub-cultured onto fresh plates of the same growth medium (passage 1; P2). Twenty-four hours later, colonies on the P2 plates were large enough to be picked, and were sub-cultured onto fresh plates of CGM agar supplemented with 1 μg/ml uracil and 400 μg/ml 5-fluoroorotic acid (FOA), under the assumption that these colonies were highly enriched for the desired cells in which the first recombination event had occurred, and would contain a small number of cells in which the second recombination event had occurred (passage 3; P3).

Seventy-two hours after inoculation, colonies on the P3 plates were large enough to be picked, and were sub-cultured onto fresh plates of the same growth medium (passage 4; P4). Growth on the P3 plates was presumed to correspond to a pyrF− phenotype, resulting from a desired second recombination event. Sub-culturing onto the P4 plates served to purify such clones. Twenty-four hours later, colonies on the P4 plates were large enough to be picked, and were used to inoculate overnight cultures in CGM broth supplemented with 20 μg/ml uracil. Four clones reached this stage of the procedure, while two had failed to sub-culture at a previous step. After overnight growth, the four clones were sub-cultured from the liquid culture onto fresh plates of CGM agar and fresh plates of CGM agar supplemented with 20 μg/ml uracil to maintain the strain and verify the pyrF− phenotype, indicated by weaker growth without the supplementary uracil. The overnight cultures were also used to purify genomic DNA from each clone, which was used as template in PCR experiments to identify clones in which both the desired homologous recombination events had occurred.

In a first 'right-hand crossover' PCR experiment the primers used were lacZalpha-sF2 (5' to 3' sequence ACTGGCCGTCGTTTTACAACGTCGTG (SEQ ID NO: 13)) which binds to the plasmid lacZα sequence in the forward orientation; and Cac-pyrD-sR1 (5' to 3' sequence AGCCATATCCACTATATCCTCTGCATTAGG (SEQ ID NO: 14)) which binds to the *C. acetobutylicum* ATCC824 chromosome downstream of the right-hand homology arm in the reverse orientation. This pair of primers can amplify a PCR product of ~1400 bp from genomic DNA of cells in which a homologous recombination event has occurred at the right-hand homology arm, localising the primer binding sites to the same DNA molecule ~1400 bp apart.

In a second 'left-hand crossover' PCR experiment the primers used were M13F (5' to 3' sequence TGTAAAACGACGGCCAGT (SEQ ID NO: 15)) which binds to the plasmid lacZα sequence in the reverse orientation; and Cac-pyrI-sF1 (5' to 3' sequence TGTGATGAAATATATAAGGGAGCAAAGGCGC (SEQ ID NO: 16)) which binds to the *C. acetobutylicum* ATCC824 chromosome upstream of the left-hand homology arm in the forward orientation. This pair of primers can amplify a PCR product of ~500 bp from genomic DNA of cells in which a homologous recombination event has occurred at the left-hand homology arm, localising the primer binding sites to the same DNA molecule ~500 bp apart.

All four clones screened produced the expected specific PCR products in both the left-hand and right-hand PCR experiments, indicating that these were the desired 'double-crossover' clones in which homologous recombination events had occurred at both the left and right homology arms, completing the allelic exchange procedure, and stably localising the lacZα sequence to the chromosome. The results of the PCR experiments for one such clone are shown in FIGS. 6C and 6D. The specific PCR products for this clone were gel-purified and sequenced, which confirmed that both the homologous recombination events had occurred. Finally, the same clone was shown to be thiamphenicol-sensitive by replica-plating single colonies onto plates of CGM agar supplemented with 20 μg/ml uracil and plates of CGM agar supplemented with 15 μg/ml thiamphenicol and 20 μg/ml uracil. The thiamphenicol-sensitive phenotype indicates that the plasmid sequence outside the homology arms, including the catP gene, is not present in the cell.

Allelic Exchange in *C. acetobutylicum* ATCC824 Using Derivatives of pMTL-JH2 Containing Lambda Cargo Sequences Having established that pMTL-JH2 could be used to perform an allelic exchange procedure in *C. acetobutylicum* ATCC824 to introduce the lacZ-alpha gene as cargo DNA into the host chromosome, it is now demonstrated that the size of the cargo sequence can be increased; at least within the size range where other required procedures, such as construction of plasmids by cloning and transfer of plasmids into the intended host organism, remain practical. Several derivatives of pMTL-JH2 containing lambda (cl857ind1 Sam 7) DNA cargo sequences were constructed, and used in separate allelic exchange procedures in *C. acetobutylicum* ATCC824. These plasmids were pMTL-JH2-lambda2.0 (FIG. 6E), pMTL-JH2-lambda2.3 (FIG. 6F), pMTL-JH2-lambda4.3 (FIG. 6G) and pMTL-JH2-lambda6.5 (FIG. 6H).

The plasmids containing phage lambda (cl857ind1 Sam 7) DNA were constructed by inserting fragments of phage lambda (cl857ind1 Sam 7) DNA between the homology arms of pMTL-JH2, such that they would be localised to the chromosome in an allelic exchange procedure.

A commercial preparation of phage lambda (cl857ind1 Sam 7) DNA, digested to completion with HindIII, was purchased from New England Biolabs (NEB). The mixture of fragments in this preparation was heated to 60° C. to separate the lambda cohesive ends of the fragments derived from the ends of the lambda chromosome, treated with T4 polymerase (NEB) to convert the HindIII cohesive ends and lambda cohesive ends to blunt ends, then individual blunt fragments were purified by agarose gel electrophoresis.

Selected blunt fragments of lambda DNA were cloned separately into recipient plasmids which had been linearised at the unique StuI site within the lacZα multiple-cloning site, and treated with antarctic phosphatase (NEB) to prevent recircularisation.

The lambda DNA fragments of approximately 2.0 kbp, 2.3 kbp, 4.3 kbp and 6.5 kbp were each separately cloned into pMTL-JH2 to construct plasmids pMTL-JH2-lambda2.0, pMTL-JH2-lambda2.3, pMTL-JH2-lambda4.3 and pMTL-JH2-lambda6.5 respectively. These plasmids were constructed in order to verify that increasing the size of the cargo sequence does not decrease the facility of the method to deliver the cargo sequence to the chromosome; at least within the size range where other required procedures, such as construction of plasmids by cloning and transfer of plasmids into the intended host organism, remain practical.

The allelic exchange procedures were performed exactly as described for pMTL-JH2. PCR, sequencing and thiamphenicol-sensitivity phenotype were used to identify and verify the clones of cells in which the allelic exchange had occurred. In the cases of pMTL-JH2-lambda2.0, pMTL-JH2-lambda2.3 and pMTL-JH2-lambda6.5; six transformant clones were successfully sub-cultured throughout the entire procedure, so all six clones were analysed at the end of the procedure. In the case of pMTL-JH2-lambda4.3, six transformant clones were picked from the transformation plates, of which three were successfully sub-cultured throughout the entire procedure, so three clones were analysed at the end of the procedure. Clones obtained using the four different plasmids were analysed using different PCR experiments.

In a 'right-hand crossover' PCR experiment to analyse clones obtained using pMTL-JH2-lambda2.0 the primers used were lambda2.0-sR1 (5' to 3' sequence AAGAAAATGATCTATATTTTTTGTCTGTCCTATATCACC (SEQ ID NO: 17)) which binds to the plasmid 2.0 kbp lambda sequence in the forward orientation; and Cac-pyrD-sR1 (5' to 3' sequence AGCCATATCCACTATATCCTCTGCATTAGG (SEQ ID NO: 18)) which binds to the *C. acetobutylicum* ATCC824 chromosome downstream of the right-hand homology arm in the reverse orientation. This pair of primers can amplify a PCR product of ~1600 bp from genomic DNA of cells in which a homologous recombination event has occurred at the right-hand homology arm, localising the primer binding sites to the same DNA molecule ~1600 bp apart.

In a 'left-hand crossover' PCR experiment to analyse clones obtained using pMTL-JH2-lambda2.0 the primers used were lambda2.0-sF1 (5' to 3' sequence AATATGACAATAAAATAATTCCTGAAGATATTAAAGAGCG (SEQ ID NO: 19)) which binds to the plasmid 2.0 kbp lambda sequence in the reverse orientation; and Cac-pyrI-sF1 (5' to 3' sequence TGTGATGAAATATATAAGGGAGCAAAGGCGC (SEQ ID NO: 20)) which binds to the *C. acetobutylicum* ATCC824 chromosome upstream of the left-hand homology arm in the forward orientation. This pair of primers can amplify a PCR product of ~600 bp from genomic DNA of cells in which a homologous recombination event has occurred at the left-hand homology arm, localising the primer binding sites to the same DNA molecule ~600 bp apart.

In a 'right-hand crossover' PCR experiment to analyse clones obtained using pMTL-JH2-lambda2.3 the primers used were lambda2.3-sR1 (5' to 3' sequence GAATATTAAGCTCGACAGGTCAGTTATTTACCTACG (SEQ ID NO: 21)) which binds to the plasmid 2.3 kbp lambda sequence in the forward orientation; and Cac-pyrD-sR1 (5' to 3' sequence AGCCATATCCACTATATCCTCTGCATTAGG (SEQ ID NO: 22)) which binds to the *C. acetobutylicum* ATCC824 chromosome downstream of the right-hand homology arm in the reverse orientation. This pair of primers can amplify a PCR product of ~1550 bp from genomic DNA of cells in which a homologous recombination event has occurred at the right-hand homology arm, localising the primer binding sites to the same DNA molecule ~1550 bp apart.

In a 'left-hand crossover' PCR experiment to analyse clones obtained using pMTL-JH2-lambda2.3 the primers used were lambda2.3-sF1 (5' to 3' sequence GGGAAGTCGTGAAAGAAAAGAAGTCAGC (SEQ ID NO: 23)) which binds to the plasmid 2.3 kbp lambda sequence in the reverse orientation; and Cac-pyrI-sF1 (5' to 3' sequence TGTGATGAAATATATAAGGGAGCAAAGGCGC (SEQ ID NO: 24)) which binds to the *C. acetobutylicum* ATCC824 chromosome upstream of the left-hand homology arm in the forward orientation. This pair of primers can amplify a PCR product of ~600 bp from genomic DNA of cells in which a homologous recombination event has occurred at the left-hand homology arm, localising the primer binding sites to the same DNA molecule ~600 bp apart.

In a 'right-hand crossover PCR experiment to analyse clones obtained using pMTL-JH2-lambda4.3 the primers used were lambda4.3-sR1 (5' to 3' sequence CGTCATAATTGATTATTTGACGTGGTTTGATGG (SEQ ID NO: 25)) which binds to the plasmid 4.3 kbp lambda sequence in the forward orientation; and Cac-pyrD-sR1 (5' to 3' sequence AGCCATATCCACTATATCCTCTGCATTAGG (SEQ ID NO: 26)) which binds to the *C. acetobutylicum* ATCC824 chromosome downstream of the right-hand homology arm in the reverse orientation. This pair of primers can amplify a PCR product of ~1600 bp from genomic DNA of cells in which a homologous recombination event has occurred at the right-hand homology arm, localising the primer binding sites to the same DNA molecule ~1600 bp apart.

In a 'left-hand crossover' PCR experiment to analyse clones obtained using pMTL-JH2-lambda4.3 the primers used were lambda4.3-sF1 (5' to 3' sequence TACCATGGCAATCTCTGCATCTTGCCC (SEQ ID NO: 27)) which binds to the plasmid 4.3 kbp lambda sequence in the reverse orientation; and Cac-pyrI-sF1 (5' to 3' sequence TGTGATGAAATATATAAGGGAGCAAAGGCGC (SEQ ID NO: 28)) which binds to the *C. acetobutylicum* ATCC824 chromosome upstream of the left-hand homology arm in the forward orientation. This pair of primers can amplify a PCR product of ~600 bp from genomic DNA of cells in which a homologous recombination event has occurred at the left-hand homology arm, localising the primer binding sites to the same DNA molecule ~600 bp apart.

In a 'right-hand crossover PCR experiment to analyse clones obtained using pMTL-JH2-lambda6.5 the primers used were lambda6.5-sR1 (5' to 3' sequence GGTAAGCACGAACTCAGCCAGAACG (SEQ ID NO: 29)) which binds to the plasmid 6.5 kbp lambda sequence in the forward orientation; and Cac-pyrD-sR1 (5' to 3' sequence AGCCATATCCACTATATCCTCTGCATTAGG (SEQ ID NO: 30)) which binds to the *C. acetobutylicum* ATCC824 chromosome downstream of the right-hand homology arm in the reverse orientation. This pair of primers can amplify a PCR product of ~1550 bp from genomic DNA of cells in which a homologous recombination event has occurred at the right-hand homology arm, localising the primer binding sites to the same DNA molecule ~1550 bp apart.

In a 'left-hand crossover' PCR experiment to analyse clones obtained using pMTL-JH2-lambda6.5 the primers used were lambda6.5-sF2 (5' to 3' sequence TATGAGTACCCTGTTTTTTCTCATGTTCAGG (SEQ ID NO: 31)) which binds to the plasmid 6.5 kbp lambda sequence in the reverse orientation; and Cac-pyrI-sF1 (5' to 3' sequence TGTGATGAAATATATAAGGGAGCAAAGGCGC (SEQ ID NO: 32)) which binds to the *C. acetobutylicum* ATCC824 chromosome upstream of the left-hand homology arm in the forward orientation. This pair of primers can amplify a PCR product of ~550 bp from genomic DNA of cells in which a homologous recombination event has occurred at the left-hand homology arm, localising the primer binding sites to the same DNA molecule ~550 bp apart.

One of six clones obtained using pMTL-JH2-lambda2.0, two of six clones obtained using pMTL-JH2-lambda2.3, three of three clones obtained using pMTL-JH2-lambda4.3 and three of six clones obtained using pMTL-JH2-lambda6.5 produced the expected specific PCR products in both the left-hand and right-hand PCR experiments. This result indicated that these were the desired 'double-crossover' clones in which homologous recombination events had occurred at both the left and right homology arms, completing the allelic exchange procedure, and stably localising the cargo sequence including the lambda DNA to the chromosome.

The results of the PCR screening experiments are shown in FIGS. 10A to 10H.

The specific PCR products of one double-crossover clone from each of the four allelic exchange experiments were sequenced, and in all cases the allele exchange was confirmed. Finally, the same clones were shown to be thiamphenicol-sensitive by replica-plating single colonies onto plates of CGM agar supplemented with 20 μg/ml uracil and plates of CGM agar supplemented with 15 μg/ml thiamphenicol and 20 μg/ml uracil. The thiamphenicol-sensitive phenotype indicated that the plasmid sequence outside the homology arms, including the catP gene, is not present in the cell.

Double-crossover clones were obtained easily, and at similar frequencies, using all four plasmids. This finding confirms that the procedure has no intrinsic limitation on the size of the DNA sequence which may be delivered to the chromosome in a single step. In fact, perhaps surprisingly/counter-intuitively, the first phase of the procedure was if anything more effective with the larger DNA inserts, as the larger plasmids seemed to have a more severe replication defect. This led to a greater growth rate advantage of the desired clones in which a first recombination event had occurred (localising the catP gene to the chromosome) relative to cells containing the free plasmid, so colonies growing faster and larger than their neighbours were more obvious on the P1 and P2 plates when using the larger plasmids than when using the smaller plasmids.

A Set of Four Plasmids for the pyrE Locus of *Clostridium difficile*

A set of four plasmids was designed and constructed to facilitate allelic exchange at the pyrE locus of *C. difficile* 630 and derivatives thereof. These plasmids allow allelic exchange in *C. difficile* using the pyrE locus, in a method analogous to that used in *C. acetobutylicum* using the pyrF locus. In typical use, but not necessarily, 'cargo' sequence will be inserted between the left-hand homology arm and right-hand homology arm of a plasmid, such that after the allelic exchange procedure is complete, the cargo sequence will be stably localised to the chromosome.

A long left-hand homology region corresponding to almost the entire pyrE ORF of *C. difficile* 630 was designed. The first 50 bp of the pyrE ORF were omitted, thereby ensuring that neither the start codon nor possible secondary start codons were not present in the portion of the pyrE ORF used in the left-hand homology region, and therefore that this left-hand homology region alone could not confer a pyrE+ phenotype. The long left-hand homology arm was purchased from the DNA synthesis company DNA 2.0 Inc., then sub-cloned using the restriction endonucleases SbfI and NotI into the shuttle vector pMTL83151 (FIG. 6I) yielding plasmid pMTL-JH19 (FIG. 6J).

A right-hand homology region corresponding to the 1200 bp immediately downstream of the pyrE ORF of *C. difficile* 630, including the CD0188 ORF and a small part of the CD0189 ORF, was designed. The right-hand homology arm was purchased from the DNA synthesis company DNA 2.0 Inc., and then sub-cloned using the restriction endonucleases NheI and AscI into the plasmid pMTL-JH19 yielding plasmid pMTL-JH20 (FIG. 6K).

A short left-hand homology region corresponding to an internal portion of the pyrE ORF of *C. difficile* 630 was designed. Both the first 50 bp of the pyrE ORF and a substantial 3' portion of the pyrE ORF were omitted. This design ensured that a homologous recombination event between this internal portion of the pyrE ORF and the full-length pyrE ORF would lead to two non-functional derivatives of the pyrE ORF: one foreshortened derivative lacking the first 50 bp of the pyrF ORF, which includes both the start codon and possible secondary start codons; and the other derivative truncated, lacking a substantial 3' portion of the pyrE ORF. The short left-hand homology arm was purchased from the DNA synthesis company DNA 2.0 Inc., then sub-cloned using the restriction endonucleases SbfI and NotI into the shuttle vector pMTL83151 yielding plasmid pMTL-JH17 (FIG. 6L). The same right-hand homology region described above, corresponding to the 1200 bp immediately downstream of the pyrE ORF, was sub-cloned using the restriction endonucleases NheI and AscI into the plasmid pMTL-JH17 yielding plasmid pMTL-JH18 (FIG. 6M).

Each of the four plasmids is designed for use in an allelic exchange procedure at the pyrE locus in which the first of two homologous recombination events is directed by a long right-hand homology arm. Plasmids pMTL-JH18 and pMTL-JH20 already contain such a long right-hand homology arm, whereas plasmids pMTL-JH17 and pMTL-JH19 serve as precursors to plasmids for use in derivatives of *C. difficile* 630 in which the chromosome has previously been modified such that the sequence immediately downstream of the pyrE ORF differs from the wild-type. In such cases, a right-hand homology arm could be constructed corresponding to the region immediately downstream of the pyrE ORF in the modified derivative of *C. difficile* 630, and inserted into pMTL-JH17 or pMTL-JH19 as appropriate. The right-hand homology arm may be designed to be longer than the left-hand homology arm so that the right-hand homology arm is more likely to direct the first of the two homologous recombination events.

During a first phase of the allelic exchange procedure, cells in which a first homologous recombination event has occurred are enriched relative to cells containing free plasmid by culture on growth medium supplemented with the antibiotic thiamphenicol. Thiamphenicol-resistance is encoded by the plasmid-borne catP gene, but the plasmids have a replication defect which limits the growth rate of cells containing free plasmid under these conditions. Those cells in which a first homologous recombination event has occurred are not under this growth rate limitation, as the catP gene is localised to the chromosome. This growth rate difference provides the basis for enrichment of cells in which a first homologous recombination event has occurred.

During a second phase of the allelic exchange procedure, cells in which a second homologous recombination event has occurred are selected. The second homologous recombination event is directed by the left-hand homology arm.

In the case of pMTL-JH18 or a suitable derivative of pMTL-JH17, the second recombination event is between the internal portion of pyrE originating from the plasmid and the equivalent region of the full-length, functional pyrE ORF originating from the host cell chromosome. Such a host strain may be the wild-type, or may have been previously constructed using pMTL-JH20 or a suitable derivative of pMTL-JH19. After this recombination event, the cell contains no functional copies of the pyrE ORF, in contrast to the cell prior to this event, and develops a pyrE− phenotype. Such cells are selected by sub-culturing onto growth medium supplemented with appropriate concentrations of fluoroorotic acid (FOA) and uracil. Under these conditions, cells with a pyrE+ phenotype convert FOA into a more toxic substance and grow very poorly if at all; while cells with a pyrE− phenotype do not catalyze this conversion, and their growth is selected.

In the case of pMTL-JH20 or a suitable derivative of pMTL-JH19, the second recombination event is between some or all of the foreshortened pyrE ORF originating from the plasmid, lacking the start codon and possible secondary start codons, and the equivalent region of the truncated pyrE ORF originating from the host cell chromosome. Such a host strain may have been previously constructed using pMTL-JH18 or a suitable derivative of pMTL-JH17. After this recombination event, the cell contains a functional copy of the pyrE ORF, in contrast to the cell prior to this event, and develops a pyrE+ phenotype. Such cells are selected by sub-culturing onto minimal growth medium containing no or low levels of uracil. Under these conditions, cells with a pyrE− phenotype, which cannot synthesize uracil de novo, grow very poorly if at all; while cells with a pyrE+ phenotype can synthesize uracil de novo, and their growth is selected.

Allelic Exchange Using pMTL-JH18-Lambda6.5 in *C. difficile* 630Δerm

An allelic exchange procedure was attempted using pMTL-JH18-lambda6.5 in *C. difficile* 630Δerm in a similar way as described for pMTL-JH12 in *C. acetobutylicum* ATCC824. Allelic exchange requires two homologous recombination events; one between each of two pairs of homology arms. In a first phase of the procedure cells in which a first recombination event had occurred were enriched for. In a second phase of the procedure cells in which a second recombination event had occurred were selected.

Plasmid pMTL-JH18-lambda6.5 was generated by inserting a 6.5 kb lambda DNA fragment into the multiple cloning site within the lacZ-alpha gene in pMTL-JH18, thereby interrupting the lacZ-alpha gene. This plasmid was then transformed by electroporation into *E. coli* CA434 cells, which can act as a conjugation donor for plasmids with a suitable origin of transfer, such as pMTL-JH18-lambda6.5 (Heap et al 2007). pMTL-JH18-lambda6.5 was then transferred from the CA434 cells to *C. difficile* 630Δerm by conjugation (Heap et al 2007). *C. difficile* 630Δerm recipients of pMTL-JH18-lambda6.5, which includes the thiamphenicol-resistance gene catP, were selected by plating the cell mixture after conjugation onto fresh plates of BHI agar supplemented with 250 μg/ml D-cycloserine, 8 μg/ml cefoxitin and 15 μg/ml thiamphenicol. Several transconjugant colonies were obtained.

It was anticipated that if sub-cultured on the same medium, the growth rate of these transconjugants would be limited by the replication defect of the plasmid; while cells in which the catP gene was localised to the chromosome by a first recombination event would not be under this growth rate limitation. This growth rate differential provides a basis for the enrichment of the desired cells in which the first recombination event has occurred.

Forty-eight hours after the conjugation, six of the largest colonies were sub-cultured onto fresh plates of the same growth medium (passage 1; P1). These clones and their derivatives were treated independently in all subsequent steps of the procedure. Twenty-four hours later, colonies on the P1 plates were large enough to be picked, and were sub-cultured onto fresh plates of the same growth medium (passage 1; P2). Twenty-four hours later, colonies on the P2 plates were large enough to be picked. Colonies from the P2 plates were sub-cultured onto fresh plates of CDM (complete defined medium—Karlsson et al. (1999) Microbiology 145:1683-1693) supplemented with 5 μg/ml uracil and 2 mg/ml fluoroorotic acid (FOA), under the assumption that these colonies were highly enriched for the desired cells in which the first recombination event had occurred, and would contain a small number of cells in which the second recombination event had occurred (passage 3; P3). Overnight cultures in BHIS broth were also inoculated from the P2 plate of each of the six clones, one of which failed to grow. Genomic DNA was purified from the five remaining overnight cultures to be used as templates in a PCR experiment later.

Twenty-four hours after inoculation, colonies on the P3 plates were large enough to be picked, and were sub-cultured onto fresh plates of the same growth medium (passage 4; P4). Growth on the P3 plates was presumed to correspond to a pyrE− phenotype, resulting from a desired second recombination event. Sub-culturing onto the P4 plates served to purify such clones. Twenty-four hours later, colonies on the P4 plates were large enough to be picked, and were used to inoculate overnight cultures in BHIS broth. Six clones reached this stage of the procedure, but one of the final overnight cultures failed to grow. Genomic DNA was purified from the five remaining overnight cultures and used as templates in PCR experiments to identify clones in which both the desired homologous recombination events had occurred.

In a first 'right-hand crossover' PCR experiment the primers used were lacZalpha-sF2 (5' to 3' sequence ACTGGCCGTCGTTTTACAACGTCGTG (SEQ ID NO: 33)) which binds to the plasmid lacZα sequence in the forward orientation; and Cdi630-CD0189-SR3 (5' to 3' sequence ccaagctctatgacagacagctcattgtttagaac (SEQ ID NO: 34)) which binds to the *C. difficile* 630Δerm chromosome downstream of the right-hand homology arm in the reverse orientation. This pair of primers can amplify a PCR product of ~1500 bp from genomic DNA of cells in which a homologous recombination event has occurred at the right-hand homology arm, localising the primer binding sites to the same DNA molecule ~1500 bp apart.

In a second 'left-hand crossover' PCR experiment the primers used were lambda6.5-sF2 (5' to 3' sequence cctgaacatgagaaaaaacagggtactcata (SEQ ID NO: 35)) which binds to the plasmid 6.5 kbp lambda sequence in the reverse orientation; and Cdi630-pyrD-SF1 (5' to 3' sequence tagagaaggaataaaaagtttagacgaaataagagg (SEQ ID NO: 36)) which binds to the *C. difficile* 630Δerm chromosome upstream of the left-hand homology arm in the forward orientation. This pair of primers can amplify a PCR product of ~600 bp from genomic DNA of cells in which a homologous recombination event has occurred at the left-hand homology arm, localising the primer binding sites to the same DNA molecule ~600 bp apart.

All five candidate double crossover clones screened produced the expected specific PCR products in both the left-hand and right-hand PCR experiments, indicating that these were the desired double-crossover clones in which homologous recombination events had occurred at both the left and right homology arms, completing the allelic exchange procedure, and stably localising the cargo sequence including the lambda DNA to the chromosome. The results of the PCR screening experiments are shown in FIGS. 6O and 6P.

The specific PCR products of one double-crossover clone were sequenced, and the sequencing data confirmed the allele exchange. Finally, the same clone was shown to be thiamphenicol-sensitive by replica-plating single colonies onto plates of BHIS agar supplemented with 250 μg/ml D-cycloserine and 8 μg/ml cefoxitin and plates of BHIS agar supplemented with 250 μg/ml D-cycloserine, 8 μg/ml cefoxitin and 15 μg/ml thiamphenicol. The thiamphenicol-sensitive phenotype indicated that the plasmid sequence outside the homology arms, including the catP gene, is not present in the cell.

These findings demonstrate that the method of the invention can be applied in *C. difficile* 630Δerm.

A Set of Four Plasmids for the pyrE Locus of *Clostridium acetobutylicum*

A set of four plasmids was designed and constructed to facilitate allelic exchange at the pyrE locus of *C. acetobutylicum* ATCC 824 and derivatives thereof. In typical use, but not necessarily, 'cargo' sequence will be inserted between the left-hand homology arm and right-hand homology arm of a plasmid, such that after the allelic exchange procedure is complete, the cargo sequence will be stably localised to the chromosome.

A long left-hand homology region corresponding to almost the entire pyrE ORF was PCR-amplified from *C. acetobutylicum* ATCC 824 genomic DNA template using primers pyrE-LHAv1.0-F1 (5' to 3' sequence cctgcaggAGAGTAATGTACTTACCTTTGGGGATTTCATAAC (SEQ ID NO: 37)) and pyrE-LHAv1.0long-R1 (5' to 3' sequence gcggccgcTTACTATTTTACTCCATACTCTTTATAGTACTCATTAATTC (SEQ ID NO: 38)). These primers were designed to omit the first 40 bp of the pyrE ORF, thereby ensuring that both the start codon and a possible secondary start codon were not present in the portion of the pyrE ORF used in the left-hand homology region, and therefore that this left-hand homology region alone could not confer a pyrE+ phenotype. The PCR product was cloned into plasmid pCR2.1-TA and its sequence verified. The long left-hand homology arm was then sub-cloned using the restriction endonucleases SbfI and NotI into the shuttle vector pMTL85141 yielding plasmid pMTL-JH13 (FIG. 6S).

A right-hand homology region corresponding to the 1200 bp immediately downstream of the pyrE ORF, including part of the hydA ORF, was PCR-amplified from *C. acetobutylicum* ATCC 824 genomic DNA template using primers hydA-RHAv1.0-F2 (5' to 3' sequence gctagctaaaataaatgtgcctcaacttagatgttaaggcacatttattttatatattattcatg (SEQ ID NO: 39)) and hydA-RHAv1.0-R2 (5' to 3' sequence ggcgcgccTGTTGCTGCTTTAAAAGAAAAATCCCATATAGAAAAAGTTCAAGAAGC (SEQ ID NO: 40)). The PCR product was cloned into plasmid pCR2.1-TA and its sequence verified. The right-hand homology arm was then sub-cloned using the restriction endonucleases NheI and AscI into the plasmid pMTL-JH13 yielding plasmid pMTL-JH14 (FIG. 6T).

A short left-hand homology region corresponding to an internal portion of the pyrE ORF near the 5' end was PCR-amplified from *C. acetobutylicum* ATCC 824 genomic DNA template using primer pyrE-LHAv1.0-F1 described above and primer pyrE-LHAv1.0short-R1 (5' to 3' sequence gcggccgcCAAGAAGTATTCCCTTATCACCGTGATCTTTAAC (SEQ ID NO: 41)). These primers were designed to omit both the first 40 bp of the pyrE ORF and a substantial 3' portion of the pyrE ORF. This design ensures that a homologous recombination event between this internal portion of the pyrE ORF and the full-length pyrE ORF would lead to two non-functional derivatives of the pyrE ORF: one foreshortened derivative lacking the first 40 bp of the pyrF ORF, which includes both the start codon and a possible secondary start codon; and the other derivative truncated, lacking a substantial 3' portion of the pyrE ORF. The PCR product was cloned into plasmid pCR2.1-TA and its sequence verified. The short left-hand homology arm was then sub-cloned using the restriction endonucleases SbfI and NotI into the shuttle vector pMTL85141 yielding plasmid pMTL-JH11 (FIG. 6Q). The same right-hand homology region described above, corresponding to the 1200 bp immediately downstream of the pyrE ORF, was sub-cloned using the restriction endonucleases NheI and AscI into the plasmid pMTL-JH11 yielding plasmid pMTL-JH12 (FIG. 6R).

Each of the four plasmids is designed for use in an allelic exchange procedure at the pyrE locus in which the first of two homologous recombination events is directed by a long right-hand homology arm. Plasmids pMTL-JH12 and pMTL-JH14 already contain such a long right-hand homology arm, whereas plasmids pMTL-JH11 and pMTL-JH13 serve as precursors to plasmids for use in derivatives of *C. acetobutylicum* ATCC 824 in which the chromosome has previously been modified such that the sequence immediately downstream of the pyrE ORF differs from the wild-type. In such cases, a right-hand homology arm would be constructed corresponding to the region immediately downstream of the pyrE ORF in the modified derivative of *C. acetobutylicum* ATCC 824, and inserted into pMTL-JH11 or pMTL-JH13 as appropriate. Whenever possible, the right-hand homology arm is designed to be longer than the left-hand homology arm so that the right-hand homology arm is more likely to direct the first of the two homologous recombination events.

During a first phase of the allelic exchange procedure, cells in which a first homologous recombination event has occurred are enriched relative to cells containing free plasmid by culture on growth medium supplemented with the antibiotic thiamphenicol. Thiamphenicol-resistance is encoded by the plasmid-borne catP gene, but the plasmids have a replication defect which limits the growth rate of cells containing free plasmid under these conditions. Those cells in which a first homologous recombination event has occurred are not under this growth rate limitation, as the catP gene is localised to the chromosome. This growth rate difference provides the basis for enrichment of cells in which a first homologous recombination event has occurred.

During a second phase of the allelic exchange procedure, cells in which a second homologous recombination event has occurred are selected. The second homologous recombination event is directed by the left-hand homology arm.

In the case of pMTL-JH12 or a suitable derivative of pMTL-JH11, the second recombination event is between the internal portion of pyrE originating from the plasmid and the equivalent region of the full-length, functional pyrE ORF originating from the host cell chromosome. Such a host strain may be the wild-type, or may have been previously constructed using pMTL-JH14 or a suitable derivative of pMTL-JH13. After this recombination event, the cell contains no functional copies of the pyrE ORF, in contrast to the cell prior to this event, and develops a pyrE− phenotype. Such cells are selected by sub-culturing onto growth medium supplemented with appropriate concentrations of fluoroorotic acid (FOA) and uracil. Under these conditions, cells with a pyrE+ phenotype convert FOA into a more toxic substance and grow very poorly if at all; while cells with a pyrE− phenotype do not catalyze this conversion, and their growth is selected.

In the case of pMTL-JH14 or a suitable derivative of pMTL-JH13, the second recombination event is between some or all of the foreshortened pyrE ORF originating from the plasmid, lacking both the start codon and a possible secondary start codon, and the equivalent region of the truncated pyrE ORF originating from the host cell chromosome. Such a host strain may have been previously constructed using pMTL-JH12 or a suitable derivative of pMTL-JH11. After this recombination event, the cell contains a functional copy of the pyrE ORF, in contrast to the cell prior to this event, and develops a pyrE+ phenotype. Such cells are selected by sub-culturing onto minimal growth medium containing no or low levels of uracil. Under these conditions, cells with a pyrE− phenotype, which cannot synthesize uracil de novo, grow very poorly if at all; while cells with a pyrE+ phenotype can synthesize uracil de novo, and their growth is selected.

EXAMPLE 5

Figure 7:
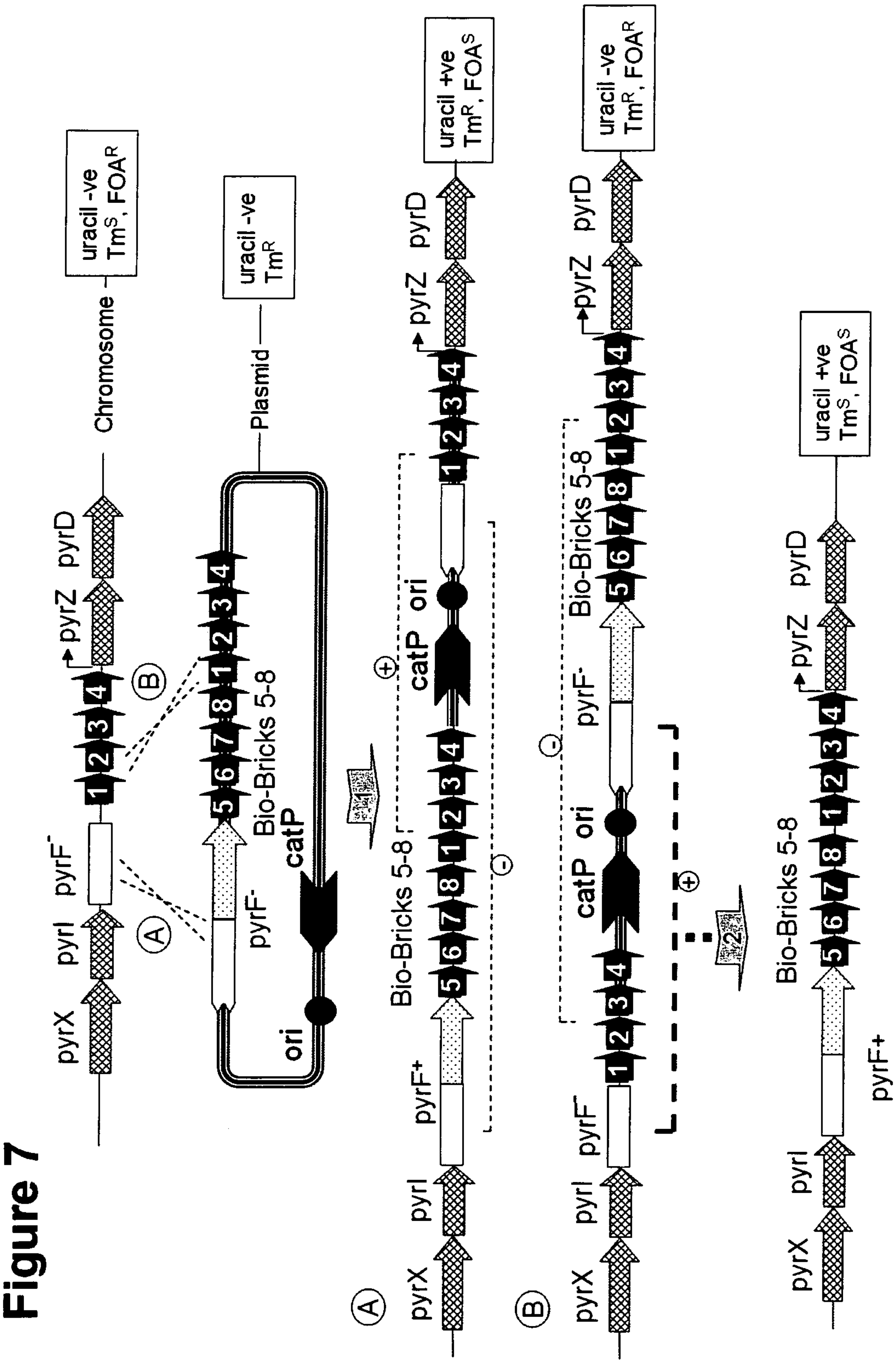

Alternative Scheme for Inserting Cargo DNA by Selection for Restoration of pyrF The pyrF− *C. acetobutylicum* strain obtained as the product of the method of Example 4 could be used in further round of double homologous recombination with a vector as illustrated in FIG. 7, and the second recombination event counter selected for by restoration of the pyrF gene. The vector would be of similar construction to the vector described in Example 1 and illustrated in FIG. 2.

The plasmid illustrated in FIG. 7 contains an allelic exchange cassette with an upstream homology arm corresponding to the 5' part of the pyrF ORF but lacking the first 47 bp. Immediately downstream is the 3' part of pyrF, for which there is no corresponding region in the host cell chromosome. Cargo sequence marked as Bio-Bricks 5-8 is located downstream of the truncated pyrF. Downstream of the Bio-Bricks 5-8 cargo sequence is a downstream homology arm corresponding in this example to the Bio-Bricks 1-4 sequence. The donor DNA molecule also contains a catP antibiotic resistance gene that confers resistance to the antibiotic thiamphenicol.

Host cells transformed with the plasmid would grow on rich medium containing thiamphenicol, although the growth rate of these cells would be limited by the replication defect of the catP-containing plasmid. A type (A) or (B) recombination event would integrate the plasmid into the chromosome, each yielding a different product DNA molecule as shown. Either of these events would confer a growth advantage to the host cell in the presence of thiamphenicol, since the catP gene becomes linked to the efficient replication of the chromosome. Cells in which a type (A) or (B) recombination event has occurred, although initially relatively rare, would be readily enriched and selected by re-streaking one or more times.

Products of type (A) recombination events would contain both a truncated, non-functional pyrF allele and a full-length pyrF allele. A full-length pyrF allele confers dominant uracil prototrophy and FOA-sensitivity in cells containing the product of type (A) events. Products of type (B) recombination events do not contain a full-length pyrF allele. To ensure that only cells containing a pyrF− phenotype are obtained, the enrichment and selection for cells in which an integration event has occurred would be performed using rich medium containing thiamphenicol, uracil and FOA. The cells obtained containing the products of type (B) integration events would be re-streaked onto rich media containing uracil, but lacking thiamphenicol or FOA. This process would allow second recombination events to occur without selection for thiamphenicol-resistance or FOA-resistance.

Depending upon which pair of homology arms directed the second recombination event, different chromosomal arrangements would result. In a final step, cells would be re-streaked onto un-supplemented minimal medium. Prototrophic cells growing after this final step would be selected as the desired double-crossover integrant containing the cargo sequence, derived from cells in which a type (B) event directed the initial plasmid integration.

The desired product is pyrF+ and could be subjected to a further round of double homologous recombination as described in Example 4. Cargo DNA could be added iteratively by successively performing the Example 4 and 5 methods. Of course, with each successive iteration, the plasmid would need to be adapted such that the downstream homology arm corresponded to the cargo DNA inserted during the preceding iteration.

EXAMPLE 6

Scheme for Iteratively Inserting Cargo DNA by Positive Selection Using Alternative Antibiotic Resistance Genes According to the method illustrated in FIG. 8A, cargo DNA could be iteratively inserted at a selected site in the host DNA molecule. It would not be necessary to insert DNA in the vicinity of pyrF, or other positively and negatively selectable allele. The only requirement would be that the region contains a suitable promoter which would act as a second element of a selectable allele, in conjunction with a first element of the selectable allele, which is the coding region of a positively selectable allele, and is provided by the donor DNA molecule. Only positive selection would be applied to select for desired products. Therefore, the method could be applied in organisms for which no counter selectable marker has been identified.

The chromosomal region illustrated in FIG. 8A includes a transcriptional promoter, in this example immediately upstream of 'gene A', and 'gene B' immediately downstream of 'gene A'. The donor DNA molecule, a plasmid, contains an allelic exchange cassette with an upstream homology arm corresponding to sequence downstream of the transcriptional promoter, in this example some or all of the 'gene A' ORF, but not the transcriptional promoter itself. Downstream of the upstream homology arm on the donor molecule is the ORF of an antibiotic resistance gene lacking a promoter 'Ab1', followed by cargo sequence marked as Bio-Bricks 1-4, followed by a downstream homology arm corresponding in this example to some or all of 'gene B'. The donor DNA molecule also contains in this example the catP antibiotic resistance gene that confers resistance to the antibiotic thiamphenicol.

Host cells containing the described plasmid and chromosomal region would grow on medium containing thiamphenicol, although the growth rate of these cells would be limited by the replication defect of the catP-containing plasmid. A type (A) or (B) recombination event would integrate the plasmid into the chromosome, yielding a product DNA molecule as shown in FIG. 8A. Either of these events confers a growth advantage to the host cell in the presence of thiamphenicol, since the catP gene is now linked to the efficient replication of the chromosome. Cells in which a type (A) or (B) recombination event has occurred, although initially relatively rare, could be readily enriched and selected by re-streaking one or more times.

Type (A) recombination events cause the operable linkage of the transcriptional promoter originating from the chromosome with the 'Ab1' ORF originating from the plasmid, thereby forming a complete, functional 'Ab1' gene, which was not previously present in the cell. This event causes the acquisition of resistance to the associated antibiotic(s). There is no means to select for a second recombination event in such clones. Type (B) recombination events do not cause the formation of a complete, functional 'Ab1' gene nor the associated change in phenotype. Clones containing the type (B) recombination product would be identified by replica plating onto media with and without the antibiotic to which a complete Ab1 gene confers resistance. In either case, thiamphenicol would be included to select against the second recombination event occurring prematurely. If a clone was unable to grow in the presence of the antibiotic to which a complete Ab1 gene confers resistance, the corresponding clone from the replica plate lacking the antibiotic would be selected as deriving from the type (B) recombination event.

Cells containing the product of a type (B) integration event would be re-streaked onto media lacking thiamphenicol. This process would allow second recombination events to occur without selection for thiamphenicol-resistance. Depending upon which pair of homology arms direct the second recombination event, different chromosomal arrangements would result. In a final step, cells containing the products of type (B) integration events would be re-streaked onto media containing selective concentration(s) of the antibiotic(s) associated with the 'Ab1' gene. Resistant cells would contain the desired double-crossover product of the second recombination event.

The desired Ab1 resistant product obtained by the above method may be subjected to a further round of double homologous recombination as described below and as illustrated in FIG. 9, in which resistance to a different antibiotic Ab2 forms the basis of selection for the second recombination event. This further round uses essentially the same method as the first round, with the substitution of Ab2 for Ab1. Preferably, and as illustrated in FIG. 9, the donor DNA molecule is designed to allow for loss of Ab1 in the second recombination event. Where Ab1 is lost in this second iteration, the product of the second iteration may be subjected to a further round of double homologous recombination, in which resistance to antibiotic Ab2 forms the basis of selection for the second recombination event The chromosomal region illustrated in FIG. 9 includes a transcriptional promoter immediately upstream of 'gene A', followed by the coding region of Ab1 and Bio-Bricks 1-4 inserted in the first iteration of the method, and 'gene B' immediately downstream. The donor DNA molecule, a plasmid, contains an allelic exchange cassette with an upstream homology arm corresponding to the sequence downstream of the transcriptional promoter, in this example some or all of the 'gene A' ORF, but not the transcriptional promoter itself. Downstream of the upstream homology arm on the donor molecule is the ORF of an antibiotic resistance gene lacking a promoter 'Ab2', followed by cargo sequence marked as Bio-Bricks 5-8, followed by a downstream homology arm corresponding to previously inserted Bio-Bricks 1-4. Because the Ab1 coding region lies between the two homology arms in the chromosome, it is lost during the double homologous recombination method. The plasmid also contains the catP antibiotic resistance gene that confers resistance to the antibiotic thiamphenicol.

Host cells containing the described plasmid and chromosomal region would grow on medium containing thiamphenicol, although the growth rate of these cells would be limited by the replication defect of the catP-containing plasmid. A type (A) or (B) recombination event would integrate the plasmid into the chromosome, yielding a different product DNA molecule as shown in FIG. 9. Either of these events would confer a growth advantage to the host cell in the presence of thiamphenicol, since the catP gene is now linked to the efficient replication of the chromosome. Cells in which a type (A) or (B) recombination event has occurred, although initially relatively rare, are readily enriched and selected by re-streaking one or more times.

Type (A) recombination events cause the operable linkage of the transcriptional promoter originating from the chromosome with the 'Ab2' ORF originating from the plasmid, thereby forming a complete, functional 'Ab2' gene, which was not previously present in the cell. This event causes the acquisition of resistance to the associated antibiotic(s). There is no means to select for a second recombination event in such clones. Type (B) recombination events do not cause the formation of a complete, functional 'Ab2' gene nor the associated change in phenotype. Clones containing the type (B) recombination product could be identified by replica plating onto media with and without the antibiotic to which a complete Ab2 gene confers resistance. In either case, thiamphenicol would be included to select against the second recombination event occurring prematurely. If a clone was unable to grow in the presence of the antibiotic to which a complete Ab1 gene confers resistance, the corresponding clone from the replica plate lacking the antibiotic would be selected as deriving from the type (B) recombination event. Alternatively, clones containing type (B) recombination products could be selected for by virtue of resistance to Ab1, as only type (B) and not type (A) recombination products confer resistance to Ab1.

Cells containing the product of a type (B) integration event would be re-streaked onto media lacking thiamphenicol. This process would allow second recombination events to occur without selection for thiamphenicol-resistance. Depending upon which pair of homology arms direct the second recombination event, different chromosomal arrangements would result. In a final step, cells containing the products of type (B) integration events would be re-streaked onto media containing selective concentration(s) of the antibiotic(s) associated with the 'Ab2' gene. Resistant cells would contain the desired double-crossover product of the second recombination event.

Importantly, such cells have also lost the 'Ab1' gene and associated phenotype, allowing the 'Ab1' ORF to be 'recycled' in further steps in which 'Ab1' and 'Ab2' are alternated, facilitating the sequential insertion of cargo sequences ad infinitum.

Typically, to perform one iteration of this scheme requires the use of selectable markers that confer resistance on two different antibiotics. A first selectable marker selects for the first recombination event (in the above example catP conferring resistance on thiamphenicol) and a second selectable marker selects for the second recombination event (in the above example Ab1 or Ab2). If the method is to be used iteratively, typically three selectable markers are required. Erythromycin, thiamphenicol, spectinomycin, tetracycline and lincomycin resistance markers are suitable selectable alleles in Clostridia. Alternative selectable markers may be used in other host classes.

In this scheme, a suitable promoter (i.e. a second element of the selectable allele) is required to cause sufficient expression of the selectable marker (i.e. the first element of the selectable allele) when the two elements are combined in single copy on the chromosome, to alter the phenotype of the host cell. For example, the promoter may be one which, when present in a single copy in the bacterial chromosome, and when in operable linkage with the coding region of the selectable marker, expresses the selectable marker in a detectable amount. *Clostridium* sp. Suitable promoters for use in *Clostridium* sp. include the fdx gene promoter of *C. perfringens* (Takamizawa et al (2004) *Protein Expression Purification* 36: 70-75); the ptb, thl and the adc promoters of *C. acetobutylicum* (Tummala et al (1999) *App. Environ. Microbiol.* 65: 3793-3799) and the cpe promoter of *C. perfringens* (Melville, Labbe and Sonenshein (1994) *Infection and Immunity* 62: 5550-5558) and the thiolase promoter from *C. acetobutylicum* (Winzer et al (2000) *J. Mol. Microbiol. Biotechnol.* 2: 531-541). The promoter of the thl gene of *C. acetobutylicum* is strong enough to cause sufficient expression of the product of the ermB gene of *Enterococcus faecalis* plasmid pAMβ1 at single copy level to confer resistance to erythromycin on Clostridia (Heap et al (2007) supra.)

To test whether a promoter is likely to be effective as a second element of a selectable allele, the first element of the selectable allele may be placed under its transcriptional control and introduced into the Clostridia to be targeted at a low copy number, preferably equivalent to the copy number of the chromosome. This can be achieved by using a low copy number plasmid, such as the low copy number derivatives of plasmid pAMβ1 described in Swinfield et al (1990) Gene. 87:79-90 or more ideally using a conjugative transposon and the method described in Mullany et al (*Plasmid* (1994) 31: 320-323) and Roberts et al (*J Microbiol Methods* (2003) 55: 617-624). To achieve the latter, the second and first elements of the selectable allele may be cloned into a vector that is unable to replicate in a Gram-positive bacterium but which carries an antibiotic resistance gene (eg catP) and a segment of DNA derived from a conjugative transposon, such as Tn916. The plasmid is then transformed into a *Bacillus subtilis* cell that carries the appropriate conjugative transposon in its genome (Tn916), and transformants selected on plates containing chloramphenicol. As the plasmid cannot replicate, the only way that chloramphenicol resistant colonies can arise is if the plasmid integrates into the genome as a consequence of homologous recombination between Tn916 and the region of homology carried by the plasmid. This results in a transposon::plasmid cointegrate carrying the second and first elements of the selectable allele that is located in a single copy in the genome. The *Bacillus subtilis* transconjugant obtained may now be used as a donor in a conjugation with the host Clostridia. In these matings, transfer of the transposon::plasmid cointegrate into the Clostridia recipient can be selected on the basis of acquisition of resistance to thiamphenicol. Once obtained, transconjugants may be tested for the resistance encoded by selectable allele, e.g., erythromycin. It may be necessary to evaluate promoters for suitability as elements of the selectable allele in other host species, or indeed to evaluate other components for suitability as elements of a selectable allele. The above approach may readily be adapted to this end by the skilled person.

A Set of Two Plasmids for the thl Locus of *Clostridium acetobutylicum*

To exemplify the scheme described in Example 6a set of two plasmids was designed and constructed to facilitate allelic exchange at the thl locus of *C. acetobutylicum* ATCC 824 and derivatives thereof. In typical use, but not necessarily, 'cargo' sequence will be inserted between the left-hand homology arm and right-hand homology arm of a plasmid, such that after the allelic exchange procedure is complete, the cargo sequence will be stably localised to the chromosome.

A left-hand homology region corresponding to the last 300 bp of the thl ORF was PCR-amplified from *C. acetobutylicum* ATCC 824 genomic DNA template using primers Cac-thl-LHAv1.0-F1 (5' to 3' sequence taaattGATATCtatgcaacaaaag-cagctattgaaaaagcagg (SEQ ID NO: 42)) and Cac-thl-LHAv1.0-R1 (5' to 3' sequence CTCCTTCTTAatcgatCTAG-CACTTTTCTAGCAATATTGCTGTTCC (SEQ ID NO: 43)), and the PCR product was gel-purified. The ermB ORF with its ribosome-binding site (RBS) was PCR-amplified from pMTL21E DNA template using primers ClaI-ermB-F1 (5' to 3' sequence GTGCTAGatcgatTAAGAAGGAGTGAT-TACATGAACAAAAATATAAAATATTCTC SEQ ID NO: 44)) and ermB-AfeI-R1 (5' to 3' sequence ATTCTTTagcgctT-TATTTCCTCCCGTTAAATAATAGATAAC-TATTAAAAATAGAC (SEQ ID NO: 45)), and the PCR product was gel-purified. Primers Cac-thl-LHAv1.0-R1 and ClaI-ermB-F1 were designed to produce a region of sequence identity between the 3' end of the thl PCR product and the 5' end of the ermB PCR product, which allowed these two purified PCR products to be used as templates in a splicing by overlap (SOE) PCR with primers Cac-thl-LHAv1.0-F1 and ermB-AfeI-R1. The resultant thl-ermB SOE PCR product was cloned into plasmid pCR2.1-TA and its sequence verified. The thl-ermB sequence was then sub-cloned using the restriction endonucleases EcoRV and AfeI, which generate blunt DNA ends; into the shuttle vector pMTL85141, linearised with NotI and blunted with T4 DNA polymerase; yielding plasmid pMTL-JH15 (FIG. 8B). This strategy was designed to regenerate only a single NotI site in pMTL-JH15, to the right-hand (3') side of the thl-ermB sequence; and also to retain the transcriptional terminator, originating from pMTL85141, to the left-hand (5') side of the thl-ermB sequence. The unique NotI site may prove useful in future cloning strategies, and the transcriptional terminator prevents or reduces undesirable transcriptional read-through into ermB, either on the plasmid, or in plasmid derivatives, or in other derivatives, such as a cointegrate molecule formed by a plasmid and a chromosome during an allelic exchange procedure.

A right-hand homology region corresponding to the 1200 bp immediately downstream of the thl ORF of *C. acetobutylicum* ATCC 824, including the CAC2872 ORF and part of the atpB ORF, was designed. The right-hand homology arm was purchased from the DNA synthesis company DNA 2.0 Inc., then sub-cloned using the restriction endonucleases NheI and AscI into the plasmid pMTL-JH15 yielding plasmid pMTL-JH16 (FIG. 8C).

Further plasmids similar to pMTL-JH15 and pMTL-JH16, but with an alternative selectable marker ORF and RBS in place of the ermB ORF and RBS, could be constructed. This would allow a series of allelic exchange procedures to be performed by alternating between different selectable markers, as illustrated in FIGS. 8A and 9.

Construction of such plasmids would be facilitated by the suitably positioned unique ClaI and NotI sites in pMTL-JH15 and pMTL-JH16. An alternative antibiotic-resistance ORF and RBS would be a suitable selectable marker. A heterologous pyrF ORF and RBS or pyrE ORF and RBS would be a suitable selectable marker for use in a pyrF− or pyrE− host strain respectively.

Plasmids pMTL-JH15 and pMTL-JH16, and similar plasmids which could be constructed as described above, are designed for use in an allelic exchange procedure at the thl locus in which the first of two homologous recombination events is directed by a long right-hand homology arm.

Plasmid pMTL-JH16 already contains such a long right-hand homology arm, whereas plasmid pMTL-JH15 can serve as a precursor to plasmids for use in derivatives of *C. acetobutylicum* ATCC 824 in which the chromosome has previously been modified such that the sequence immediately downstream of the thl ORF differs from the wild-type. In such cases, a right-hand homology arm could be constructed corresponding to the region immediately downstream of the thl ORF in the modified derivative of *C. acetobutylicum* ATCC 824, and inserted as appropriate into pMTL-JH15 or similar plasmids which could be constructed as described above. The right-hand homology arm may be designed to be longer than the left-hand homology arm so that the right-hand homology arm is more likely to direct the first of the two homologous recombination events.

During a first phase of the allelic exchange procedure, cells in which a first homologous recombination event has occurred are enriched relative to cells containing free plasmid by culture on growth medium supplemented with the antibiotic thiamphenicol. Thiamphenicol-resistance is encoded by the plasmid-borne catP gene, but the plasmids have a replication defect which limits the growth rate of cells containing free plasmid under these conditions. Those cells in which a first homologous recombination event has occurred are not under this growth rate limitation, as the catP gene is localised to the chromosome. This growth rate difference provides the basis for enrichment of cells in which a first homologous recombination event has occurred.

During a second phase of the allelic exchange procedure, cells in which a second homologous recombination event has occurred are selected. The second homologous recombination event is directed by the left-hand homology arm.

The second recombination event is between the region originating from the plasmid corresponding to the last 300 bp of thl ORF, and the equivalent region of the full-length thl ORF originating from the host cell chromosome.

In the case of pMTL-JH16 or a plasmid derived from pMTL-JH15 by the addition of a suitable right-hand homology arm, the host strain must be an appropriate macrolide-lincosamide-streptogramin (MLS) sensitive derivative of *C. acetobutylicum* ATCC 824. Such a host strain may be the wild-type, or may have been previously constructed using a suitable derivative of pMTL-JH15 as described above, in which an alternative selectable marker gene was used to select for the second recombination event.

After this recombination event, the ermB ORF is placed under the control of the strong chromosomal thl promoter, leading to transcription and translation of the ermB ORF, in contrast to the cell prior to this event, and the cell develops an MLS-resistant phenotype. Such cells are selected by sub-culturing onto growth medium supplemented with appropriate concentrations of an MLS antibiotic such as erythromycin. Under these conditions, cells with an MLS-sensitive phenotype grow very poorly if at all, while the growth of cells with a MLS-resistant phenotype is selected.

In the case of a plasmid derived from pMTL-JH16 by replacement of the ermB ORF and RBS with an alternative suitable selectable marker ORF and RBS; or derived from pMTL-JH15 by replacement of the ermB ORF and RBS with an alternative suitable selectable marker ORF and RBS and the addition of a suitable right-hand homology arm; the second recombination event would place the alternative selectable marker ORF under the control of the strong chromosomal thl promoter. This would lead to transcription and translation of the alternative selectable marker, and the cell would develop the corresponding selectable phenotype which could be used to select the cells in which the second recombination event had occurred.

Allelic Exchange Using pMTL-JH16 in *C. acetobutylicum* ATCC824

To exemplify the scheme described in Example 6 an allelic exchange procedure was performed using pMTL-JH16 (FIG. 8C) in *C. acetobutylicum* ATCC824. Allelic exchange requires two homologous recombination events; one between each of two pairs of homology arms. In a first phase of the procedure cells in which a first recombination event had occurred were enriched for, and in a second phase of the procedure cells in which a second recombination event had occurred were selected. Finally, PCR, sequencing and the thiamphenicol-sensitivity phenotype was used to identify and verify the clones of cells in which the allelic exchange had occurred.

Plasmid pMTL-JH16 was transformed by electroporation into *E. coli* TOP10 cells already harbouring plasmid pAN2, thereby protectively methylating it against the *C. acetobutylicum* ATCC824 Cac8241 DNA restriction system which would otherwise hinder the next step (Heap et al 2007). Methylated plasmid DNA was re-isolated from these transformed *E. coli* cells and used to transform *C. acetobutylicum* ATCC824 by electroporation, in accordance with the procedure described by Mermelstein and Papoutsakis, 1993. Cells transformed by pMTL-JH16, which includes the thiamphenicol-resistance gene catP, were selected by plating the transformation mixture onto CGM agar supplemented with 15 μg/ml thiamphenicol, and several transformant colonies were obtained.

It was anticipated that if sub-cultured on the same medium, the growth rate of these transformants would be limited by the replication defect of the plasmid; while cells in which the catP gene was localised to the chromosome by a first recombination event would not be under this growth rate limitation. This growth rate differential provides a basis for the enrichment of the desired cells in which the first recombination event has occurred. Accordingly, the largest colonies on each plate, especially those obviously larger than neighbouring colonies, would be indicative of clones of cells able to grow faster due to the localisation of the catP gene to the chromosome by a first recombination event. Therefore we sub-cultured transformants on the same medium, and preferentially sub-cultured such colonies.

Forty-eight hours after the transformation, six of the largest colonies were sub-cultured onto fresh plates of the same growth medium (passage 1; P1). These clones and their derivatives were treated independently in all subsequent steps of the procedure. Twenty-four hours later, colonies on the P1 plates were large enough to be picked, and were sub-cultured onto fresh plates of the same growth medium (passage 1; P2). Twenty-four hours later, colonies on the P2 plates were large enough to be picked, and it was assumed that these colonies were highly enriched for the desired cells in which the first recombination event had occurred, and would contain a small number of cells in which the second recombination event had occurred. Therefore, large colonies were sub-cultured onto fresh plates of CGM agar supplemented with 2.5 μg/ml erythromycin, CGM agar supplemented with 10 μg/ml erythromycin and CGM agar supplemented with 20 μg/ml erythromycin (passage 3; P3).

Seventy-two hours after inoculation, colonies on the P3 plates at all erythromycin concentrations were large enough to be picked, so were sub-cultured from the 20 μg/ml erythromycin P3 plates onto fresh plates of CGM agar supplemented with 20 μg/ml erythromycin and CGM agar supplemented with 40 μg/ml erythromycin (passage 4; P4). Growth on the P3 plates was presumed to correspond to an erythromycin-resistant phenotype resulting from a desired second recombination event, in which the ermB ORF is placed under the control of the strong chromosomal thl promoter. Subculturing onto the P4 plates served to purify these desired clones. Twenty-four hours later, colonies on the 40 μg/ml erythromycin P4 plates were large enough to be picked, and were used to inoculate overnight cultures in CGM broth supplemented with 40 μg/ml erythromycin.

Six transformant clones were successfully sub-cultured throughout the entire procedure, so all six clones were analysed at the end of the procedure. After overnight growth, the six clones were sub-cultured from the liquid culture onto fresh plates of CGM agar supplemented with 40 μg/ml erythromycin to maintain the strains. The overnight cultures were also used to purify genomic DNA from each clone, which was used as template in PCR experiments to identify clones in which both the desired homologous recombination events had occurred.

In a first 'right-hand crossover' PCR experiment the primers used were lacZalpha-sF2 (5' to 3' sequence ACTGGCCGTCGTTTTACAACGTCGTG (SEQ ID NO: 46)) which binds to the plasmid lacZα sequence in the forward orientation; and Cac-atpB-sR1 (5' to 3' sequence ATGATACTGGTATTGTAACCTTTTCTAAAAGGTTCATAGG (SEQ ID NO: 47)) which binds to the *C. acetobutylicum* ATCC824 chromosome downstream of the right-hand homology arm in the reverse orientation. This pair of primers can amplify a PCR product of ~1450 bp from genomic DNA of cells in which a homologous recombination event has occurred at the right-hand homology arm, localising the primer binding sites to the same DNA molecule ~1450 bp apart.

In a second 'left-hand crossover' PCR experiment the primers used were M13F (5' to 3' sequence TGTAAAACGACGGCCAGT (SEQ ID NO: 48)) which binds to the plasmid lacZα sequence in the reverse orientation; and Cac-thl-sF1 (5' to 3' sequence ACTTGCTAAGATAGTTTCTTATGGTTCAGCAGG (SEQ ID NO: 49)) which binds to the *C. acetobutylicum* ATCC824 chromosome upstream of the left-hand homology arm in the forward orientation. This pair of primers can amplify a PCR product of ~1250 bp from genomic DNA of cells in which a homologous recombination event has occurred at the left-hand homology arm, localising the primer binding sites to the same DNA molecule ~1250 bp apart.

All six clones screened produced the expected specific PCR products in both the left-hand and right-hand PCR experiments, indicating that these were the desired 'double-crossover' clones in which homologous recombination events had occurred at both the left and right homology ams, completing the allelic exchange procedure, and stably localising the ermB and lacZα sequences to the chromosome. The results of the PCR screening experiments are shown in FIGS. 8D and 8E.

The specific PCR products of one double-crossover clone were sequenced, and the sequencing data confirmed the allele exchange. Finally, the same clone was shown to be thiamphenicol-sensitive by replica-plating single colonies onto plates of CGM agar supplemented with 20 μg/ml erythromycin and plates of CGM agar supplemented with 15 μg/ml thiamphenicol. The thiamphenicol-sensitive phenotype indicated that the plasmid sequence outside the homology arms, including the catP gene, is not present in the cell.

These findings demonstrate that the method of the invention can be used where one element of the selectable allele is a promoter, and the other element of the selectable allele is a suitable ORF and RBS lacking its own promoter. This principle is illustrated in FIGS. 8A and 9.

The invention claimed is:

1. A method of forming a selectable allele by double cross-over homologous recombination in a host cell comprising: inserting into the host cell a donor DNA molecule comprising a first element of a first selectable allele, and at least two homology arms;

wherein the donor DNA molecule can induce a first homologous recombination event between the donor DNA molecule and an acceptor DNA molecule comprising a second element of the first selectable allele in the host cell, thereby to form a product of the first homologous recombination event in the host cell; and wherein the donor DNA molecule can induce a second homologous recombination event within the product of the first homologous recombination event, thereby to form a product of the second homologous recombination event in the host cell which confers a selectable phenotype on the host cell, wherein the selectable phenotype arises following and in dependency on the formation of a selectable allele from the first and second elements of the first selectable allele; and wherein the host cell is a prokaryote.

2. The method of claim 1 wherein the first homology arm can induce a first homologous recombination with the acceptor DNA molecule at a first recombination site upstream of the first element of the first selectable allele, and the second homology arm can induce a second homologous recombination with the acceptor DNA molecule at a second recombination site downstream of the first element of the first selectable allele; and wherein the acceptor DNA molecule comprises homology arms corresponding to the homology arms of the donor DNA molecule and the second element of the first selectable allele is located upstream of the first recombination site or downstream of the second recombination site.

3. The method of claim 1 wherein the donor DNA molecule comprises cargo DNA, wherein the cargo DNA is included in the product of the first recombination event and is retained in the product of the second recombination event.

4. The method of claim 3 wherein the first homology arm can induce homologous recombination with the acceptor DNA molecule at a first recombination site upstream of the first element of the first selectable allele, and the second homology arm can induce homologous recombination with the acceptor DNA molecule at a second recombination site downstream of the first element of the first selectable marker allele; and wherein the acceptor DNA molecule comprises homology arms corresponding to the homology arms of the donor DNA molecule and the second element of the first selectable allele is located upstream of the first recombination site or downstream of the second recombination site; and wherein the cargo DNA is located in the donor DNA molecule downstream of the first recombination site and upstream of the second recombination site.

5. The method of claim 1 wherein the donor DNA molecule comprises a selectable marker gene and the first recombination event confers a selectable phenotype on the host cell, based on the incorporation of the selectable marker gene into the product of the first homologous recombination event.

6. The method of claim 5 wherein the selectable marker gene is not retained in the product of the second recombination event.

7. The method of claim 6 wherein the donor DNA molecule comprises at least two homology arms, wherein the first homology arm induces homologous recombination with the acceptor DNA molecule at a first recombination site upstream of the first element of the first selectable allele, and the second homology arm induces homologous recombination with the acceptor DNA molecule at a second recombination site downstream of the first element of the first selectable allele; and wherein the acceptor DNA molecule comprises homology arms corresponding to the homology arms of the donor DNA molecule and the second element of the first selectable allele is located upstream of the first recombination site or downstream of the second recombination site; and wherein the selectable marker gene is located in the donor DNA molecule upstream of the homology arm that induces the first recombination site, or downstream of the homology arm that induces the second recombination site.

8. The method of claim 1 wherein the selectable allele is either:

(i) a gene which can confer either a selective advantage or a selective disadvantage on the host cell as compared to a host cell lacking the selectable allele, depending on the conditions in which the host cell is maintained; or (ii) a disrupted or partial form of such a gene, which does not confer the selective advantage or the selective disadvantage conferred by the gene.

9. The method of claim 8 wherein the selective advantage is uracil prototrophy and the selective disadvantage is sensitivity to fluoroorotic acid.

10. The method of claim 9 wherein the gene is pyrF or a homologue thereof.

11. The method of claim 1 wherein the selectable allele is an antibiotic resistance gene which confers a selective advantage on the host cell.

12. The method of claim 1 wherein following the first recombination event, the host cell in which the selectable phenotype has not been conferred by the product of the first recombination event is selected.

13. The method of claim 1 further comprising isolating the host cell comprising the product of the second homologous recombination event by selecting an altered phenotype conferred by the selectable allele, so as to provide an isolated host cell.

14. The method of claim 13 further comprising modifying the product of the second homologous recombination event in the isolated host cell, so as to generate a new first element of a selectable allele, in the altered isolated host cell.

15. A method of producing an altered host cell, the method comprising providing a host cell and carrying out the method of claim 13.

16. The method of claim 13, wherein a plurality of cargo DNA is iteratively inserted into the acceptor DNA molecule in the host cell, the method further comprising the steps of:

(i) isolating the host cell by virtue of an altered phenotype conferred by the selectable allele;

(ii) disrupting the selectable allele so that it does not confer the selective advantage on the host cell, so as to form in the host cell a modified acceptor DNA molecule comprising the cargo DNA;

(iii) inserting a second donor DNA molecule into the host cell, wherein the second donor DNA molecule comprises a second cargo DNA molecule, a first element of a second selectable allele, and at least two homology arms;

and wherein the second donor DNA molecule can induce a first homologous recombination event between the second donor DNA molecule and the modified acceptor DNA molecule comprising a second element of the second selectable allele in the host cell, thereby to form a product of the first homologous recombination event in the host cell; and wherein the second donor DNA molecule can further induce a second homologous recombination event within the product of the first homologous recombination event, thereby to form a product of the second homologous recombination event in the host cell which confers a selectable phenotype on the host cell, wherein the selectable phenotype arises following and in dependency on the formation of a selectable allele from the first and second elements of the second selectable allele, thereby forming in the host cell a further modified acceptor DNA molecule comprising the second selectable allele, the first cargo DNA and the second cargo DNA;

or the steps of:

(i) isolating the host cell by virtue of an altered phenotype conferred by the first selectable allele;

(ii) inserting a second donor DNA into the host cell, wherein the second donor DNA molecule comprises a second cargo DNA molecule, a first element of a second selectable allele, and at least two homology arms;

and wherein the second donor DNA molecule can induce a first homologous recombination event between the donor DNA molecule and the modified acceptor DNA molecule comprising a second element of the second selectable allele in the host cell, thereby to form a product of the first homologous recombination event in the host cell; and can induce a second homologous recombination event within the product of the first homologous recombination event, thereby to form a product of the second homologous recombination event in the host cell which confers a second selectable phenotype on the host cell, wherein the second selectable phenotype arises following and in dependency on the formation of a selectable allele from the first and second elements of the second selectable allele thereby forming in the host cell a further modified acceptor DNA molecule comprising a second selectable allele, the first cargo DNA and the second cargo DNA, wherein the second selectable allele confers a different altered phenotype on the host cell than the first selectable allele.

17. The method of claim 16 wherein one of the first selectable allele or the second selectable alleleis a gene which can confer a selective advantage or a selective disadvantage on the host cell as compared to a host cell lacking the first selectable allele or the second selectable allele, depending on the conditions in which the host cell is maintained;

and the other of the first selectable allele or the second selectable allele is a disrupted or partial form of such a gene, which does not confer the selective advantage or the selective disadvantage conferred by the gene.

18. The method of claim 17 wherein the selective advantage is uracil prototrophy and the selective disadvantage is sensitivity to fluoroorotic acid.

19. The method of claim 18 wherein the gene is pyrF or a homologous gene.

20. The method of claim 16 further comprising isolating the host cell comprising the further modified acceptor DNA molecule by virtue of an altered phenotype conferred by the second selectable allele.

21. A method of producing an altered host cell containing cargo DNA, the method comprising providing an isolated altered host cell according to claim 20.

22. The method of claim 20 further comprising:

inserting a third donor DNA into the host cell, wherein the third donor DNA molecule comprises a third cargo DNA molecule, a first element of a third selectable allele, and at least two homology arms;

and wherein the third donor DNA molecule can induce a first homologous recombination event between the third donor DNA molecule and the further modified acceptor DNA molecule comprising a second element of the third selectable allele in the host cell, thereby to form a product of the first homologous recombination event in the host cell; and further can induce a second homologous recombination event within the product of the first homologous recombination event, thereby to form a product of the second homologous recombination event between the third donor DNA and the further modified acceptor DNA molecule in the host cell which confers a selectable phenotype on the host cell, wherein the selectable phenotype arises following and in dependency on the formation of a selectable allele from the first and second elements of the third selectable allele thereby forming in the host cell a further modified acceptor DNA molecule comprising the third selectable allele, the first cargo DNA, the second cargo DNA and the third cargo DNA.

23. The method of claim 16 wherein the first selectable allele and the second selectable allele are retained subsequent to homologous recombination; and optionally wherein the first selectable allele and the second selectable allele each confer resistance to a different antibiotic on the host cell; and optionally wherein the first selectable allele is not retained in the product of the second recombination event in step (ii).

24. The method of claim 23 further comprising isolating the host cell comprising the further modified acceptor DNA molecule by virtue of an altered phenotype conferred by the second selectable allele.

25. A method of producing an altered host cell containing cargo DNA, the method comprising providing an isolated altered host cell according to claim 24.

26. The method of claim 23 wherein the first selectable allele is not retained in the product of the second recombination event in step (ii) further comprising:

inserting a third cargo DNA into the further modified acceptor DNA molecule by the method of double crossover homologous recombination between a third donor DNA molecule and the further modified acceptor DNA molecule, thereby forming in the host cell a modified acceptor DNA molecule comprising the first selectable allele, the first cargo DNA, the second cargo DNA and the third cargo DNA, wherein the method comprises:

inserting a third donor DNA into the host cell, wherein the third donor DNA molecule comprises a third cargo DNA molecule, a first element of a third selectable allele, and at least two homology arms;

and wherein the third donor DNA molecule can induce a first homologous recombination event between the third donor DNA molecule and the further modified acceptor DNA molecule comprising a second element of the third selectable allele in the host cell, thereby to form a product of the first homologous recombination event in the host cell; and which can induce a second homologous recombination event within the product of the first homologous recombination event, thereby to form a product of the second homologous recombination event between the third donor DNA and the further modified acceptor DNA molecule in the host cell which confers a selectable phenotype on the host cell, wherein the selectable phenotype arises following and in dependency on the formation of a selectable allele from the first and second elements of the third selectable allele.

27. The method of claim 1 wherein the host cell is a Gram positive bacterium.

28. The method claim 1 wherein the acceptor DNA molecule is a chromosome and/or the donor DNA molecule is a plasmid.

29. The method of claim 27, wherein the Gram positive bacterium is *Clostridium.*

30. The method of claim 28, wherein the acceptor DNA molecule is a non-replicative plasmid, a replication-defective plasmid or a conditional plasmid.

* * * * *

SEQUENCE LISTING

```
<160> NUMBER OF SEQ ID NOS: 70

<210> SEQ ID NO 1
<211> LENGTH: 10
<212> TYPE: DNA
<213> ORGANISM: Artificial Sequence
<220> FEATURE:
<223> OTHER INFORMATION: 10-nt sequence in pIM13

<400> SEQUENCE: 1

acgaccaaaa                                                          10


<210> SEQ ID NO 2
<211> LENGTH: 56
<212> TYPE: DNA
<213> ORGANISM: Artificial Sequence
<220> FEATURE:
<223> OTHER INFORMATION: Primer

<400> SEQUENCE: 2

taatacctgc agggtgttta ggacttgata ctgatattac ttatgtacca gaagag        56


<210> SEQ ID NO 3
<211> LENGTH: 51
<212> TYPE: DNA
<213> ORGANISM: Artificial Sequence
<220> FEATURE:
<223> OTHER INFORMATION: Primer
```

<400> SEQUENCE: 3
ataagcggcc gctcataaag tttttctgat ctcgtctctc atattaatcg c 51

<210> SEQ ID NO 4
<211> LENGTH: 47
<212> TYPE: DNA
<213> ORGANISM: Artificial Sequence
<220> FEATURE:
<223> OTHER INFORMATION: Primer

<400> SEQUENCE: 4
ataaagctag cattttgggg gaattttgat gaaggaaaag tatacag 47

<210> SEQ ID NO 5
<211> LENGTH: 57
<212> TYPE: DNA
<213> ORGANISM: Artificial Sequence
<220> FEATURE:
<223> OTHER INFORMATION: Primer

<400> SEQUENCE: 5
attggcgcgc cttgtgatac aacattataa gcaacttctg attttattcc aaaagcc 57

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
tgtgatgaaa tatataaggg agcaaaggcg c 31

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
agccatatcc actatatcct ctgcattagg 30

<210> SEQ ID NO 8
<211> LENGTH: 56
<212> TYPE: DNA
<213> ORGANISM: Artificial Sequence
<220> FEATURE:
<223> OTHER INFORMATION: Primer

<400> SEQUENCE: 8
taatacctgc agggtgttta ggacttgata ctgatattac ttatgtacca gaagag 56

<210> SEQ ID NO 9
<211> LENGTH: 51
<212> TYPE: DNA
<213> ORGANISM: Artificial Sequence
<220> FEATURE:
<223> OTHER INFORMATION: Primer

<400> SEQUENCE: 9
ataagcggcc gctcataaag tttttctgat ctcgtctctc atattaatcg c 51

<210> SEQ ID NO 10
<211> LENGTH: 47

<212> TYPE: DNA
<213> ORGANISM: Artificial Sequence
<220> FEATURE:
<223> OTHER INFORMATION: Primer

<400> SEQUENCE: 10
ataaagctag cattttgggg gaattttgat gaaggaaaag tatacag 47

<210> SEQ ID NO 11
<211> LENGTH: 57
<212> TYPE: DNA
<213> ORGANISM: Artificial Sequence
<220> FEATURE:
<223> OTHER INFORMATION: Primer

<400> SEQUENCE: 11
attggcgcgc cttgtgatac aacattataa gcaacttctg attttattcc aaaagcc 57

<210> SEQ ID NO 12
<211> LENGTH: 48
<212> TYPE: DNA
<213> ORGANISM: Artificial Sequence
<220> FEATURE:
<223> OTHER INFORMATION: Primer

<400> SEQUENCE: 12
tgcggccgct cattaacctt caaagtgagc tttagcatac atttcagc 48

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
actggccgtc gttttacaac gtcgtg 26

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
agccatatcc actatatcct ctgcattagg 30

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
tgtaaaacga cggccagt 18

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
tgtgatgaaa tatataaggg agcaaaggcg c 31

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
aagaaaatga tctatatttt ttgtctgtcc tatatcacc 39

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
agccatatcc actatatcct ctgcattagg 30

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
aatatgacaa taaaataatt cctgaagata ttaaagagcg 40

<210> SEQ ID NO 20
<211> LENGTH: 31
<212> TYPE: DNA
<213> ORGANISM: Artificial Sequence
<220> FEATURE:
<223> OTHER INFORMATION: Primer

<400> SEQUENCE: 20
tgtgatgaaa tatataaggg agcaaaggcg c 31

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
gaatattaag ctcgacaggt cagttattta cctacg 36

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
agccatatcc actatatcct ctgcattagg 30

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
gggaagtcgt gaaagaaaag aagtcagc 28

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
tgtgatgaaa tatataaggg agcaaaggcg c 31

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25
cgtcataatt gattatttga cgtggtttga tgg 33

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
agccatatcc actatatcct ctgcattagg 30

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
taccatggca atctctgcat cttgccc 27

<210> SEQ ID NO 28
<211> LENGTH: 31
<212> TYPE: DNA
<213> ORGANISM: Artificial Sequence
<220> FEATURE:
<223> OTHER INFORMATION: Primer

<400> SEQUENCE: 28
tgtgatgaaa tatataaggg agcaaaggcg c 31

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
ggtaagcacg aactcagcca gaacg 25

<210> SEQ ID NO 30
<211> LENGTH: 30

```
<212> TYPE: DNA
<213> ORGANISM: Artificial Sequence
<220> FEATURE:
<223> OTHER INFORMATION: Primer

<400> SEQUENCE: 30

agccatatcc actatatcct ctgcattagg                              30

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31

tatgagtacc ctgttttttc tcatgttcag g                            31

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32

tgtgatgaaa tatataaggg agcaaaggcg c                            31

<210> SEQ ID NO 33
<211> LENGTH: 26
<212> TYPE: DNA
<213> ORGANISM: Artificial Sequence
<220> FEATURE:
<223> OTHER INFORMATION: Primer

<400> SEQUENCE: 33

actggccgtc gttttacaac gtcgtg                                  26

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34

ccaagctcta tgacagacag ctcattgttt agaac                        35

<210> SEQ ID NO 35
<211> LENGTH: 31
<212> TYPE: DNA
<213> ORGANISM: Artificial Sequence
<220> FEATURE:
<223> OTHER INFORMATION: Primer

<400> SEQUENCE: 35

cctgaacatg agaaaaaaca gggtactcat a                            31

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36

tagagaagga ataaaaagtt tagacgaaat aagagg                       36
```

<210> SEQ ID NO 37
<211> LENGTH: 42
<212> TYPE: DNA
<213> ORGANISM: Artificial Sequence
<220> FEATURE:
<223> OTHER INFORMATION: Primer

<400> SEQUENCE: 37
cctgcaggag agtaatgtac ttacctttgg ggatttcata ac 42

<210> SEQ ID NO 38
<211> LENGTH: 49
<212> TYPE: DNA
<213> ORGANISM: Artificial Sequence
<220> FEATURE:
<223> OTHER INFORMATION: Primer

<400> SEQUENCE: 38
gcggccgctt actattttac tccatactct ttatagtact cattaattc 49

<210> SEQ ID NO 39
<211> LENGTH: 65
<212> TYPE: DNA
<213> ORGANISM: Artificial Sequence
<220> FEATURE:
<223> OTHER INFORMATION: Primer

<400> SEQUENCE: 39
gctagctaaa ataaatgtgc ctcaacttag atgttaaggc acatttattt tatatattat 60
tcatg 65

<210> SEQ ID NO 40
<211> LENGTH: 56
<212> TYPE: DNA
<213> ORGANISM: Artificial Sequence
<220> FEATURE:
<223> OTHER INFORMATION: Primer

<400> SEQUENCE: 40
ggcgcgcctg ttgctgcttt aaaagaaaaa tcccatatag aaaaagttca agaagc 56

<210> SEQ ID NO 41
<211> LENGTH: 42
<212> TYPE: DNA
<213> ORGANISM: Artificial Sequence
<220> FEATURE:
<223> OTHER INFORMATION: Primer

<400> SEQUENCE: 41
gcggccgcca agaagtattc ccttatcacc gtgatcttta ac 42

<210> SEQ ID NO 42
<211> LENGTH: 44
<212> TYPE: DNA
<213> ORGANISM: Artificial Sequence
<220> FEATURE:
<223> OTHER INFORMATION: Primer

<400> SEQUENCE: 42
taaattgata tctatgcaac aaaagcagct attgaaaaag cagg 44

<210> SEQ ID NO 43
<211> LENGTH: 46
<212> TYPE: DNA
<213> ORGANISM: Artificial Sequence

```
<220> FEATURE:
<223> OTHER INFORMATION: Primer

<400> SEQUENCE: 43

ctccttctta atcgatctag cacttttcta gcaatattgc tgttcc                46


<210> SEQ ID NO 44
<211> LENGTH: 55
<212> TYPE: DNA
<213> ORGANISM: Artificial Sequence
<220> FEATURE:
<223> OTHER INFORMATION: Primer

<400> SEQUENCE: 44

gtgctagatc gattaagaag gagtgattac atgaacaaaa atataaaata ttctc      55


<210> SEQ ID NO 45
<211> LENGTH: 56
<212> TYPE: DNA
<213> ORGANISM: Artificial Sequence
<220> FEATURE:
<223> OTHER INFORMATION: Primer

<400> SEQUENCE: 45

attctttagc gctttatttc ctcccgttaa ataatagata actattaaaa atagac     56


<210> SEQ ID NO 46
<211> LENGTH: 26
<212> TYPE: DNA
<213> ORGANISM: Artificial Sequence
<220> FEATURE:
<223> OTHER INFORMATION: Primers

<400> SEQUENCE: 46

actggccgtc gttttacaac gtcgtg                                      26


<210> SEQ ID NO 47
<211> LENGTH: 40
<212> TYPE: DNA
<213> ORGANISM: Artificial Sequence
<220> FEATURE:
<223> OTHER INFORMATION: Primer

<400> SEQUENCE: 47

atgatactgg tattgtaacc ttttctaaaa ggttcatagg                        40


<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48

tgtaaaacga cggccagt                                                18


<210> SEQ ID NO 49
<211> LENGTH: 33
<212> TYPE: DNA
<213> ORGANISM: Artificial Sequence
<220> FEATURE:
<223> OTHER INFORMATION: Primer

<400> SEQUENCE: 49

acttgctaag atagtttctt atggttcagc agg                               33
```

<210> SEQ ID NO 50
<211> LENGTH: 2963
<212> TYPE: DNA
<213> ORGANISM: Artificial Sequence
<220> FEATURE:
<223> OTHER INFORMATION: Shuttle plasmid pMTL85141

<400> SEQUENCE: 50
ggataaaaaa attgtagata aattttataa aatagtttta tctacaattt ttttatcagg 60
aaacagctat gaccgcggcc gctgtatcca tatgaccatg attacgaatt cgagctcggt 120
acccggggat cctctagagt cgacgtcacg cgtccatgga gatctcgagg cctgcagaca 180
tgcaagcttg gcactggccg tcgttttaca acgtcgtgac tgggaaaacc ctggcgttac 240
ccaacttaat cgccttgcag cacatccccc tttcgccagc tggcgtaata gcgaagaggc 300
ccgcaccgat cgcccttccc aacagttgcg cagcctgaat ggcgaatggc gctagcataa 360
aaataagaag cctgcatttg caggcttctt atttttatgg cgcgccgcat tcacttcttt 420
tctatataaa tatgagcgaa gcgaataagc gtcggaaaag cagcaaaaag tttccttttt 480
gctgttggag catgggggtt caggggggtgc agtatctgac gtcaatgccg agcgaaagcg 540
agccgaaggg tagcatttac gttagataac cccctgatat gctccgacgc tttatataga 600
aaagaagatt caactaggta aaatcttaat ataggttgag atgataaggt ttataaggaa 660
tttgtttgtt ctaatttttc actcattttg ttctaatttc ttttaacaaa tgttcttttt 720
tttttagaac agttatgata tagttagaat agtttaaaat aaggagtgag aaaaagatga 780
aagaaagata tggaacagtc tataaaggct ctcagaggct catagacgaa gaaagtggag 840
aagtcataga ggtagacaag ttataccgta aacaaacgtc tggtaacttc gtaaaggcat 900
atatagtgca attaataagt atgttagata tgattggcgg aaaaaaactt aaaatcgtta 960
actatatcct agataatgtc cacttaagta acaatacaat gatagctaca acaagagaaa 1020
tagcaaaagc tacaggaaca agtctacaaa cagtaataac aacacttaaa atcttagaag 1080
aaggaaatat tataaaaaga aaaactggag tattaatgtt aaaccctgaa ctactaatga 1140
gaggcgacga ccaaaaacaa aaatacctct tactcgaatt tgggaacttt gagcaagagg 1200
caaatgaaat agattgacct cccaataaca ccacgtagtt attgggaggt caatctatga 1260
aatgcgatta agggccggcc agtgggcaag ttgaaaaatt cacaaaaatg tggtataata 1320
tctttgttca ttagagcgat aaacttgaat ttgagaggga acttagatgg tatttgaaaa 1380
aattgataaa aatagttgga acagaaaaga gtattttgac cactactttg caagtgtacc 1440
ttgtacctac agcatgaccg ttaaagtgga tatcacacaa ataaaggaaa agggaatgaa 1500
actatatcct gcaatgcttt attatattgc aatgattgta aaccgccatt cagagtttag 1560
gacggcaatc aatcaagatg gtgaattggg gatatatgat gagatgatac caagctatac 1620
aatatttcac aatgatactg aaacattttc cagcctttgg actgagtgta agtctgactt 1680
taaatcattt ttagcagatt atgaaagtga tacgcaacgg tatggaaaca atcatagaat 1740
ggaaggaaag ccaaatgctc cggaaaacat ttttaatgta tctatgatac cgtggtcaac 1800
cttcgatggc tttaatctga atttgcagaa aggatatgat tatttgattc ctatttttac 1860
tatggggaaa tattataaag aagataacaa aattatactt cctttggcaa ttcaagttca 1920
tcacgcagta tgtgacggat ttcacatttg ccgttttgta aacgaattgc aggaattgat 1980
aaatagttaa cttcaggttt gtctgtaact aaaaacaagt atttaagcaa aaacatcgta 2040
gaaatacggt gtttttttgtt accctaagtt taaactcctt tttgataatc tcatgaccaa 2100
aatcccttaa cgtgagtttt cgttccactg agcgtcagac cccgtagaaa agatcaaagg 2160

-continued atcttcttga gatccttttt ttctgcgcgt aatctgctgc ttgcaaacaa aaaaaccacc 2220
gctaccagcg gtggtttgtt tgccggatca agagctacca actctttttc cgaaggtaac 2280
tggcttcagc agagcgcaga taccaaatac tgtccttcta gtgtagccgt agttaggcca 2340
ccacttcaag aactctgtag caccgcctac atacctcgct ctgctaatcc tgttaccagt 2400
ggctgctgcc agtggcgata agtcgtgtct taccgggttg gactcaagac gatagttacc 2460
ggataaggcg cagcggtcgg gctgaacggg gggttcgtgc acacagccca gcttggagcg 2520
aacgacctac accgaactga gatacctaca gcgtgagcat tgagaaagcg ccacgcttcc 2580
cgaagggaga aaggcggaca ggtatccggt aagcggcagg gtcggaacag gagagcgcac 2640
gagggagctt ccagggggaa acgcctggta tctttatagt cctgtcgggt ttcgccacct 2700
ctgacttgag cgtcgatttt tgtgatgctc gtcagggggg cggagcctat ggaaaaacgc 2760
cagcaacgcg gcctttttac ggttcctggc cttttgctgg ccttttgctc acatgttctt 2820
tcctgcgtta tcccctgatt ctgtggataa ccgtattacc gcctttgagt gagctgatac 2880
cgctcgccgc agccgaacga ccgagcgcag cgagtcagtg agcgaggaag cggaagagcg 2940
cccaatacgc agggccccct gca 2963

<210> SEQ ID NO 51
<211> LENGTH: 4863
<212> TYPE: DNA
<213> ORGANISM: Artificial Sequence
<220> FEATURE:
<223> OTHER INFORMATION: Shuttle plasmid pMTL-JH4

<400> SEQUENCE: 51
gggtgtttag gacttgatac tgatattact tatgtaccag aagagttttg taagaaattt 60
aatagtatag aagatgctat atttaatttt aataagaaaa taattgatgc gactttagat 120
gttgtttcat gttataaggt gcaaattgca tattatgaag cttatggttt aaaaggactt 180
ttggcctata aaaggacact tgaatatttg agagaaaaaa aggctattgc aattgctgat 240
ataaaaagag gagatatagc taaaacagct gaaatgtatg ctaaagctca ctttgaaggt 300
gattttgaag cggattttgt tacgttaaat ccttacatgg ggttagatgg tatagagcct 360
tatatgcctt atattgaaaa aatggaaaaa ggattattta ttttgcttag aacatcgaat 420
aaaggagcct atgatataca atatataaag actcagggcg gaaaaaacgt atatgatgag 480
gttggagaaa aaatatatga tttaggtcaa aaggctacgg gaaggagcaa gtattcttca 540
ataggagcag tagttggatg tactcacgtt gaagaaggcg ttgaaattag aaataaattt 600
aaaaatatgt tttttctaat tccaggctat ggagcacaag gtggaactgc aaaggaagta 660
agtttgtatt taagagaagg taatggtgga gtggtaaatt cctcaagggg aatacttctt 720
gcttataaaa aagaagaaaa cggtgaaaaa atatttgatg agtgtgcaag gcttgcagcg 780
attaatatga gagacgagat cagaaaaact ttatgagcgg ccgctgtatc catatgacca 840
tgattacgaa ttcgagctcg gtacccgggg atcctctaga gtcgacgtca cgcgtccatg 900
gagatctcga ggcctgcaga catgcaagct tggcactggc cgtcgtttta caacgtcgtg 960
actgggaaaa ccctggcgtt acccaactta atcgccttgc agcacatccc cctttcgcca 1020
gctggcgtaa tagcgaagag gcccgcaccg atcgcccttc ccaacagttg cgcagcctga 1080
atggcgaatg gcgctagcat ttgggggaa ttttgatgaa ggaaaagtat acagtagaaa 1140
aagtatatga aaatataaaa gttgaagatg gtatatacaa acttagtata aagggtgaat 1200
ttgaggtgag gccaggacaa ttttatcttt taagagcttg ggatatagaa ccaacacttt 1260

-continued

```
ctagacctat tagtatatat gatgcagatg acgaaaaaat atcgttctta tactctgttg   1320
ttggaaaagg aactgaaatt ttatctaaat taaagagcgg cgatgaaata aagataacag   1380
gacctttagg aaatggattt aacgtaaaaa ggataagtgg aaaagtggct atagtttgtg   1440
gtggtatagg tgtagcacca atggtatatc tggctaaaaa cttaaaaaat tgtaatgttg   1500
atttttatgc tggcttcaaa actgtgagta aaactgtgga taatgtggaa aaatatgtta   1560
aagagttaaa gttgtccaca gaagatggaa gtattggaca taaggggtat gtaacagata   1620
actttaagcc agaagaatac gattatgttt tatgctgcgg acctgagata atgatgtata   1680
aagttgttaa aatgtgtgaa caaaagaatg ttcctgtata tatttcaatg gagaaaaaaa   1740
tggcatgtgg aataggtgca tgccttgtat gcacttgtaa aactaagggt ggaagaagaa   1800
gagcttgtaa agagggccca gtatttttag gaagtgagtt gatattaaat gactaaagta   1860
aatatttgtg gaatagattt taagaacccc gttattgctg cttctggcac ctttggattt   1920
ggagaagagt ttagtaagta ttttgatgtt tcaaggcttg gtggcatatc ttcaaaggga   1980
cttacattga atcctaagga aggtaatgat ggtgcaagag tttttgaggt cacaggcgga   2040
atgatgaata gtgtaggact tcaaaatcct ggagttaaag agtttataaa aaaagaactt   2100
cctaagatga aaaaaataga tacagtatgt attgttaacc ttggtggaag ctgtgaggat   2160
gattatttaa ggggcatgga gcttcttgag aatacagatg ctgatatgat agaacttaat   2220
atatcctgtc ctaatgtaaa gcacggcggc atggcttttg gaataaaatc agaagttgct   2280
tataatgttg tatcacaagg cgcgccgcat tcacttcttt tctatataaa tatgagcgaa   2340
gcgaataagc gtcggaaaag cagcaaaaag tttccttttt gctgttggag catgggggtt   2400
caggggggtgc agtatctgac gtcaatgccg agcgaaagcg agccgaaggg tagcatttac   2460
gttagataac cccctgatat gctccgacgc tttatataga aaagaagatt caactaggta   2520
aaatcttaat ataggttgag atgataaggt ttataaggaa tttgtttgtt ctaatttttc   2580
actcattttg ttctaatttc ttttaacaaa tgttcttttt tttttagaac agttatgata   2640
tagttagaat agtttaaaat aaggagtgag aaaaagatga aagaaagata tggaacagtc   2700
tataaaggct ctcagaggct catagacgaa gaaagtggag aagtcataga ggtagacaag   2760
ttataccgta aacaaacgtc tggtaacttc gtaaaggcat atatagtgca attaataagt   2820
atgttagata tgattggcgg aaaaaaactt aaaatcgtta actatatcct agataatgtc   2880
cacttaagta acaatacaat gatagctaca acaagagaaa tagcaaaagc tacaggaaca   2940
agtctacaaa cagtaataac aacacttaaa atcttagaag aaggaaatat tataaaaaga   3000
aaaactggag tattaatgtt aaaccctgaa ctactaatga gaggcgacga ccaaaaacaa   3060
aaatacctct tactcgaatt tgggaacttt gagcaagagg caaatgaaat agattgacct   3120
cccaataaca ccacgtagtt attgggaggt caatctatga aatgcgatta agggccggcc   3180
agtgggcaag ttgaaaaatt cacaaaaatg tggtataata tctttgttca ttagagcgat   3240
aaacttgaat ttgagaggga acttagatgg tatttgaaaa aattgataaa aatagttgga   3300
acagaaaaga gtattttgac cactactttg caagtgtacc ttgtacctac agcatgaccg   3360
ttaaagtgga tatcacacaa ataaaggaaa agggaatgaa actatatcct gcaatgcttt   3420
attatattgc aatgattgta aaccgccatt cagagtttag gacggcaatc aatcaagatg   3480
gtgaattggg gatatatgat gagatgatac caagctatac aatatttcac aatgatactg   3540
aaacattttc cagcctttgg actgagtgta agtctgactt taaatcattt ttagcagatt   3600
atgaaagtga tacgcaacgg tatggaaaca atcatagaat ggaaggaaag ccaaatgctc   3660
```

```
cggaaaacat ttttaatgta tctatgatac cgtggtcaac cttcgatggc tttaatctga   3720

atttgcagaa aggatatgat tatttgattc ctatttttac tatggggaaa tattataaag   3780

aagataacaa aattatactt cctttggcaa ttcaagttca tcacgcagta tgtgacggat   3840

ttcacatttg ccgttttgta aacgaattgc aggaattgat aaatagttaa cttcaggttt   3900

gtctgtaact aaaaacaagt atttaagcaa aaacatcgta gaaatacggt gtttttttgtt   3960

accctaagtt taaactcctt tttgataatc tcatgaccaa aatcccttaa cgtgagtttt   4020

cgttccactg agcgtcagac cccgtagaaa agatcaaagg atcttcttga gatccttttt   4080

ttctgcgcgt aatctgctgc ttgcaaacaa aaaaaccacc gctaccagcg gtggtttgtt   4140

tgccggatca agagctacca actctttttc cgaaggtaac tggcttcagc agagcgcaga   4200

taccaaatac tgtccttcta gtgtagccgt agttaggcca ccacttcaag aactctgtag   4260

caccgcctac atacctcgct ctgctaatcc tgttaccagt ggctgctgcc agtggcgata   4320

agtcgtgtct taccgggttg gactcaagac gatagttacc ggataaggcg cagcggtcgg   4380

gctgaacggg gggttcgtgc acacagccca gcttggagcg aacgacctac accgaactga   4440

gatacctaca gcgtgagcat tgagaaagcg ccacgcttcc cgaagggaga aaggcggaca   4500

ggtatccggt aagcggcagg gtcggaacag gagagcgcac gagggagctt ccagggggaa   4560

acgcctggta tctttatagt cctgtcgggt ttcgccacct ctgacttgag cgtcgatttt   4620

tgtgatgctc gtcagggggg cggagcctat ggaaaaacgc cagcaacgcg gcctttttac   4680

ggttcctggc cttttgctgg ccttttgctc acatgttctt tcctgcgtta tcccctgatt   4740

ctgtggataa ccgtattacc gcctttgagt gagctgatac cgctcgccgc agccgaacga   4800

ccgagcgcag cgagtcagtg agcgaggaag cggaagagcg cccaatacgc agggcccccct   4860

gca                                                                 4863


<210> SEQ ID NO 52
<211> LENGTH: 4353
<212> TYPE: DNA
<213> ORGANISM: Artificial Sequence
<220> FEATURE:
<223> OTHER INFORMATION: Shuttle plasmid pMTL-JH2

<400> SEQUENCE: 52

gggtgtttag gacttgatac tgatattact tatgtaccag aagagttttg taagaaattt     60

aatagtatag aagatgctat atttaatttt aataagaaaa taattgatgc gactttagat    120

gttgtttcat gttataaggt gcaaattgca tattatgaag cttatggttt aaaaggactt    180

ttggcctata aaaggacact tgaatatttg agagaaaaaa aggctattgc aattgctgat    240

ataaaaagag gagatatagc taaaacagct gaaatgtatg ctaaagctca ctttgaaggt    300

taatgagcgg ccgctgtatc catatgacca tgattacgaa ttcgagctcg gtacccgggg    360

atcctctaga gtcgacgtca cgcgtccatg gagatctcga ggcctgcaga catgcaagct    420

tggcactggc cgtcgtttta caacgtcgtg actgggaaaa ccctggcgtt acccaactta    480

atcgccttgc agcacatccc cctttcgcca gctggcgtaa tagcgaagag gcccgcaccg    540

atcgcccttc ccaacagttg cgcagcctga atggcgaatg gcgctagcat tttgggggaa    600

ttttgatgaa ggaaaagtat acagtagaaa aagtatatga aaatataaaa gttgaagatg    660

gtatatacaa acttagtata aagggtgaat ttgaggtgag gccaggacaa ttttatcttt    720

taagagcttg ggatatagaa ccaacacttt ctagacctat tagtatatat gatgcagatg    780

acgaaaaaat atcgttctta tactctgttg ttggaaaagg aactgaaatt ttatctaaat    840
```

-continued

```
taaagagcgg cgatgaaata aagataacag gacctttagg aaatggattt aacgtaaaaa    900
ggataagtgg aaaagtggct atagtttgtg gtggtatagg tgtagcacca atggtatatc    960
tggctaaaaa cttaaaaaat tgtaatgttg atttttatgc tggcttcaaa actgtgagta   1020
aaactgtgga taatgtggaa aaatatgtta aagagttaaa gttgtccaca gaagatggaa   1080
gtattggaca taaggggtat gtaacagata actttaagcc agaagaatac gattatgttt   1140
tatgctgcgg acctgagata atgatgtata aagttgttaa aatgtgtgaa caaaagaatg   1200
ttcctgtata tatttcaatg gagaaaaaaa tggcatgtgg aataggtgca tgccttgtat   1260
gcacttgtaa aactaagggt ggaagaagaa gagcttgtaa agagggccca gtatttttag   1320
gaagtgagtt gatattaaat gactaaagta aatatttgtg gaatagattt taagaacccc   1380
gttattgctg cttctggcac ctttggattt ggagaagagt ttagtaagta ttttgatgtt   1440
tcaaggcttg gtggcatatc ttcaaaggga cttacattga atcctaagga aggtaatgat   1500
ggtgcaagag tttttgaggt cacaggcgga atgatgaata gtgtaggact tcaaaatcct   1560
ggagttaaag agtttataaa aaaagaactt cctaagatga aaaaaataga tacagtatgt   1620
attgttaacc ttggtggaag ctgtgaggat gattatttaa ggggcatgga gcttcttgag   1680
aatacagatg ctgatatgat agaacttaat atatcctgtc ctaatgtaaa gcacggcggc   1740
atggcttttg gaataaaatc agaagttgct tataatgttg tatcacaagg cgcgccgcat   1800
tcacttcttt tctatataaa tatgagcgaa gcgaataagc gtcggaaaag cagcaaaaag   1860
tttccttttt gctgttggag catggggggtt cagggggtgc agtatctgac gtcaatgccg   1920
agcgaaagcg agccgaaggg tagcatttac gttagataac cccctgatat gctccgacgc   1980
tttatataga aaagaagatt caactaggta aaatcttaat ataggttgag atgataaggt   2040
ttataaggaa tttgtttgtt ctaatttttc actcattttg ttctaatttc ttttaacaaa   2100
tgttcttttt tttttagaac agttatgata tagttagaat agtttaaaat aaggagtgag   2160
aaaaagatga aagaaagata tggaacagtc tataaaggct ctcagaggct catagacgaa   2220
gaaagtggag aagtcataga ggtagacaag ttataccgta aacaaacgtc tggtaacttc   2280
gtaaaggcat atatagtgca attaataagt atgttagata tgattggcgg aaaaaaactt   2340
aaaatcgtta actatatcct agataatgtc cacttaagta acaatacaat gatagctaca   2400
acaagagaaa tagcaaaagc tacaggaaca agtctacaaa cagtaataac aacacttaaa   2460
atcttagaag aaggaaatat tataaaaaga aaaactggag tattaatgtt aaaccctgaa   2520
ctactaatga gaggcgacga ccaaaaacaa aaatacctct tactcgaatt tgggaacttt   2580
gagcaagagg caaatgaaat agattgacct cccaataaca ccacgtagtt attgggaggt   2640
caatctatga aatgcgatta agggccggcc agtgggcaag ttgaaaaatt cacaaaaatg   2700
tggtataata tctttgttca ttagagcgat aaacttgaat ttgagaggga acttagatgg   2760
tatttgaaaa aattgataaa aatagttgga acagaaaaga gtattttgac cactactttg   2820
caagtgtacc ttgtacctac agcatgaccg ttaaagtgga tatcacacaa ataaaggaaa   2880
agggaatgaa actatatcct gcaatgcttt attatattgc aatgattgta aaccgccatt   2940
cagagtttag gacggcaatc aatcaagatg gtgaattggg gatatatgat gagatgatac   3000
caagctatac aatatttcac aatgatactg aaacattttc cagcctttgg actgagtgta   3060
agtctgactt taaatcattt ttagcagatt atgaaagtga tacgcaacgg tatggaaaca   3120
atcatagaat ggaaggaaag ccaaatgctc cggaaaacat ttttaatgta tctatgatac   3180
cgtggtcaac cttcgatggc tttaatctga atttgcagaa aggatatgat tatttgattc   3240
```

ctatttttac tatggggaaa tattataaag aagataacaa aattatactt cctttggcaa 3300
ttcaagttca tcacgcagta tgtgacggat ttcacatttg ccgttttgta aacgaattgc 3360
aggaattgat aaatagttaa cttcaggttt gtctgtaact aaaaacaagt atttaagcaa 3420
aaacatcgta gaaatacggt gtttttttgtt accctaagtt taaactcctt tttgataatc 3480
tcatgaccaa aatcccttaa cgtgagtttt cgttccactg agcgtcagac cccgtagaaa 3540
agatcaaagg atcttcttga gatccttttt ttctgcgcgt aatctgctgc ttgcaaacaa 3600
aaaaaccacc gctaccagcg gtggtttgtt tgccggatca agagctacca actctttttc 3660
cgaaggtaac tggcttcagc agagcgcaga taccaaatac tgtccttcta gtgtagccgt 3720
agttaggcca ccacttcaag aactctgtag caccgcctac atacctcgct ctgctaatcc 3780
tgttaccagt ggctgctgcc agtggcgata agtcgtgtct taccgggttg gactcaagac 3840
gatagttacc ggataaggcg cagcggtcgg gctgaacggg gggttcgtgc acacagccca 3900
gcttggagcg aacgacctac accgaactga gatacctaca gcgtgagcat tgagaaagcg 3960
ccacgcttcc cgaagggaga aaggcggaca ggtatccggt aagcggcagg gtcggaacag 4020
gagagcgcac gagggagctt ccagggggaa acgcctggta tctttatagt cctgtcgggt 4080
ttcgccacct ctgacttgag cgtcgatttt tgtgatgctc gtcagggggg cggagcctat 4140
ggaaaaacgc cagcaacgcg gcctttttac ggttcctggc cttttgctgg ccttttgctc 4200
acatgttctt tcctgcgtta tcccctgatt ctgtggataa ccgtattacc gcctttgagt 4260
gagctgatac cgctcgccgc agccgaacga ccgagcgcag cgagtcagtg agcgaggaag 4320
cggaagagcg cccaatacgc agggcccccct gca 4353

<210> SEQ ID NO 53
<211> LENGTH: 6384
<212> TYPE: DNA
<213> ORGANISM: Artificial Sequence
<220> FEATURE:
<223> OTHER INFORMATION: Shuttle plasmid pMTL-JH2-lambda2.0

<400> SEQUENCE: 53
gggtgtttag gacttgatac tgatattact tatgtaccag aagagttttg taagaaattt 60
aatagtatag aagatgctat atttaatttt aataagaaaa taattgatgc gactttagat 120
gttgtttcat gttataaggt gcaaattgca tattatgaag cttatggttt aaaaggactt 180
ttggcctata aaaggacact tgaatatttg agagaaaaaa aggctattgc aattgctgat 240
ataaaaagag gagatatagc taaaacagct gaaatgtatg ctaaagctca ctttgaaggt 300
taatgagcgg ccgctgtatc catatgacca tgattacgaa ttcgagctcg gtacccgggg 360
atcctctaga gtcgacgtca cgcgtccatg gagatctcga ggagcttggc tgtatagtca 420
actaactctt ctgtcgaagt gatattttta ggcttatcta ccagttttag acgctcttta 480
atatcttcag gaattatttt attgtcatat tgtatcatgc taaatgacaa tttgcttatg 540
gagtaatctt ttaattttaa ataagttatt ctcctggctt catcaaataa agagtcgaat 600
gatgttggcg aaatcacatc gtcacccatt ggattgttta tttgtatgcc aagagagtta 660
cagcagttat acattctgcc atagattata gctaaggcat gtaataattc gtaatctttt 720
agcgtattag cgacccatcg tctttctgat ttaataatag atgattcagt taaatatgaa 780
ggtaatttct tttgtgcaag tctgactaac ttttttatac caatgtttaa catactttca 840
tttgtaataa actcaatgtc attttcttca atgtaagatg aaataagagt agcctttgcc 900
tcgctataca tttctaaatc gccttgtttt tctatcgtat tgcgagaatt tttagcccaa 960

-continued

```
gccattaatg gatcattttt ccatttttca ataacattat tgttatacca aatgtcatat   1020
cctataatct ggtttttgtt tttttgaata ataaatgtta ctgttcttgc ggtttggagg   1080
aattgattca aattcaagcg aaataattca gggtcaaaat atgtatcaat gcagcatttg   1140
agcaagtgcg ataaatcttt aagtcttctt tcccatggtt ttttagtcat aaaactctcc   1200
attttgatag gttgcatgct agatgctgat atattttaga ggtgataaaa ttaactgctt   1260
aactgtcaat gtaatacaag ttgtttgatc tttgcaatga ttcttatcag aaaccatata   1320
gtaaattagt tacacaggaa atttttaata ttattattat cattcattat gtattaaaat   1380
tagagttgtg gcttggctct gctaacacgt tgctcatagg agatatggta gagccgcaga   1440
cacgtcgtat gcaggaacgt gctgcggctg gctggtgaac ttccgatagt gcgggtgttg   1500
aatgatttcc agttgctacc gattttacat atttttttgca tgagagaatt tgtaccacct   1560
cccaccgacc atctatgact gtacgccact gtccctagga ctgctatgtg ccggagcgga   1620
cattacaaac gtccttctcg gtgcatgcca ctgttgccaa tgacctgcct aggaattggt   1680
tagcaagtta ctaccggatt ttgtaaaaac agccctcctc atataaaaag tattcgttca   1740
cttccgataa gcgtcgtaat ttctatcttt tcatcatatt ctagatccct ctgaaaaaat   1800
cttccgagtt tgctaggcac tgatacataa ctcttttcca ataattgggg aagtcattca   1860
aatctataat aggtttcaga tttgcttcaa taaattctga ctgtagctgc tgaaacgttg   1920
cggttgaact atatttcctt ataactttta cgaaagagtt tctttgagta atcacttcac   1980
tcaagtgctt ccctgcctcc aaacgatacc tgttagcaat atttaatagc ttgaaatgat   2040
gaagagctct gtgtttgtct tcctgcctcc agttcgccgg gcattcaaca taaaaactga   2100
tagcacccgg agttccggaa acgaaatttg catataccca ttgctcacga aaaaaaatgt   2160
ccttgtcgat atagggatga atcgcttggt gtacctcatc tactgcgaaa acttgacctt   2220
tctctcccat attgcagtcg cggcacgatg gaactaaatt aataggcatc accgaaaatt   2280
caggataatg tgcaatagga agaaaatgat ctatattttt tgtctgtcct atatcaccac   2340
aaaatggaca tttttcacct gatgaaacaa gcatgtcatc gtaatatgtt ctagcgggtt   2400
tgtttttatc tcggagatta ttttcataaa gctcctgcag acatgcaagc ttggcactgg   2460
ccgtcgtttt acaacgtcgt gactgggaaa accctggcgt tacccaactt aatcgccttg   2520
cagcacatcc ccctttcgcc agctggcgta atagcgaaga ggcccgcacc gatcgccctt   2580
cccaacagtt gcgcagcctg aatggcgaat ggcgctagca ttttggggga attttgatga   2640
aggaaaagta tacagtagaa aaagtatatg aaaatataaa agttgaagat ggtatataca   2700
aacttagtat aaagggtgaa tttgaggtga ggccaggaca attttatctt ttaagagctt   2760
gggatataga accaacactt tctagaccta ttagtatata tgatgcagat gacgaaaaaa   2820
tatcgttctt atactctgtt gttggaaaag gaactgaaat tttatctaaa ttaaagagcg   2880
gcgatgaaat aaagataaca ggacctttag gaaatggatt taacgtaaaa aggataagtg   2940
gaaaagtggc tatagtttgt ggtggtatag gtgtagcacc aatggtatat ctggctaaaa   3000
acttaaaaaa ttgtaatgtt gatttttatg ctggcttcaa aactgtgagt aaaactgtgg   3060
ataatgtgga aaaatatgtt aaagagttaa agttgtccac agaagatgga agtattggac   3120
ataaggggta tgtaacagat aactttaagc cagaagaata cgattatgtt ttatgctgcg   3180
gacctgagat aatgatgtat aaagttgtta aaatgtgtga acaaaagaat gttcctgtat   3240
atatttcaat ggagaaaaaa atggcatgtg gaataggtgc atgccttgta tgcacttgta   3300
aaactaaggg tggaagaaga agagcttgta aagagggccc agtattttta ggaagtgagt   3360
```

-continued

```
tgatattaaa tgactaaagt aaatatttgt ggaatagatt ttaagaaccc cgttattgct   3420
gcttctggca cctttggatt tggagaagag tttagtaagt attttgatgt ttcaaggctt   3480
ggtggcatat cttcaaaggg acttacattg aatcctaagg aaggtaatga tggtgcaaga   3540
gtttttgagg tcacaggcgg aatgatgaat agtgtaggac ttcaaaatcc tggagttaaa   3600
gagtttataa aaaaagaact tcctaagatg aaaaaaatag atacagtatg tattgttaac   3660
cttggtggaa gctgtgagga tgattattta aggggcatgg agcttcttga gaatacagat   3720
gctgatatga tagaacttaa tatatcctgt cctaatgtaa agcacggcgg catggctttt   3780
ggaataaaat cagaagttgc ttataatgtt gtatcacaag gcgcgccgca ttcacttctt   3840
ttctatataa atatgagcga agcgaataag cgtcggaaaa gcagcaaaaa gtttcctttt   3900
tgctgttgga gcatgggggt tcagggggtg cagtatctga cgtcaatgcc gagcgaaagc   3960
gagccgaagg gtagcattta cgttagataa cccccctgata tgctccgacg ctttatatag   4020
aaaagaagat tcaactaggt aaaatcttaa tataggttga gatgataagg tttataagga   4080
atttgtttgt tctaattttt cactcatttt gttctaattt cttttaacaa atgttctttt   4140
ttttttagaa cagttatgat atagttagaa tagtttaaaa taaggagtga gaaaaagatg   4200
aaagaaagat atggaacagt ctataaaggc tctcagaggc tcatagacga agaaagtgga   4260
gaagtcatag aggtagacaa gttataccgt aaacaaacgt ctggtaactt cgtaaaggca   4320
tatatagtgc aattaataag tatgttagat atgattggcg gaaaaaaact taaaatcgtt   4380
aactatatcc tagataatgt ccacttaagt aacaatacaa tgatagctac aacaagagaa   4440
atagcaaaag ctacaggaac aagtctacaa acagtaataa caacacttaa aatcttagaa   4500
gaaggaaata ttataaaaag aaaaactgga gtattaatgt taaaccctga actactaatg   4560
agaggcgacg accaaaaaca aaaatacctc ttactcgaat ttgggaactt tgagcaagag   4620
gcaaatgaaa tagattgacc tcccaataac accacgtagt tattgggagg tcaatctatg   4680
aaatgcgatt aagggccggc cagtgggcaa gttgaaaaat tcacaaaaat gtggtataat   4740
atctttgttc attagagcga taaacttgaa tttgagaggg aacttagatg gtatttgaaa   4800
aaattgataa aaatagttgg aacagaaaag agtattttga ccactacttt gcaagtgtac   4860
cttgtaccta cagcatgacc gttaaagtgg atatcacaca aataaaggaa aagggaatga   4920
aactatatcc tgcaatgctt tattatattg caatgattgt aaaccgccat tcagagttta   4980
ggacggcaat caatcaagat ggtgaattgg ggatatatga tgagatgata ccaagctata   5040
caatatttca caatgatact gaaacatttt ccagcctttg gactgagtgt aagtctgact   5100
ttaaatcatt tttagcagat tatgaaagtg atacgcaacg gtatggaaac aatcatagaa   5160
tggaaggaaa gccaaatgct ccggaaaaca tttttaatgt atctatgata ccgtggtcaa   5220
ccttcgatgg ctttaatctg aatttgcaga aaggatatga ttatttgatt cctatttttta   5280
ctatggggaa atattataaa gaagataaca aaattatact tcctttggca attcaagttc   5340
atcacgcagt atgtgacgga tttcacattt gccgttttgt aaacgaattg caggaattga   5400
taaatagtta acttcaggtt tgtctgtaac taaaaacaag tatttaagca aaaacatcgt   5460
agaaatacgg tgtttttgt taccctaagt ttaaactcct ttttgataat ctcatgacca   5520
aaatccctta acgtgagttt tcgttccact gagcgtcaga ccccgtagaa aagatcaaag   5580
gatcttcttg agatcctttt tttctgcgcg taatctgctg cttgcaaaca aaaaaaccac   5640
cgctaccagc ggtggtttgt ttgccggatc aagagctacc aactcttttt ccgaaggtaa   5700
ctggcttcag cagagcgcag ataccaaata ctgtccttct agtgtagccg tagttaggcc   5760
```

```
accacttcaa gaactctgta gcaccgccta catacctcgc tctgctaatc ctgttaccag   5820

tggctgctgc cagtggcgat aagtcgtgtc ttaccgggtt ggactcaaga cgatagttac   5880

cggataaggc gcagcggtcg ggctgaacgg ggggttcgtg cacacagccc agcttggagc   5940

gaacgaccta caccgaactg agatacctac agcgtgagca ttgagaaagc gccacgcttc   6000

ccgaagggag aaaggcggac aggtatccgg taagcggcag ggtcggaaca ggagagcgca   6060

cgagggagct tccaggggga aacgcctggt atctttatag tcctgtcggg tttcgccacc   6120

tctgacttga gcgtcgattt ttgtgatgct cgtcaggggg gcggagccta tggaaaaacg   6180

ccagcaacgc ggccttttta cggttcctgg ccttttgctg gccttttgct cacatgttct   6240

ttcctgcgtt atcccctgat tctgtggata accgtattac cgcctttgag tgagctgata   6300

ccgctcgccg cagccgaacg accgagcgca gcgagtcagt gagcgaggaa gcggaagagc   6360

gcccaatacg cagggccccc tgca                                          6384
```

```
<210> SEQ ID NO 54
<211> LENGTH: 6679
<212> TYPE: DNA
<213> ORGANISM: Artificial Sequence
<220> FEATURE:
<223> OTHER INFORMATION: Shuttle plasmid pMTL-JH2-lambda2.3

<400> SEQUENCE: 54
```

```
gggtgtttag gacttgatac tgatattact tatgtaccag aagagttttg taagaaattt     60

aatagtatag aagatgctat atttaatttt aataagaaaa taattgatgc gactttagat    120

gttgtttcat gttataaggt gcaaattgca tattatgaag cttatggttt aaaaggactt    180

ttggcctata aaaggacact tgaatatttg agagaaaaaa aggctattgc aattgctgat    240

ataaaaagag gagatatagc taaaacagct gaaatgtatg ctaaagctca ctttgaaggt    300

taatgagcgg ccgctgtatc catatgacca tgattacgaa ttcgagctcg gtacccgggg    360

atcctctaga gtcgacgtca cgcgtccatg gagatctcga ggagctttgt gtgccaccca    420

ctacgacctg cataaccagt aagaagatag cagtgatgtc aaacgacgca gctgacttct    480

tttctttcac gacttcccca cacccagcat gcataccttt ccgccataac tgtagtgaat    540

gtctgttatg agcgaggagc ggaagttaac acttatgaaa aatggctacg aagtccgtgg    600

ctatctatcg gcttattagt acttgaaacg cttcttcaga agcctgaaga gctaatcgtt    660

cggcgatact atatatgcat taatagacta tatcgttggt ataaacagtg caccatgcaa    720

catgaataac agtgggttat ccaaaaggaa gcagaaagct aaatatggaa aactacaata    780

cgatgccccg ttaagttcaa tactactaat ttttagatgg aaaacgtatg taatagagag    840

taacttaaaa gagagatcct gtgttgccgc caaataaatt gcggttattt taataaaatt    900

aagggttact atatgttgga gtttagtgtt attgaaagag gcgggtatat tcctgcagta    960

gaaaaaaata aggcattcct acgagcagat ggttggaatg actattcctt tgttacaatg   1020

ttttatctta ctgtctttga tgagcatggt gaaaaatgcg atatcggaaa tgttaaaatt   1080

ggttttgtag gtcaaaaaga agaagtaagc acttattcat taatagataa aaaattcagt   1140

caactccctg aaatgttttt ttccttaggt gaaagcattg actactatgt taatctcagc   1200

aaattaagcg atggttttaa acataacctt cttaaagcta ttcaggattt agtagtatgg   1260

ccaaatcgat tagccgacat tgaaaatgaa agcgtcctta acacctcatt acttagaggg   1320

gtaactcttt cagaaattca tggacagttc gcacgtgtgt taaatggttt gccagaattg   1380

tcagatttcc acttttcatt taatagaaaa agtgctcccg gattcagtga tttaactata   1440
```

-continued

```
ccttttgagg tgacggttaa ttctatgccc agcacgaaca ttcatgcttt tatcgggcgg   1500
aatgggtgtg gtaaaacaac aattttgaat ggaatgattg gtgcaatcac caacccagaa   1560
aacaatgaat attttttctc tgaaaataat agacttatcg agtcaagaat cccaaaggga   1620
tattttcgat cgcttgtttc agtttcgttt agtgcatttg atccttttac tcctcctaaa   1680
gaacaacctg acccagcaaa aggtacacaa tacttttata ttggactcaa gaatgctgcc   1740
agcaatagtt taaaatcact aggcgatctc cgcttagaat tcatttcagc atttattggt   1800
tgtatgagag tagatagaaa aagacaactc tggcttgaag ctatcaaaaa actaagtagt   1860
gatgaaaact tttcaaatat ggaactcatc agcctcattt ctaaatatga agagttaaga   1920
cgtaatgaac cacagattca agtggacgat gataaattca ctaaattgtt ttatgacaat   1980
atccagaaat atctgcttcg aatgagctct ggacatgcaa ttgtttttatt tactatcaca   2040
agattagtag atgtcgttgg cgaaaagtca ttagttttat tcgatgaacc agaggttcat   2100
ctgcatccac ctttgctctc tgctttttta cgaacattaa gcgacttact cgatgcacgc   2160
aatggtgtag caataattgc aactcattcc ccagtagtac tgcaagaggt tccaaaatcc   2220
tgcatgtgga aagtcctacg gtcaagagaa gcaataaata ttatccgtcc ggatattgag   2280
acattcggtg agaacttagg tgttttaact cgtgaggtgt ttttacttga agtgacaaat   2340
tctggatacc accacttatt atcgcagtcc gttgattcag agctttctta tgaaaccatt   2400
ctaaaaaatt ataatggtca gataggatta gaaggtcgaa ccgtttttaaa agcgatgata   2460
atgaacagag atgaaggtaa agtacaatga aaaaactacc tcttccagcg agaacttata   2520
gcgaaatgct taataaatgc tcggaaggta tgatgcagat aaatgttaga aataatttca   2580
ttactcactt ccccactttt ttgcagaaag aacaacaata tagaatatta agctcgacag   2640
gtcagttatt tacctacgac aggacacacc ctcttgagcc tacaacctta gtagttggta   2700
acctgacaaa ggttaaatta gaaaagctcc tgcagacatg caagcttggc actggccgtc   2760
gttttacaac gtcgtgactg ggaaaaccct ggcgttaccc aacttaatcg ccttgcagca   2820
catccccctt tcgccagctg gcgtaatagc gaagaggccc gcaccgatcg cccttcccaa   2880
cagttgcgca gcctgaatgg cgaatggcgc tagcattttg gggaatttt gatgaaggaa   2940
aagtatacag tagaaaaagt atatgaaaat ataaaagttg aagatggtat atacaaactt   3000
agtataaagg gtgaatttga ggtgaggcca ggacaatttt atcttttaag agcttgggat   3060
atagaaccaa cactttctag acctattagt atatatgatg cagatgacga aaaaatatcg   3120
ttcttatact ctgttgttgg aaaaggaact gaaattttat ctaaattaaa gagcggcgat   3180
gaaataaaga taacaggacc tttaggaaat ggatttaacg taaaaaggat aagtggaaaa   3240
gtggctatag tttgtggtgg tataggtgta gcaccaatgg tatatctggc taaaaactta   3300
aaaaattgta atgttgattt ttatgctggc ttcaaaactg tgagtaaaac tgtggataat   3360
gtggaaaaat atgttaaaga gttaaagttg tccacagaag atggaagtat tggacataag   3420
gggtatgtaa cagataactt taagccagaa gaatacgatt atgttttatg ctgcggacct   3480
gagataatga tgtataaagt tgttaaaatg tgtgaacaaa agaatgttcc tgtatatatt   3540
tcaatggaga aaaaaatggc atgtggaata ggtgcatgcc ttgtatgcac ttgtaaaact   3600
aagggtggaa gaagaagagc ttgtaaagag ggcccagtat ttttaggaag tgagttgata   3660
ttaaatgact aaagtaaata tttgtggaat agattttaag aaccccgtta ttgctgcttc   3720
tggcaccttt ggatttggag aagagtttag taagtatttt gatgtttcaa ggcttggtgg   3780
catatcttca aagggactta cattgaatcc taaggaaggt aatgatggtg caagagtttt   3840
```

-continued

```
tgaggtcaca ggcggaatga tgaatagtgt aggacttcaa aatcctggag ttaaagagtt   3900
tataaaaaaa gaacttccta agatgaaaaa aatagataca gtatgtattg ttaaccttgg   3960
tggaagctgt gaggatgatt atttaagggg catggagctt cttgagaata cagatgctga   4020
tatgatagaa cttaatatat cctgtcctaa tgtaaagcac ggcggcatgg cttttggaat   4080
aaaatcagaa gttgcttata atgttgtatc acaaggcgcg ccgcattcac ttcttttcta   4140
tataaatatg agcgaagcga ataagcgtcg gaaaagcagc aaaaagtttc ctttttgctg   4200
ttggagcatg gggttcagg gggtgcagta tctgacgtca atgccgagcg aaagcgagcc   4260
gaagggtagc atttacgtta gataaccccc tgatatgctc cgacgcttta tatagaaaag   4320
aagattcaac taggtaaaat cttaatatag gttgagatga taaggtttat aaggaatttg   4380
tttgttctaa tttttcactc attttgttct aatttctttt aacaaatgtt cttttttttt   4440
tagaacagtt atgatatagt tagaatagtt taaaataagg agtgagaaaa agatgaaaga   4500
aagatatgga acagtctata aaggctctca gaggctcata gacgaagaaa gtggagaagt   4560
catagaggta gacaagttat accgtaaaca aacgtctggt aacttcgtaa aggcatatat   4620
agtgcaatta ataagtatgt tagatatgat tggcggaaaa aaacttaaaa tcgttaacta   4680
tatcctagat aatgtccact taagtaacaa tacaatgata gctacaacaa gagaaatagc   4740
aaaagctaca ggaacaagtc tacaaacagt aataacaaca cttaaaatct tagaagaagg   4800
aaatattata aaaagaaaaa ctggagtatt aatgttaaac cctgaactac taatgagagg   4860
cgacgaccaa aaacaaaaat acctcttact cgaatttggg aactttgagc aagaggcaaa   4920
tgaaatagat tgacctccca ataacaccac gtagttattg ggaggtcaat ctatgaaatg   4980
cgattaaggg ccggccagtg ggcaagttga aaaattcaca aaaatgtggt ataatatctt   5040
tgttcattag agcgataaac ttgaatttga gagggaactt agatggtatt tgaaaaaatt   5100
gataaaaata gttggaacag aaaagagtat tttgaccact actttgcaag tgtaccttgt   5160
acctacagca tgaccgttaa agtggatatc acacaaataa aggaaaaggg aatgaaacta   5220
tatcctgcaa tgctttatta tattgcaatg attgtaaacc gccattcaga gtttaggacg   5280
gcaatcaatc aagatggtga attggggata tatgatgaga tgataccaag ctatacaata   5340
tttcacaatg atactgaaac attttccagc ctttggactg agtgtaagtc tgactttaaa   5400
tcatttttag cagattatga aagtgatacg caacggtatg gaaacaatca tagaatggaa   5460
ggaaagccaa atgctccgga aaacattttt aatgtatcta tgataccgtg gtcaaccttc   5520
gatggcttta atctgaattt gcagaaagga tatgattatt tgattcctat ttttactatg   5580
gggaaatatt ataaagaaga taacaaaatt atacttcctt tggcaattca agttcatcac   5640
gcagtatgtg acggatttca catttgccgt tttgtaaacg aattgcagga attgataaat   5700
agttaacttc aggtttgtct gtaactaaaa acaagtattt aagcaaaaac atcgtagaaa   5760
tacggtgttt tttgttaccc taagtttaaa ctccttttg ataatctcat gaccaaaatc   5820
ccttaacgtg agttttcgtt ccactgagcg tcagaccccg tagaaaagat caaaggatct   5880
tcttgagatc cttttttct gcgcgtaatc tgctgcttgc aaacaaaaaa accaccgcta   5940
ccagcggtgg tttgtttgcc ggatcaagag ctaccaactc tttttccgaa ggtaactggc   6000
ttcagcagag cgcagatacc aaatactgtc cttctagtgt agccgtagtt aggccaccac   6060
ttcaagaact ctgtagcacc gcctacatac ctcgctctgc taatcctgtt accagtggct   6120
gctgccagtg gcgataagtc gtgtcttacc gggttggact caagacgata gttaccggat   6180
aaggcgcagc ggtcgggctg aacgggggt tcgtgcacac agcccagctt ggagcgaacg   6240
```

-continued

```
acctacaccg aactgagata cctacagcgt gagcattgag aaagcgccac gcttcccgaa   6300

gggagaaagg cggacaggta tccggtaagc ggcagggtcg gaacaggaga gcgcacgagg   6360

gagcttccag ggggaaacgc ctggtatctt tatagtcctg tcgggtttcg ccacctctga   6420

cttgagcgtc gatttttgtg atgctcgtca ggggggcgga gcctatggaa aaacgccagc   6480

aacgcggcct ttttacggtt cctggccttt tgctggcctt ttgctcacat gttctttcct   6540

gcgttatccc ctgattctgt ggataaccgt attaccgcct ttgagtgagc tgataccgct   6600

cgccgcagcc gaacgaccga gcgcagcgag tcagtgagcg aggaagcgga agagcgccca   6660

atacgcaggg cccccctgca                                               6679
```

<210> SEQ ID NO 55
<211> LENGTH: 8726
<212> TYPE: DNA
<213> ORGANISM: Artificial Sequence
<220> FEATURE:
<223> OTHER INFORMATION: Shuttle plasmid pMTL-JH2-lambda4.3

<400> SEQUENCE: 55

```
gggtgtttag gacttgatac tgatattact tatgtaccag aagagttttg taagaaattt     60

aatagtatag aagatgctat atttaatttt aataagaaaa taattgatgc gactttagat    120

gttgtttcat gttataaggt gcaaattgca tattatgaag cttatggttt aaaaggactt    180

ttggcctata aaaggacact tgaatatttg agagaaaaaa aggctattgc aattgctgat    240

ataaaaagag gagatatagc taaaacagct gaaatgtatg ctaaagctca ctttgaaggt    300

taatgagcgg ccgctgtatc catatgacca tgattacgaa ttcgagctcg gtacccgggg    360

atcctctaga gtcgacgtca cgcgtccatg gagatctcga ggagcttgaa ggaaatacta    420

aggcaaaggt actgcaagtg ctcgcaacat tcgcttatgc ggattattgc cgtagtgccg    480

cgacgccggg ggcaagatgc agagattgcc atggtacagg ccgtgcggtt gatattgcca    540

aaacagagct gtgggggaga gttgtcgaga aagagtgcgg aagatgcaaa ggcgtcggct    600

attcaaggat gccagcaagc gcagcatatc gcgctgtgac gatgctaatc ccaaacctta    660

cccaacccac ctggtcacgc actgttaagc cgctgtatga cgctctggtg gtgcaatgcc    720

acaaagaaga gtcaatcgca gacaacattt tgaatgcggt cacacgttag cagcatgatt    780

gccacggatg gcaacatatt aacggcatga tattgactta ttgaataaaa ttgggtaaat    840

ttgactcaac gatgggttaa ttcgctcgtt gtggtagtga gatgaaaaga ggcggcgctt    900

actaccgatt ccgcctagtt ggtcacttcg acgtatcgtc tggaactcca accatcgcag    960

gcagagaggt ctgcaaaatg caatcccgaa acagttcgca ggtaatagtt agagcctgca   1020

taacggtttc gggatttttt atatctgcac aacaggtaag agcattgagt cgataatcgt   1080

gaagagtcgg cgagcctggt tagccagtgc tctttccgtt gtgctgaatt aagcgaatac   1140

cggaagcaga accggatcac caaatgcgta caggcgtcat cgccgcccag caacagcaca   1200

acccaaactg agccgtagcc actgtctgtc ctgaattcat tagtaatagt tacgctgcgg   1260

ccttttacac atgaccttcg tgaaagcggg tggcaggagg tcgcgctaac aacctcctgc   1320

cgttttgccc gtgcatatcg gtcacgaaca aatctgatta ctaaacacag tagcctggat   1380

ttgttctatc agtaatcgac cttattccta attaaataga gcaaatcccc ttattggggg   1440

taagacatga agatgccaga aaaacatgac ctgttggccg ccattctcgc ggcaaaggaa   1500

caaggcatcg ggcaatcct tgcgtttgca atggcgtacc ttcgcggcag atataatggc   1560

ggtgcgttta caaaaacagt aatcgacgca acgatgtgcg ccattatcgc ctggttcatt   1620
```

-continued

```
cgtgaccttc tcgacttcgc cggactaagt agcaatctcg cttatataac gagcgtgttt   1680
atcggctaca tcggtactga ctcgattggt tcgcttatca aacgcttcgc tgctaaaaaa   1740
gccggagtag aagatggtag aaatcaataa tcaacgtaag gcgttcctcg atatgctggc   1800
gtggtcggag ggaactgata acggacgtca gaaaaccaga aatcatggtt atgacgtcat   1860
tgtaggcgga gagctattta ctgattactc cgatcaccct cgcaaacttg tcacgctaaa   1920
cccaaaactc aaatcaacag gcgccggacg ctaccagctt ctttcccgtt ggtgggatgc   1980
ctaccgcaag cagcttggcc tgaaagactt ctctccgaaa agtcaggacg ctgtggcatt   2040
gcagcagatt aaggagcgtg gcgctttacc tatgattgat cgtggtgata tccgtcaggc   2100
aatcgaccgt tgcagcaata tctgggcttc actgccgggc gctggttatg gtcagttcga   2160
gcataaggct gacagcctga ttgcaaaatt caaagaagcg ggcggaacgg tcagagagat   2220
tgatgtatga gcagagtcac cgcgattatc tccgctctgg ttatctgcat catcgtctgc   2280
ctgtcatggg ctgttaatca ttaccgtgat aacgccatta cctacaaagc ccagcgcgac   2340
aaaaatgcca gagaactgaa gctggcgaac gcggcaatta ctgacatgca gatgcgtcag   2400
cgtgatgttg ctgcgctcga tgcaaaatac acgaaggagt tagctgatgc taaagctgaa   2460
aatgatgctc tgcgtgatga tgttgccgct ggtcgtcgtc ggttgcacat caaagcagtc   2520
tgtcagtcag tgcgtgaagc caccaccgcc tccggcgtgg ataatgcagc ctccccccga   2580
ctggcagaca ccgctgaacg ggattatttc accctcagag agaggctgat cactatgcaa   2640
aaacaactgg aaggaaccca gaagtatatt aatgagcagt gcagatagag ttgcccatat   2700
cgatgggcaa ctcatgcaat tattgtgagc aatacacacg cgcttccagc ggagtataaa   2760
tgcctaaagt aataaaaccg agcaatccat ttacgaatgt ttgctgggtt tctgttttaa   2820
caacattttc tgcgccgcca caaattttgg ctgcatcgac agttttcttc tgcccaattc   2880
cagaaacgaa gaaatgatgg gtgatggttt cctttggtgc tactgctgcc ggtttgtttt   2940
gaacagtaaa cgtctgttga gcacatcctg taataagcag ggccagcgca gtagcgagta   3000
gcattttttt catggtgtta ttcccgatgc tttttgaagt tcgcagaatc gtatgtgtag   3060
aaaattaaac aaaccctaaa caatgagttg aaatttcata ttgttaatat ttattaatgt   3120
atgtcaggtg cgatgaatcg tcattgtatt cccggattaa ctatgtccac agccctgacg   3180
gggaacttct ctgcgggagt gtccgggaat aattaaaacg atgcacacag ggtttagcgc   3240
gtacacgtat tgcattatgc caacgccccg gtgctgacac ggaagaaacc ggacgttatg   3300
atttagcgtg gaaagatttg tgtagtgttc tgaatgctct cagtaaatag taatgaatta   3360
tcaaaggtat agtaatatct tttatgttca tggatatttg taacccatcg gaaaactcct   3420
gctttagcaa gattttccct gtattgctga aatgtgattt ctcttgattt caacctatca   3480
taggacgttt ctataagatg cgtgtttctt gagaatttaa catttacaac ctttttaagt   3540
ccttttatta acacggtgtt atcgttttct aacacgatgt gaatattatc tgtggctaga   3600
tagtaaatat aatgtgagac gttgtgacgt tttagttcag aataaaacaa ttcacagtct   3660
aaatcttttc gcacttgatc gaatatttct ttaaaaatgg caacctgagc cattggtaaa   3720
accttccatg tgatacgagg gcgcgtagtt tgcattatcg tttttatcgt ttcaatctgg   3780
tctgacctcc ttgtgttttg ttgatgattt atgtcaaata ttaggaatgt tttcacttaa   3840
tagtattggt tgcgtaacaa agtgcggtcc tgctggcatt ctggagggaa atacaaccga   3900
cagatgtatg taaggccaac gtgctcaaat cttcatacag aaagatttga agtaatattt   3960
taaccgctag atgaagagca agcgcatgga gcgacaaaat gaataaagaa caatctgctg   4020
```

```
atgatccctc cgtggatctg attcgtgtaa aaaatatgct taatagcacc atttctatga   4080
gttaccctga tgttgtaatt gcatgtatag aacataaggt gtctctggaa gcattcagag   4140
caattgaggc agcgttggtg aagcacgata ataatatgaa ggattattcc ctggtggttg   4200
actgatcacc ataactgcta atcattcaaa ctatttagtc tgtgacagag ccaacacgca   4260
gtctgtcact gtcaggaaag tggtaaaact gcaactcaat tactgcaatg ccctcgtaat   4320
taagtgaatt tacaatatcg tcctgttcgg agggaagaac gcgggatgtt cattcttcat   4380
cacttttaat tgatgtatat gctctctttt ctgacgttag tctccgacgg caggcttcaa   4440
tgacccaggc tgagaaattc ccggaccctt tttgctcaag agcgatgtta atttgttcaa   4500
tcatttggtt aggaaagcgg atgttgcggg ttgttgttct gcgggttctg ttcttcgttg   4560
acatgaggtt gccccgtatt cagtgtcgct gatttgtatt gtctgaagtt gtttttacgt   4620
taagttgatg cagatcaatt aatacgatac ctgcgtcata attgattatt tgacgtggtt   4680
tgatggcctc cacgcacgtt gtgatatgta gatgataatc attatcactt tacgggtcct   4740
ttccggtgat ccgacaggtt acggggcggc gacctcctgc agacatgcaa gcttggcact   4800
ggccgtcgtt ttacaacgtc gtgactggga aaaccctggc gttacccaac ttaatcgcct   4860
tgcagcacat ccccctttcg ccagctggcg taatagcgaa gaggcccgca ccgatcgccc   4920
ttcccaacag ttgcgcagcc tgaatggcga atggcgctag cattttgggg gaattttgat   4980
gaaggaaaag tatacagtag aaaaagtata tgaaaatata aaagttgaag atggtatata   5040
caaacttagt ataaagggtg aatttgaggt gaggccagga caatttttatc ttttaagagc   5100
ttgggatata gaaccaacac tttctagacc tattagtata tatgatgcag atgacgaaaa   5160
aatatcgttc ttatactctg ttgttggaaa aggaactgaa attttatcta aattaaagag   5220
cggcgatgaa ataaagataa caggaccttt aggaaatgga tttaacgtaa aaaggataag   5280
tggaaaagtg gctatagttt gtggtggtat aggtgtagca ccaatggtat atctggctaa   5340
aaacttaaaa aattgtaatg ttgattttta tgctggcttc aaaactgtga gtaaaactgt   5400
ggataatgtg gaaaaatatg ttaaagagtt aaagttgtcc acagaagatg gaagtattgg   5460
acataagggg tatgtaacag ataactttaa gccagaagaa tacgattatg ttttatgctg   5520
cggacctgag ataatgatgt ataaagttgt taaaatgtgt gaacaaaaga atgttcctgt   5580
atatatttca atggagaaaa aaatggcatg tggaataggt gcatgccttg tatgcacttg   5640
taaaactaag ggtggaagaa gaagagcttg taaagagggc ccagtatttt taggaagtga   5700
gttgatatta aatgactaaa gtaaatattt gtggaataga ttttaagaac cccgttattg   5760
ctgcttctgg cacctttgga tttggagaag agtttagtaa gtattttgat gtttcaaggc   5820
ttggtggcat atcttcaaag ggacttacat tgaatcctaa ggaaggtaat gatggtgcaa   5880
gagtttttga ggtcacaggc ggaatgatga atagtgtagg acttcaaaat cctggagtta   5940
aagagtttat aaaaaaagaa cttcctaaga tgaaaaaaat agatacagta tgtattgtta   6000
accttggtgg aagctgtgag gatgattatt taaggggcat ggagcttctt gagaatacag   6060
atgctgatat gatagaactt aatatatcct gtcctaatgt aaagcacggc ggcatggctt   6120
ttggaataaa atcagaagtt gcttataatg ttgtatcaca aggcgcgccg cattcacttc   6180
ttttctatat aaatatgagc gaagcgaata agcgtcggaa aagcagcaaa aagtttcctt   6240
tttgctgttg gagcatgggg gttcaggggg tgcagtatct gacgtcaatg ccgagcgaaa   6300
gcgagccgaa gggtagcatt tacgttagat aaccccctga tatgctccga cgctttatat   6360
agaaaagaag attcaactag gtaaaatctt aatataggtt gagatgataa ggtttataag   6420
```

gaatttgttt gttctaattt ttcactcatt ttgttctaat ttcttttaac aaatgttctt 6480
ttttttttag aacagttatg atatagttag aatagtttaa aataaggagt gagaaaaaga 6540
tgaaagaaag atatggaaca gtctataaag gctctcagag gctcatagac gaagaaagtg 6600
gagaagtcat agaggtagac aagttatacc gtaaacaaac gtctggtaac ttcgtaaagg 6660
catatatagt gcaattaata agtatgttag atatgattgg cggaaaaaaa cttaaaatcg 6720
ttaactatat cctagataat gtccacttaa gtaacaatac aatgatagct acaacaagag 6780
aaatagcaaa agctacagga acaagtctac aaacagtaat aacaacactt aaaatcttag 6840
aagaaggaaa tattataaaa agaaaaactg gagtattaat gttaaaccct gaactactaa 6900
tgagaggcga cgaccaaaaa caaaaatacc tcttactcga atttgggaac tttgagcaag 6960
aggcaaatga aatagattga cctcccaata acaccacgta gttattggga ggtcaatcta 7020
tgaaatgcga ttaagggccg gccagtgggc aagttgaaaa attcacaaaa atgtggtata 7080
atatctttgt tcattagagc gataaacttg aatttgagag ggaacttaga tggtatttga 7140
aaaaattgat aaaaatagtt ggaacagaaa agagtatttt gaccactact ttgcaagtgt 7200
accttgtacc tacagcatga ccgttaaagt ggatatcaca caaataaagg aaaagggaat 7260
gaaactatat cctgcaatgc tttattatat tgcaatgatt gtaaaccgcc attcagagtt 7320
taggacggca atcaatcaag atggtgaatt ggggatatat gatgagatga taccaagcta 7380
tacaatattt cacaatgata ctgaaacatt ttccagcctt tggactgagt gtaagtctga 7440
ctttaaatca tttttagcag attatgaaag tgatacgcaa cggtatggaa acaatcatag 7500
aatggaagga aagccaaatg ctccggaaaa catttttaat gtatctatga taccgtggtc 7560
aaccttcgat ggctttaatc tgaatttgca gaaaggatat gattatttga ttcctatttt 7620
tactatgggg aaatattata aagaagataa caaaattata cttcctttgg caattcaagt 7680
tcatcacgca gtatgtgacg gatttcacat ttgccgtttt gtaaacgaat tgcaggaatt 7740
gataaatagt taacttcagg tttgtctgta actaaaaaca agtatttaag caaaaacatc 7800
gtagaaatac ggtgtttttt gttaccctaa gtttaaactc ctttttgata atctcatgac 7860
caaaatccct taacgtgagt tttcgttcca ctgagcgtca gaccccgtag aaaagatcaa 7920
aggatcttct tgagatcctt tttttctgcg cgtaatctgc tgcttgcaaa caaaaaaacc 7980
accgctacca gcggtggttt gtttgccgga tcaagagcta ccaactcttt ttccgaaggt 8040
aactggcttc agcagagcgc agataccaaa tactgtcctt ctagtgtagc cgtagttagg 8100
ccaccacttc aagaactctg tagcaccgcc tacatacctc gctctgctaa tcctgttacc 8160
agtggctgct gccagtggcg ataagtcgtg tcttaccggg ttggactcaa gacgatagtt 8220
accggataag gcgcagcggt cgggctgaac ggggggttcg tgcacacagc ccagcttgga 8280
gcgaacgacc tacaccgaac tgagatacct acagcgtgag cattgagaaa gcgccacgct 8340
tcccgaaggg agaaaggcgg acaggtatcc ggtaagcggc agggtcggaa caggagagcg 8400
cacgagggag cttccagggg gaaacgcctg gtatctttat agtcctgtcg ggtttcgcca 8460
cctctgactt gagcgtcgat ttttgtgatg ctcgtcaggg gggcggagcc tatggaaaaa 8520
cgccagcaac gcggcctttt tacggttcct ggccttttgc tggccttttg ctcacatgtt 8580
ctttcctgcg ttatcccctg attctgtgga taaccgtatt accgcctttg agtgagctga 8640
taccgctcgc cgcagccgaa cgaccgagcg cagcgagtca gtgagcgagg aagcggaaga 8700
gcgcccaata cgcagggccc cctgca 8726

<210> SEQ ID NO 56
<211> LENGTH: 10909
<212> TYPE: DNA
<213> ORGANISM: Artificial Sequence
<220> FEATURE:
<223> OTHER INFORMATION: Shuttle plasmid pMTL-JH2-lambda6.5

<400> SEQUENCE: 56
gggtgtttag gacttgatac tgatattact tatgtaccag aagagttttg taagaaattt 60
aatagtatag aagatgctat atttaatttt aataagaaaa taattgatgc gactttagat 120
gttgtttcat gttataaggt gcaaattgca tattatgaag cttatggttt aaaaggactt 180
ttggcctata aaaggacact tgaatatttg agagaaaaaa aggctattgc aattgctgat 240
ataaaaagag gagatatagc taaaacagct gaaatgtatg ctaaagctca ctttgaaggt 300
taatgagcgg ccgctgtatc catatgacca tgattacgaa ttcgagctcg gtacccgggg 360
atcctctaga gtcgacgtca cgcgtccatg gagatctcga ggagcttagg tgagaacatc 420
cctgcctgaa catgagaaaa aacagggtac tcatactcac ttctaagtga cggctgcata 480
ctaaccgctt catacatctc gtagatttct ctggcgattg aagggctaaa ttcttcaacg 540
ctaactttga gaatttttgt aagcaatgcg gcgttataag catttaatgc attgatgcca 600
ttaaataaag caccaacgcc tgactgcccc atccccatct tgtctgcgac agattcctgg 660
gataagccaa gttcattttt cttttttca taaattgctt taaggcgacg tgcgtcctca 720
agctgctctt gtgttaatgg tttctttttt gtgctcatac gttaaatcta tcaccgcaag 780
ggataaatat ctaacaccgt gcgtgttgac tattttacct ctggcggtga taatggttgc 840
atgtactaag gaggttgtat ggaacaacgc ataaccctga aagattatgc aatgcgcttt 900
gggcaaacca agacagctaa agatctcggc gtatatcaaa gcgcgatcaa caaggccatt 960
catgcaggcc gaaagatttt tttaactata aacgctgatg gaagcgttta tgcggaagag 1020
gtaaagccct tcccgagtaa caaaaaaaca acagcataaa taaccccgct cttacacatt 1080
ccagccctga aaaagggcat caaattaaac cacacctatg gtgtatgcat ttatttgcat 1140
acattcaatc aattgttatc taaggaaata cttacatatg gttcgtgcaa acaaacgcaa 1200
cgaggctcta cgaatcgaga gtgcgttgct taacaaaatc gcaatgcttg gaactgagaa 1260
gacagcggaa gctgtgggcg ttgataagtc gcagatcagc aggtggaaga gggactggat 1320
tccaaagttc tcaatgctgc ttgctgttct tgaatggggg gtcgttgacg acgacatggc 1380
tcgattggcg cgacaagttg ctgcgattct caccaataaa aaacgcccgg cggcaaccga 1440
gcgttctgaa caaatccaga tggagttctg aggtcattac tggatctatc aacaggagtc 1500
attatgacaa atacagcaaa aatactcaac ttcggcagag gtaactttgc cggacaggag 1560
cgtaatgtgg cagatctcga tgatggttac gccagactat caaatatgct gcttgaggct 1620
tattcgggcg cagatctgac caagcgacag tttaaagtgc tgcttgccat tctgcgtaaa 1680
acctatgggt ggaataaacc aatggacaga atcaccgatt ctcaacttag cgagattaca 1740
aagttacctg tcaaacggtg caatgaagcc aagttagaac tcgtcagaat gaatattatc 1800
aagcagcaag gcggcatgtt tggaccaaat aaaaacatct cagaatggtg catccctcaa 1860
aacgagggaa aatcccctaa aacgagggat aaaacatccc tcaaattggg ggattgctat 1920
ccctcaaaac agggggacac aaaagacact attacaaaag aaaaaagaaa agattattcg 1980
tcagagaatt ctggcgaatc ctctgaccag ccagaaaacg acctttctgt ggtgaaaccg 2040
gatgctgcaa ttcagagcgg cagcaagtgg gggacagcag aagacctgac cgccgcagag 2100
tggatgtttg acatggtgaa gactatcgca ccatcagcca gaaaaccgaa ttttgctggg 2160
tgggctaacg atatccgcct gatgcgtgaa cgtgacggac gtaaccaccg cgacatgtgt 2220
gtgctgttcc gctgggcatg ccaggacaac ttctggtccg gtaacgtgct gagcccggcc 2280
aaactccgcg ataagtggac ccaactcgaa atcaaccgta acaagcaaca ggcaggcgtg 2340
acagccagca aaccaaaact cgacctgaca aacacagact ggatttacgg ggtggatcta 2400
tgaaaaacat cgccgcacag atggttaact ttgaccgtga gcagatgcgt cggatcgcca 2460
acaacatgcc ggaacagtac gacgaaaagc cgcaggtaca gcaggtagcg cagatcatca 2520
acggtgtgtt cagccagtta ctggcaactt tcccggcgag cctggctaac cgtgaccaga 2580
acgaagtgaa cgaaatccgt cgccagtggg ttctggcttt tcgggaaaac gggatcacca 2640
cgatggaaca ggttaacgca ggaatgcgcg tagcccgtcg gcagaatcga ccatttctgc 2700
catcacccgg gcagtttgtt gcatggtgcc gggaagaagc atccgttacc gccggactgc 2760
caaacgtcag cgagctggtt gatatggttt acgagtattg ccggaagcga ggcctgtatc 2820
cggatgcgga gtcttatccg tggaaatcaa acgcgcacta ctggctggtt accaacctgt 2880
atcagaacat gcgggccaat gcgcttactg atgcggaatt acgccgtaag gccgcagatg 2940
agcttgtcca tatgactgcg agaattaacc gtggtgaggc gatccctgaa ccagtaaaac 3000
aacttcctgt catgggcggt agacctctaa atcgtgcaca ggctctggcg aagatcgcag 3060
aaatcaaagc taagttcgga ctgaaaggag caagtgtatg acgggcaaag aggcaattat 3120
tcattacctg gggacgcata atagcttctg tgcgccggac gttgccgcgc taacaggcgc 3180
aacagtaacc agcataaatc aggccgcggc taaaatggca cgggcaggtc ttctggttat 3240
cgaaggtaag gtctggcgaa cggtgtatta ccggtttgct accagggaag aacgggaagg 3300
aaagatgagc acgaacctgg tttttaagga gtgtcgccag agtgccgcga tgaaacgggt 3360
attggcggta tatggagtta aaagatgacc atctacatta ctgagctaat aacaggcctg 3420
ctggtaatcg caggcctttt tatttggggg agagggaagt catgaaaaaa ctaacctttg 3480
aaattcgatc tccagcacat cagcaaaacg ctattcacgc agtacagcaa atccttccag 3540
acccaaccaa accaatcgta gtaaccattc aggaacgcaa ccgcagctta gaccaaaaca 3600
ggaagctatg ggcctgctta ggtgacgtct ctcgtcaggt tgaatggcat ggtcgctggc 3660
tggatgcaga aagctggaag tgtgtgttta ccgcagcatt aaagcagcag gatgttgttc 3720
ctaaccttgc cgggaatggc tttgtggtaa taggccagtc aaccagcagg atgcgtgtag 3780
gcgaatttgc ggagctatta gagcttatac aggcattcgg tacagagcgt ggcgttaagt 3840
ggtcagacga agcgagactg gctctggagt ggaaagcgag atggggagac agggctgcat 3900
gataaatgtc gttagtttct ccggtggcag gacgtcagca tatttgctct ggctaatgga 3960
gcaaaagcga cgggcaggta aagacgtgca ttacgttttc atggatacag gttgtgaaca 4020
tccaatgaca tatcggtttg tcagggaagt tgtgaagttc tgggatatac cgctcaccgt 4080
attgcaggtt gatatcaacc cggagcttgg acagccaaat ggttatacgg tatgggaacc 4140
aaaggatatt cagacgcgaa tgcctgttct gaagccattt atcgatatgg taaagaaata 4200
tggcactcca tacgtcggcg gcgcgttctg cactgacaga ttaaaactcg ttcccttcac 4260
caaatactgt gatgaccatt tcgggcgagg gaattacacc acgtggattg gcatcagagc 4320
tgatgaaccg aagcggctaa agccaaagcc tggaatcaga tatcttgctg aactgtcaga 4380
ctttgagaag gaagatatcc tcgcatggtg gaagcaacaa ccattcgatt tgcaaatacc 4440
ggaacatctc ggtaactgca tattctgcat taaaaaatca acgcaaaaaa tcggacttgc 4500
ctgcaaagat gaggagggat tgcagcgtgt ttttaatgag gtcatcacgg gatcccatgt 4560

-continued

```
gcgtgacgga catcgggaaa cgccaaagga gattatgtac cgaggaagaa tgtcgctgga   4620
cggtatcgcg aaaatgtatt cagaaaatga ttatcaagcc ctgtatcagg acatggtacg   4680
agctaaaaga ttcgataccg gctcttgttc tgagtcatgc gaaatatttg gagggcagct   4740
tgatttcgac ttcgggaggg aagctgcatg atgcgatgtt atcggtgcgg tgaatgcaaa   4800
gaagataacc gcttccgacc aaatcaacct tactggaatc gatggtgtct ccggtgtgaa   4860
agaacaccaa caggggtgtt accactaccg caggaaaagg aggacgtgtg gcgagacagc   4920
gacgaagtat caccgacata atctgcgaaa actgcaaata ccttccaacg aaacgcacca   4980
gaaataaacc caagccaatc ccaaaagaat ctgacgtaaa aaccttcaac tacacggctc   5040
acctgtggga tatccggtgg ctaagacgtc gtgcgaggaa aacaaggtga ttgaccaaaa   5100
tcgaagttac gaacaagaaa gcgtcgagcg agctttaacg tgcgctaact gcggtcagaa   5160
gctgcatgtg ctggaagttc acgtgtgtga gcactgctgc gcagaactga tgagcgatcc   5220
gaatagctcg atgcacgagg aagaagatga tggctaaacc agcgcgaaga cgatgtaaaa   5280
acgatgaatg ccgggaatgg tttcaccctg cattcgctaa tcagtggtgg tgctctccag   5340
agtgtggaac caagatagca ctcgaacgac gaagtaaaga acgcgaaaaa gcggaaaaag   5400
cagcagagaa gaaacgacga cgagaggagc agaaacagaa agataaactt aagattcgaa   5460
aactcgcctt aaagccccgc agttactgga ttaaacaagc ccaacaagcc gtaaacgcct   5520
tcatcagaga aagagaccgc gacttaccat gtatctcgtg cggaacgctc acgtctgctc   5580
agtgggatgc cggacattac cggacaactg ctgcggcacc tcaactccga tttaatgaac   5640
gcaatattca caagcaatgc gtggtgtgca accagcacaa aagcggaaat ctcgttccgt   5700
atcgcgtcga actgattagc cgcatcgggc aggaagcagt agacgaaatc gaatcaaacc   5760
ataaccgcca tcgctggact atcgaagagt gcaaggcgat caaggcagag taccaacaga   5820
aactcaaaga cctgcgaaat agcagaagtg aggccgcatg acgttctcag taaaaaccat   5880
tccagacatg ctcgttgaag catacggaaa tcagacagaa gtagcacgca gactgaaatg   5940
tagtcgcggt acggtcagaa aatacgttga tgataaagac gggaaaatgc acgccatcgt   6000
caacgacgtt ctcatggttc atcgcggatg gagtgaaaga gatgcgctat tacgaaaaaa   6060
ttgatggcag caaataccga aatatttggg tagttggcga tctgcacgga tgctacacga   6120
acctgatgaa caaactggat acgattggat tcgacaacaa aaaagacctg cttatctcgg   6180
tgggcgattt ggttgatcgt ggtgcagaga acgttgaatg cctggaatta atcacattcc   6240
cctggttcag agctgtacgt ggaaaccatg agcaaatgat gattgatggc ttatcagagc   6300
gtggaaacgt taatcactgg ctgcttaatg gcggtggctg gttctttaat ctcgattacg   6360
acaaagaaat tctggctaaa gctcttgccc ataaagcaga tgaacttccg ttaatcatcg   6420
aactggtgag caaagataaa aaatatgtta tctgccacgc cgattatccc tttgacgaat   6480
acgagtttgg aaagccagtt gatcatcagc aggtaatctg gaaccgcgaa cgaatcagca   6540
actcacaaaa cgggatcgtg aaagaaatca aaggcgcgga cacgttcatc tttggtcata   6600
cgccagcagt gaaaccactc aagtttgcca accaaatgta tatcgatacc ggcgcagtgt   6660
tctgcggaaa cctaacattg attcaggtac agggagaagg cgcatgagac tcgaaagcgt   6720
agctaaattt cattcgccaa aaagcccgat gatgagcgac tcaccacggg ccacggcttc   6780
tgactctctt tccggtactg atgtgatggc tgctatgggg atggcgcaat cacaagccgg   6840
attcggtatg gctgcattct gcggtaagca cgaactcagc cagaacgaca aacaaaaggc   6900
tatcaactat ctgatgcaat ttgcacacaa ggtatcgggg aaataccgtg gtgtggcacc   6960
```

-continued

```
tgcagacatg caagcttggc actggccgtc gttttacaac gtcgtgactg ggaaaaccct   7020
ggcgttaccc aacttaatcg ccttgcagca catccccctt tcgccagctg gcgtaatagc   7080
gaagaggccc gcaccgatcg cccttcccaa cagttgcgca gcctgaatgg cgaatggcgc   7140
tagcattttg gggaatttt gatgaaggaa aagtatacag tagaaaaagt atatgaaaat   7200
ataaaagttg aagatggtat atacaaactt agtataaagg gtgaatttga ggtgaggcca   7260
ggacaatttt atcttttaag agcttgggat atagaaccaa cactttctag acctattagt   7320
atatatgatg cagatgacga aaaaatatcg ttcttatact ctgttgttgg aaaaggaact   7380
gaaattttat ctaaattaaa gagcggcgat gaaataaaga taacaggacc tttaggaaat   7440
ggatttaacg taaaaaggat aagtggaaaa gtggctatag tttgtggtgg tataggtgta   7500
gcaccaatgg tatatctggc taaaaactta aaaaattgta atgttgattt ttatgctggc   7560
ttcaaaactg tgagtaaaac tgtggataat gtggaaaaat atgttaaaga gttaaagttg   7620
tccacagaag atggaagtat tggacataag ggtatgtaa cagataactt taagccagaa   7680
gaatacgatt atgttttatg ctgcggacct gagataatga tgtataaagt tgttaaaatg   7740
tgtgaacaaa agaatgttcc tgtatatatt tcaatggaga aaaaaatggc atgtggaata   7800
ggtgcatgcc ttgtatgcac ttgtaaaact aagggtggaa gaagaagagc ttgtaaagag   7860
ggcccagtat ttttaggaag tgagttgata ttaaatgact aaagtaaata tttgtggaat   7920
agattttaag aaccccgtta ttgctgcttc tggcaccttt ggatttggag aagagtttag   7980
taagtatttt gatgtttcaa ggcttggtgg catatcttca aagggactta cattgaatcc   8040
taaggaaggt aatgatggtg caagagtttt tgaggtcaca ggcggaatga tgaatagtgt   8100
aggacttcaa aatcctggag ttaaagagtt tataaaaaaa gaacttccta agatgaaaaa   8160
aatagataca gtatgtattg ttaaccttgg tggaagctgt gaggatgatt atttaagggg   8220
catggagctt cttgagaata cagatgctga tatgatagaa cttaatatat cctgtcctaa   8280
tgtaaagcac ggcggcatgg cttttggaat aaaatcagaa gttgcttata atgttgtatc   8340
acaaggcgcg ccgcattcac ttcttttcta tataaatatg agcgaagcga ataagcgtcg   8400
gaaaagcagc aaaaagtttc ctttttgctg ttggagcatg ggggttcagg gggtgcagta   8460
tctgacgtca atgccgagcg aaagcgagcc gaagggtagc atttacgtta gataaccccc   8520
tgatatgctc cgacgcttta tatagaaaag aagattcaac taggtaaaat cttaatatag   8580
gttgagatga taaggtttat aaggaatttg tttgttctaa tttttcactc attttgttct   8640
aatttctttt aacaaatgtt cttttttttt tagaacagtt atgatatagt tagaatagtt   8700
taaaataagg agtgagaaaa agatgaaaga aagatatgga acagtctata aaggctctca   8760
gaggctcata gacgaagaaa gtggagaagt catagaggta gacaagttat accgtaaaca   8820
aacgtctggt aacttcgtaa aggcatatat agtgcaatta ataagtatgt tagatatgat   8880
tggcggaaaa aaacttaaaa tcgttaacta tatcctagat aatgtccact taagtaacaa   8940
tacaatgata gctacaacaa gagaaatagc aaaagctaca ggaacaagtc tacaaacagt   9000
aataacaaca cttaaaatct tagaagaagg aaatattata aaaagaaaaa ctggagtatt   9060
aatgttaaac cctgaactac taatgagagg cgacgaccaa aaacaaaaat acctcttact   9120
cgaatttggg aactttgagc aagaggcaaa tgaaatagat tgacctccca ataacaccac   9180
gtagttattg ggaggtcaat ctatgaaatg cgattaaggg ccggccagtg ggcaagttga   9240
aaaattcaca aaaatgtggt ataatatctt tgttcattag agcgataaac ttgaatttga   9300
gagggaactt agatggtatt tgaaaaaatt gataaaaata gttggaacag aaaagagtat   9360
```

```
tttgaccact actttgcaag tgtaccttgt acctacagca tgaccgttaa agtggatatc   9420

acacaaataa aggaaaaggg aatgaaacta tatcctgcaa tgctttatta tattgcaatg   9480

attgtaaacc gccattcaga gtttaggacg gcaatcaatc aagatggtga attggggata   9540

tatgatgaga tgataccaag ctatacaata tttcacaatg atactgaaac attttccagc   9600

ctttggactg agtgtaagtc tgactttaaa tcatttttag cagattatga aagtgatacg   9660

caacggtatg gaaacaatca tagaatggaa ggaaagccaa atgctccgga aaacattttt   9720

aatgtatcta tgataccgtg gtcaaccttc gatggcttta atctgaattt gcagaaagga   9780

tatgattatt tgattcctat ttttactatg ggaaatattt ataaagaaga taacaaaatt   9840

atacttcctt tggcaattca agttcatcac gcagtatgtg acggatttca catttgccgt   9900

tttgtaaacg aattgcagga attgataaat agttaacttc aggtttgtct gtaactaaaa   9960

acaagtattt aagcaaaaac atcgtagaaa tacggtgttt tttgttaccc taagtttaaa  10020

ctccttttg ataatctcat gaccaaaatc ccttaacgtg agttttcgtt ccactgagcg  10080

tcagaccccg tagaaaagat caaaggatct tcttgagatc cttttttct gcgcgtaatc  10140

tgctgcttgc aaacaaaaaa accaccgcta ccagcggtgg tttgtttgcc ggatcaagag  10200

ctaccaactc tttttccgaa ggtaactggc ttcagcagag cgcagatacc aaatactgtc  10260

cttctagtgt agccgtagtt aggccaccac ttcaagaact ctgtagcacc gcctacatac  10320

ctcgctctgc taatcctgtt accagtggct gctgccagtg gcgataagtc gtgtcttacc  10380

gggttggact caagacgata gttaccggat aaggcgcagc ggtcgggctg aacggggggt  10440

tcgtgcacac agcccagctt ggagcgaacg acctacaccg aactgagata cctacagcgt  10500

gagcattgag aaagcgccac gcttcccgaa gggagaaagg cggacaggta tccggtaagc  10560

ggcagggtcg gaacaggaga gcgcacgagg gagcttccag ggggaaacgc ctggtatctt  10620

tatagtcctg tcgggtttcg ccacctctga cttgagcgtc gatttttgtg atgctcgtca  10680

gggggcgga gcctatggaa aaacgccagc aacgcggcct ttttacggtt cctggccttt  10740

tgctggcctt ttgctcacat gttctttcct gcgttatccc ctgattctgt ggataaccgt  10800

attaccgcct ttgagtgagc tgataccgct cgccgcagcc gaacgaccga gcgcagcgag  10860

tcagtgagcg aggaagcgga agagcgccca atacgcaggg cccctgca              10909
```

<210> SEQ ID NO 57
<211> LENGTH: 4476
<212> TYPE: DNA
<213> ORGANISM: Artificial Sequence
<220> FEATURE:
<223> OTHER INFORMATION: Shuttle plasmid pMTL83151

<400> SEQUENCE: 57

```
ggataaaaaa attgtagata aattttataa aatagtttta tctacaattt ttttatcagg     60

aaacagctat gaccgcggcc gctgtatcca tatgaccatg attacgaatt cgagctcggt    120

acccggggat cctctagagt cgacgtcacg cgtccatgga gatctcgagg cctgcagaca    180

tgcaagcttg gcactggccg tcgttttaca acgtcgtgac tgggaaaacc ctggcgttac    240

ccaacttaat cgccttgcag cacatccccc tttcgccagc tggcgtaata gcgaagaggc    300

ccgcaccgat cgcccttccc aacagttgcg cagcctgaat ggcgaatggc gctagcataa    360

aaataagaag cctgcatttg caggcttctt atttttatgg cgcgccgcca ttattttttt    420

gaacaattga caattcattt cttatttttt attaagtgat agtcaaaagg cataacagtg    480

ctgaatagaa agaaatttac agaaaagaaa attatagaat ttagtatgat taattatact    540
```

```
catttatgaa tgtttaattg aatacaaaaa aaaatacttg ttatgtattc aattacgggt    600
taaaatatag acaagttgaa aaatttaata aaaaaataag tcctcagctc ttatatatta    660
agctaccaac ttagtatata agccaaaact taaatgtgct accaacacat caagccgtta    720
gagaactcta tctatagcaa tatttcaaat gtaccgacat acaagagaaa cattaactat    780
atatattcaa tttatgagat tatcttaaca gatataaatg taaattgcaa taagtaagat    840
ttagaagttt atagcctttg tgtattggaa gcagtacgca aaggcttttt tatttgataa    900
aaattagaag tatatttatt ttttcataat taatttatga aaatgaaagg gggtgagcaa    960
agtgacagag gaaagcagta tcttatcaaa taacaaggta ttagcaatat cattattgac   1020
tttagcagta aacattatga cttttatagt gcttgtagct aagtagtacg aaagggggag   1080
ctttaaaaag ctccttggaa tacatagaat tcataaatta atttatgaaa agaagggcgt   1140
atatgaaaac ttgtaaaaat tgcaaagagt ttattaaaga tactgaaata tgcaaaatac   1200
attcgttgat gattcatgat aaaacagtag caacctattg cagtaaatac aatgagtcaa   1260
gatgtttaca taaagggaaa gtccaatgta ttaattgttc aaagatgaac cgatatggat   1320
ggtgtgccat aaaaatgaga tgttttacag aggaagaaca gaaaaaagaa cgtacatgca   1380
ttaaatatta tgcaaggagc tttaaaaaag ctcatgtaaa gaagagtaaa aagaaaaaat   1440
aatttattta ttaatttaat attgagagtg ccgacacagt atgcactaaa aaatatatct   1500
gtggtgtagt gagccgatac aaaaggatag tcactcgcat tttcataata catcttatgt   1560
tatgattatg tgtcggtggg acttcacgac gaaaacccac aataaaaaaa gagttcgggg   1620
tagggttaag catagttgag gcaactaaac aatcaagcta ggatatgcag tagcagaccg   1680
taaggtcgtt gtttaggtgt gttgtaatac atacgctatt aagatgtaaa aatacggata   1740
ccaatgaagg gaaaagtata atttttggat gtagtttgtt tgttcatcta tgggcaaact   1800
acgtccaaag ccgtttccaa atctgctaaa aagtatatcc tttctaaaat caaagtcaag   1860
tatgaaatca taaataaagt ttaattttga agttattatg atattatgtt tttctattaa   1920
aataaattaa gtatatagaa tagtttaata atagtatata cttaatgtga taagtgtctg   1980
acagtgtcac agaaaggatg attgttatgg attataagcg gccggccagt gggcaagttg   2040
aaaaattcac aaaaatgtgg tataatatct ttgttcatta gagcgataaa cttgaatttg   2100
agagggaact tagatggtat ttgaaaaaat tgataaaaat agttggaaca gaaaagagta   2160
ttttgaccac tactttgcaa gtgtaccttg tacctacagc atgaccgtta aagtggatat   2220
cacacaaata aaggaaaagg gaatgaaact atatcctgca atgctttatt atattgcaat   2280
gattgtaaac cgccattcag agtttaggac ggcaatcaat caagatggtg aattggggat   2340
atatgatgag atgataccaa gctatacaat atttcacaat gatactgaaa catttttccag   2400
cctttggact gagtgtaagt ctgactttaa atcattttta gcagattatg aaagtgatac   2460
gcaacggtat ggaaacaatc atagaatgga aggaaagcca aatgctccgg aaaacatttt   2520
taatgtatct atgataccgt ggtcaacctt cgatggcttt aatctgaatt tgcagaaagg   2580
atatgattat ttgattccta tttttactat ggggaaatat tataaagaag ataacaaaat   2640
tatacttcct ttggcaattc aagttcatca cgcagtatgt gacggatttc acatttgccg   2700
ttttgtaaac gaattgcagg aattgataaa tagttaactt caggtttgtc tgtaactaaa   2760
aacaagtatt taagcaaaaa catcgtagaa atacggtgtt ttttgttacc ctaagtttaa   2820
actccttttt gataatctca tgaccaaaat cccttaacgt gagttttcgt tccactgagc   2880
gtcagacccc gtagaaaaga tcaaaggatc ttcttgagat cctttttttc tgcgcgtaat   2940
```

```
ctgctgcttg caaacaaaaa aaccaccgct accagcggtg gtttgtttgc cggatcaaga   3000

gctaccaact ctttttccga aggtaactgg cttcagcaga gcgcagatac caaatactgt   3060

ccttctagtg tagccgtagt taggccacca cttcaagaac tctgtagcac cgcctacata   3120

cctcgctctg ctaatcctgt taccagtggc tgctgccagt ggcgataagt cgtgtcttac   3180

cgggttggac tcaagacgat agttaccgga taaggcgcag cggtcgggct gaacgggggg   3240

ttcgtgcaca cagcccagct tggagcgaac gacctacacc gaactgagat acctacagcg   3300

tgagcattga gaaagcgcca cgcttcccga agggagaaag gcggacaggt atccggtaag   3360

cggcagggtc ggaacaggag agcgcacgag ggagcttcca gggggaaacg cctggtatct   3420

ttatagtcct gtcgggtttc gccacctctg acttgagcgt cgatttttgt gatgctcgtc   3480

aggggggcgg agcctatgga aaaacgccag caacgcggcc tttttacggt tcctggcctt   3540

ttgctggcct tttgctcaca tgttctttcc tgcgttatcc cctgattctg tggataaccg   3600

tattaccgcc tttgagtgag ctgataccgc tcgccgcagc cgaacgaccg agcgcagcga   3660

gtcagtgagc gaggaagcgg aagagcgccc aatacgcagg gccccctgct tcggggtcat   3720

tatagcgatt ttttcggtat atccatcctt tttcgcacga tatacaggat tttgccaaag   3780

ggttcgtgta gactttcctt ggtgtatcca acggcgtcag ccgggcagga taggtgaagt   3840

aggcccaccc gcgagcgggt gttccttctt cactgtccct tattcgcacc tggcggtgct   3900

caacgggaat cctgctctgc gaggctggcc ggctaccgcc ggcgtaacag atgagggcaa   3960

gcggatggct gatgaaacca agccaaccag gaagggcagc ccacctatca aggtgtactg   4020

ccttccagac gaacgaagag cgattgagga aaaggcggcg gcggccggca tgagcctgtc   4080

ggcctacctg ctggccgtcg gccagggcta caaaatcacg ggcgtcgtgg actatgagca   4140

cgtccgcgag ctggcccgca tcaatggcga cctgggccgc ctgggcggcc tgctgaaact   4200

ctggctcacc gacgacccgc gcacggcgcg gttcggtgat gccacgatcc tcgccctgct   4260

ggcgaagatc gaagagaagc aggacgagct tggcaaggtc atgatgggcg tggtccgccc   4320

gagggcagag ccatgacttt tttagccgct aaaacggccg gggggtgcgc gtgattgcca   4380

agcacgtccc catgcgctcc atcaagaaga gcgacttcgc ggagctggtg aagtacatca   4440

ccgacgagca aggcaagacc gatcgggccc cctgca                             4476
```

<210> SEQ ID NO 58
<211> LENGTH: 4942
<212> TYPE: DNA
<213> ORGANISM: Artificial Sequence
<220> FEATURE:
<223> OTHER INFORMATION: Shuttle plasmid pMTL-JH19

<400> SEQUENCE: 58

```
ggggagggac atttttattt atcttcagga aaacacagta atagatacgt acaatgtgca     60

aaagtattaa gattcccaga atatgctgct gaggtattaa gtacagttgt tgaacaaata    120

aaagacttag atatagactt agtagtagga ccagctatgg gtggagtaat agtttcttat    180

gagttaggaa gacaattagg aaaagaagct gtatttactg agagaaaaga caatacaatg    240

gagttaagaa gaggatttga agttaaaaaa ggagcaaaga taataattgc tgaagacgtt    300

gtaactactg gtaaatcaac tatggagaca aaaagagtat tagaagcctt aggtggagaa    360

gttgtaggtg ttgcatgtat agcagataga actaatcatg atataggtat gcctatatat    420

agtgctataa aacttgatat tcaagtttat gaatctgatg agtgtccttt atgtaaggaa    480

ggaaaattac cagttgttaa gcctggaagt agagagttca aggaattagg gatgtaataa    540
```

-continued

```
gcggccgctg tatccatatg accatgatta cgaattcgag ctcggtaccc ggggatcctc    600
tagagtcgac gtcacgcgtc catggagatc tcgaggcctg cagacatgca agcttggcac    660
tggccgtcgt tttacaacgt cgtgactggg aaaaccctgg cgttacccaa cttaatcgcc    720
ttgcagcaca tccccctttc gccagctggc gtaatagcga agaggcccgc accgatcgcc    780
cttcccaaca gttgcgcagc ctgaatggcg aatggcgcta gcataaaaat aagaagcctg    840
catttgcagg cttcttattt ttatggcgcg ccgccattat ttttttgaac aattgacaat    900
tcatttctta tttttatta agtgatagtc aaaaggcata acagtgctga atagaaagaa    960
atttacagaa aagaaaatta tagaatttag tatgattaat tatactcatt tatgaatgtt   1020
taattgaata caaaaaaaaa tacttgttat gtattcaatt acgggttaaa atatagacaa   1080
gttgaaaaat ttaataaaaa aataagtcct cagctcttat atattaagct accaacttag   1140
tatataagcc aaaacttaaa tgtgctacca acacatcaag ccgttagaga actctatcta   1200
tagcaatatt tcaaatgtac cgacatacaa gagaaacatt aactatatat attcaattta   1260
tgagattatc ttaacagata taaatgtaaa ttgcaataag taagatttag aagtttatag   1320
cctttgtgta ttggaagcag tacgcaaagg ctttttttatt tgataaaaat tagaagtata   1380
tttattttt cataattaat ttatgaaaat gaaagggggt gagcaaagtg acagaggaaa   1440
gcagtatctt atcaaataac aaggtattag caatatcatt attgacttta gcagtaaaca   1500
ttatgacttt tatagtgctt gtagctaagt agtacgaaag gggagcttt aaaaagctcc   1560
ttggaataca tagaattcat aaattaattt atgaaaagaa gggcgtatat gaaaacttgt   1620
aaaaattgca aagagtttat taaagatact gaaatatgca aaatacattc gttgatgatt   1680
catgataaaa cagtagcaac ctattgcagt aaatacaatg agtcaagatg tttacataaa   1740
gggaaagtcc aatgtattaa ttgttcaaag atgaaccgat atggatggtg tgccataaaa   1800
atgagatgtt ttacagagga agaacagaaa aaagaacgta catgcattaa atattatgca   1860
aggagcttta aaaaagctca tgtaaagaag agtaaaaaga aaaaataatt tatttattaa   1920
tttaatattg agagtgccga cacagtatgc actaaaaaat atatctgtgg tgtagtgagc   1980
cgatacaaaa ggatagtcac tcgcattttc ataatacatc ttatgttatg attatgtgtc   2040
ggtgggactt cacgacgaaa acccacaata aaaaaagagt tcggggtagg gttaagcata   2100
gttgaggcaa ctaaacaatc aagctaggat atgcagtagc agaccgtaag gtcgttgttt   2160
aggtgtgttg taatacatac gctattaaga tgtaaaaata cggataccaa tgaagggaaa   2220
agtataattt ttggatgtag tttgtttgtt catctatggg caaactacgt ccaaagccgt   2280
ttccaaatct gctaaaaagt atatcctttc taaaatcaaa gtcaagtatg aaatcataaa   2340
taaagtttaa ttttgaagtt attatgatat tatgtttttc tattaaaata aattaagtat   2400
atagaatagt ttaataatag tatatactta atgtgataag tgtctgacag tgtcacagaa   2460
aggatgattg ttatggatta taagcggccg gccagtgggc aagttgaaaa attcacaaaa   2520
atgtggtata atatctttgt tcattagagc gataaacttg aatttgagag ggaacttaga   2580
tggtatttga aaaaattgat aaaaatagtt ggaacagaaa agagtatttt gaccactact   2640
ttgcaagtgt accttgtacc tacagcatga ccgttaaagt ggatatcaca caaataaagg   2700
aaaagggaat gaaactatat cctgcaatgc tttattatat tgcaatgatt gtaaaccgcc   2760
attcagagtt taggacggca atcaatcaag atggtgaatt ggggatatat gatgagatga   2820
taccaagcta tacaatattt cacaatgata ctgaaacatt ttccagcctt tggactgagt   2880
gtaagtctga ctttaaatca tttttagcag attatgaaag tgatacgcaa cggtatggaa   2940
```

acaatcatag aatggaagga aagccaaatg ctccggaaaa catttttaat gtatctatga 3000
taccgtggtc aaccttcgat ggctttaatc tgaatttgca gaaaggatat gattatttga 3060
ttcctatttt tactatgggg aaatattata aagaagataa caaaattata cttcctttgg 3120
caattcaagt tcatcacgca gtatgtgacg gatttcacat ttgccgtttt gtaaacgaat 3180
tgcaggaatt gataaatagt taacttcagg tttgtctgta actaaaaaca agtatttaag 3240
caaaaacatc gtagaaatac ggtgtttttt gttaccctaa gtttaaactc ctttttgata 3300
atctcatgac caaaatccct taacgtgagt tttcgttcca ctgagcgtca gaccccgtag 3360
aaaagatcaa aggatcttct tgagatcctt tttttctgcg cgtaatctgc tgcttgcaaa 3420
caaaaaaacc accgctacca gcggtggttt gtttgccgga tcaagagcta ccaactcttt 3480
ttccgaaggt aactggcttc agcagagcgc agataccaaa tactgtcctt ctagtgtagc 3540
cgtagttagg ccaccacttc aagaactctg tagcaccgcc tacatacctc gctctgctaa 3600
tcctgttacc agtggctgct gccagtggcg ataagtcgtg tcttaccggg ttggactcaa 3660
gacgatagtt accggataag gcgcagcggt cgggctgaac ggggggttcg tgcacacagc 3720
ccagcttgga gcgaacgacc tacaccgaac tgagatacct acagcgtgag cattgagaaa 3780
gcgccacgct tcccgaaggg agaaaggcgg acaggtatcc ggtaagcggc agggtcggaa 3840
caggagagcg cacgagggag cttccagggg gaaacgcctg gtatctttat agtcctgtcg 3900
ggtttcgcca cctctgactt gagcgtcgat ttttgtgatg ctcgtcaggg gggcggagcc 3960
tatggaaaaa cgccagcaac gcggcctttt tacggttcct ggccttttgc tggccttttg 4020
ctcacatgtt ctttcctgcg ttatcccctg attctgtgga taaccgtatt accgcctttg 4080
agtgagctga taccgctcgc cgcagccgaa cgaccgagcg cagcgagtca gtgagcgagg 4140
aagcggaaga gcgcccaata cgcagggccc cctgcttcgg ggtcattata gcgatttttt 4200
cggtatatcc atcctttttc gcacgatata caggattttg ccaaagggtt cgtgtagact 4260
ttccttggtg tatccaacgg cgtcagccgg gcaggatagg tgaagtaggc ccacccgcga 4320
gcgggtgttc cttcttcact gtcccttatt cgcacctggc ggtgctcaac gggaatcctg 4380
ctctgcgagg ctggccggct accgccggcg taacagatga gggcaagcgg atggctgatg 4440
aaaccaagcc aaccaggaag ggcagcccac ctatcaaggt gtactgcctt ccagacgaac 4500
gaagagcgat tgaggaaaag gcggcggcgg ccggcatgag cctgtcggcc tacctgctgg 4560
ccgtcggcca gggctacaaa atcacgggcg tcgtggacta tgagcacgtc cgcgagctgg 4620
cccgcatcaa tggcgacctg ggccgcctgg gcggcctgct gaaactctgg ctcaccgacg 4680
acccgcgcac ggcgcggttc ggtgatgcca cgatcctcgc cctgctggcg aagatcgaag 4740
agaagcagga cgagcttggc aaggtcatga tgggcgtggt ccgcccgagg gcagagccat 4800
gactttttta gccgctaaaa cggccggggg gtgcgcgtga ttgccaagca cgtccccatg 4860
cgctccatca agaagagcga cttcgcggag ctggtgaagt acatcaccga cgagcaaggc 4920
aagaccgatc gggccccctg ca 4942

<210> SEQ ID NO 59
<211> LENGTH: 6100
<212> TYPE: DNA
<213> ORGANISM: Artificial Sequence
<220> FEATURE:
<223> OTHER INFORMATION: Shuttle plasmid pMTL-JH20

<400> SEQUENCE: 59
ggggagggac atttttatt atcttcagga aaacacagta atagatacgt acaatgtgca 60

```
aaagtattaa gattcccaga atatgctgct gaggtattaa gtacagttgt tgaacaaata    120
aaagacttag atatagactt agtagtagga ccagctatgg gtggagtaat agtttcttat    180
gagttaggaa gacaattagg aaaagaagct gtatttactg agagaaaaga caatacaatg    240
gagttaagaa gaggatttga agttaaaaaa ggagcaaaga taataattgc tgaagacgtt    300
gtaactactg gtaaatcaac tatggagaca aaaagagtat tagaagcctt aggtggagaa    360
gttgtaggtg ttgcatgtat agcagataga actaatcatg atataggtat gcctatatat    420
agtgctataa aacttgatat tcaagtttat gaatctgatg agtgtccttt atgtaaggaa    480
ggaaaattac cagttgttaa gcctggaagt agagagttca aggaattagg gatgtaataa    540
gcggccgctg tatccatatg accatgatta cgaattcgag ctcggtaccc ggggatcctc    600
tagagtcgac gtcacgcgtc catggagatc tcgaggcctg cagacatgca agcttggcac    660
tggccgtcgt tttacaacgt cgtgactggg aaaaccctgg cgttacccaa cttaatcgcc    720
ttgcagcaca tccccctttc gccagctggc gtaatagcga agaggcccgc accgatcgcc    780
cttcccaaca gttgcgcagc ctgaatggcg aatggcgcta gcaaacttaa ttatttatag    840
tgttacttaa aaaatgtaaa ttttttagag taaaaatttg taatataaca tataacttaa    900
aaataaaaag cagttagcct tataaatgaa ggttagctgt ttttttgtt aaaaatatat    960
ttacaaaata agagatagta gcagtacaat ataagtataa ggtaaaagta ttatatatta   1020
gggaggggta agtatgaaaa atcaattaaa tgaaaataat aaaaaggttg tattttttgg   1080
agtaggtgct gtaggagcta cttttgcaga acaatttttt aactctaaat atgattttaa   1140
aattctttgt gataatgaaa gaaagaaaag atatttagaa gaaggattta taataaatgg   1200
aaaaaggtat gattttgatt atgtaactaa agatgagtat aaacaagagg ctgattttat   1260
aattataggt ctaaaatata ataatttaaa agaaaatata aaagaattag atggattagt   1320
tggaaaaaat acagttataa tgtctctgct aaatggagtt gatagcgaag agataatagg   1380
agaaagattt ggaattgaaa aaatggtata ttcatatgtt accaatatag atgcaaagaa   1440
aatcaataat aatattatac acactactaa tgggataatt gtatttggta acaaagataa   1500
tagtgaagat agaaaaacta atataataac cgaagtcttt gatgatgtaa atatagaata   1560
tactttatca aaagatattc aacgagatat gtggtggaag tacatggtta atattggtgt   1620
aaatcaaact tcagctatac ttggtgcacc ttatggagtt tttcagagtt ctgagcattt   1680
aagagaatta gcaaaatctg caatgaggga agttgttgct atagcacaag caaaagacat   1740
atctcttaca gaagatgatg tggaacattc attacataga atactagaac attcaaaaga   1800
aggaagaaca tcaatgcttc aagatgtgga agctcataga cttacagaag tagatatgtt   1860
ttctaagaat atctgtaaac ttggaaaaaa atataacata cctactccta taaatcagac   1920
tttcttttat atgataaaag taattgaaag tagattttaa aggggctttg taagaaatat   1980
tgataattat tgattttaaa ttttattaat gttatatact atggcgcgcc gccattattt   2040
ttttgaacaa ttgacaattc atttcttatt ttttattaag tgatagtcaa aaggcataac   2100
agtgctgaat agaaagaaat ttacagaaaa gaaaattata gaatttagta tgattaatta   2160
tactcattta tgaatgttta attgaataca aaaaaaaata cttgttatgt attcaattac   2220
gggttaaaat atagacaagt tgaaaaattt aataaaaaaa taagtcctca gctcttatat   2280
attaagctac caacttagta tataagccaa aacttaaatg tgctaccaac acatcaagcc   2340
gttagagaac tctatctata gcaatatttc aaatgtaccg acatacaaga gaaacattaa   2400
ctatatatat tcaatttatg agattatctt aacagatata aatgtaaatt gcaataagta   2460
```

```
agatttagaa gtttatagcc tttgtgtatt ggaagcagta cgcaaaggct tttttatttg   2520
ataaaaatta gaagtatatt tattttttca taattaattt atgaaaatga aagggggtga   2580
gcaaagtgac agaggaaagc agtatcttat caaataacaa ggtattagca atatcattat   2640
tgactttagc agtaaacatt atgactttta tagtgcttgt agctaagtag tacgaaaggg   2700
ggagctttaa aaagctcctt ggaatacata gaattcataa attaatttat gaaaagaagg   2760
gcgtatatga aaacttgtaa aaattgcaaa gagtttatta aagatactga aatatgcaaa   2820
atacattcgt tgatgattca tgataaaaca gtagcaacct attgcagtaa atacaatgag   2880
tcaagatgtt tacataaagg gaaagtccaa tgtattaatt gttcaaagat gaaccgatat   2940
ggatggtgtg ccataaaaat gagatgtttt acagaggaag aacagaaaaa agaacgtaca   3000
tgcattaaat attatgcaag gagctttaaa aaagctcatg taaagaagag taaaaagaaa   3060
aaataattta tttattaatt taatattgag agtgccgaca cagtatgcac taaaaaatat   3120
atctgtggtg tagtgagccg atacaaaagg atagtcactc gcattttcat aatacatctt   3180
atgttatgat tatgtgtcgg tgggacttca cgacgaaaac ccacaataaa aaaagagttc   3240
ggggtagggt taagcatagt tgaggcaact aaacaatcaa gctaggatat gcagtagcag   3300
accgtaaggt cgttgtttag gtgtgttgta atacatacgc tattaagatg taaaaatacg   3360
gataccaatg aagggaaaag tataattttt ggatgtagtt tgtttgttca tctatgggca   3420
aactacgtcc aaagccgttt ccaaatctgc taaaaagtat atcctttcta aaatcaaagt   3480
caagtatgaa atcataaata aagtttaatt ttgaagttat tatgatatta tgtttttcta   3540
ttaaaataaa ttaagtatat agaatagttt aataatagta tatacttaat gtgataagtg   3600
tctgacagtg tcacagaaag gatgattgtt atggattata agcggccggc cagtgggcaa   3660
gttgaaaaat tcacaaaaat gtggtataat atctttgttc attagagcga taaacttgaa   3720
tttgagaggg aacttagatg gtatttgaaa aaattgataa aaatagttgg aacagaaaag   3780
agtattttga ccactacttt gcaagtgtac cttgtaccta cagcatgacc gttaaagtgg   3840
atatcacaca aataaaggaa aagggaatga aactatatcc tgcaatgctt tattatattg   3900
caatgattgt aaaccgccat tcagagttta ggacggcaat caatcaagat ggtgaattgg   3960
ggatatatga tgagatgata ccaagctata caatatttca caatgatact gaaacatttt   4020
ccagcctttg gactgagtgt aagtctgact ttaaatcatt tttagcagat tatgaaagtg   4080
atacgcaacg gtatggaaac aatcatagaa tggaaggaaa gccaaatgct ccggaaaaca   4140
tttttaatgt atctatgata ccgtggtcaa ccttcgatgg ctttaatctg aatttgcaga   4200
aaggatatga ttatttgatt cctattttta ctatggggaa atattataaa gaagataaca   4260
aaattatact tcctttggca attcaagttc atcacgcagt atgtgacgga tttcacattt   4320
gccgttttgt aaacgaattg caggaattga taaatagtta acttcaggtt tgtctgtaac   4380
taaaaacaag tatttaagca aaaacatcgt agaaatacgg tgtttttttgt taccctaagt   4440
ttaaactcct ttttgataat ctcatgacca aaatccctta acgtgagttt tcgttccact   4500
gagcgtcaga ccccgtagaa aagatcaaag gatcttcttg agatcctttt tttctgcgcg   4560
taatctgctg cttgcaaaca aaaaaaccac cgctaccagc ggtggtttgt ttgccggatc   4620
aagagctacc aactcttttt ccgaaggtaa ctggcttcag cagagcgcag ataccaaata   4680
ctgtccttct agtgtagccg tagttaggcc accacttcaa gaactctgta gcaccgccta   4740
catacctcgc tctgctaatc ctgttaccag tggctgctgc cagtggcgat aagtcgtgtc   4800
ttaccgggtt ggactcaaga cgatagttac cggataaggc gcagcggtcg ggctgaacgg   4860
```

```
ggggttcgtg cacacagccc agcttggagc gaacgaccta caccgaactg agatacctac   4920
agcgtgagca ttgagaaagc gccacgcttc ccgaagggag aaaggcggac aggtatccgg   4980
taagcggcag ggtcggaaca ggagagcgca cgagggagct tccaggggga aacgcctggt   5040
atctttatag tcctgtcggg tttcgccacc tctgacttga gcgtcgattt ttgtgatgct   5100
cgtcaggggg gcggagccta tggaaaaacg ccagcaacgc ggccttttta cggttcctgg   5160
ccttttgctg gccttttgct cacatgttct ttcctgcgtt atcccctgat tctgtggata   5220
accgtattac cgcctttgag tgagctgata ccgctcgccg cagccgaacg accgagcgca   5280
gcgagtcagt gagcgaggaa gcggaagagc gcccaatacg cagggccccc tgcttcgggg   5340
tcattatagc gatttttttcg gtatatccat cctttttcgc acgatataca ggattttgcc   5400
aaagggttcg tgtagacttt ccttggtgta tccaacggcg tcagccgggc aggataggtg   5460
aagtaggccc acccgcgagc gggtgttcct tcttcactgt cccttattcg cacctggcgg   5520
tgctcaacgg gaatcctgct ctgcgaggct ggccggctac cgccggcgta acagatgagg   5580
gcaagcggat ggctgatgaa accaagccaa ccaggaaggg cagcccacct atcaaggtgt   5640
actgccttcc agacgaacga agagcgattg aggaaaaggc ggcggcggcc ggcatgagcc   5700
tgtcggccta cctgctggcc gtcggccagg gctacaaaat cacgggcgtc gtggactatg   5760
agcacgtccg cgagctggcc cgcatcaatg gcgacctggg ccgcctgggc ggcctgctga   5820
aactctggct caccgacgac ccgcgcacgg cgcggttcgg tgatgccacg atcctcgccc   5880
tgctggcgaa gatcgaagag aagcaggacg agcttggcaa ggtcatgatg ggcgtggtcc   5940
gcccgagggc agagccatga ctttttttagc cgctaaaacg gccggggggt gcgcgtgatt   6000
gccaagcacg tccccatgcg ctccatcaag aagagcgact tcgcggagct ggtgaagtac   6060
atcaccgacg agcaaggcaa gaccgatcgg gccccctgca                        6100
```

```
<210> SEQ ID NO 60
<211> LENGTH: 4704
<212> TYPE: DNA
<213> ORGANISM: Artificial Sequence
<220> FEATURE:
<223> OTHER INFORMATION: Shuttle plasmid pMTL-JH17

<400> SEQUENCE: 60
```

```
ggggagggac atttttttatt atcttcagga aaacacagta atagatacgt acaatgtgca     60
aaagtattaa gattcccaga atatgctgct gaggtattaa gtacagttgt tgaacaaata    120
aaagacttag atatagactt agtagtagga ccagctatgg gtggagtaat agtttcttat    180
gagttaggaa gacaattagg aaaagaagct gtatttactg agagaaaaga caatacaatg    240
gagttaagaa gaggatttga agttaaaaaa ggagcaaaga taataattgc tgaagacgtt    300
gtgcggccgc tgtatccata tgaccatgat tacgaattcg agctcggtac ccggggatcc    360
tctagagtcg acgtcacgcg tccatggaga tctcgaggcc tgcagacatg caagcttggc    420
actggccgtc gttttacaac gtcgtgactg ggaaaaccct ggcgttaccc aacttaatcg    480
ccttgcagca catcccccctt tcgccagctg gcgtaatagc gaagaggccc gcaccgatcg    540
cccttcccaa cagttgcgca gcctgaatgg cgaatggcgc tagcataaaa ataagaagcc    600
tgcatttgca ggcttcttat ttttatggcg cgccgccatt atttttttga acaattgaca    660
attcatttct tattttttat taagtgatag tcaaaaggca taacagtgct gaatagaaag    720
aaatttacag aaaagaaaat tatagaattt agtatgatta attatactca tttatgaatg    780
tttaattgaa tacaaaaaaa aatacttgtt atgtattcaa ttacgggtta aaatatagac    840
```

```
aagttgaaaa atttaataaa aaaataagtc ctcagctctt atatattaag ctaccaactt    900
agtatataag ccaaaactta aatgtgctac caacacatca agccgttaga gaactctatc    960
tatagcaata tttcaaatgt accgacatac aagagaaaca ttaactatat atattcaatt   1020
tatgagatta tcttaacaga tataaatgta aattgcaata agtaagattt agaagtttat   1080
agcctttgtg tattggaagc agtacgcaaa ggctttttta tttgataaaa attagaagta   1140
tatttatttt ttcataatta atttatgaaa atgaaagggg gtgagcaaag tgacagagga   1200
aagcagtatc ttatcaaata acaaggtatt agcaatatca ttattgactt tagcagtaaa   1260
cattatgact tttatagtgc ttgtagctaa gtagtacgaa agggggagct ttaaaaagct   1320
ccttggaata catagaattc ataaattaat ttatgaaaag aagggcgtat atgaaaactt   1380
gtaaaaattg caaagagttt attaaagata ctgaaatatg caaaatacat tcgttgatga   1440
ttcatgataa aacagtagca acctattgca gtaaatacaa tgagtcaaga tgtttacata   1500
aagggaaagt ccaatgtatt aattgttcaa agatgaaccg atatggatgg tgtgccataa   1560
aaatgagatg ttttacagag gaagaacaga aaaaagaacg tacatgcatt aaatattatg   1620
caaggagctt taaaaaagct catgtaaaga agagtaaaaa gaaaaaaataa tttatttatt   1680
aatttaatat tgagagtgcc gacacagtat gcactaaaaa atatatctgt ggtgtagtga   1740
gccgatacaa aaggatagtc actcgcattt tcataataca tcttatgtta tgattatgtg   1800
tcggtgggac ttcacgacga aaacccacaa taaaaaaaga gttcggggta gggttaagca   1860
tagttgaggc aactaaacaa tcaagctagg atatgcagta gcagaccgta aggtcgttgt   1920
ttaggtgtgt tgtaatacat acgctattaa gatgtaaaaa tacggatacc aatgaaggga   1980
aaagtataat ttttggatgt agtttgtttg ttcatctatg ggcaaactac gtccaaagcc   2040
gtttccaaat ctgctaaaaa gtatatcctt tctaaaatca aagtcaagta tgaaatcata   2100
aataaagttt aattttgaag ttattatgat attatgtttt tctattaaaa taaattaagt   2160
atatagaata gtttaataat agtatatact taatgtgata agtgtctgac agtgtcacag   2220
aaaggatgat tgttatggat tataagcggc cggccagtgg gcaagttgaa aaattcacaa   2280
aaatgtggta taatatcttt gttcattaga gcgataaact tgaatttgag agggaactta   2340
gatggtattt gaaaaaattg ataaaaatag ttggaacaga aaagagtatt ttgaccacta   2400
ctttgcaagt gtaccttgta cctacagcat gaccgttaaa gtggatatca cacaaataaa   2460
ggaaaaggga atgaaactat atcctgcaat gctttattat attgcaatga ttgtaaaccg   2520
ccattcagag tttaggacgg caatcaatca agatggtgaa ttggggatat atgatgagat   2580
gataccaagc tatacaatat ttcacaatga tactgaaaca ttttccagcc tttggactga   2640
gtgtaagtct gactttaaat catttttagc agattatgaa agtgatacgc aacggtatgg   2700
aaacaatcat agaatggaag gaaagccaaa tgctccggaa aacattttta atgtatctat   2760
gataccgtgg tcaaccttcg atggctttaa tctgaatttg cagaaaggat atgattattt   2820
gattcctatt tttactatgg ggaaatatta taaagaagat aacaaaatta tacttccttt   2880
ggcaattcaa gttcatcacg cagtatgtga cggatttcac atttgccgtt ttgtaaacga   2940
attgcaggaa ttgataaata gttaacttca ggtttgtctg taactaaaaa caagtattta   3000
agcaaaaaca tcgtagaaat acggtgtttt ttgttaccct aagtttaaac tcctttttga   3060
taatctcatg accaaaatcc cttaacgtga gttttcgttc cactgagcgt cagaccccgt   3120
agaaaagatc aaaggatctt cttgagatcc tttttttctg cgcgtaatct gctgcttgca   3180
aacaaaaaaa ccaccgctac cagcggtggt ttgtttgccg gatcaagagc taccaactct   3240
```

-continued

```
ttttccgaag gtaactggct tcagcagagc gcagatacca aatactgtcc ttctagtgta   3300

gccgtagtta ggccaccact tcaagaactc tgtagcaccg cctacatacc tcgctctgct   3360

aatcctgtta ccagtggctg ctgccagtgg cgataagtcg tgtcttaccg ggttggactc   3420

aagacgatag ttaccggata aggcgcagcg gtcgggctga acggggggtt cgtgcacaca   3480

gcccagcttg gagcgaacga cctacaccga actgagatac ctacagcgtg agcattgaga   3540

aagcgccacg cttcccgaag ggagaaaggc ggacaggtat ccggtaagcg gcagggtcgg   3600

aacaggagag cgcacgaggg agcttccagg gggaaacgcc tggtatcttt atagtcctgt   3660

cgggtttcgc cacctctgac ttgagcgtcg atttttgtga tgctcgtcag gggggcggag   3720

cctatggaaa aacgccagca acgcggcctt tttacggttc ctggcctttt gctggccttt   3780

tgctcacatg ttctttcctg cgttatcccc tgattctgtg gataaccgta ttaccgcctt   3840

tgagtgagct gataccgctc gccgcagccg aacgaccgag cgcagcgagt cagtgagcga   3900

ggaagcggaa gagcgcccaa tacgcagggc cccctgcttc ggggtcatta tagcgatttt   3960

ttcggtatat ccatcctttt tcgcacgata tacaggattt tgccaaaggg ttcgtgtaga   4020

ctttccttgg tgtatccaac ggcgtcagcc gggcaggata ggtgaagtag gcccacccgc   4080

gagcgggtgt tccttcttca ctgtccctta ttcgcacctg gcggtgctca acgggaatcc   4140

tgctctgcga ggctggccgg ctaccgccgg cgtaacagat gagggcaagc ggatggctga   4200

tgaaaccaag ccaaccagga agggcagccc acctatcaag gtgtactgcc ttccagacga   4260

acgaagagcg attgaggaaa aggcggcggc ggccggcatg agcctgtcgg cctacctgct   4320

ggccgtcggc cagggctaca aaatcacggg cgtcgtggac tatgagcacg tccgcgagct   4380

ggcccgcatc aatggcgacc tgggccgcct gggcggcctg ctgaaactct ggctcaccga   4440

cgacccgcgc acggcgcggt tcggtgatgc cacgatcctc gccctgctgg cgaagatcga   4500

agagaagcag gacgagcttg gcaaggtcat gatgggcgtg gtccgcccga gggcagagcc   4560

atgacttttt tagccgctaa aacggccggg gggtgcgcgt gattgccaag cacgtcccca   4620

tgcgctccat caagaagagc gacttcgcgg agctggtgaa gtacatcacc gacgagcaag   4680

gcaagaccga tcgggccccc tgca                                           4704
```

<210> SEQ ID NO 61
<211> LENGTH: 5862
<212> TYPE: DNA
<213> ORGANISM: Artificial Sequence
<220> FEATURE:
<223> OTHER INFORMATION: Shuttle plasmid pMTL-JH18

<400> SEQUENCE: 61

```
ggggagggac atttttattt atcttcagga aaacacagta atagatacgt acaatgtgca     60

aaagtattaa gattcccaga atatgctgct gaggtattaa gtacagttgt tgaacaaata    120

aaagacttag atatagactt agtagtagga ccagctatgg gtggagtaat agtttcttat    180

gagttaggaa gacaattagg aaaagaagct gtatttactg agagaaaaga caatacaatg    240

gagttaagaa gaggatttga agttaaaaaa ggagcaaaga taataattgc tgaagacgtt    300

gtgcggccgc tgtatccata tgaccatgat tacgaattcg agctcggtac ccggggatcc    360

tctagagtcg acgtcacgcg tccatggaga tctcgaggcc tgcagacatg caagcttggc    420

actggccgtc gttttacaac gtcgtgactg ggaaaaccct ggcgttaccc aacttaatcg    480

ccttgcagca catccccctt tcgccagctg gcgtaatagc gaagaggccc gcaccgatcg    540

cccttcccaa cagttgcgca gcctgaatgg cgaatggcgc tagcaaactt aattatttat    600
```

```
agtgttactt aaaaaatgta aatttttag agtaaaaatt tgtaatataa catataactt    660
aaaaataaaa agcagttagc cttataaatg aaggttagct gtttttttg ttaaaaatat    720
atttacaaaa taagagatag tagcagtaca atataagtat aaggtaaaag tattatatat    780
tagggagggg taagtatgaa aatcaatta aatgaaaata ataaaaaggt tgtatttttt    840
ggagtaggtg ctgtaggagc tacttttgca gaacaatttt ttaactctaa atatgatttt    900
aaaattcttt gtgataatga aagaaagaaa agatatttag aagaaggatt tataataaat    960
ggaaaaaggt atgattttga ttatgtaact aaagatgagt ataaacaaga ggctgatttt   1020
ataattatag gtctaaaata taataattta aaagaaaata taaaagaatt agatggatta   1080
gttggaaaaa atacagttat aatgtctctg ctaaatggag ttgatagcga agagataata   1140
ggagaaagat ttggaattga aaaaatggta tattcatatg ttaccaatat agatgcaaag   1200
aaaatcaata ataatattat acacactact aatgggataa ttgtatttgg taacaaagat   1260
aatagtgaag atagaaaaac taatataata accgaagtct ttgatgatgt aaatatagaa   1320
tatactttat caaaagatat tcaacgagat atgtggtgga agtacatggt taatattggt   1380
gtaaatcaaa cttcagctat acttggtgca ccttatggag tttttcagag ttctgagcat   1440
ttaagagaat tagcaaaatc tgcaatgagg gaagttgttg ctatagcaca agcaaaagac   1500
atatctctta cagaagatga tgtggaacat tcattacata gaatactaga acattcaaaa   1560
gaaggaagaa catcaatgct tcaagatgtg gaagctcata gacttacaga agtagatatg   1620
ttttctaaga atatctgtaa acttggaaaa aaatataaca tacctactcc tataaatcag   1680
actttctttt atatgataaa agtaattgaa agtagatttt aaagggggctt tgtaagaaat   1740
attgataatt attgatttta aattttatta atgttatata ctatggcgcg ccgccattat   1800
ttttttgaac aattgacaat tcatttctta tttttttatta agtgatagtc aaaaggcata   1860
acagtgctga atagaaagaa atttacagaa aagaaaatta tagaatttag tatgattaat   1920
tatactcatt tatgaatgtt taattgaata caaaaaaaaa tacttgttat gtattcaatt   1980
acgggttaaa atatagacaa gttgaaaaat ttaataaaaa aataagtcct cagctcttat   2040
atattaagct accaacttag tatataagcc aaaacttaaa tgtgctacca acacatcaag   2100
ccgttagaga actctatcta tagcaatatt tcaaatgtac cgacatacaa gagaaacatt   2160
aactatatat attcaattta tgagattatc ttaacagata taaatgtaaa ttgcaataag   2220
taagatttag aagtttatag cctttgtgta ttggaagcag tacgcaaagg ctttttttatt   2280
tgataaaaat tagaagtata tttatttttt cataattaat ttatgaaaat gaaagggggt   2340
gagcaaagtg acagaggaaa gcagtatctt atcaaataac aaggtattag caatatcatt   2400
attgacttta gcagtaaaca ttatgacttt tatagtgctt gtagctaagt agtacgaaag   2460
ggggagcttt aaaaagctcc ttggaataca tagaattcat aaattaattt atgaaaagaa   2520
gggcgtatat gaaaacttgt aaaaattgca aagagtttat taaagatact gaaatatgca   2580
aaatacattc gttgatgatt catgataaaa cagtagcaac ctattgcagt aaatacaatg   2640
agtcaagatg tttacataaa gggaaagtcc aatgtattaa ttgttcaaag atgaaccgat   2700
atggatggtg tgccataaaa atgagatgtt ttacagagga agaacagaaa aaagaacgta   2760
catgcattaa atattatgca aggagcttta aaaaagctca tgtaaagaag agtaaaaaga   2820
aaaaataatt tatttattaa tttaatattg agagtgccga cacagtatgc actaaaaaat   2880
atatctgtgg tgtagtgagc cgatacaaaa ggatagtcac tcgcattttc ataatacatc   2940
ttatgttatg attatgtgtc ggtgggactt cacgacgaaa acccacaata aaaaaagagt   3000
```

tcggggtagg gttaagcata gttgaggcaa ctaaacaatc aagctaggat atgcagtagc 3060
agaccgtaag gtcgttgttt aggtgtgttg taatacatac gctattaaga tgtaaaaata 3120
cggataccaa tgaagggaaa agtataattt ttggatgtag tttgtttgtt catctatggg 3180
caaactacgt ccaaagccgt ttccaaatct gctaaaaagt atatcctttc taaaatcaaa 3240
gtcaagtatg aaatcataaa taaagtttaa ttttgaagtt attatgatat tatgtttttc 3300
tattaaaata aattaagtat atagaatagt ttaataatag tatatactta atgtgataag 3360
tgtctgacag tgtcacagaa aggatgattg ttatggatta taagcggccg gccagtgggc 3420
aagttgaaaa attcacaaaa atgtggtata atatctttgt tcattagagc gataaacttg 3480
aatttgagag ggaacttaga tggtatttga aaaaattgat aaaaatagtt ggaacagaaa 3540
agagtatttt gaccactact ttgcaagtgt accttgtacc tacagcatga ccgttaaagt 3600
ggatatcaca caaataaagg aaaagggaat gaaactatat cctgcaatgc tttattatat 3660
tgcaatgatt gtaaaccgcc attcagagtt taggacggca atcaatcaag atggtgaatt 3720
ggggatatat gatgagatga taccaagcta tacaatattt cacaatgata ctgaaacatt 3780
ttccagcctt tggactgagt gtaagtctga ctttaaatca tttttagcag attatgaaag 3840
tgatacgcaa cggtatggaa acaatcatag aatggaagga aagccaaatg ctccggaaaa 3900
catttttaat gtatctatga taccgtggtc aaccttcgat ggctttaatc tgaatttgca 3960
gaaaggatat gattatttga ttcctatttt tactatgggg aaatattata aagaagataa 4020
caaaattata cttcctttgg caattcaagt tcatcacgca gtatgtgacg gatttcacat 4080
ttgccgtttt gtaaacgaat tgcaggaatt gataaatagt taacttcagg tttgtctgta 4140
actaaaaaca agtatttaag caaaaacatc gtagaaatac ggtgtttttt gttaccctaa 4200
gtttaaactc ctttttgata atctcatgac caaaatccct taacgtgagt tttcgttcca 4260
ctgagcgtca gaccccgtag aaaagatcaa aggatcttct tgagatcctt tttttctgcg 4320
cgtaatctgc tgcttgcaaa caaaaaaacc accgctacca gcggtggttt gtttgccgga 4380
tcaagagcta ccaactcttt ttccgaaggt aactggcttc agcagagcgc agataccaaa 4440
tactgtcctt ctagtgtagc cgtagttagg ccaccacttc aagaactctg tagcaccgcc 4500
tacatacctc gctctgctaa tcctgttacc agtggctgct gccagtggcg ataagtcgtg 4560
tcttaccggg ttggactcaa gacgatagtt accggataag gcgcagcggt cgggctgaac 4620
ggggggttcg tgcacacagc ccagcttgga gcgaacgacc tacaccgaac tgagatacct 4680
acagcgtgag cattgagaaa gcgccacgct tcccgaaggg agaaaggcgg acaggtatcc 4740
ggtaagcggc agggtcggaa caggagagcg cacgagggag cttccagggg gaaacgcctg 4800
gtatctttat agtcctgtcg ggtttcgcca cctctgactt gagcgtcgat ttttgtgatg 4860
ctcgtcaggg gggcggagcc tatggaaaaa cgccagcaac gcggcctttt tacggttcct 4920
ggccttttgc tggccttttg ctcacatgtt ctttcctgcg ttatcccctg attctgtgga 4980
taaccgtatt accgcctttg agtgagctga taccgctcgc cgcagccgaa cgaccgagcg 5040
cagcgagtca gtgagcgagg aagcggaaga gcgcccaata cgcagggccc cctgcttcgg 5100
ggtcattata gcgatttttt cggtatatcc atcctttttc gcacgatata caggattttg 5160
ccaaagggtt cgtgtagact ttccttggtg tatccaacgg cgtcagccgg gcaggatagg 5220
tgaagtaggc ccacccgcga gcgggtgttc cttcttcact gtcccttatt cgcacctggc 5280
ggtgctcaac gggaatcctg ctctgcgagg ctggccggct accgccggcg taacagatga 5340
gggcaagcgg atggctgatg aaaccaagcc aaccaggaag ggcagcccac ctatcaaggt 5400

```
gtactgcctt ccagacgaac gaagagcgat tgaggaaaag gcggcggcgg ccggcatgag   5460

cctgtcggcc tacctgctgg ccgtcggcca gggctacaaa atcacgggcg tcgtggacta   5520

tgagcacgtc cgcgagctgg cccgcatcaa tggcgacctg ggccgcctgg gcggcctgct   5580

gaaactctgg ctcaccgacg acccgcgcac ggcgcggttc ggtgatgcca cgatcctcgc   5640

cctgctggcg aagatcgaag agaagcagga cgagcttggc aaggtcatga tgggcgtggt   5700

ccgcccgagg gcagagccat gactttttta gccgctaaaa cggccggggg gtgcgcgtga   5760

ttgccaagca cgtccccatg cgctccatca agaagagcga cttcgcggag ctggtgaagt   5820

acatcaccga cgagcaaggc aagaccgatc gggccccctg ca                      5862
```

<210> SEQ ID NO 62
<211> LENGTH: 12412
<212> TYPE: DNA
<213> ORGANISM: Artificial Sequence
<220> FEATURE:
<223> OTHER INFORMATION: Shuttle plasmid pMTL-JH18-lambda6.5

<400> SEQUENCE: 62

```
ggggagggac atttttttatt atcttcagga aaacacagta atagatacgt acaatgtgca     60

aaagtattaa gattcccaga atatgctgct gaggtattaa gtacagttgt tgaacaaata    120

aaagacttag atatagactt agtagtagga ccagctatgg gtggagtaat agtttcttat    180

gagttaggaa gacaattagg aaaagaagct gtatttactg agagaaaaga caatacaatg    240

gagttaagaa gaggatttga agttaaaaaa ggagcaaaga taataattgc tgaagacgtt    300

gtgcggccgc tgtatccata tgaccatgat tacgaattcg agctcggtac ccggggatcc    360

tctagagtcg acgtcacgcg tccatggaga tctcgagggg tgagaacatc cctgcctgaa    420

catgagaaaa aacagggtac tcatactcac ttctaagtga cggctgcata ctaaccgctt    480

catacatctc gtagatttct ctggcgattg aagggctaaa ttcttcaacg ctaactttga    540

gaatttttgt aagcaatgcg gcgttataag catttaatgc attgatgcca ttaaataaag    600

caccaacgcc tgactgcccc atccccatct tgtctgcgac agattcctgg gataagccaa    660

gttcattttt cttttttttca taaattgctt taaggcgacg tgcgtcctca agctgctctt    720

gtgttaatgg tttctttttt gtgctcatac gttaaatcta tcaccgcaag ggataaatat    780

ctaacaccgt gcgtgttgac tattttacct ctggcggtga taatggttgc atgtactaag    840

gaggttgtat ggaacaacgc ataaccctga aagattatgc aatgcgcttt gggcaaacca    900

agacagctaa agatctcggc gtatatcaaa gcgcgatcaa caaggccatt catgcaggcc    960

gaaagatttt tttaactata aacgctgatg gaagcgttta tgcggaagag gtaaagccct   1020

tcccgagtaa caaaaaaaca acagcataaa taaccccgct cttacacatt ccagccctga   1080

aaaagggcat caaattaaac cacacctatg gtgtatgcat ttatttgcat acattcaatc   1140

aattgttatc taaggaaata cttacatatg gttcgtgcaa acaaacgcaa cgaggctcta   1200

cgaatcgaga gtgcgttgct taacaaaatc gcaatgcttg gaactgagaa gacagcggaa   1260

gctgtgggcg ttgataagtc gcagatcagc aggtggaaga gggactggat tccaaagttc   1320

tcaatgctgc ttgctgttct tgaatggggg gtcgttgacg acgacatggc tcgattggcg   1380

cgacaagttg ctgcgattct caccaataaa aaacgcccgg cggcaaccga gcgttctgaa   1440

caaatccaga tggagttctg aggtcattac tggatctatc aacaggagtc attatgacaa   1500

atacagcaaa aatactcaac ttcggcagag gtaactttgc cggacaggag cgtaatgtgg   1560

cagatctcga tgatggttac gccagactat caaatatgct gcttgaggct tattcgggcg   1620
```

-continued

```
cagatctgac caagcgacag tttaaagtgc tgcttgccat tctgcgtaaa acctatgggt   1680
ggaataaacc aatggacaga atcaccgatt ctcaacttag cgagattaca aagttacctg   1740
tcaaacggtg caatgaagcc aagttagaac tcgtcagaat gaatattatc aagcagcaag   1800
gcggcatgtt tggaccaaat aaaaacatct cagaatggtg catccctcaa aacgagggaa   1860
aatcccctaa aacgagggat aaaacatccc tcaaattggg ggattgctat ccctcaaaac   1920
agggggacac aaaagacact attacaaaag aaaaaagaaa agattattcg tcagagaatt   1980
ctggcgaatc ctctgaccag ccagaaaacg acctttctgt ggtgaaaccg gatgctgcaa   2040
ttcagagcgg cagcaagtgg gggacagcag aagacctgac cgccgcagag tggatgtttg   2100
acatggtgaa gactatcgca ccatcagcca gaaaaccgaa ttttgctggg tgggctaacg   2160
atatccgcct gatgcgtgaa cgtgacggac gtaaccaccg cgacatgtgt gtgctgttcc   2220
gctgggcatg ccaggacaac ttctggtccg gtaacgtgct gagcccggcc aaactccgcg   2280
ataagtggac ccaactcgaa atcaaccgta acaagcaaca ggcaggcgtg acagccagca   2340
aaccaaaact cgacctgaca aacacagact ggatttacgg ggtggatcta tgaaaaacat   2400
cgccgcacag atggttaact ttgaccgtga gcagatgcgt cggatcgcca acaacatgcc   2460
ggaacagtac gacgaaaagc cgcaggtaca gcaggtagcg cagatcatca acggtgtgtt   2520
cagccagtta ctggcaactt tcccggcgag cctggctaac cgtgaccaga acgaagtgaa   2580
cgaaatccgt cgccagtggg ttctggcttt tcgggaaaac gggatcacca cgatggaaca   2640
ggttaacgca ggaatgcgcg tagcccgtcg gcagaatcga ccatttctgc catcacccgg   2700
gcagtttgtt gcatggtgcc gggaagaagc atccgttacc gccggactgc caaacgtcag   2760
cgagctggtt gatatggttt acgagtattg ccggaagcga ggcctgtatc cggatgcgga   2820
gtcttatccg tggaaatcaa acgcgcacta ctggctggtt accaacctgt atcagaacat   2880
gcgggccaat gcgcttactg atgcggaatt acgccgtaag gccgcagatg agcttgtcca   2940
tatgactgcg agaattaacc gtggtgaggc gatccctgaa ccagtaaaac aacttcctgt   3000
catgggcggt agacctctaa atcgtgcaca ggctctggcg aagatcgcag aaatcaaagc   3060
taagttcgga ctgaaaggag caagtgtatg acgggcaaag aggcaattat tcattacctg   3120
gggacgcata atagcttctg tgcgccggac gttgccgcgc taacaggcgc aacagtaacc   3180
agcataaatc aggccgcggc taaaatggca cgggcaggtc ttctggttat cgaaggtaag   3240
gtctggcgaa cggtgtatta ccggtttgct accagggaag aacgggaagg aaagatgagc   3300
acgaacctgg tttttaagga gtgtcgccag agtgccgcga tgaaacgggt attggcggta   3360
tatggagtta aaagatgacc atctacatta ctgagctaat aacaggcctg ctggtaatcg   3420
caggcctttt tatttggggg agagggaagt catgaaaaaa ctaacctttg aaattcgatc   3480
tccagcacat cagcaaaacg ctattcacgc agtacagcaa atccttccag acccaaccaa   3540
accaatcgta gtaaccattc aggaacgcaa ccgcagctta gaccaaaaca ggaagctatg   3600
ggcctgctta ggtgacgtct ctcgtcaggt tgaatggcat ggtcgctggc tggatgcaga   3660
aagctggaag tgtgtgttta ccgcagcatt aaagcagcag gatgttgttc ctaaccttgc   3720
cgggaatggc tttgtggtaa taggccagtc aaccagcagg atgcgtgtag gcgaatttgc   3780
ggagctatta gagcttatac aggcattcgg tacagagcgt ggcgttaagt ggtcagacga   3840
agcgagactg gctctggagt ggaaagcgag atggggagac agggctgcat gataaatgtc   3900
gttagtttct ccggtggcag gacgtcagca tatttgctct ggctaatgga gcaaaagcga   3960
cgggcaggta aagacgtgca ttacgttttc atggatacag gttgtgaaca tccaatgaca   4020
```

-continued

```
tatcggtttg tcagggaagt tgtgaagttc tgggatatac cgctcaccgt attgcaggtt   4080
gatatcaacc cggagcttgg acagccaaat ggttatacgg tatgggaacc aaaggatatt   4140
cagacgcgaa tgcctgttct gaagccattt atcgatatgg taaagaaata tggcactcca   4200
tacgtcggcg gcgcgttctg cactgacaga ttaaaactcg ttcccttcac caaatactgt   4260
gatgaccatt tcgggcgagg gaattacacc acgtggattg gcatcagagc tgatgaaccg   4320
aagcggctaa agccaaagcc tggaatcaga tatcttgctg aactgtcaga ctttgagaag   4380
gaagatatcc tcgcatggtg gaagcaacaa ccattcgatt tgcaaatacc ggaacatctc   4440
ggtaactgca tattctgcat taaaaaatca acgcaaaaaa tcggacttgc ctgcaaagat   4500
gaggagggat tgcagcgtgt ttttaatgag gtcatcacgg gatcccatgt gcgtgacgga   4560
catcgggaaa cgccaaagga gattatgtac cgaggaagaa tgtcgctgga cggtatcgcg   4620
aaaatgtatt cagaaaatga ttatcaagcc ctgtatcagg acatggtacg agctaaaaga   4680
ttcgataccg gctcttgttc tgagtcatgc gaaatatttg gagggcagct tgatttcgac   4740
ttcgggaggg aagctgcatg atgcgatgtt atcggtgcgg tgaatgcaaa gaagataacc   4800
gcttccgacc aaatcaacct tactggaatc gatggtgtct ccggtgtgaa agaacaccaa   4860
caggggtgtt accactaccg caggaaaagg aggacgtgtg gcgagacagc gacgaagtat   4920
caccgacata atctgcgaaa actgcaaata ccttccaacg aaacgcacca gaaataaacc   4980
caagccaatc ccaaaagaat ctgacgtaaa aaccttcaac tacacggctc acctgtggga   5040
tatccggtgg ctaagacgtc gtgcgaggaa aacaaggtga ttgaccaaaa tcgaagttac   5100
gaacaagaaa gcgtcgagcg agctttaacg tgcgctaact gcggtcagaa gctgcatgtg   5160
ctggaagttc acgtgtgtga gcactgctgc gcagaactga tgagcgatcc gaatagctcg   5220
atgcacgagg aagaagatga tggctaaacc agcgcgaaga cgatgtaaaa acgatgaatg   5280
ccgggaatgg tttcaccctg cattcgctaa tcagtggtgg tgctctccag agtgtggaac   5340
caagatagca ctcgaacgac gaagtaaaga acgcgaaaaa gcggaaaaag cagcagagaa   5400
gaaacgacga cgagaggagc agaaacagaa agataaactt aagattcgaa aactcgcctt   5460
aaagccccgc agttactgga ttaaacaagc ccaacaagcc gtaaacgcct tcatcagaga   5520
aagagaccgc gacttaccat gtatctcgtg cggaacgctc acgtctgctc agtgggatgc   5580
cggacattac cggacaactg ctgcggcacc tcaactccga tttaatgaac gcaatattca   5640
caagcaatgc gtggtgtgca accagcacaa aagcggaaat ctcgttccgt atcgcgtcga   5700
actgattagc cgcatcgggc aggaagcagt agacgaaatc gaatcaaacc ataaccgcca   5760
tcgctggact atcgaagagt gcaaggcgat caaggcagag taccaacaga aactcaaaga   5820
cctgcgaaat agcagaagtg aggccgcatg acgttctcag taaaaaccat tccagacatg   5880
ctcgttgaag catacggaaa tcagacagaa gtagcacgca gactgaaatg tagtcgcggt   5940
acggtcagaa aatacgttga tgataaagac gggaaaatgc acgccatcgt caacgacgtt   6000
ctcatggttc atcgcggatg gagtgaaaga gatgcgctat tacgaaaaaa ttgatggcag   6060
caaataccga aatatttggg tagttggcga tctgcacgga tgctacacga acctgatgaa   6120
caaactggat acgattggat tcgacaacaa aaaagacctg cttatctcgg tgggcgattt   6180
ggttgatcgt ggtgcagaga acgttgaatg cctggaatta atcacattcc cctggttcag   6240
agctgtacgt ggaaaccatg agcaaatgat gattgatggc ttatcagagc gtggaaacgt   6300
taatcactgg ctgcttaatg gcggtggctg gttctttaat ctcgattacg acaaagaaat   6360
tctggctaaa gctcttgccc ataaagcaga tgaacttccg ttaatcatcg aactggtgag   6420
```

-continued caaagataaa aaatatgtta tctgccacgc cgattatccc tttgacgaat acgagtttgg 6480
aaagccagtt gatcatcagc aggtaatctg gaaccgcgaa cgaatcagca actcacaaaa 6540
cgggatcgtg aaagaaatca aaggcgcgga cacgttcatc tttggtcata cgccagcagt 6600
gaaaccactc aagtttgcca accaaatgta tatcgatacc ggcgcagtgt tctgcggaaa 6660
cctaacattg attcaggtac agggagaagg cgcatgagac tcgaaagcgt agctaaattt 6720
cattcgccaa aaagcccgat gatgagcgac tcaccacggg ccacggcttc tgactctctt 6780
tccggtactg atgtgatggc tgctatgggg atggcgcaat cacaagccgg attcggtatg 6840
gctgcattct gcggtaagca cgaactcagc cagaacgaca aacaaaaggc tatcaactat 6900
ctgatgcaat ttgcacacaa ggtatcgggg aaataccgtg gtgtggcacc tgcagacatg 6960
caagcttggc actggccgtc gttttacaac gtcgtgactg ggaaaaccct ggcgttaccc 7020
aacttaatcg ccttgcagca catccccctt tcgccagctg gcgtaatagc gaagaggccc 7080
gcaccgatcg cccttcccaa cagttgcgca gcctgaatgg cgaatggcgc tagcaaactt 7140
aattatttat agtgttactt aaaaaatgta aattttttag agtaaaaatt tgtaatataa 7200
catataactt aaaaataaaa agcagttagc cttataaatg aaggttagct gttttttttg 7260
ttaaaaatat atttacaaaa taagagatag tagcagtaca atataagtat aaggtaaaag 7320
tattatatat tagggagggg taagtatgaa aaatcaatta aatgaaaata ataaaaaggt 7380
tgtatttttt ggagtaggtg ctgtaggagc tacttttgca gaacaatttt ttaactctaa 7440
atatgatttt aaaattcttt gtgataatga aagaaagaaa agatatttag aagaaggatt 7500
tataataaat ggaaaaaggt atgattttga ttatgtaact aaagatgagt ataaacaaga 7560
ggctgatttt ataattatag gtctaaaata taataattta aaagaaaata taaaagaatt 7620
agatggatta gttggaaaaa atacagttat aatgtctctg ctaaatggag ttgatagcga 7680
agagataata ggagaaagat ttggaattga aaaaatggta tattcatatg ttaccaatat 7740
agatgcaaag aaaatcaata ataatattat acacactact aatgggataa ttgtatttgg 7800
taacaaagat aatagtgaag atagaaaaac taatataata accgaagtct ttgatgatgt 7860
aaatatagaa tatactttat caaaagatat tcaacgagat atgtggtgga agtacatggt 7920
taatattggt gtaaatcaaa cttcagctat acttggtgca ccttatggag tttttcagag 7980
ttctgagcat ttaagagaat tagcaaaatc tgcaatgagg gaagttgttg ctatagcaca 8040
agcaaaagac atatctctta cagaagatga tgtggaacat tcattacata gaatactaga 8100
acattcaaaa gaaggaagaa catcaatgct tcaagatgtg gaagctcata gacttacaga 8160
agtagatatg ttttctaaga atatctgtaa acttggaaaa aaatataaca tacctactcc 8220
tataaatcag actttctttt atatgataaa agtaattgaa agtagatttt aaaggggctt 8280
tgtaagaaat attgataatt attgatttta aattttatta atgttatata ctatggcgcg 8340
ccgccattat ttttttgaac aattgacaat tcatttctta ttttttatta agtgatagtc 8400
aaaaggcata acagtgctga atagaaagaa atttacagaa aagaaaatta tagaatttag 8460
tatgattaat tatactcatt tatgaatgtt taattgaata caaaaaaaaa tacttgttat 8520
gtattcaatt acgggttaaa atatagacaa gttgaaaaat ttaataaaaa aataagtcct 8580
cagctcttat atattaagct accaacttag tatataagcc aaaacttaaa tgtgctacca 8640
acacatcaag ccgttagaga actctatcta tagcaatatt tcaaatgtac cgacatacaa 8700
gagaaacatt aactatatat attcaattta tgagattatc ttaacagata taaatgtaaa 8760
ttgcaataag taagatttag aagtttatag cctttgtgta ttggaagcag tacgcaaagg 8820

-continued

```
cttttttatt tgataaaaat tagaagtata tttatttttt cataattaat ttatgaaaat   8880
gaaagggggt gagcaaagtg acagaggaaa gcagtatctt atcaaataac aaggtattag   8940
caatatcatt attgacttta gcagtaaaca ttatgacttt tatagtgctt gtagctaagt   9000
agtacgaaag gggggagcttt aaaaagctcc ttggaataca tagaattcat aaattaattt   9060
atgaaaagaa gggcgtatat gaaaacttgt aaaaattgca aagagtttat taaagatact   9120
gaaatatgca aaatacattc gttgatgatt catgataaaa cagtagcaac ctattgcagt   9180
aaatacaatg agtcaagatg tttacataaa gggaaagtcc aatgtattaa ttgttcaaag   9240
atgaaccgat atggatggtg tgccataaaa atgagatgtt ttacagagga agaacagaaa   9300
aaagaacgta catgcattaa atattatgca aggagcttta aaaaagctca tgtaaagaag   9360
agtaaaaaga aaaaataatt tatttattaa tttaatattg agagtgccga cacagtatgc   9420
actaaaaaat atatctgtgg tgtagtgagc cgatacaaaa ggatagtcac tcgcattttc   9480
ataatacatc ttatgttatg attatgtgtc ggtgggactt cacgacgaaa acccacaata   9540
aaaaaagagt tcggggtagg gttaagcata gttgaggcaa ctaaacaatc aagctaggat   9600
atgcagtagc agaccgtaag gtcgttgttt aggtgtgttg taatacatac gctattaaga   9660
tgtaaaaata cggataccaa tgaagggaaa agtataattt ttggatgtag tttgtttgtt   9720
catctatggg caaactacgt ccaaagccgt ttccaaatct gctaaaaagt atatcctttc   9780
taaaatcaaa gtcaagtatg aaatcataaa taaagtttaa ttttgaagtt attatgatat   9840
tatgtttttc tattaaaata aattaagtat atagaatagt ttaataatag tatatactta   9900
atgtgataag tgtctgacag tgtcacagaa aggatgattg ttatggatta taagcggccg   9960
gccagtgggc aagttgaaaa attcacaaaa atgtggtata atatctttgt tcattagagc  10020
gataaacttg aatttgagag ggaacttaga tggtatttga aaaaattgat aaaaatagtt  10080
ggaacagaaa agagtatttt gaccactact ttgcaagtgt accttgtacc tacagcatga  10140
ccgttaaagt ggatatcaca caaataaagg aaaagggaat gaaactatat cctgcaatgc  10200
tttattatat tgcaatgatt gtaaaccgcc attcagagtt taggacggca atcaatcaag  10260
atggtgaatt ggggatatat gatgagatga taccaagcta tacaatattt cacaatgata  10320
ctgaaacatt ttccagcctt tggactgagt gtaagtctga ctttaaatca tttttagcag  10380
attatgaaag tgatacgcaa cggtatggaa acaatcatag aatggaagga aagccaaatg  10440
ctccggaaaa catttttaat gtatctatga taccgtggtc aaccttcgat ggctttaatc  10500
tgaatttgca gaaaggatat gattatttga ttcctatttt tactatgggg aaatattata  10560
aagaagataa caaaattata cttcctttgg caattcaagt tcatcacgca gtatgtgacg  10620
gatttcacat ttgccgtttt gtaaacgaat tgcaggaatt gataaatagt taacttcagg  10680
tttgtctgta actaaaaaca agtatttaag caaaaacatc gtagaaatac ggtgtttttt  10740
gttaccctaa gtttaaactc ctttttgata atctcatgac caaaatccct taacgtgagt  10800
tttcgttcca ctgagcgtca gaccccgtag aaaagatcaa aggatcttct tgagatcctt  10860
tttttctgcg cgtaatctgc tgcttgcaaa caaaaaaacc accgctacca gcggtggttt  10920
gtttgccgga tcaagagcta ccaactcttt ttccgaaggt aactggcttc agcagagcgc  10980
agataccaaa tactgtcctt ctagtgtagc cgtagttagg ccaccacttc aagaactctg  11040
tagcaccgcc tacatacctc gctctgctaa tcctgttacc agtggctgct gccagtggcg  11100
ataagtcgtg tcttaccggg ttggactcaa gacgatagtt accggataag gcgcagcggt  11160
cgggctgaac ggggggttcg tgcacacagc ccagcttgga gcgaacgacc tacaccgaac  11220
```

```
tgagatacct acagcgtgag cattgagaaa gcgccacgct tcccgaaggg agaaaggcgg  11280
acaggtatcc ggtaagcggc agggtcggaa caggagagcg cacgagggag cttccagggg  11340
gaaacgcctg gtatctttat agtcctgtcg ggtttcgcca cctctgactt gagcgtcgat  11400
ttttgtgatg ctcgtcaggg gggcggagcc tatggaaaaa cgccagcaac gcggcctttt  11460
tacggttcct ggccttttgc tggccttttg ctcacatgtt ctttcctgcg ttatcccctg  11520
attctgtgga taaccgtatt accgcctttg agtgagctga taccgctcgc cgcagccgaa  11580
cgaccgagcg cagcgagtca gtgagcgagg aagcggaaga gcgcccaata cgcagggccc  11640
cctgcttcgg ggtcattata gcgatttttt cggtatatcc atcctttttc gcacgatata  11700
caggattttg ccaaagggtt cgtgtagact ttccttggtg tatccaacgg cgtcagccgg  11760
gcaggatagg tgaagtaggc ccacccgcga gcgggtgttc cttcttcact gtcccttatt  11820
cgcacctggc ggtgctcaac gggaatcctg ctctgcgagg ctggccggct accgccggcg  11880
taacagatga gggcaagcgg atggctgatg aaaccaagcc aaccaggaag ggcagcccac  11940
ctatcaaggt gtactgcctt ccagacgaac gaagagcgat tgaggaaaag gcggcggcgg  12000
ccggcatgag cctgtcggcc tacctgctgg ccgtcggcca gggctacaaa atcacgggcg  12060
tcgtggacta tgagcacgtc cgcgagctgg cccgcatcaa tggcgacctg ggccgcctgg  12120
gcggcctgct gaaactctgg ctcaccgacg acccgcgcac ggcgcggttc ggtgatgcca  12180
cgatcctcgc cctgctggcg aagatcgaag agaagcagga cgagcttggc aaggtcatga  12240
tgggcgtggt ccgcccgagg gcagagccat gactttttta gccgctaaaa cggccggggg  12300
gtgcgcgtga ttgccaagca cgtccccatg cgctccatca agaagagcga cttcgcggag  12360
ctggtgaagt acatcaccga cgagcaaggc aagaccgatc gggccccctg ca          12412
```

<210> SEQ ID NO 63
<211> LENGTH: 3191
<212> TYPE: DNA
<213> ORGANISM: Artificial Sequence
<220> FEATURE:
<223> OTHER INFORMATION: Shuttle plasmid pMTL-JH11

<400> SEQUENCE: 63

```
ggagagtaat gtacttacct ttggggattt cataactaaa agcggcagaa gaacaccatt     60
ttttataaat acaggtaact acaagacagg taatcaatta aataagttgg ctaagtttta    120
tgctaaagca atatatgata attttggaga tgattttgat attttatttg ggcctgcata    180
taaaggaata cctttaagtg tttcagtagc tatggcactt gataatattt atggaattaa    240
tgcagcttat tgttcaaata gaaaagaagt taaagatcac ggtgataagg gaatacttct    300
tggcggccgc tgtatccata tgaccatgat tacgaattcg agctcggtac ccggggatcc    360
tctagagtcg acgtcacgcg tccatggaga tctcgaggcc tgcagacatg caagcttggc    420
actggccgtc gttttacaac gtcgtgactg ggaaaaccct ggcgttaccc aacttaatcg    480
ccttgcagca catccccctt tcgccagctg gcgtaatagc gaagaggccc gcaccgatcg    540
cccttcccaa cagttgcgca gcctgaatgg cgaatggcgc tagcataaaa ataagaagcc    600
tgcatttgca ggcttcttat ttttatggcg cgccgcattc acttcttttc tatataaata    660
tgagcgaagc gaataagcgt cggaaaagca gcaaaaagtt tcctttttgc tgttggagca    720
tgggggttca gggggtgcag tatctgacgt caatgccgag cgaaagcgag ccgaagggta    780
gcatttacgt tagataaccc cctgatatgc tccgacgctt tatatagaaa agaagattca    840
actaggtaaa atcttaatat aggttgagat gataaggttt ataaggaatt tgtttgttct    900
```

-continued

```
aatttttcac tcattttgtt ctaatttctt ttaacaaatg ttcttttttt tttagaacag    960
ttatgatata gttagaatag tttaaaataa ggagtgagaa aaagatgaaa gaaagatatg   1020
gaacagtcta taaaggctct cagaggctca tagacgaaga aagtggagaa gtcatagagg   1080
tagacaagtt ataccgtaaa caaacgtctg gtaacttcgt aaaggcatat atagtgcaat   1140
taataagtat gttagatatg attggcggaa aaaaacttaa aatcgttaac tatatcctag   1200
ataatgtcca cttaagtaac aatacaatga tagctacaac aagagaaata gcaaaagcta   1260
caggaacaag tctacaaaca gtaataacaa cacttaaaat cttagaagaa ggaaatatta   1320
taaaaagaaa aactggagta ttaatgttaa accctgaact actaatgaga ggcgacgacc   1380
aaaaacaaaa atacctctta ctcgaatttg ggaactttga gcaagaggca aatgaaatag   1440
attgacctcc caataacacc acgtagttat tgggaggtca atctatgaaa tgcgattaag   1500
ggccggccag tgggcaagtt gaaaaattca caaaaatgtg gtataatatc tttgttcatt   1560
agagcgataa acttgaattt gagagggaac ttagatggta tttgaaaaaa ttgataaaaa   1620
tagttggaac agaaaagagt attttgacca ctactttgca agtgtacctt gtacctacag   1680
catgaccgtt aaagtggata tcacacaaat aaaggaaaag ggaatgaaac tatatcctgc   1740
aatgctttat tatattgcaa tgattgtaaa ccgccattca gagtttagga cggcaatcaa   1800
tcaagatggt gaattgggga tatatgatga gatgatacca agctatacaa tatttcacaa   1860
tgatactgaa acattttcca gcctttggac tgagtgtaag tctgacttta aatcattttt   1920
agcagattat gaaagtgata cgcaacggta tggaaacaat catagaatgg aaggaaagcc   1980
aaatgctccg gaaaacattt ttaatgtatc tatgataccg tggtcaacct tcgatggctt   2040
taatctgaat ttgcagaaag gatatgatta tttgattcct atttttacta tggggaaata   2100
ttataaagaa gataacaaaa ttatacttcc tttggcaatt caagttcatc acgcagtatg   2160
tgacggattt cacatttgcc gttttgtaaa cgaattgcag gaattgataa atagttaact   2220
tcaggtttgt ctgtaactaa aaacaagtat ttaagcaaaa acatcgtaga aatacggtgt   2280
tttttgttac cctaagttta aactcctttt tgataatctc atgaccaaaa tcccttaacg   2340
tgagttttcg ttccactgag cgtcagaccc cgtagaaaag atcaaaggat cttcttgaga   2400
tccttttttt ctgcgcgtaa tctgctgctt gcaaacaaaa aaaccaccgc taccagcggt   2460
ggtttgtttg ccggatcaag agctaccaac tctttttccg aaggtaactg gcttcagcag   2520
agcgcagata ccaaatactg tccttctagt gtagccgtag ttaggccacc acttcaagaa   2580
ctctgtagca ccgcctacat acctcgctct gctaatcctg ttaccagtgg ctgctgccag   2640
tggcgataag tcgtgtctta ccgggttgga ctcaagacga tagttaccgg ataaggcgca   2700
gcggtcgggc tgaacggggg gttcgtgcac acagcccagc ttggagcgaa cgacctacac   2760
cgaactgaga tacctacagc gtgagcattg agaaagcgcc acgcttcccg aagggagaaa   2820
ggcggacagg tatccggtaa gcggcagggt cggaacagga gagcgcacga gggagcttcc   2880
agggggaaac gcctggtatc tttatagtcc tgtcgggttt cgccacctct gacttgagcg   2940
tcgatttttg tgatgctcgt caggggggcg gagcctatgg aaaaacgcca gcaacgcggc   3000
ctttttacgg ttcctggcct tttgctggcc ttttgctcac atgttctttc ctgcgttatc   3060
ccctgattct gtggataacc gtattaccgc ctttgagtga gctgataccg ctcgccgcag   3120
ccgaacgacc gagcgcagcg agtcagtgag cgaggaagcg gaagagcgcc caatacgcag   3180
ggccccctgc a                                                        3191
```

-continued

<210> SEQ ID NO 64
<211> LENGTH: 4349
<212> TYPE: DNA
<213> ORGANISM: Artificial Sequence
<220> FEATURE:
<223> OTHER INFORMATION: Shuttle plasmid pMTL-JH12

<400> SEQUENCE: 64

```
ggagagtaat gtacttacct ttggggattt cataactaaa agcggcagaa gaacaccatt     60

ttttataaat acaggtaact acaagacagg taatcaatta aataagttgg ctaagtttta    120

tgctaaagca atatatgata attttggaga tgattttgat attttatttg ggcctgcata    180

taaaggaata cctttaagtg tttcagtagc tatggcactt gataatattt atggaattaa    240

tgcagcttat tgttcaaata gaaaagaagt taaagatcac ggtgataagg gaatacttct    300

tggcggccgc tgtatccata tgaccatgat tacgaattcg agctcggtac ccggggatcc    360

tctagagtcg acgtcacgcg tccatggaga tctcgaggcc tgcagacatg caagcttggc    420

actggccgtc gttttacaac gtcgtgactg ggaaaaccct ggcgttaccc aacttaatcg    480

ccttgcagca catccccctt tcgccagctg gcgtaatagc gaagaggccc gcaccgatcg    540

cccttcccaa cagttgcgca gcctgaatgg cgaatggcgc tagctaaaat aaatgtgcct    600

caacttagat gttaaggcac atttatttta tatattattc atgttttgaa acatttttat    660

cttttgtgta ttttacgtgt agtaatttgt gagcaagtcc ttcacctggt tttccaaagt    720

agctatcata cattttaata atagctggat tatcatgtga ctttctcttt gaaagaacat    780

ttttatcttg gttgtataat actgatgctc ttagttttct gtaatcaaca ttttctctat    840

caagagcatt tacgtgaggt tgacctccac catttataca tccaccaggg caagccatta    900

cttctataaa gtgatattgt ttttcgttca tttttccaga tttcataaac tcgaagaagt    960

tagaagcacc atttataaca gcaacgttta gtttatttcc agcaatttca acttccgctt   1020

cttttatgcc tttaaagcct cttacttcag tgtaatcaac attttcaagt tctttatttt   1080

cagcaaagtc tttagctgat cttattgcag cttccataac gccaccggtt gcaccaaaga   1140

tagctccagc accactgtaa gtacccatag caggatcaac ttcaccatct tcaagatctg   1200

caaatttaat ttttgcatct ttaatcattt ttgcaagctc tcttgtagtt aaggatgcat   1260

caatatctct taagctgtta gtttccatga aaggaatatc tgcttcatat tttttatcat   1320

tacaaggcat gatagtaact gtataaacat cttctggagc tattcctgaa attgaaggat   1380

agtaagtttt tgatgcagta ccaaatattt gttgtggtga ttttgctgat gaaagattat   1440

ctaataattc aggatgataa ttttgagcta atcttaccca tgcaggacag caagatgtaa   1500

acatagggaa tgggccatta tttttaactc tgcctaaaag ttcagtagct tcttccatta   1560

tagtcatatc tgcaccaaag tttatatcaa atactttatc aaagcctaac attctaagtg   1620

cagtatatag ttttcctgtt acatcttttc catatcccat tttgaataat tcgcccatag   1680

cagttcttac tgatggagcc attgcaacaa tgacatgttt tttagggtca ttaagagctt   1740

cttgaacttt ttctatatgg gatttttctt ttaaagcagc aacaggcgcg ccgcattcac   1800

ttcttttcta tataaatatg agcgaagcga ataagcgtcg gaaaagcagc aaaaagtttc   1860

ctttttgctg ttggagcatg ggggttcagg gggtgcagta tctgacgtca atgccgagcg   1920

aaagcgagcc gaagggtagc atttacgtta gataaccccc tgatatgctc cgacgcttta   1980

tatagaaaag aagattcaac taggtaaaat cttaatatag gttgagatga taaggtttat   2040

aaggaatttg tttgttctaa tttttcactc attttgttct aatttctttt aacaaatgtt   2100

cttttttttt tagaacagtt atgatatagt tagaatagtt taaaataagg agtgagaaaa   2160
```

```
agatgaaaga aagatatgga acagtctata aaggctctca gaggctcata gacgaagaaa   2220
gtggagaagt catagaggta gacaagttat accgtaaaca aacgtctggt aacttcgtaa   2280
aggcatatat agtgcaatta ataagtatgt tagatatgat tggcggaaaa aaacttaaaa   2340
tcgttaacta tatcctagat aatgtccact taagtaacaa tacaatgata gctacaacaa   2400
gagaaatagc aaaagctaca ggaacaagtc tacaaacagt aataacaaca cttaaaatct   2460
tagaagaagg aaatattata aaaagaaaaa ctggagtatt aatgttaaac cctgaactac   2520
taatgagagg cgacgaccaa aaacaaaaat acctcttact cgaatttggg aactttgagc   2580
aagaggcaaa tgaaatagat tgacctccca ataacaccac gtagttattg ggaggtcaat   2640
ctatgaaatg cgattaaggg ccggccagtg ggcaagttga aaaattcaca aaaatgtggt   2700
ataatatctt tgttcattag agcgataaac ttgaatttga gagggaactt agatggtatt   2760
tgaaaaaatt gataaaaata gttggaacag aaaagagtat tttgaccact actttgcaag   2820
tgtaccttgt acctacagca tgaccgttaa agtggatatc acacaaataa aggaaaaggg   2880
aatgaaacta tatcctgcaa tgctttatta tattgcaatg attgtaaacc gccattcaga   2940
gtttaggacg gcaatcaatc aagatggtga attggggata tatgatgaga tgataccaag   3000
ctatacaata tttcacaatg atactgaaac attttccagc ctttggactg agtgtaagtc   3060
tgactttaaa tcatttttag cagattatga aagtgatacg caacggtatg gaaacaatca   3120
tagaatggaa ggaaagccaa atgctccgga aaacattttt aatgtatcta tgataccgtg   3180
gtcaaccttc gatggcttta atctgaattt gcagaaagga tatgattatt tgattcctat   3240
ttttactatg ggaaatatt ataaagaaga taacaaaatt atacttcctt tggcaattca   3300
agttcatcac gcagtatgtg acggatttca catttgccgt tttgtaaacg aattgcagga   3360
attgataaat agttaacttc aggtttgtct gtaactaaaa acaagtattt aagcaaaaac   3420
atcgtagaaa tacggtgttt tttgttaccc taagtttaaa ctcctttttg ataatctcat   3480
gaccaaaatc ccttaacgtg agttttcgtt ccactgagcg tcagaccccg tagaaaagat   3540
caaaggatct tcttgagatc cttttttct gcgcgtaatc tgctgcttgc aaacaaaaaa   3600
accaccgcta ccagcggtgg tttgtttgcc ggatcaagag ctaccaactc tttttccgaa   3660
ggtaactggc ttcagcagag cgcagatacc aaatactgtc cttctagtgt agccgtagtt   3720
aggccaccac ttcaagaact ctgtagcacc gcctacatac ctcgctctgc taatcctgtt   3780
accagtggct gctgccagtg gcgataagtc gtgtcttacc gggttggact caagacgata   3840
gttaccggat aaggcgcagc ggtcgggctg aacggggggt tcgtgcacac agcccagctt   3900
ggagcgaacg acctacaccg aactgagata cctacagcgt gagcattgag aaagcgccac   3960
gcttcccgaa gggagaaagg cggacaggta tccggtaagc ggcagggtcg gaacaggaga   4020
gcgcacgagg gagcttccag ggggaaacgc ctggtatctt tatagtcctg tcgggtttcg   4080
ccacctctga cttgagcgtc gatttttgtg atgctcgtca ggggggcgga gcctatggaa   4140
aaacgccagc aacgcggcct ttttacggtt cctggccttt tgctggcctt ttgctcacat   4200
gttctttcct gcgttatccc ctgattctgt ggataaccgt attaccgcct ttgagtgagc   4260
tgataccgct cgccgcagcc gaacgaccga gcgcagcgag tcagtgagcg aggaagcgga   4320
agagcgccca atacgcaggg cccccctgca                                    4349
```

<210> SEQ ID NO 65
<211> LENGTH: 3529
<212> TYPE: DNA
<213> ORGANISM: Artificial Sequence -continued
<220> FEATURE:
<223> OTHER INFORMATION: Shuttle plasmid pMTL-JH13

<400> SEQUENCE: 65

```
ggagagtaat gtacttacct ttggggattt cataactaaa agcggcagaa gaacaccatt     60
ttttataaat acaggtaact acaagacagg taatcaatta aataagttgg ctaagtttta    120
tgctaaagca atatatgata attttggaga tgattttgat attttatttg ggcctgcata    180
taaaggaata cctttaagtg tttcagtagc tatggcactt gataatattt atggaattaa    240
tgcagcttat tgttcaaata gaaaagaagt taaagatcac ggtgataagg gaatacttct    300
tggagcaaag cttgaagaag gagacagagt tataattgta gaagatgtca caacagctgg    360
tacatcagta tacgaaacaa tgcctatact taaatcacag gctgaggttg atgtaaaggg    420
aatcataata tcagtggata gaatggaaag aggtaaggga gataagagtg ccttaactga    480
acttaaagaa aagtttggat ttaaaacatg ttctattgtt actatggaag aggtagtaga    540
atatttgtat aagaaaaata tcaatggcaa agtaatcata gatgataaaa tgaaagatag    600
aattaatgag tactataaag agtatggagt aaaatagtaa gcggccgctg tatccatatg    660
accatgatta cgaattcgag ctcggtaccc ggggatcctc tagagtcgac gtcacgcgtc    720
catggagatc tcgaggcctg cagacatgca agcttggcac tggccgtcgt tttacaacgt    780
cgtgactggg aaaaccctgg cgttacccaa cttaatcgcc ttgcagcaca tccccctttc    840
gccagctggc gtaatagcga agaggcccgc accgatcgcc cttcccaaca gttgcgcagc    900
ctgaatggcg aatggcgcta gcataaaaat aagaagcctg catttgcagg cttcttattt    960
ttatggcgcg ccgcattcac ttcttttcta tataaatatg agcgaagcga ataagcgtcg   1020
gaaaagcagc aaaaagtttc ctttttgctg ttggagcatg ggggttcagg gggtgcagta   1080
tctgacgtca atgccgagcg aaagcgagcc gaagggtagc atttacgtta gataaccccc   1140
tgatatgctc cgacgcttta tatagaaaag aagattcaac taggtaaaat cttaatatag   1200
gttgagatga taaggtttat aaggaatttg tttgttctaa tttttcactc attttgttct   1260
aatttctttt aacaaatgtt cttttttttt tagaacagtt atgatatagt tagaatagtt   1320
taaaataagg agtgagaaaa agatgaaaga aagatatgga acagtctata aaggctctca   1380
gaggctcata gacgaagaaa gtggagaagt catagaggta gacaagttat accgtaaaca   1440
aacgtctggt aacttcgtaa aggcatatat agtgcaatta ataagtatgt tagatatgat   1500
tggcggaaaa aaacttaaaa tcgttaacta tatcctagat aatgtccact taagtaacaa   1560
tacaatgata gctacaacaa gagaaatagc aaaagctaca ggaacaagtc tacaaacagt   1620
aataacaaca cttaaaatct tagaagaagg aaatattata aaaagaaaaa ctggagtatt   1680
aatgttaaac cctgaactac taatgagagg cgacgaccaa aaacaaaaat acctcttact   1740
cgaatttggg aactttgagc aagaggcaaa tgaaatagat tgacctccca ataacaccac   1800
gtagttattg ggaggtcaat ctatgaaatg cgattaaggg ccggccagtg ggcaagttga   1860
aaaattcaca aaaatgtggt ataatatctt tgttcattag agcgataaac ttgaatttga   1920
gagggaactt agatggtatt tgaaaaaatt gataaaaata gttggaacag aaaagagtat   1980
tttgaccact actttgcaag tgtaccttgt acctacagca tgaccgttaa agtggatatc   2040
acacaaataa aggaaaaggg aatgaaacta tatcctgcaa tgctttatta tattgcaatg   2100
attgtaaacc gccattcaga gtttaggacg gcaatcaatc aagatggtga attggggata   2160
tatgatgaga tgataccaag ctatacaata tttcacaatg atactgaaac attttccagc   2220
ctttggactg agtgtaagtc tgactttaaa tcatttttag cagattatga aagtgatacg   2280
```

caacggtatg gaaacaatca tagaatggaa ggaaagccaa atgctccgga aaacattttt 2340
aatgtatcta tgataccgtg gtcaaccttc gatggcttta atctgaattt gcagaaagga 2400
tatgattatt tgattcctat ttttactatg gggaaatatt ataaagaaga taacaaaatt 2460
atacttcctt tggcaattca agttcatcac gcagtatgtg acggatttca catttgccgt 2520
tttgtaaacg aattgcagga attgataaat agttaacttc aggtttgtct gtaactaaaa 2580
acaagtattt aagcaaaaac atcgtagaaa tacggtgttt tttgttaccc taagtttaaa 2640
ctcctttttg ataatctcat gaccaaaatc ccttaacgtg agttttcgtt ccactgagcg 2700
tcagaccccg tagaaaagat caaaggatct tcttgagatc ctttttttct gcgcgtaatc 2760
tgctgcttgc aaacaaaaaa accaccgcta ccagcggtgg tttgtttgcc ggatcaagag 2820
ctaccaactc tttttccgaa ggtaactggc ttcagcagag cgcagatacc aaatactgtc 2880
cttctagtgt agccgtagtt aggccaccac ttcaagaact ctgtagcacc gcctacatac 2940
ctcgctctgc taatcctgtt accagtggct gctgccagtg gcgataagtc gtgtcttacc 3000
gggttggact caagacgata gttaccggat aaggcgcagc ggtcgggctg aacggggggt 3060
tcgtgcacac agcccagctt ggagcgaacg acctacaccg aactgagata cctacagcgt 3120
gagcattgag aaagcgccac gcttcccgaa gggagaaagg cggacaggta tccggtaagc 3180
ggcagggtcg gaacaggaga gcgcacgagg gagcttccag ggggaaacgc ctggtatctt 3240
tatagtcctg tcgggtttcg ccacctctga cttgagcgtc gatttttgtg atgctcgtca 3300
ggggggcgga gcctatggaa aaacgccagc aacgcggcct ttttacggtt cctggccttt 3360
tgctggcctt ttgctcacat gttctttcct gcgttatccc ctgattctgt ggataaccgt 3420
attaccgcct ttgagtgagc tgataccgct cgccgcagcc gaacgaccga gcgcagcgag 3480
tcagtgagcg aggaagcgga agagcgccca atacgcaggg ccccctgca 3529

<210> SEQ ID NO 66
<211> LENGTH: 4687
<212> TYPE: DNA
<213> ORGANISM: Artificial Sequence
<220> FEATURE:
<223> OTHER INFORMATION: Shuttle plasmid pMTL-JH14

<400> SEQUENCE: 66
ggagagtaat gtacttacct ttggggattt cataactaaa agcggcagaa gaacaccatt 60
ttttataaat acaggtaact acaagacagg taatcaatta aataagttgg ctaagtttta 120
tgctaaagca atatatgata attttggaga tgattttgat attttatttg ggcctgcata 180
taaaggaata cctttaagtg tttcagtagc tatggcactt gataatattt atggaattaa 240
tgcagcttat tgttcaaata gaaaagaagt taaagatcac ggtgataagg gaatacttct 300
tggagcaaag cttgaagaag gagacagagt tataattgta gaagatgtca caacagctgg 360
tacatcagta tacgaaacaa tgcctatact taaatcacag gctgaggttg atgtaaaggg 420
aatcataata tcagtggata gaatggaaag aggtaaggga gataagagtg ccttaactga 480
acttaaagaa aagtttggat ttaaaacatg ttctattgtt actatggaag aggtagtaga 540
atatttgtat aagaaaaata tcaatggcaa agtaatcata gatgataaaa tgaaagatag 600
aattaatgag tactataaag agtatggagt aaaatagtaa gcggccgctg tatccatatg 660
accatgatta cgaattcgag ctcggtaccc ggggatcctc tagagtcgac gtcacgcgtc 720
catggagatc tcgaggcctg cagacatgca agcttggcac tggccgtcgt tttacaacgt 780
cgtgactggg aaaaccctgg cgttacccaa cttaatcgcc ttgcagcaca tccccctttc 840

```
gccagctggc gtaatagcga agaggcccgc accgatcgcc cttcccaaca gttgcgcagc    900
ctgaatggcg aatggcgcta gctaaaataa atgtgcctca acttagatgt taaggcacat    960
ttattttata tattattcat gttttgaaac atttttatct tttgtgtatt ttacgtgtag   1020
taatttgtga gcaagtcctt cacctggttt tccaaagtag ctatcataca ttttaataat   1080
agctggatta tcatgtgact ttctctttga aagaacattt ttatcttggt tgtataatac   1140
tgatgctctt agttttctgt aatcaacatt ttctctatca agagcattta cgtgaggttg   1200
acctccacca tttatacatc caccagggca agccattact tctataaagt gatattgttt   1260
ttcgttcatt tttccagatt tcataaactc gaagaagtta gaagcaccat ttataacagc   1320
aacgtttagt ttatttccag caatttcaac ttccgcttct tttatgcctt taaagcctct   1380
tacttcagtg taatcaacat tttcaagttc tttattttca gcaaagtctt tagctgatct   1440
tattgcagct tccataacgc caccggttgc accaaagata gctccagcac cactgtaagt   1500
acccatagca ggatcaactt caccatcttc aagatctgca aatttaattt ttgcatcttt   1560
aatcattttt gcaagctctc ttgtagttaa ggatgcatca atatctctta agctgttagt   1620
ttccatgaaa ggaatatctg cttcatattt tttatcatta caaggcatga tagtaactgt   1680
ataaacatct tctggagcta ttcctgaaat tgaaggatag taagtttttg atgcagtacc   1740
aaatatttgt tgtggtgatt ttgctgatga aagattatct aataattcag gatgataatt   1800
ttgagctaat cttacccatg caggacagca agatgtaaac atagggaatg ggccattatt   1860
tttaactctg cctaaaagtt cagtagcttc ttccattata gtcatatctg caccaaagtt   1920
tatatcaaat actttatcaa agcctaacat tctaagtgca gtatatagtt ttcctgttac   1980
atcttttcca tatcccattt tgaataattc gcccatagca gttcttactg atggagccat   2040
tgcaacaatg acatgttttt tagggtcatt aagagcttct tgaacttttt ctatatggga   2100
tttttctttt aaagcagcaa caggcgcgcc gcattcactt cttttctata taaatatgag   2160
cgaagcgaat aagcgtcgga aaagcagcaa aaagtttcct tttgctgttg ggagcatggg   2220
ggttcagggg gtgcagtatc tgacgtcaat gccgagcgaa agcgagccga agggtagcat   2280
ttacgttaga taacccccctg atatgctccg acgctttata tagaaaagaa gattcaacta   2340
ggtaaaatct taatataggt tgagatgata aggtttataa ggaatttgtt tgttctaatt   2400
tttcactcat tttgttctaa tttcttttaa caaatgttct tttttttta gaacagttat   2460
gatatagtta gaatagttta aaataaggag tgagaaaaag atgaaagaaa gatatggaac   2520
agtctataaa ggctctcaga ggctcataga cgaagaaagt ggagaagtca tagaggtaga   2580
caagttatac cgtaaacaaa cgtctggtaa cttcgtaaag gcatatatag tgcaattaat   2640
aagtatgtta gatatgattg gcggaaaaaa acttaaaatc gttaactata tcctagataa   2700
tgtccactta agtaacaata caatgatagc tacaacaaga gaaatagcaa aagctacagg   2760
aacaagtcta caaacagtaa taacaacact taaaatctta gaagaaggaa atattataaa   2820
aagaaaaact ggagtattaa tgttaaaccc tgaactacta atgagaggcg acgaccaaaa   2880
acaaaaatac ctcttactcg aatttgggaa ctttgagcaa gaggcaaatg aaatagattg   2940
acctcccaat aacaccacgt agttattggg aggtcaatct atgaaatgcg attaagggcc   3000
ggccagtggg caagttgaaa aattcacaaa aatgtggtat aatatctttg ttcattagag   3060
cgataaactt gaatttgaga gggaacttag atggtatttg aaaaaattga taaaaatagt   3120
tggaacagaa aagagtattt tgaccactac tttgcaagtg taccttgtac ctacagcatg   3180
accgttaaag tggatatcac acaaataaag gaaaagggaa tgaaactata tcctgcaatg   3240
```

```
ctttattata ttgcaatgat tgtaaaccgc cattcagagt ttaggacggc aatcaatcaa   3300

gatggtgaat tggggatata tgatgagatg ataccaagct atacaatatt tcacaatgat   3360

actgaaacat tttccagcct ttggactgag tgtaagtctg actttaaatc atttttagca   3420

gattatgaaa gtgatacgca acggtatgga aacaatcata gaatggaagg aaagccaaat   3480

gctccggaaa acatttttaa tgtatctatg ataccgtggt caaccttcga tggctttaat   3540

ctgaatttgc agaaaggata tgattatttg attcctattt ttactatggg gaaatattat   3600

aaagaagata acaaaattat acttcctttg gcaattcaag ttcatcacgc agtatgtgac   3660

ggatttcaca tttgccgttt tgtaaacgaa ttgcaggaat tgataaatag ttaacttcag   3720

gtttgtctgt aactaaaaac aagtatttaa gcaaaaacat cgtagaaata cggtgttttt   3780

tgttacccta agtttaaact cctttttgat aatctcatga ccaaaatccc ttaacgtgag   3840

ttttcgttcc actgagcgtc agaccccgta gaaaagatca aaggatcttc ttgagatcct   3900

tttttctgc gcgtaatctg ctgcttgcaa acaaaaaaac caccgctacc agcggtggtt   3960

tgtttgccgg atcaagagct accaactctt tttccgaagg taactggctt cagcagagcg   4020

cagataccaa atactgtcct tctagtgtag ccgtagttag gccaccactt caagaactct   4080

gtagcaccgc ctacatacct cgctctgcta atcctgttac cagtggctgc tgccagtggc   4140

gataagtcgt gtcttaccgg gttggactca agacgatagt taccggataa ggcgcagcgg   4200

tcgggctgaa cggggggttc gtgcacacag cccagcttgg agcgaacgac ctacaccgaa   4260

ctgagatacc tacagcgtga gcattgagaa agcgccacgc ttcccgaagg gagaaaggcg   4320

gacaggtatc cggtaagcgg cagggtcgga acaggagagc gcacgaggga gcttccaggg   4380

ggaaacgcct ggtatcttta tagtcctgtc gggtttcgcc acctctgact tgagcgtcga   4440

tttttgtgat gctcgtcagg ggggcggagc ctatggaaaa acgccagcaa cgcggccttt   4500

ttacggttcc tggccttttg ctggcctttt gctcacatgt tctttcctgc gttatcccct   4560

gattctgtgg ataaccgtat taccgccttt gagtgagctg ataccgctcg ccgcagccga   4620

acgaccgagc gcagcgagtc agtgagcgag gaagcggaag agcgcccaat acgcagggcc   4680

ccctgca                                                             4687
```

```
<210> SEQ ID NO 67
<211> LENGTH: 3195
<212> TYPE: DNA
<213> ORGANISM: Artificial Sequence
<220> FEATURE:
<223> OTHER INFORMATION: Shuttle plasmid pMTL-JH1

<400> SEQUENCE: 67

gggtgtttag gacttgatac tgatattact tatgtaccag aagagttttg taagaaattt     60

aatagtatag aagatgctat atttaatttt aataagaaaa taattgatgc gactttagat    120

gttgtttcat gttataaggt gcaaattgca tattatgaag cttatggttt aaaaggactt    180

ttggcctata aaaggacact tgaatatttg agagaaaaaa aggctattgc aattgctgat    240

ataaaaagag gagatatagc taaaacagct gaaatgtatg ctaaagctca ctttgaaggt    300

taatgagcgg ccgctgtatc catatgacca tgattacgaa ttcgagctcg gtacccgggg    360

atcctctaga gtcgacgtca cgcgtccatg gagatctcga ggcctgcaga catgcaagct    420

tggcactggc cgtcgtttta caacgtcgtg actgggaaaa ccctggcgtt acccaactta    480

atcgccttgc agcacatccc cctttcgcca gctggcgtaa tagcgaagag gcccgcaccg    540

atcgcccttc ccaacagttg cgcagcctga atggcgaatg gcgctagcat aaaaataaga    600
```

-continued

```
agcctgcatt tgcaggcttc ttatttttat ggcgcgccgc attcacttct tttctatata    660
aatatgagcg aagcgaataa gcgtcggaaa agcagcaaaa agtttccttt ttgctgttgg    720
agcatggggg ttcagggggt gcagtatctg acgtcaatgc cgagcgaaag cgagccgaag    780
ggtagcattt acgttagata accccctgat atgctccgac gctttatata gaaaagaaga    840
ttcaactagg taaaatctta atataggttg agatgataag gtttataagg aatttgtttg    900
ttctaatttt tcactcattt tgttctaatt tcttttaaca aatgttcttt ttttttaga    960
acagttatga tatagttaga atagtttaaa ataaggagtg agaaaaagat gaaagaaaga   1020
tatggaacag tctataaagg ctctcagagg ctcatagacg aagaaagtgg agaagtcata   1080
gaggtagaca agttataccg taaacaaacg tctggtaact tcgtaaaggc atatatagtg   1140
caattaataa gtatgttaga tatgattggc ggaaaaaaac ttaaaatcgt taactatatc   1200
ctagataatg tccacttaag taacaataca atgatagcta caacaagaga aatagcaaaa   1260
gctacaggaa caagtctaca aacagtaata acaacactta aaatcttaga agaaggaaat   1320
attataaaaa gaaaaactgg agtattaatg ttaaaccctg aactactaat gagaggcgac   1380
gaccaaaaac aaaaatacct cttactcgaa tttgggaact ttgagcaaga ggcaaatgaa   1440
atagattgac ctcccaataa caccacgtag ttattgggag gtcaatctat gaaatgcgat   1500
taagggccgg ccagtgggca agttgaaaaa ttcacaaaaa tgtggtataa tatctttgtt   1560
cattagagcg ataaacttga atttgagagg gaacttagat ggtatttgaa aaaattgata   1620
aaaatagttg gaacagaaaa gagtattttg accactactt tgcaagtgta ccttgtacct   1680
acagcatgac cgttaaagtg gatatcacac aaataaagga aaagggaatg aaactatatc   1740
ctgcaatgct ttattatatt gcaatgattg taaaccgcca ttcagagttt aggacggcaa   1800
tcaatcaaga tggtgaattg ggatatatg atgagatgat accaagctat acaatatttc   1860
acaatgatac tgaaacattt tccagccttt ggactgagtg taagtctgac tttaaatcat   1920
ttttagcaga ttatgaaagt gatacgcaac ggtatggaaa caatcataga atggaaggaa   1980
agccaaatgc tccggaaaac atttttaatg tatctatgat accgtggtca accttcgatg   2040
gctttaatct gaatttgcag aaaggatatg attatttgat tcctattttt actatgggga   2100
aatattataa agaagataac aaaattatac ttcctttggc aattcaagtt catcacgcag   2160
tatgtgacgg atttcacatt tgccgttttg taaacgaatt gcaggaattg ataaatagtt   2220
aacttcaggt ttgtctgtaa ctaaaaacaa gtatttaagc aaaaacatcg tagaaatacg   2280
gtgtttttg ttaccctaag tttaaactcc tttttgataa tctcatgacc aaaatccctt   2340
aacgtgagtt ttcgttccac tgagcgtcag accccgtaga aaagatcaaa ggatcttctt   2400
gagatccttt ttttctgcgc gtaatctgct gcttgcaaac aaaaaaacca ccgctaccag   2460
cggtggtttg tttgccggat caagagctac caactctttt tccgaaggta actggcttca   2520
gcagagcgca gataccaaat actgtccttc tagtgtagcc gtagttaggc caccacttca   2580
agaactctgt agcaccgcct acatacctcg ctctgctaat cctgttacca gtggctgctg   2640
ccagtggcga taagtcgtgt cttaccgggt tggactcaag acgatagtta ccggataagg   2700
cgcagcggtc gggctgaacg gggggttcgt gcacacagcc cagcttggag cgaacgacct   2760
acaccgaact gagataccta cagcgtgagc attgagaaag cgccacgctt cccgaaggga   2820
gaaaggcgga caggtatccg gtaagcggca gggtcggaac aggagagcgc acgagggagc   2880
ttccaggggg aaacgcctgg tatctttata gtcctgtcgg gtttcgccac ctctgacttg   2940
agcgtcgatt tttgtgatgc tcgtcagggg ggcggagcct atggaaaaac gccagcaacg   3000
```

```
cggccttttt acggttcctg gccttttgct ggccttttgc tcacatgttc tttcctgcgt   3060

tatcccctga ttctgtggat aaccgtatta ccgcctttga gtgagctgat accgctcgcc   3120

gcagccgaac gaccgagcgc agcgagtcag tgagcgagga agcggaagag cgcccaatac   3180

gcagggcccc ctgca                                                    3195


<210> SEQ ID NO 68
<211> LENGTH: 3705
<212> TYPE: DNA
<213> ORGANISM: Artificial Sequence
<220> FEATURE:
<223> OTHER INFORMATION: Shuttle plasmid pMTL-JH3

<400> SEQUENCE: 68

gggtgtttag gacttgatac tgatattact tatgtaccag aagagttttg taagaaattt     60

aatagtatag aagatgctat atttaatttt aataagaaaa taattgatgc gactttagat    120

gttgtttcat gttataaggt gcaaattgca tattatgaag cttatggttt aaaaggactt    180

ttggcctata aaaggacact tgaatatttg agagaaaaaa aggctattgc aattgctgat    240

ataaaaagag gagatatagc taaaacagct gaaatgtatg ctaaagctca ctttgaaggt    300

gattttgaag cggattttgt tacgttaaat ccttacatgg ggttagatgg tatagagcct    360

tatatgcctt atattgaaaa aatggaaaaa ggattattta ttttgcttag aacatcgaat    420

aaaggagcct atgatataca atatataaag actcagggcg gaaaaaacgt atatgatgag    480

gttggagaaa aaatatatga tttaggtcaa aaggctacgg gaaggagcaa gtattcttca    540

ataggagcag tagttggatg tactcacgtt gaagaaggcg ttgaaattag aaataaattt    600

aaaaatatgt tttttctaat tccaggctat ggagcacaag gtggaactgc aaaggaagta    660

agtttgtatt taagagaagg taatggtgga gtggtaaatt cctcaagggg aatacttctt    720

gcttataaaa aagaagaaaa cggtgaaaaa atatttgatg agtgtgcaag gcttgcagcg    780

attaatatga gagacgagat cagaaaaact ttatgagcgg ccgctgtatc catatgacca    840

tgattacgaa ttcgagctcg gtacccgggg atcctctaga gtcgacgtca cgcgtccatg    900

gagatctcga ggcctgcaga catgcaagct tggcactggc cgtcgtttta caacgtcgtg    960

actgggaaaa ccctggcgtt acccaactta atcgccttgc agcacatccc cctttcgcca   1020

gctggcgtaa tagcgaagag gcccgcaccg atcgcccttc ccaacagttg cgcagcctga   1080

atggcgaatg gcgctagcat aaaaataaga agcctgcatt tgcaggcttc ttatttttat   1140

ggcgcgccgc attcacttct tttctatata aatatgagcg aagcgaataa gcgtcggaaa   1200

agcagcaaaa agtttccttt ttgctgttgg agcatggggg ttcagggggt gcagtatctg   1260

acgtcaatgc cgagcgaaag cgagccgaag ggtagcattt acgttagata accccctgat   1320

atgctccgac gctttatata gaaaagaaga ttcaactagg taaaatctta atataggttg   1380

agatgataag gtttataagg aatttgtttg ttctaatttt tcactcattt tgttctaatt   1440

tcttttaaca aatgttcttt ttttttaga acagttatga tatagttaga atagtttaaa   1500

ataaggagtg agaaaaagat gaaagaaaga tatggaacag tctataaagg ctctcagagg   1560

ctcatagacg aagaaagtgg agaagtcata gaggtagaca agttataccg taaacaaacg   1620

tctggtaact tcgtaaaggc atatatagtg caattaataa gtatgttaga tatgattggc   1680

ggaaaaaaac ttaaaatcgt taactatatc ctagataatg tccacttaag taacaataca   1740

atgatagcta caacaagaga aatagcaaaa gctacaggaa caagtctaca aacagtaata   1800

acaacactta aaatcttaga agaaggaaat attataaaaa gaaaaactgg agtattaatg   1860
```

ttaaaccctg aactactaat gagaggcgac gaccaaaaac aaaaatacct cttactcgaa 1920
tttgggaact ttgagcaaga ggcaaatgaa atagattgac ctcccaataa caccacgtag 1980
ttattgggag gtcaatctat gaaatgcgat taagggccgg ccagtgggca agttgaaaaa 2040
ttcacaaaaa tgtggtataa tatctttgtt cattagagcg ataaacttga atttgagagg 2100
gaacttagat ggtatttgaa aaaattgata aaaatagttg gaacagaaaa gagtattttg 2160
accactactt tgcaagtgta ccttgtacct acagcatgac cgttaaagtg gatatcacac 2220
aaataaagga aaagggaatg aaactatatc ctgcaatgct ttattatatt gcaatgattg 2280
taaaccgcca ttcagagttt aggacggcaa tcaatcaaga tggtgaattg gggatatatg 2340
atgagatgat accaagctat acaatatttc acaatgatac tgaaacattt tccagccttt 2400
ggactgagtg taagtctgac tttaaatcat ttttagcaga ttatgaaagt gatacgcaac 2460
ggtatggaaa caatcataga atggaaggaa agccaaatgc tccggaaaac atttttaatg 2520
tatctatgat accgtggtca accttcgatg gctttaatct gaatttgcag aaaggatatg 2580
attatttgat tcctattttt actatgggga aatattataa agaagataac aaaattatac 2640
ttcctttggc aattcaagtt catcacgcag tatgtgacgg atttcacatt tgccgttttg 2700
taaacgaatt gcaggaattg ataaatagtt aacttcaggt ttgtctgtaa ctaaaaacaa 2760
gtatttaagc aaaaacatcg tagaaatacg gtgtttttttg ttaccctaag tttaaactcc 2820
tttttgataa tctcatgacc aaaatccctt aacgtgagtt ttcgttccac tgagcgtcag 2880
accccgtaga aaagatcaaa ggatcttctt gagatccttt ttttctgcgc gtaatctgct 2940
gcttgcaaac aaaaaaacca ccgctaccag cggtggtttg tttgccggat caagagctac 3000
caactctttt tccgaaggta actggcttca gcagagcgca gataccaaat actgtccttc 3060
tagtgtagcc gtagttaggc caccacttca agaactctgt agcaccgcct acatacctcg 3120
ctctgctaat cctgttacca gtggctgctg ccagtggcga taagtcgtgt cttaccgggt 3180
tggactcaag acgatagtta ccggataagg cgcagcggtc gggctgaacg gggggttcgt 3240
gcacacagcc cagcttggag cgaacgacct acaccgaact gagataccta cagcgtgagc 3300
attgagaaag cgccacgctt cccgaaggga gaaaggcgga caggtatccg gtaagcggca 3360
gggtcggaac aggagagcgc acgagggagc ttccaggggg aaacgcctgg tatctttata 3420
gtcctgtcgg gtttcgccac ctctgacttg agcgtcgatt tttgtgatgc tcgtcagggg 3480
ggcggagcct atggaaaaac gccagcaacg cggccttttt acggttcctg gccttttgct 3540
ggccttttgc tcacatgttc tttcctgcgt tatcccctga ttctgtggat aaccgtatta 3600
ccgcctttga gtgagctgat accgctcgcc gcagccgaac gaccgagcgc agcgagtcag 3660
tgagcgagga agcggaagag cgcccaatac gcagggcccc ctgca 3705

<210> SEQ ID NO 69
<211> LENGTH: 4034
<212> TYPE: DNA
<213> ORGANISM: Artificial Sequence
<220> FEATURE:
<223> OTHER INFORMATION: Shuttle vector pMTL-JH15

<400> SEQUENCE: 69
ggataaaaaa attgtagata aattttataa aatagtttta tctacaattt ttttatcagg 60
aaacagctat gaccgcggcc atctatgcaa caaaagcagc tattgaaaaa gcaggttgga 120
cagttgatga attagattta atagaatcaa atgaagcttt tgcagctcaa agtttagcag 180
tagcaaaaga tttaaaattt gatatgaata aagtaaatgt aaatggagga gctattgccc 240

```
ttggtcatcc aattggagca tcaggtgcaa gaatactcgt tactcttgta cacgcaatgc    300
aaaaaagaga tgcaaaaaaa ggcttagcaa ctttatgtat aggtggcgga caaggaacag    360
caatattgct agaaaagtgc tagatcgatt aagaaggagt gattacatga acaaaaatat    420
aaaatattct caaaactttt taacgagtga aaaagtactc aaccaaataa taaaacaatt    480
gaatttaaaa gaaaccgata ccgtttacga aattggaaca ggtaaagggc atttaacgac    540
gaaactggct aaaataagta aacaggtaac gtctattgaa ttagacagtc atctattcaa    600
cttatcgtca gaaaaattaa aactgaatac tcgtgtcact ttaattcacc aagatattct    660
acagtttcaa ttccctaaca aacagaggta taaaattgtt gggagtattc cttaccattt    720
aagcacacaa attattaaaa aagtggtttt tgaaagccat gcgtctgaca tctatctgat    780
tgttgaagaa ggattctaca agcgtacctt ggatattcac cgaacactag ggttgctctt    840
gcacactcaa gtctcgattc agcaattgct taagctgcca gcggaatgct ttcatcctaa    900
accaaaagta aacagtgtct taataaaact tacccgccat accacagatg ttccagataa    960
atattggaag ctatatacgt actttgtttc aaaatgggtc aatcgagaat atcgtcaact   1020
gtttactaaa aatcagtttc atcaagcaat gaaacacgcc aaagtaaaca atttaagtac   1080
cgttacttat gagcaagtat tgtctatttt taatagttat ctattattta acgggaggaa   1140
ataaagcggc cgctgtatcc atatgaccat gattacgaat tcgagctcgg tacccgggga   1200
tcctctagag tcgacgtcac gcgtccatgg agatctcgag gcctgcagac atgcaagctt   1260
ggcactggcc gtcgttttac aacgtcgtga ctgggaaaac cctggcgtta cccaacttaa   1320
tcgccttgca gcacatcccc ctttcgccag ctggcgtaat agcgaagagg cccgcaccga   1380
tcgcccttcc caacagttgc gcagcctgaa tggcgaatgg cgctagcata aaaataagaa   1440
gcctgcattt gcaggcttct tatttttatg gcgcgccgca ttcacttctt ttctatataa   1500
atatgagcga agcgaataag cgtcggaaaa gcagcaaaaa gtttcctttt tgctgttgga   1560
gcatgggggt tcagggggtg cagtatctga cgtcaatgcc gagcgaaagc gagccgaagg   1620
gtagcattta cgttagataa ccccctgata tgctccgacg ctttatatag aaaagaagat   1680
tcaactaggt aaaatcttaa tataggttga gatgataagg tttataagga atttgtttgt   1740
tctaattttt cactcatttt gttctaattt cttttaacaa atgttctttt tttttagaa    1800
cagttatgat atagttagaa tagtttaaaa taaggagtga gaaaaagatg aaagaaagat   1860
atggaacagt ctataaaggc tctcagaggc tcatagacga agaaagtgga gaagtcatag   1920
aggtagacaa gttataccgt aaacaaacgt ctggtaactt cgtaaaggca tatatagtgc   1980
aattaataag tatgttagat atgattggcg gaaaaaaact taaaatcgtt aactatatcc   2040
tagataatgt ccacttaagt aacaatacaa tgatagctac aacaagagaa atagcaaaag   2100
ctacaggaac aagtctacaa acagtaataa caacacttaa aatcttagaa gaaggaaata   2160
ttataaaaag aaaaactgga gtattaatgt taaaccctga actactaatg agaggcgacg   2220
accaaaaaca aaaatacctc ttactcgaat ttgggaactt tgagcaagag gcaaatgaaa   2280
tagattgacc tcccaataac accacgtagt tattgggagg tcaatctatg aaatgcgatt   2340
aagggccggc cagtgggcaa gttgaaaaat tcacaaaaat gtggtataat atctttgttc   2400
attagagcga taaacttgaa tttgagaggg aacttagatg gtatttgaaa aaattgataa   2460
aaatagttgg aacagaaaag agtattttga ccactacttt gcaagtgtac cttgtaccta   2520
cagcatgacc gttaaagtgg atatcacaca aataaaggaa aagggaatga aactatatcc   2580
tgcaatgctt tattatattg caatgattgt aaaccgccat tcagagttta ggacggcaat   2640
```

caatcaagat ggtgaattgg ggatatatga tgagatgata ccaagctata caatatttca 2700
caatgatact gaaacatttt ccagcctttg gactgagtgt aagtctgact ttaaatcatt 2760
tttagcagat tatgaaagtg atacgcaacg gtatggaaac aatcatagaa tggaaggaaa 2820
gccaaatgct ccggaaaaca tttttaatgt atctatgata ccgtggtcaa ccttcgatgg 2880
ctttaatctg aatttgcaga aaggatatga ttatttgatt cctatttta ctatggggaa 2940 atattataaa gaagataaca aaattatact tcctttggca attcaagttc atcacgcagt 3000
atgtgacgga tttcacattt gccgttttgt aaacgaattg caggaattga taaatagtta 3060
acttcaggtt tgtctgtaac taaaaacaag tatttaagca aaaacatcgt agaaatacgg 3120 tgtttttgt taccctaagt ttaaactcct tttgataat ctcatgacca aaatccctta 3180
acgtgagttt tcgttccact gagcgtcaga ccccgtagaa aagatcaaag gatcttcttg 3240
agatcctttt tttctgcgcg taatctgctg cttgcaaaca aaaaaaccac cgctaccagc 3300
ggtggtttgt ttgccggatc aagagctacc aactcttttt ccgaaggtaa ctggcttcag 3360
cagagcgcag ataccaaata ctgtccttct agtgtagccg tagttaggcc accacttcaa 3420
gaactctgta gcaccgccta catacctcgc tctgctaatc ctgttaccag tggctgctgc 3480
cagtggcgat aagtcgtgtc ttaccgggtt ggactcaaga cgatagttac cggataaggc 3540
gcagcggtcg ggctgaacgg ggggttcgtg cacacagccc agcttggagc gaacgaccta 3600
caccgaactg agatacctac agcgtgagca ttgagaaagc gccacgcttc ccgaagggag 3660
aaaggcggac aggtatccgg taagcggcag ggtcggaaca ggagagcgca cgagggagct 3720
tccaggggga aacgcctggt atctttatag tcctgtcggg tttcgccacc tctgacttga 3780
gcgtcgattt ttgtgatgct cgtcaggggg gcggagccta tggaaaaacg ccagcaacgc 3840
ggccttttta cggttcctgg ccttttgctg gccttttgct cacatgttct ttcctgcgtt 3900
atcccctgat tctgtggata accgtattac cgcctttgag tgagctgata ccgctcgccg 3960
cagccgaacg accgagcgca gcgagtcagt gagcgaggaa gcggaagagc gcccaatacg 4020
cagggccccc tgca 4034

<210> SEQ ID NO 70
<211> LENGTH: 5192
<212> TYPE: DNA
<213> ORGANISM: Artificial Sequence
<220> FEATURE:
<223> OTHER INFORMATION: Shuttle plasmid pMTL-JH16

<400> SEQUENCE: 70
ggataaaaaa attgtagata aattttataa aatagtttta tctacaattt ttttatcagg 60
aaacagctat gaccgcggcc atctatgcaa caaaagcagc tattgaaaaa gcaggttgga 120
cagttgatga attagattta atagaatcaa atgaagcttt tgcagctcaa agtttagcag 180
tagcaaaaga tttaaaattt gatatgaata aagtaaatgt aaatggagga gctattgccc 240
ttggtcatcc aattggagca tcaggtgcaa gaatactcgt tactcttgta cacgcaatgc 300
aaaaaagaga tgcaaaaaaa ggcttagcaa ctttatgtat aggtggcgga caaggaacag 360
caatattgct agaaaagtgc tagatcgatt aagaaggagt gattacatga acaaaaatat 420
aaaatattct caaaactttt taacgagtga aaaagtactc aaccaaataa taaaacaatt 480
gaatttaaaa gaaaccgata ccgtttacga aattggaaca ggtaaagggc atttaacgac 540
gaaactggct aaaataagta aacaggtaac gtctattgaa ttagacagtc atctattcaa 600
cttatcgtca gaaaaattaa aactgaatac tcgtgtcact ttaattcacc aagatattct 660

-continued

```
acagtttcaa ttccctaaca aacagaggta taaaattgtt gggagtattc cttaccattt    720
aagcacacaa attattaaaa aagtggtttt tgaaagccat gcgtctgaca tctatctgat    780
tgttgaagaa ggattctaca agcgtacctt ggatattcac cgaacactag ggttgctctt    840
gcacactcaa gtctcgattc agcaattgct taagctgcca gcggaatgct ttcatcctaa    900
accaaaagta aacagtgtct taataaaact tacccgccat accacagatg ttccagataa    960
atattggaag ctatatacgt actttgtttc aaaatgggtc aatcgagaat atcgtcaact   1020
gtttactaaa aatcagtttc atcaagcaat gaaacacgcc aaagtaaaca atttaagtac   1080
cgttacttat gagcaagtat tgtctatttt taatagttat ctattattta acgggaggaa   1140
ataaagcggc cgctgtatcc atatgaccat gattacgaat tcgagctcgg tacccgggga   1200
tcctctagag tcgacgtcac gcgtccatgg agatctcgag gcctgcagac atgcaagctt   1260
ggcactggcc gtcgttttac aacgtcgtga ctgggaaaac cctggcgtta cccaacttaa   1320
tcgccttgca gcacatcccc ctttcgccag ctggcgtaat agcgaagagg cccgcaccga   1380
tcgcccttcc caacagttgc gcagcctgaa tggcgaatgg cgctagcaaa gtattgttaa   1440
aaataactct gtagaattat aaattagttc tacagagtta tttttaaaa aaattctaaa   1500
cttatgtata aaaaatacga taagaatgta gaattaaaac taaagacagt tcaatttctt   1560
ttagaataat ttagttagtg tggtaaaaaa atgtcataat gatatttatg ttgaaatttg   1620
tataaaattc agaaaatgaa tatattttat caattttcag tcatttgaaa gattatgagg   1680
ctaatgcagt actaggcgta aattgaattt ataattacta tagcgataag aaatggccta   1740
aaaacgtttg cagtaatgaa agaaccgtaa atattataaa aaaaatctta aaacagagtt   1800
ttatttataa aaatttaaga tatataattt aaataacgtg ttaaaatagt ggaggaagta   1860
atttgaatct gaatattaaa agaatgttaa aggttgtaac tctttatgat gcaattattg   1920
ctgcaatagt ttcagtaata cttttgtttg ctgctaatta taagatttcg ttaatagtga   1980
ttatagggat tttttcagca atatttaatt tttatttaag taatttaaca gctgatttcg   2040
tttttgtaaa aaaaatggga aatacgtcac ttatatttct tagttcaatt tttagagtaa   2100
tacttgtttt ttttataggt attattcttt ataaaatata taaatattat ttaatagcct   2160
acttaggagg atatagtgct cattttatag cccttataat ttatgggtca ctagtaaata   2220
aacgatgaaa ggaagtgatt gaatggagct aggtgcaaag acagtatttt cgatgaagct   2280
tggaagttac aactttgcta taacagaaac tgtagtatta cagtggatta tcatggcagt   2340
tataatatta cttgcaatat ttcttactaa aaatcttaag aaagtaccaa ataggaaaca   2400
aagcgtaata gaaatgattg ttaacttaat aaatggattg gtaaaagaaa atatgggaga   2460
gaaattcatg aatttcgttc caattatcgg tactatggca gtgtttatac ttttcttaaa   2520
tttaacaggg ctagtaggta tcgaaccagc aacaaaggat attagtgtta cagcaggctt   2580
tgctttagta agtgcatttt taataaatgc aactgcaata aaaagaaggc gcgccgcatt   2640
cacttctttt ctatataaat atgagcgaag cgaataagcg tcggaaaagc agcaaaaagt   2700
ttcctttttg ctgttggagc atgggggttc agggggtgca gtatctgacg tcaatgccga   2760
gcgaaagcga gccgaagggt agcatttacg ttagataacc ccctgatatg ctccgacgct   2820
ttatatagaa aagaagattc aactaggtaa aatcttaata taggttgaga tgataaggtt   2880
tataaggaat ttgtttgttc taatttttca ctcattttgt tctaatttct tttaacaaat   2940
gttctttttt ttttagaaca gttatgatat agttagaata gtttaaaata aggagtgaga   3000
aaaagatgaa agaaagatat ggaacagtct ataaaggctc tcagaggctc atagacgaag   3060
```

-continued

```
aaagtggaga agtcatagag gtagacaagt tataccgtaa acaaacgtct ggtaacttcg   3120
taaaggcata tatagtgcaa ttaataagta tgttagatat gattggcgga aaaaaactta   3180
aaatcgttaa ctatatccta gataatgtcc acttaagtaa caatacaatg atagctacaa   3240
caagagaaat agcaaaagct acaggaacaa gtctacaaac agtaataaca acacttaaaa   3300
tcttagaaga aggaaatatt ataaaaagaa aaactggagt attaatgtta aaccctgaac   3360
tactaatgag aggcgacgac caaaaacaaa aatacctctt actcgaattt gggaactttg   3420
agcaagaggc aaatgaaata gattgacctc ccaataacac cacgtagtta ttgggaggtc   3480
aatctatgaa atgcgattaa gggccggcca gtgggcaagt tgaaaaattc acaaaaatgt   3540
ggtataatat ctttgttcat tagagcgata aacttgaatt tgagagggaa cttagatggt   3600
atttgaaaaa attgataaaa atagttggaa cagaaaagag tattttgacc actactttgc   3660
aagtgtacct tgtacctaca gcatgaccgt taaagtggat atcacacaaa taaaggaaaa   3720
gggaatgaaa ctatatcctg caatgcttta ttatattgca atgattgtaa accgccattc   3780
agagtttagg acggcaatca atcaagatgg tgaattgggg atatatgatg agatgatacc   3840
aagctataca atatttcaca atgatactga aacattttcc agcctttgga ctgagtgtaa   3900
gtctgacttt aaatcatttt tagcagatta tgaaagtgat acgcaacggt atggaaacaa   3960
tcatagaatg gaaggaaagc caaatgctcc ggaaaacatt tttaatgtat ctatgatacc   4020
gtggtcaacc ttcgatggct ttaatctgaa tttgcagaaa ggatatgatt atttgattcc   4080
tatttttact atggggaaat attataaaga agataacaaa attatacttc ctttggcaat   4140
tcaagttcat cacgcagtat gtgacggatt tcacatttgc cgttttgtaa acgaattgca   4200
ggaattgata aatagttaac ttcaggtttg tctgtaacta aaaacaagta tttaagcaaa   4260
aacatcgtag aaatacggtg ttttttgtta ccctaagttt aaactccttt ttgataatct   4320
catgaccaaa atcccttaac gtgagttttc gttccactga gcgtcagacc ccgtagaaaa   4380
gatcaaagga tcttcttgag atcctttttt tctgcgcgta atctgctgct tgcaaacaaa   4440
aaaaccaccg ctaccagcgg tggtttgttt gccggatcaa gagctaccaa ctctttttcc   4500
gaaggtaact ggcttcagca gagcgcagat accaaatact gtccttctag tgtagccgta   4560
gttaggccac cacttcaaga actctgtagc accgcctaca tacctcgctc tgctaatcct   4620
gttaccagtg gctgctgcca gtggcgataa gtcgtgtctt accgggttgg actcaagacg   4680
atagttaccg gataaggcgc agcggtcggg ctgaacgggg ggttcgtgca cacagcccag   4740
cttggagcga acgacctaca ccgaactgag atacctacag cgtgagcatt gagaaagcgc   4800
cacgcttccc gaagggagaa aggcggacag gtatccggta agcggcaggg tcggaacagg   4860
agagcgcacg agggagcttc caggggggaaa cgcctggtat ctttatagtc ctgtcgggtt   4920
tcgccacctc tgacttgagc gtcgattttt gtgatgctcg tcaggggggc ggagcctatg   4980
gaaaaacgcc agcaacgcgg cctttttacg gttcctggcc ttttgctggc cttttgctca   5040
catgttcttt cctgcgttat cccctgattc tgtggataac cgtattaccg cctttgagtg   5100
agctgatacc gctcgccgca gccgaacgac cgagcgcagc gagtcagtga gcgaggaagc   5160
ggaagagcgc ccaatacgca gggcccctg ca                                 5192
```